United States Patent
Peer Mohamed et al.

(10) Patent No.: US 10,912,780 B2
(45) Date of Patent: Feb. 9, 2021

(54) HETEROCYCLIC COMPOUNDS USEFUL AS ANTI-BACTERIAL AGENTS AND METHOD FOR PRODUCTION THEREOF

(71) Applicant: Bugworks Research, Inc., Wilmington, DE (US)

(72) Inventors: Shahul Hameed Peer Mohamed, Bengaluru (IN); Nagakumar Bharatham, Bengaluru (IN); Nainesh Katagihallimath, Bengaluru (IN); Sreevalli Sharma, Bengaluru (IN); Radha Nandishaiah, Bengaluru (IN); Vasanthi Ramachandran, Bengaluru (IN); Balasubramanian Venkataraman, Bengaluru (IN)

(73) Assignee: Bugworks Research, Inc., Wilmington, DE (US)

( * ) Notice: Subject to any disclaimer, the term of this patent is extended or adjusted under 35 U.S.C. 154(b) by 0 days.

(21) Appl. No.: 16/487,317

(22) PCT Filed: Jun. 8, 2018

(86) PCT No.: PCT/IN2018/050381
§ 371 (c)(1),
(2) Date: Aug. 20, 2019

(87) PCT Pub. No.: WO2018/225097
PCT Pub. Date: Dec. 13, 2018

(65) Prior Publication Data
US 2020/0085834 A1    Mar. 19, 2020

(30) Foreign Application Priority Data

Jun. 8, 2017 (IN) .............................. 201741020214

(51) Int. Cl.
| | | |
|---|---|---|
| *A61K 31/5383* | (2006.01) | |
| *A61K 45/06* | (2006.01) | |
| *C07D 498/04* | (2006.01) | |
| *C07D 519/00* | (2006.01) | |
| *A61P 31/00* | (2006.01) | |
| *A61P 31/04* | (2006.01) | |

(52) U.S. Cl.
CPC .......... *A61K 31/5383* (2013.01); *A61K 45/06* (2013.01); *A61P 31/04* (2018.01); *C07D 498/04* (2013.01); *C07D 519/00* (2013.01)

(58) Field of Classification Search
CPC .. A61K 31/5383; A61K 45/06; C07D 498/04; C07D 519/00; A61P 31/00; A61P 31/04
See application file for complete search history.

(56) References Cited

FOREIGN PATENT DOCUMENTS

| WO | WO 2008/126024 A2 | 10/2008 |
| WO | WO 2010/041194 A1 | 4/2010 |
| WO | WO 2010/055348 A1 | 5/2010 |
| WO | WO 2013/068948 A1 | 5/2013 |

OTHER PUBLICATIONS

Hubschwerlen et al., 2013, caplus an 2013:237515.*

* cited by examiner

*Primary Examiner* — Sun Jae Yoo
(74) *Attorney, Agent, or Firm* — Cooley LLP; Ivor R. Elrifi; Heidi A. Erlacher

(57) ABSTRACT

The present disclosure relates to compounds of Formula I, or their stereoisomers, pharmaceutically acceptable salts, complexes, hydrates, solvates, tautomers, polymorphs, racemic mixtures, optically active forms and pharmaceutically active derivatives thereof, and pharmaceutical compositions containing them as the active ingredient which can be used as medicaments. The aforementioned substances can also be used in the manufacture of medicaments for treatment, prevention or suppression of diseases, and conditions mediated by microbes. The present disclosure also relates to the synthesis and characterization of aforementioned substances.

Formula I

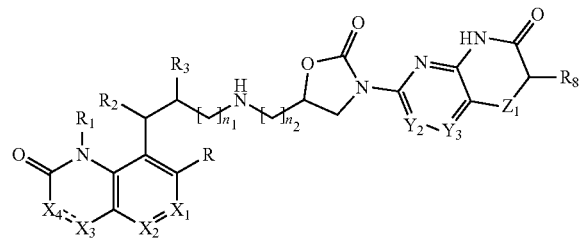

20 Claims, No Drawings

HETEROCYCLIC COMPOUNDS USEFUL AS ANTI-BACTERIAL AGENTS AND METHOD FOR PRODUCTION THEREOF

RELATED APPLICATIONS

This application is a U.S. National Phase application, filed under 35 U.S.C. § 371, of International Application No. PCT/IN2018/050381, filed on Jun. 8, 2018, which claims priority to and the benefit of Indian Application 201741020214, filed on Jun. 8, 2017, the entire contents of each of which are incorporated herein by reference in their entireties.

FIELD OF INVENTION

The present invention relates to the field of medicinal chemistry and more particularly to the development of antimicrobial compounds effective against bacteria, virus, fungi and protozoa including a spectrum of Gram-negative and Gram-positive pathogens. The present disclosure relates to compounds of Formula I, and their stereoisomers, pharmaceutically acceptable salts, complexes, hydrates, solvates, tautomers, polymorphs, racemic mixtures, optically active forms and pharmaceutically active derivatives thereof and pharmaceutical compositions containing them as the active ingredient. The present disclosure further relates to the synthesis and characterization of aforementioned compounds.

The compounds of the present disclosure are useful as medicaments and their use in the manufacture of medicaments for treatment, prevention or suppression of diseases, and conditions mediated by microbes. The present invention also provides evidence for treating infection caused by microbes.

BACKGROUND

Due to increasing antibiotic resistance, novel classes of antibacterial agents are acutely needed for the treatment of bacterial infection. In general, broad spectrum antibiotic compounds, which possess effective activity against both Gram-positive and Gram-negative pathogens are need of the hour. Current antibacterial drugs used to treat and prevent bacterial infections have been found to have limited effect. Further, there is a continuing need to identify new compounds with potent antibacterial activity with reduced possibility of pathogens developing resistance, which possess improved efficacy against bacterial infections that resist treatment with currently available antibiotics, or which possess selectivity against target microorganisms.

From the foregoing discussion, it is clear that compounds used in the state of the art to treat and prevent bacterial infection have been found to have limited effect.

SUMMARY

The present disclosure is based on the surprising discovery that compounds of Formula I (see below) exhibit advantageous antimicrobial properties. Thus, the present disclosure provides a compound of Formula I

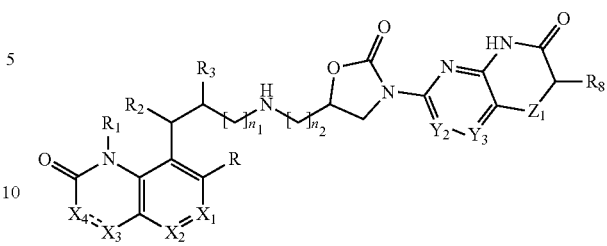

Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

The present disclosure further relates to a compound of Formula I, or its stereoisomers, pharmaceutically acceptable salts, complexes, hydrates, solvates, tautomers, polymorphs, racemic mixtures, optically active forms and pharmaceutically active derivatives thereof, for use in killing or inhibiting the growth of a microorganism selected from the group consisting of bacteria, virus, fungi, and protozoa.

The present disclosure further relates to use of a compound of Formula I, or its stereoisomers, pharmaceutically acceptable salts, complexes, hydrates, solvates, tautomers, polymorphs, racemic mixtures, optically active forms and pharmaceutically active derivatives thereof, in killing or inhibiting the growth of a microorganism selected from the group consisting of bacteria, virus, fungi and protozoa.

The present disclosure further relates to a compound of Formula I, or its stereoisomers, pharmaceutically acceptable salts, complexes, hydrates, solvates, tautomers, polymorphs, racemic mixtures, optically active forms and pharmaceutically active derivatives thereof, for use in treating a disease or condition in a patient wherein said disease or condition is caused by a microorganism selected from the group consisting of Gram positive, and Gram negative pathogens.

The present disclosure further relates to use of a compound of Formula I, or its stereoisomers, pharmaceutically acceptable salts, complexes, hydrates, solvates, tautomers, polymorphs, racemic mixtures, optically active forms and pharmaceutically active derivatives thereof, in treating disease or condition in a patient, wherein said disease or condition is caused by a microorganism selected from the group consisting of Gram positive, and Gram negative pathogens. The patient is typically a mammal, preferably a human.

The present disclosure further relates to a method of treating a bacterial infection or condition in a subject, said method comprising administering to a subject a compound of Formula I, or its stereoisomers, pharmaceutically acceptable salts, complexes, hydrates, solvates, tautomers, polymorphs, racemic mixtures, optically active forms and pharmaceutically active derivatives thereof, wherein said bacterial infection or condition is caused by a microorganism selected from the group consisting of Gram positive, and Gram negative pathogens.

The present disclosure relates to a composition comprising a compound of Formula I, or its stereoisomers, pharmaceutically acceptable salts, complexes, hydrates, solvates, tautomers, polymorphs, racemic mixtures, optically active forms, and pharmaceutically active derivatives thereof together with a carrier.

The present disclosure relates to a pharmaceutical composition comprising a compound of Formula I, or its stereoisomers, pharmaceutically acceptable salts, complexes, hydrates, solvates, tautomers, polymorphs, racemic mixtures, optically active forms, and pharmaceutically active derivatives thereof, together with a pharmaceutically acceptable carrier, optionally in combination with one or more other pharmaceutical compositions.

The present disclosure relates to a process of preparation of compound of Formula I, or its stereoisomers, pharmaceutically acceptable salts, complexes, hydrates, solvates, tautomers, polymorphs, racemic mixtures, optically active forms, and pharmaceutically active derivatives thereof.

The present disclosure relates to a process of preparation of a composition comprising a compound of Formula I, or its stereoisomers, pharmaceutically acceptable salts, complexes, hydrates, solvates, tautomers, polymorphs, racemic mixtures, optically active forms, and pharmaceutically active derivatives thereof together with a carrier.

The present disclosure relates to a process of preparation of pharmaceutical composition comprising a compound of Formula I, or its stereoisomers, pharmaceutically acceptable salts, complexes, hydrates, solvates, tautomers, polymorphs, racemic mixtures, optically active forms, and pharmaceutically active derivatives thereof, together with a pharmaceutically acceptable carrier, optionally in combination with one or more other pharmaceutical compositions.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

In this specification, the prefix $C_{x-y}$ as used in terms such as $C_{x-y}$alkyl and the like (where x and y are integers) indicates the numerical range of carbon atoms that are present in the group; for example, $C_{1-6}$ alkyl includes $C_1$alkyl (methyl), $C_2$alkyl (ethyl), $C_3$alkyl (propyl and isopropyl) and $C_4$alkyl (butyl, 1-methylpropyl, 2-methylpropyl, and t-butyl). Unless specifically stated, the bonding atom of a group may be any suitable atom of that group; for example, propyl includes prop-1-yl and prop-2-yl.

The term "alkyl" refers to a monoradical branched or unbranched saturated hydrocarbon chain having from 1 to 10 carbon atoms. This term is exemplified by groups such as n-butyl, iso-butyl, t-butyl, n-hexyl, n-decyl, and the like. The groups may be optionally substituted.

The term "haloalkyl" as used herein refers to an alkyl group in which one or more hydrogen atoms are replaced by the same number of identical or different halogen atoms. The term "haloalkyl" is exemplified by groups such as chloromethyl, trifluoromethyl, 1-fluoroethyl, 2,2,2-trifluoroethyl, and the like.

The term "alkylene" refers to a diradical branched or unbranched saturated hydrocarbon chain having from 1 to 6 carbon atoms. This term is exemplified by groups such as methylene, ethylene, propylene, butylene, hexylene, and the like. The groups may be optionally substituted. Representative substituted alkylene groups include amino substituted alkylenes.

The term "alkenyl" refers to a monoradical of a branched or unbranched unsaturated hydrocarbon group preferably having from 2, 3, 4, 5, or 6 carbon atoms and having 1, 2, or 3, double bond (vinyl), preferably 1 double bond. The groups may be optionally substituted.

The term "cycloalkyl" refers to carbocyclic groups of from 3 to 12 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, and the like, or multiple ring structures or carbocyclic groups to which is fused an aryl group, for example indane, and the like. The groups may be optionally substituted.

The terms "alkoxyl" or "alkoxy" refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether, either is, or resembles an alkoxyl, such as can be represented by one of —O-alkyl, —O-alkenyl, —O-alkynyl.

"Halo" or "Halogen", alone or in combination with any other term means halogens such as chloro (Cl), fluoro (F), bromo (Br) and iodo (I).

The term "heteroaryl" refers to an heteroaromatic carbocyclic group of 3 to 10 carbon atoms having a single ring (e.g. pyridine) or multiple rings (e.g. isoquinoline), or multiple condensed (fused) rings. Preferred heteroaryls include thiophene, pyrazole, thiazole, pyridine, and the like. The groups may be optionally substituted.

The term "carbocyclyl" or "carbocycle" refers to a saturated, unsaturated ring having 4 to 7 carbon atoms as a monocycle. Representative carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocyclyl" refers to a "carbocyclyl" as defined herein, wherein one or more carbon atoms have been replaced with a heteroatom selected from O, N, or S.

The term "haloalkoxy" refers to an alkoxy group as defined above further attached via halo linkage. For example, $C_{1-6}$ haloalkoxy refers to an alkoxy group having from 1-6 carbon atoms, or 1-3 carbon atoms further attached via halo linkage. Preferred haloalkoxy groups include, without limitation, —OCH$_2$Cl, —OCHCl$_2$, and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form, and mixtures thereof. Accordingly, the chemical structures depicted herein encompass all possible tautomeric forms of the illustrated or identified compounds.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

The compounds discussed herein in many instances may have been named and/or checked with ACD/Name by ACD/Labs® and/or Chemdraw by CambridgeSoft®.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "solvate", as used herein, refers to a crystal form of a substance which contains solvent.

The term "hydrate" refers to a solvate wherein the solvent is water.

The present disclosure relates to a compound of Formula I

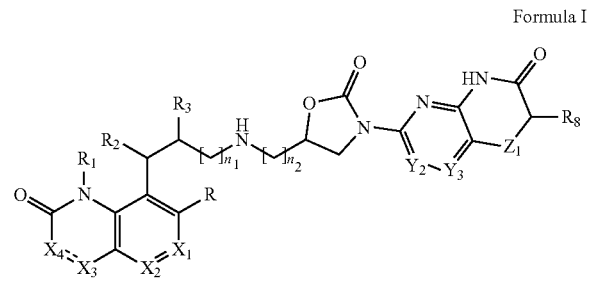

Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-4}$ alkyl, fluorine, $OC_{1-4}$ alkyl, hydroxyl, and amino;

R is selected from the group consisting of hydrogen, fluorine, cyano, $OC_{1-4}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-2}$ alkyl, fluorine, $OC_{1-2}$ alkyl, hydroxyl, and amino;

R is selected from the group consisting of hydrogen, fluorine, cyano, $OC_{1-2}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di($C_{1-6}$ alkyl)amino;

$R_2$ and $R_3$ are independently selected from the group consisting of hydrogen, fluorine, methoxy, hydroxyl, and amino; provided that at least one of $R_2$ and $R_3$ is hydrogen;

R is selected from the group consisting of hydrogen, fluorine, methoxy, cyano, and hydroxyl;

$X_1$ is N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di($C_{1-6}$ alkyl)amino;

$R_2$ and $R_3$ are independently selected from the group consisting of hydrogen, fluorine, methoxy, hydroxyl, and amino; provided that at least one of $R_2$ and $R_3$ is hydrogen;

R is selected from the group consisting of hydrogen, fluorine, methoxy, cyano, and hydroxyl;

$X_1$ is N or $CR_4$;

$R_4$ is selected from the group consisting of hydrogen, halogen, cyano, —$OC_{1-4}$ alkyl, $C_{1-4}$ haloalkyl, —$OC_{1-6}$ haloalkyl, and $C_{1-6}$ alkyl;

$X_2$ is N or $CR_5$;

$R_5$ is selected from the group consisting of hydrogen, halogen, cyano, —$OC_{1-4}$ alkyl, $C_{1-4}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di($C_{1-6}$ alkyl)amino;

$R_2$ and $R_3$ are independently selected from the group consisting of hydrogen, hydroxyl, fluorine, methyl, methoxy, and amino; provided that at least one of $R_2$ and $R_3$ is hydrogen;

R is selected from the group consisting of hydrogen, fluorine, methoxy, cyano, and hydroxyl;

$X_1$ is —N or $CR_4$;

$R_4$ is selected from the group consisting of hydrogen, fluorine, cyano, —$OC_{1-3}$ alkyl, and $C_{1-3}$ alkyl;

$X_2$ is —N or $CR_5$;

$R_5$ is selected from the group consisting of hydrogen, fluorine, cyano, —$OC_{1-3}$ alkyl, and $C_{1-3}$ alkyl;

$X_3$ is N or $CR_6$; and $X_4$ is CH or C—$CH_3$ wherein dotted line ( ---- ) represents a bond;

$R_6$ is selected from the group consisting of hydrogen, fluorine, cyano, —$OC_{1-3}$ alkyl, and $C_{1-3}$ alkyl, wherein $C_{1-3}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-3}$ alkyl, and $C_{1-3}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of $CH_3$, $CH_2CH_3$, $CH(CH_3)_2$, cylopropyl, cyclobutyl, $CH_2CF_3$, CH₂CHFCH₃, CH₂CF₂CH₃, CH₂CH(OH)CH₃, CH₂CH₂OH, CH₂CH₂OCH₃, CH₂CH(OCH₃)CH₃, CH₂CH₂NH₂, CH₂CH₂NHCH₃, CH₂CH(NH₂)CH₃, CH₂CH₂N(CH₃)₂, CH₂CHFCH₂NH₂, CH₂CF₂CH₂NH₂, CH₂CH₂SO₂CH₃,

[structures: cyclopropylmethyl, cyclobutylmethyl, cyclobutyl-OH, oxetanyl, oxetanylmethyl, tetrahydrofuranyl, tetrahydropyranyl, cyclobutyl-NH₂, cyclopropyl-NH₂, 1-aminocyclopropylmethyl, cyclopropylmethyl-NH₂, azetidinyl-NH, N-methylazetidinyl, azetidinylmethyl-NH]

$R_2$ and $R_3$ are independently selected from the group consisting of hydrogen, hydroxyl, fluorine, methyl, methoxy, and amino; provided that at least one of $R_2$ and $R_3$ is hydrogen;

R is selected from the group consisting of hydrogen, fluorine, methoxy, cyano, and hydroxyl;

$X_1$ is —N or $CR_4$;

$R_4$ is selected from the group consisting of hydrogen, fluorine, cyano, —$OC_{1-3}$ alkyl, and $C_{1-3}$ alkyl;

$X_2$ is —N or $CR_5$;

$R_5$ is selected from the group consisting of hydrogen, fluorine, cyano, —$OC_{1-3}$ alkyl, and $C_{1-3}$ alkyl;

$X_3$ is N or $CR_6$; and $X_4$ is CH or C—CH₃ wherein dotted line (----) represents a bond;

$R_6$ is selected from the group consisting of hydrogen, fluorine, cyano, —$OC_{1-3}$ alkyl, and $C_{1-3}$ alkyl, wherein $C_{1-3}$ alkyl is optionally substituted with hydroxyl or amino;

$X_4$ is CH₂ or O; and $X_3$ is CH₂ when dotted line (---) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-3}$ alkyl, and $C_{1-3}$ alkyl;

$Z_1$ is selected from the group consisting of O, S, and CH₂; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of CH₃, CH₂CH₃, CH(CH₃)₂, cylopropyl, cyclobutyl, CH₂CF₃, CH₂CHFCH₃, CH₂CF₂CH₃, CH₂CH(OH)CH₃, CH₂CH₂OH, CH₂CH₂OCH₃, CH₂CH(OCH₃)CH₃, CH₂CH₂NH₂, CH₂CH₂NHCH₃, CH₂CH(NH₂)CH₃, CH₂CH₂N(CH₃)₂, CH₂CHFCH₂NH₂, CH₂CF₂CH₂NH₂, CH₂CH₂SO₂CH₃,

[structures: cyclopropylmethyl, cyclobutylmethyl, cyclobutyl-OH, oxetanyl, oxetanylmethyl, tetrahydrofuranyl, tetrahydropyranyl, cyclobutyl-NH₂, cyclopropyl-NH₂, 1-aminocyclopropylmethyl, cyclopropylmethyl-NH₂, azetidinyl-NH, N-methylazetidinyl, azetidinylmethyl-NH]

$R_2$ and $R_3$ are independently selected from the group consisting of hydrogen, fluorine, $C_{1-6}$ alkyl, $OC_{1-6}$ alkyl, hydroxyl, and amino; provided that at least one of $R_2$ and $R_3$ is hydrogen;

R is selected from the group consisting of hydrogen, fluorine, cyano, $OC_{1-6}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;

$X_3$ is N or $CR_6$; and $X_4$ is CH or C—$C_{1-6}$ alkyl wherein dotted line (----) represents a bond;

$R_6$ is selected from the group consisting of hydrogen, halogen, cyano, —$OC_{1-3}$ alkyl, and $C_{1-6}$ alkyl, wherein $C_{1-3}$ alkyl is optionally substituted with hydroxyl or amino;

$X_4$ is CH₂ or O; and $X_3$ is CH₂ when dotted line (---) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-3}$ alkyl, and $C_{1-3}$ alkyl;

$Z_1$ is selected from the group consisting of O, S, and CH₂; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of CH₃, CH₂CH₃, CH(CH₃)₂, cylopropyl, cyclobutyl, CH₂CF₃, CH₂CHFCH₃, CH₂CF₂CH₃, CH₂CH(OH)CH₃, CH₂CH₂OH, CH₂CH₂OCH₃, CH₂CH(OCH₃)CH₃, CH₂CH₂NH₂, CH₂CH₂NHCH₃, CH₂CH(NH₂)CH₃, CH₂CH₂N(CH₃)₂, CH₂CHFCH₂NH₂, CH₂CF₂CH₂NH₂, CH₂CH₂SO₂CH₃,

[structures: cyclopropylmethyl, cyclobutylmethyl, cyclobutyl-OH, oxetanyl]

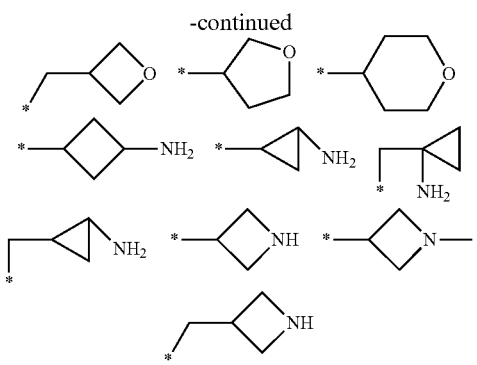

R₂ and R₃ are independently selected from the group consisting of hydrogen, fluorine, $OC_{1-4}$ alkyl, hydroxyl, and amino; provided that at least one of R₂ and R₃ is hydrogen;
R is selected from the group consisting of hydrogen, fluorine, cyano, $OC_{1-6}$ alkyl, and hydroxyl;
$X_1$ is —N or $CR_4$;
$R_4$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_2$ is —N or $CR_5$;
$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_3$ is N or $CR_6$; and $X_4$ is CH or C—$C_{1-6}$ alkyl wherein dotted line ( ---- ) represents a bond;
$R_6$ is selected from the group consisting of hydrogen, halogen, cyano, —$OC_{1-3}$ alkyl, and $C_{1-3}$ alkyl, wherein $C_{1-3}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, halogen, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CH_2SO_2CH_3$,

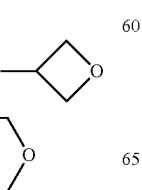

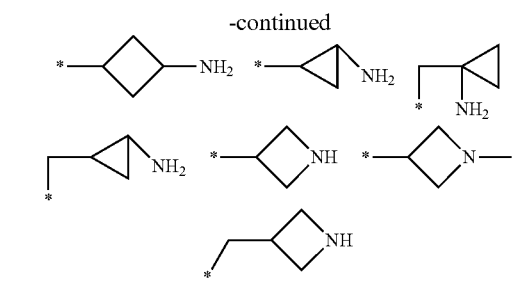

R₂ and R₃ are is independently selected from the group consisting of hydrogen, hydroxyl, methoxy, fluorine, and amino; provided that at least one of R₂ and R₃ is hydrogen;
R is selected from the group consisting of hydrogen, fluorine, methoxy, cyano, and hydroxyl;
$X_1$ is N or $CR_4$;
$R_4$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_2$ is N or $CR_5$;
$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_3$ is N or $CR_6$; and $X_4$ is CH or C—$CH_3$ wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, halogen, cyano, $C_{1-6}$ alkoxy, $C_{1-6}$ haloalkyl, $OC_{1-6}$ haloalkyl, and $C_{1-6}$ alkyl;
$Z_1$ is selected from the group consisting of O, S, and $CH_2$; and
$R_8$ is selected from the group consisting of hydrogen, methyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is independently selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CH_2SO_2CH_3$,

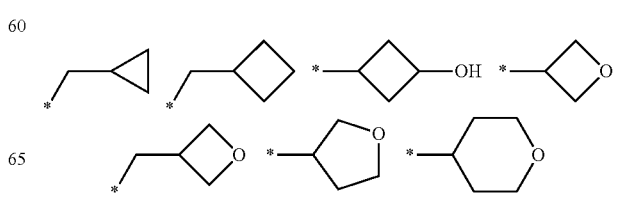

-continued

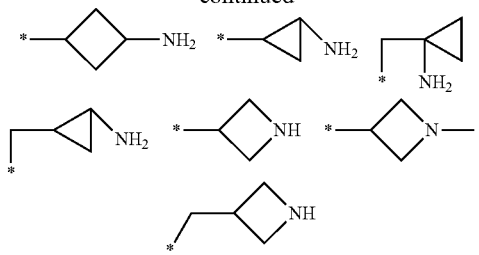

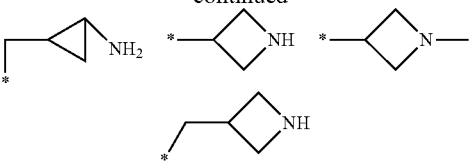

R₂ and R₃ are is independently selected from the group consisting of hydrogen, hydroxyl, fluorine, and amino; provided that at least one of R₂ and R₃ is hydrogen;
R is selected from the group consisting of hydrogen, fluorine, methoxy, cyano, and hydroxyl;
$X_1$ is —N or $CR_4$;
$R_4$ is selected from the group consisting of hydrogen, halogen, cyano, —$OC_{1-6}$ alkyl, and $C_{1-6}$ alkyl;
$X_2$ is N or $CR_5$;
$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_3$ is N or $CR_6$; and $X_4$ is CH or C—$CH_3$ wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, halogen, cyano, —$OC_{1-3}$ alkyl, $C_{1-3}$ haloalkyl, $OC_{1-6}$ haloalkyl, and $C_{1-3}$ alkyl;
$Z_1$ is selected from the group consisting of O, S, and $CH_2$; and
$R_8$ is selected from the group consisting of hydrogen, methyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$,

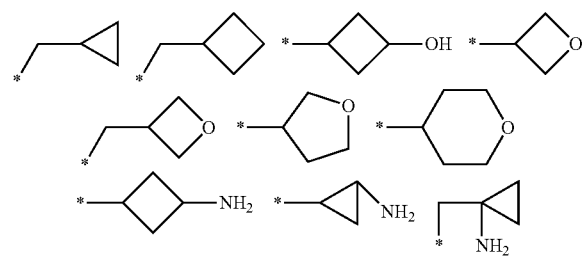

R₂ and R₃ are independently selected from the group consisting of hydrogen, hydroxyl, methyl, methoxy, and amino; provided that at least one of R₂ and R₃ is hydrogen;
R is selected from the group consisting of hydrogen, fluorine, cyano, and hydroxyl;
$X_1$ is —N or $CR_4$;
$R_4$ is selected from the group consisting of hydrogen, fluorine, cyano, —$OC_{1-3}$ alkyl, and $C_{1-3}$ alkyl;
$X_2$ is —N or $CR_5$;
$R_5$ is selected from the group consisting of hydrogen, fluorine, cyano, —$OC_{1-3}$ alkyl, and $C_{1-3}$ alkyl;
$X_3$ is N or $CR_6$; and $X_4$ is CH or C—$CH_3$ wherein dotted line ( ---- ) represents a bond;
$R_6$ is selected from the group consisting of hydrogen, fluorine, cyano, —$OC_{1-3}$ alkyl, and $C_{1-3}$ alkyl, wherein $C_{1-3}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, fluorine, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, methyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$,

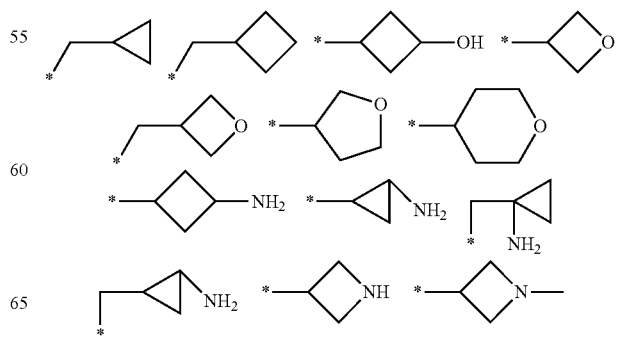

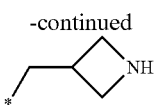

R₂ and R₃ are independently selected from the group consisting of hydrogen, hydroxyl, methoxy, and amino; provided that at least one of R₂ and R₃ is hydrogen;
R is selected from the group consisting of hydrogen, fluorine, cyano, and hydroxyl;
$X_1$ is —N or $CR_4$;
$R_4$ is selected from the group consisting of hydrogen, fluorine, cyano, —$OC_{1-3}$ alkyl, and $C_{1-3}$ alkyl;
$X_2$ is —N or $CR_5$;
$R_5$ is selected from the group consisting of hydrogen, fluorine, cyano, —$OC_{1-3}$ alkyl, and $C_{1-3}$ alkyl;
$X_3$ is N or $CR_6$; and $X_4$ is CH or C—$CH_3$ wherein dotted line ( ---- ) represents a bond;
$R_6$ is selected from the group consisting of hydrogen, fluorine, cyano, —$OC_{1-3}$ alkyl, $CH_2OH$, $CH_2NH_2$;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, fluorine, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, methyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$,

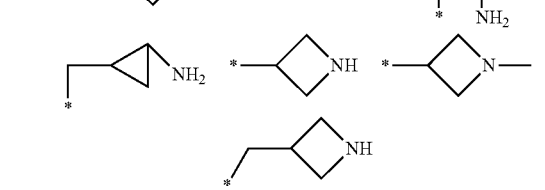

R₂ and R₃ are independently selected from the group consisting of hydrogen, methoxy, fluorine, and hydroxyl; provided that at least one of R₂ and R₃ is hydrogen;
R is selected from the group consisting of hydrogen, fluorine, methoxy, cyano, and hydroxyl;
$X_1$ is —N or $CR_4$;
$R_4$ is selected from the group consisting of hydrogen, fluorine, cyano, —$OC_{1-3}$ alkyl, and $C_{1-3}$ alkyl;
$X_2$ is —N or $CR_5$;
$R_5$ is selected from the group consisting of hydrogen, fluorine, cyano, —$OC_{1-3}$ alkyl, and $C_{1-3}$ alkyl;
$X_3$ is N or $CR_6$; and $X_4$ is CH or C—$CH_3$ wherein dotted line ( ---- ) represents a bond;
$R_6$ is selected from the group consisting of hydrogen, fluorine, cyano, —$OC_{1-3}$ alkyl, and $C_{1-3}$ alkyl, wherein $C_{1-3}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, fluorine, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein
$R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$, R₂ and R₃ are independently selected from the group consisting of hydrogen, methoxy, fluorine, and hydroxyl; provided that at least one of R₂ and R₃ is hydrogen;
R is selected from the group consisting of hydrogen, fluorine, methoxy, cyano, and hydroxyl;
$X_1$ is —N or $CR_4$;

$R_4$ is selected from the group consisting of hydrogen, fluorine, cyano, —$OC_{1-2}$ alkyl, and $C_{1-2}$ alkyl;

$X_2$ is —N or $CR_5$;

$R_5$ is selected from the group consisting of hydrogen, fluorine, cyano, —$OC_{1-2}$ alkyl, and $C_{1-2}$ alkyl;

$X_3$ is N or $CR_6$; and $X_4$ is CH or C—$CH_3$ wherein dotted line ( ---- ) represents a bond;

$R_6$ is selected from the group consisting of hydrogen, fluorine, cyano, —$OC_{1-2}$ alkyl, and $C_{1-3}$ alkyl, wherein $C_{1-2}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, fluorine, cyano, —$OC_{1-2}$ alkyl, and $C_{1-2}$ alkyl;

$Z_1$ is selected from the group consisting of O, and $CH_2$; and $R_8$ is selected from the group consisting of hydrogen, $C_{1-4}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$,

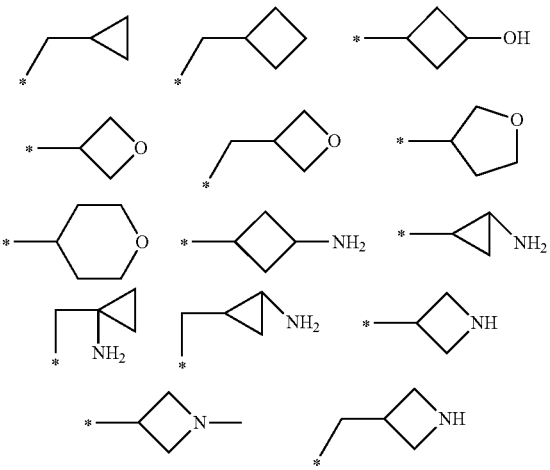

$R_2$ and $R_3$ are independently selected from the group consisting of hydrogen, fluorine, methoxy, amino, and hydroxyl; provided that at least one of $R_2$ and $R_3$ is hydrogen;

R is selected from the group consisting of hydrogen, fluorine, cyano methoxy, and hydroxyl;

$X_1$ is —N or $CR_4$;

$R_4$ is selected from the group consisting of hydrogen, fluorine, cyano, methoxy, and methyl;

$X_2$ is —N or $CR_5$;

$R_5$ is selected from the group consisting of hydrogen, fluorine, cyano, methoxy, and methyl;

$X_3$ is N or $CR_6$; and $X_4$ is CH or C—$CH_3$ wherein dotted line ( ---- ) represents a bond;

$R_6$ is selected from the group consisting of hydrogen, fluorine, cyano, methoxy, methyl, $CH_2OH$, and $CH_2NH_2$;

$X_4$ is $CH_2$ or O; and $X_3$ is $CH_2$ when dotted line ( --- ) represents no bond;

$n_1$ is 0 or 1;

$n_2$ is 0 to 2;

$Y_1$ is —N or CH; $Y_2$ is —N or $CR_7$;

$R_7$ is selected from the group consisting of hydrogen, fluorine, cyano, methoxy, and methyl;

$Z_1$ is 0; and $R_8$ is selected from the group consisting of hydrogen, methyl, and fluorine.

According to an embodiment the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl wherein dotted line ( ---- ) represents a bond;

$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof,
wherein
$R_1$ is selected from the group consisting of, $C_{1-6}$ alkyl, $C_{2-6}$ alkenyl, $C_{3-6}$ cycloalkyl, $C_{1-6}$ alkylamino, $C_{1-6}$ aminoalkylene, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, $C_{3-6}$ cycloalkylamino, $C_{3-6}$ aminocycloalkyl, $C_{1-6}$ alkylamino, or di ($C_{1-6}$ alkyl) amino;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is —N or $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is N or $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is N or $CR_6$; and $X_4$ is CH or C—$C_{1-6}$ alkyl wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof,
wherein
$R_1$ is selected from the group consisting of, $C_{1-6}$ alkyl, $C_{2-6}$ alkenyl, each of which is unsubstituted or substituted with 1 to 3 groups independently selected from $SO_3H$, $COOR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, $C_{3-6}$ cycloalkylamino, $C_{3-6}$ aminocycloalkyl, $C_{1-6}$ alkylamino, or di ($C_{1-6}$ alkyl)amino;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is —N or $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is N or $CR_6$; and $X_4$ is CH or C—$C_{1-6}$ alkyl wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 0 to 2;
$Y_2$ and $Y_3$ are independently selected from —N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof,
wherein
$R_1$ is selected from the group consisting of, $C_{1-6}$ alkyl, $C_{3-6}$ cycloalkyl, each of which is unsubstituted or substituted with 1 to 3 groups independently selected from amino, hydroxyl, $C_{1-6}$ alkoxy;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is —N or $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is —N or $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is $CR_6$; and $X_4$ is CH or C—$C_{1-6}$ alkyl wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$n_1$ is 0 or 1;
$n_2$ is 0 to 2;
$Y_2$ and $Y_3$ are independently selected from —N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of, $C_{1-6}$ alkyl, $C_{2-6}$ alkenyl, $C_{3-6}$ cycloalkyl, each of which is unsubstituted or substituted with 1 to 3 groups independently selected from $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is —N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is —N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl when dotted line ( ---- ) represents a bond, wherein $R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is N or $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl when dotted line ( ---- ) represents a bond, wherein
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 1;
$n_2$ is 0 to 2;
$Y_2$ and $Y_3$ are independently selected from —N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof,
wherein
$R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is N or $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is N or $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is N or $CR_6$; and $X_4$ is CH or C—$C_{1-6}$ alkyl when dotted line ( ---- ) represents a bond,
wherein
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 1;
$Y_2$ and $Y_3$ are independently selected from —N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof,
wherein
$R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is N or $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is N or $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is N or $CR_6$; and $X_4$ is CH or C—$C_{1-6}$ alkyl when dotted line ( ---- ) represents a bond,
wherein
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is $CH_2$ or O; and $X_3$ is $CH_2$ when dotted line ( --- ) represents no bond;
$n_1$ is 0 or 1;
$n_2$ is 2;
$Y_2$ and $Y_3$ are independently selected from —N or $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof,
wherein $R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is N $X_3$ is N or $CR_6$; and $X_4$ is CH or C—$C_{1-6}$ alkyl when dotted line ( ---- ) represents a bond,
wherein $R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof,
wherein $R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino;

$R_2$ and $R_3$ are independently selected from the group consisting of hydrogen, $C_{1-6}$ alkyl, fluorine, $OC_{1-6}$ alkyl, hydroxyl, and amino;

R is selected from the group consisting of hydrogen, fluorine, cyano, $OC_{1-6}$ alkyl, and hydroxyl;

$X_1$ is N or $CR_4$;

$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is $CR_5$;

$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_3$ is N or $CR_6$; and $X_4$ is CH or C—$C_{1-6}$ alkyl when dotted line ( ---- ) represents a bond,
wherein $R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;

$X_4$ is $CH_2$ or O; and $X_3$ is $CH_2$ when dotted line ( --- ) represents no bond;

$n_1$ is 0 or 1;

$n_2$ is 0 to 2;

$Y_2$ and $Y_3$ are independently selected from —N or $CR_7$;

$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$Z_1$ is selected from the group consisting of O, S, and $CH_2$; and $R_8$ is selected from the group consisting of hydrogen, $C_{1-6}$ alkyl, and fluorine.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, wherein $R_1$ is selected from the group consisting of $CH_3$, $CH_2CH_3$, $CH(CH_3)_2$, cylopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$, $R_2$ and $R_3$ are independently selected from the group consisting of hydrogen, fluorine, methoxy, amino, and hydroxyl; provided that at least one of $R_2$ and $R_3$ is hydrogen;

R is selected from the group consisting of hydrogen, fluorine, cyano methoxy, and hydroxyl;

$X_1$ is $CR_4$;

$R_4$ is selected from the group consisting of hydrogen, fluorine, cyano, methoxy, and methyl;

$X_2$ is N or $CR_5$;

$R_5$ is selected from the group consisting of hydrogen, methoxy, and methyl;

$X_3$ is N or $CR_6$; and $X_4$ is CH or C—$CH_3$ wherein dotted line ( ---- ) represents a bond;

$R_6$ is selected from the group consisting of hydrogen, fluorine, cyano, methoxy, methyl, $CH_2OH$, and $CH_2NH_2$;

$X_4$ is $CH_2$ or O; and $X_3$ is $CH_2$ when dotted line ( --- ) represents no bond;

$n_1$ is 0 or 1;
$n_2$ is 0 to 2;
$Y_1$ is —N or CH; $Y_2$ is —N or $CR_7$;
$R_7$ is selected from the group consisting of hydrogen, fluorine, cyano, methoxy, and methyl;
$Z_1$ is 0; and
$R_8$ is selected from the group consisting of hydrogen, methyl, and fluorine.

According to an embodiment, the present disclosure relates to a compound of Formula I, its stereoisomers, pharmaceutically acceptable salts, complexes, hydrates, solvates, tautomers, polymorphs, racemic mixtures, optically active forms and pharmaceutically active derivatives thereof, wherein, $X_1$ is CH.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $X_2$ is N or CH.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $X_3$ is selected from CH, $CH_2$, C—$CH_2NH_2$, C—$CH_2OH$, or N.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $X_4$ is selected from CH, $CH_2$, or C—$CH_3$.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $R_1$ is selected from $CH_3$, $CH_2CH_3$, $CH_2CH_2OH$, $CH_2CH_2OCH_3$, or $CH_2CH_2SO_2CH_3$.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $R_2$ is H.

According to an embodiment, the present disclosure relates to a compound of Formula I, Ia or its stereoisomers, pharmaceutically acceptable salts, complexes, hydrates, solvates, tautomers, polymorphs, racemic mixtures, optically active forms and pharmaceutically active derivatives thereof, wherein, $R_3$ is H, or OH.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, R is fluorine.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $Y_2$ is CH or N.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $Y_3$ is CH or N.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $Z_1$ is O.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein, $R_8$ is H.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein $n_1$ is 0 or 1.

According to an embodiment, the present disclosure relates to a compound of Formula I, or its stereoisomers, pharmaceutically acceptable salts, complexes, hydrates, solvates, tautomers, polymorphs, racemic mixtures, optically active forms and pharmaceutically active derivatives thereof, wherein $n_2$ is 1 or 2.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivatives thereof, which is selected from a group consisting of:

6-(5-(((3-(3-fluoro-5-methyl-6-oxo-5,6-dihydro-1,5-naphthyridin-4-yl)propyl)amino)methyl)-2-oxooxazolidin-3-yl)-2H-pyrido[3,2-b][1,4]oxazin-3(4H)-one (Example 1)

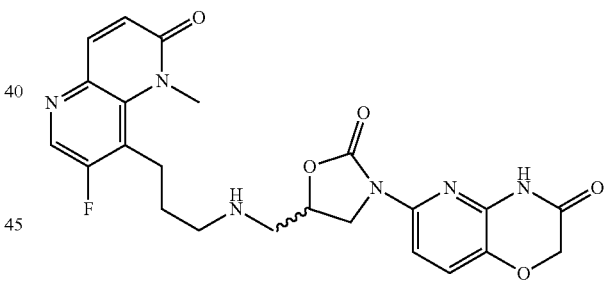

(S)-6-(5-(((2-(7-fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one (Example 2)

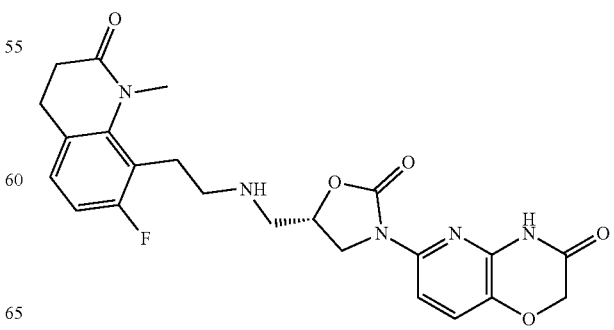

| 33 | 34 |
|---|---|
| (R)-6-(5-(((2-(7-fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one (Example 3) | (S)-6-(5-(((2-(6-fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 6) |

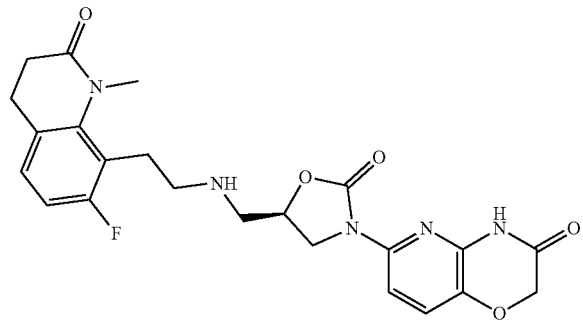 [SMILES: CN1C(=O)CCc2ccc(F)c(CCNC[C@@H]3CN(c4ccc5c(n4)NC(=O)CO5)C(=O)O3)c21]

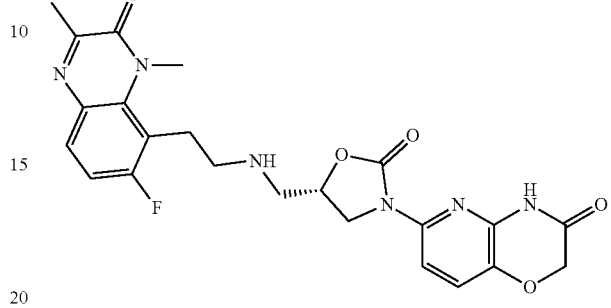

(S)-6-(5-(((2-(6-fluoro-4-methyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 4)

(R)-6-(5-(((2-(6-fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 7)

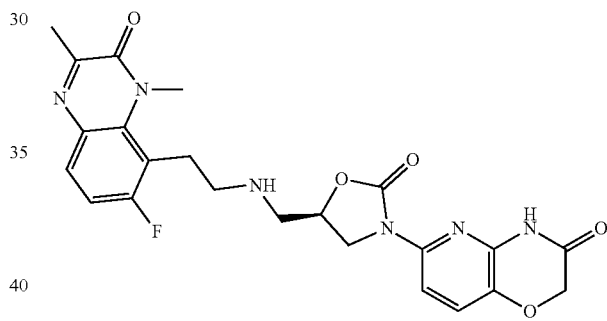

(R)-6-(5-(((2-(6-fluoro-4-methyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 5)

(S)-6-(5-(((2-(7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one (Example 8)

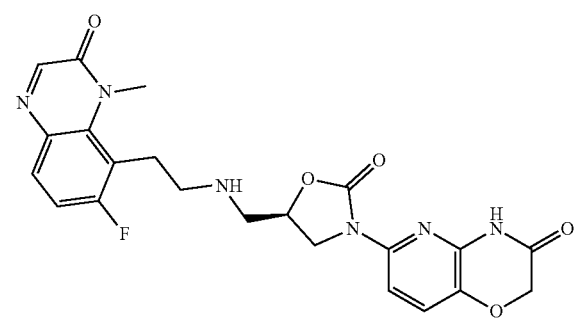 [SMILES: Cn1c(=O)cnc2ccc(F)c(CCNC[C@@H]3CN(c4ccc5c(n4)NC(=O)CO5)C(=O)O3)c21]

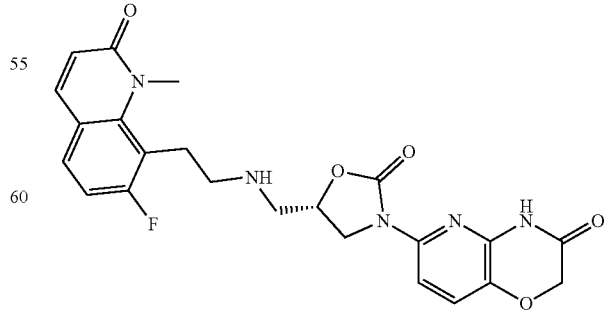

(S)-6-(5-(((2-(6-fluoro-4-(2-hydroxyethyl)-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 9)

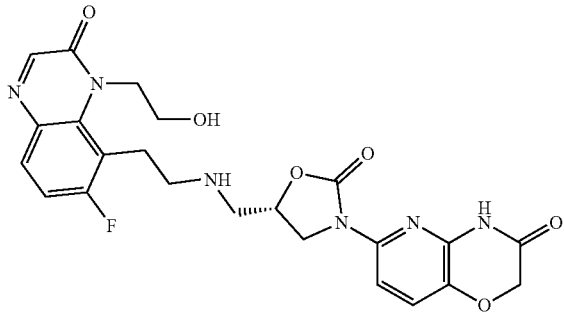 [SMILES: O=C1COc2ccc(N3C[C@H](CNCCc4c(F)ccc5ncc(=O)n(CCO)c45)OC3=O)nc2N1]

(S)-6-(5-(((2-(7-fluoro-1-(2-hydroxyethyl)-2-oxo-1,2-dihydroquinolin-8-yl)ethyl)amino)methyl)-2-oxooxazolidin-3-yl)-2H-pyrido[3,2-b][1,4]oxazin-3(4H)-one (Example 10)

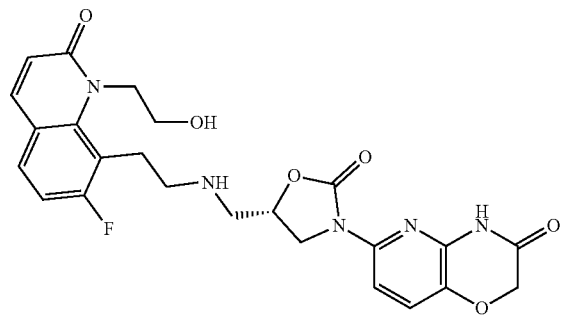 [SMILES: O=C1COc2ccc(N3C[C@H](CNCCc4c(F)ccc5ccc(=O)n(CCO)c45)OC3=O)nc2N1]

(S)-6-(5-(((2-(7-fluoro-1-(2-(methylsulfonyl)ethyl)-2-oxo-1,2-dihydroquinolin-8-yl)ethyl)amino)methyl)-2-oxooxazolidin-3-yl)-2H-pyrido[3,2-b][1,4]oxazin-3(4H)-one (Example 11)

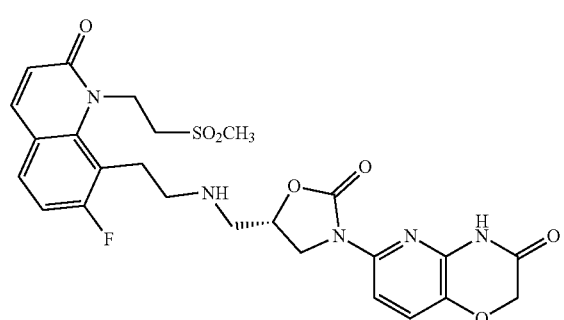

(S)-6-(5-(((2-(7-fluoro-4-(hydroxymethyl)-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one (Example 12)

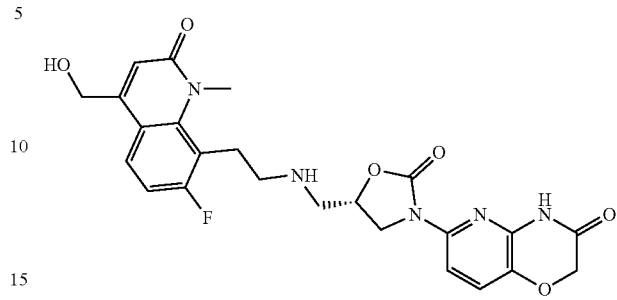

(S)-6-(5-(((2-(4-(aminomethyl)-7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one (Example 13)

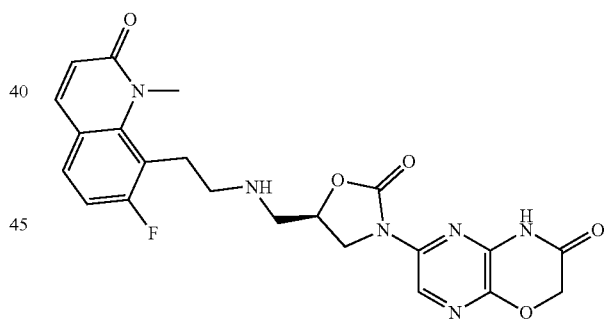

(R)-6-(5-(((2-(7-fluoro-1-methyl-2-oxo-1,2-dihydroquinolin-8-yl)ethyl)amino)methyl)-2-oxooxazolidin-3-yl)-2H-pyrazino[2,3-b][1,4]oxazin-3(4H)-one (Example 14)

(S)-6-(5-(((2-(7-fluoro-1-methyl-2-oxo-1,2-dihydroquinolin-8-yl)ethyl)amino)methyl)-2-oxooxazolidin-3-yl)-2H-pyrazino[2,3-b][1,4]oxazin-3(4H)-one (Example 15)

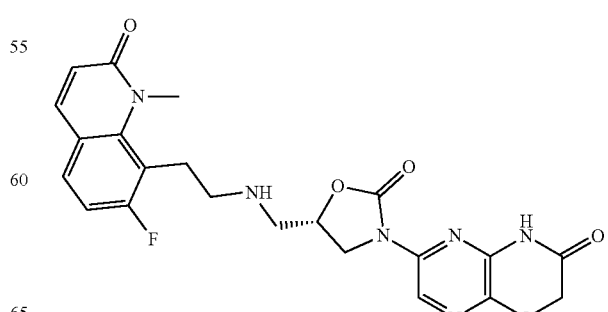

(S)-2-(5-(((2-(7-fluoro-1-methyl-2-oxo-1,2-dihydroquino-lin-8-yl)ethyl)amino)methyl)-2-oxooxazolidin-3-yl)-6H-pyrimido[5,4-b][1,4]oxazin-7(8H)-one (Example 16)

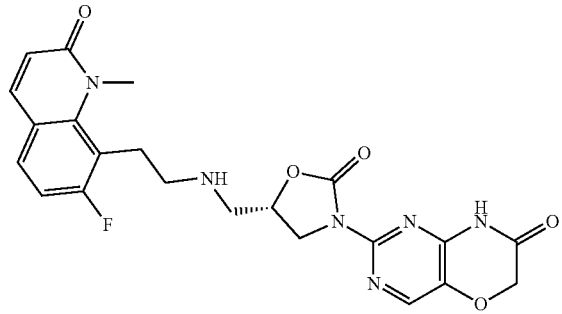 [SMILES: Cn1c(=O)ccc2ccc(F)c(CCNC[C@H]3CN(c4ncc5c(n4)NC(=O)CO5)C(=O)O3)c21]

(S)-2-(5-(((2-(6-fluoro-4-methyl-3-oxo-3,4-dihydroqui-noxalin-5-yl)ethyl)amino)methyl)-2-oxooxazolidin-3-yl)-6H-pyrimido[5,4-b][1,4]oxazin-7(8H)-one (Example 17)

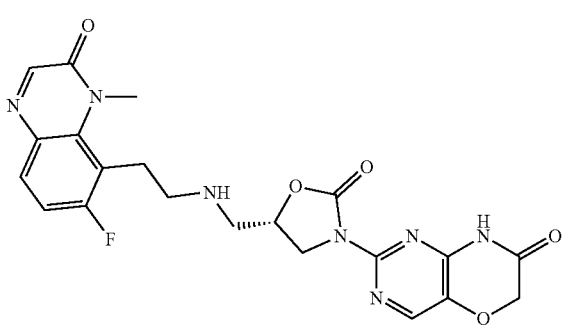 [SMILES: Cn1c(=O)cnc2ccc(F)c(CCNC[C@H]3CN(c4ncc5c(n4)NC(=O)CO5)C(=O)O3)c21]

6-((S)-5-((((S)-3-(7-fluoro-1-methyl-2-oxo-1,2-dihydroqui-nolin-8-yl)-2-hydroxypropyl)amino)methyl)-2-oxooxa-zolidin-3-yl)-2H-pyrido[3,2-b][1,4]oxazin-3(4H)-one (Example 18)

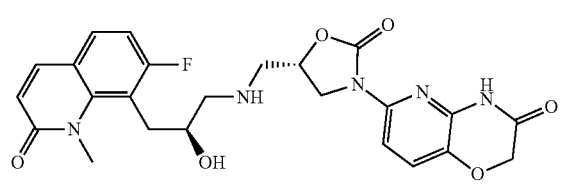 [SMILES: Cn1c(=O)ccc2ccc(F)c(C[C@H](O)CNC[C@H]3CN(c4ccc5c(n4)NC(=O)CO5)C(=O)O3)c21]

6-((S)-5-((((R)-3-(7-fluoro-1-methyl-2-oxo-1,2-dihydro-quinolin-8-yl)-2-hydroxypropyl)amino)methyl)-2-oxooxa-zolidin-3-yl)-2H-pyrido[3,2-b][1,4]oxazin-3(4H)-one (Example 19)

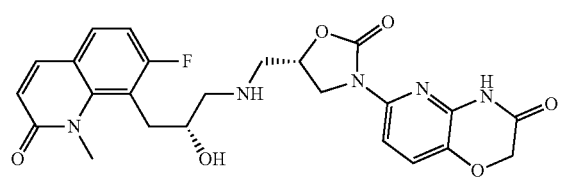 [SMILES: Cn1c(=O)ccc2ccc(F)c(C[C@@H](O)CNC[C@H]3CN(c4ccc5c(n4)NC(=O)CO5)C(=O)O3)c21]

(S)-6-(5-(((2-(7-fluoro-1-(2-hydroxyethyl)-2-oxo-1,2-dihy-droquinolin-8-yl)ethyl)amino)methyl)-2-oxooxazolidin-3-yl)-2H-pyrazino[2,3-b][1,4]oxazin-3(4H)-one (Example 20)

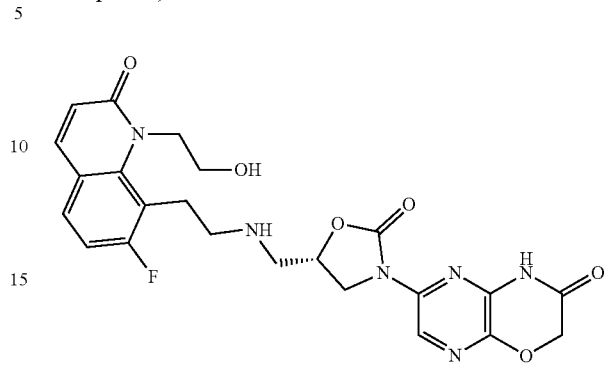

(S)-6-(5-(((2-(7-fluoro-1-(2-methoxyethyl)-2-oxo-1,2-dihy-droquinolin-8-yl)ethyl)amino)methyl)-2-oxooxazolidin-3-yl)-2H-pyrazino[2,3-b][1,4]oxazin-3(4H)-one (Example 21)

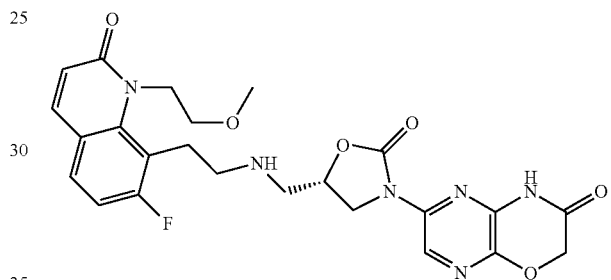

(S)-6-(5-(((3-(7-fluoro-1-methyl-2-oxo-1,2-dihydroquino-lin-8-yl)propyl)amino)methyl)-2-oxooxazolidin-3-yl)-2H-pyrazino[2,3-b][1,4]oxazin-3(4H)-one (Example 22)

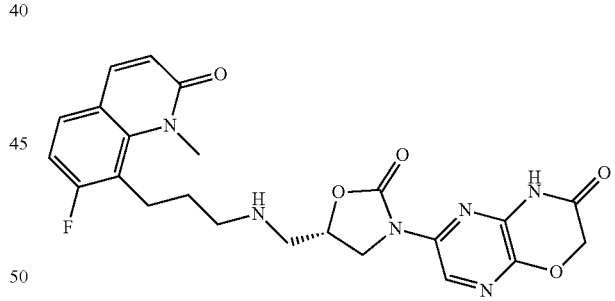

(R)-6-(5-(((3-(7-fluoro-1-methyl-2-oxo-1,2-dihydroquino-lin-8-yl)propyl)amino)methyl)-2-oxooxazolidin-3-yl)-2H-pyrazino[2,3-b][1,4]oxazin-3(4H)-one (Example 23)

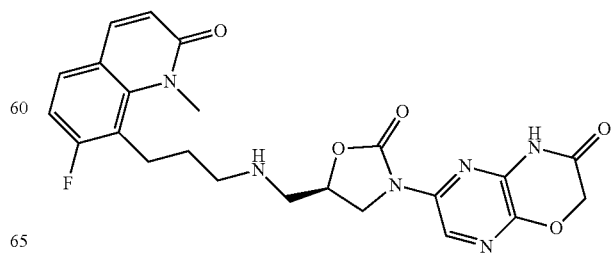

(S)-6-(5-(2-((2-(7-fluoro-1-methyl-2-oxo-1,2-dihydroqui-
nolin-8-yl)ethyl)amino)ethyl)-2-oxooxazolidin-3-yl)-2H-
pyrazino[2,3-b][1,4]oxazin-3(4H)-one (Example 24)

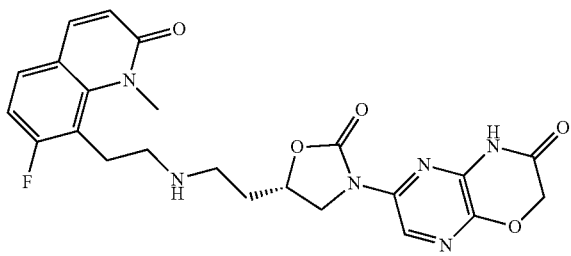 [SMILES: Cn1c(=O)ccc2ccc(F)c(CCNCC[C@H]3CN(c4cnc5c(n4)NC(=O)CO5)C(=O)O3)c21]

(R)-6-(5-(2-((2-(7-fluoro-1-methyl-2-oxo-1,2-dihydroqui-
nolin-8-yl)ethyl)amino)ethyl)-2-oxooxazolidin-3-yl)-2H-
pyrazino[2,3-b][1,4]oxazin-3(4H)-one (Example 25)

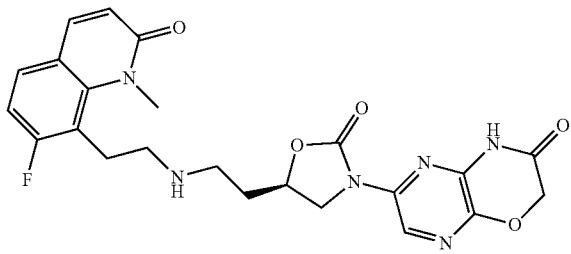 [SMILES: Cn1c(=O)ccc2ccc(F)c(CCNCC[C@@H]3CN(c4cnc5c(n4)NC(=O)CO5)C(=O)O3)c21]

(S)-6-(5-(((2-(1-ethyl-7-fluoro-2-oxo-1,2-dihydroquinolin-
8-yl)ethyl)amino)methyl)-2-oxooxazolidin-3-yl)-2H-
pyrazino[2,3-b][1,4]oxazin-3(4H)-one (Example 26)

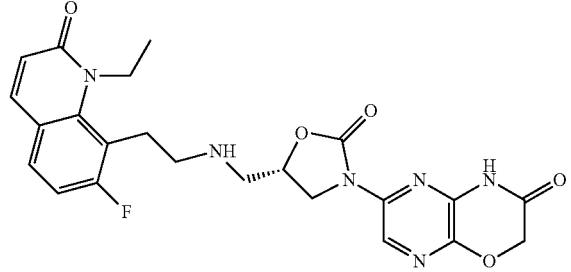 [SMILES: CCn1c(=O)ccc2ccc(F)c(CCNC[C@H]3CN(c4cnc5c(n4)NC(=O)CO5)C(=O)O3)c21]

(S)-6-(5-(2-((2-(1-ethyl-7-fluoro-2-oxo-1,2-dihydroquino-
lin-8-yl)ethyl)amino)ethyl)-2-oxooxazolidin-3-yl)-2H-
pyrazino[2,3-b][1,4]oxazin-3(4H)-one (Example 27)

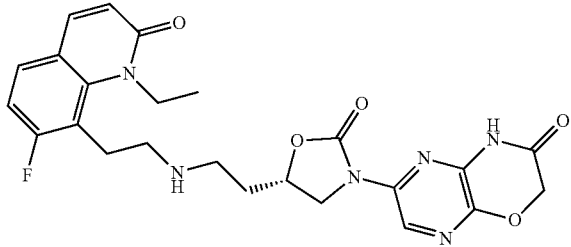 [SMILES: CCn1c(=O)ccc2ccc(F)c(CCNCC[C@H]3CN(c4cnc5c(n4)NC(=O)CO5)C(=O)O3)c21]

(S)-6-(5-(((2-(7-fluoro-1,4-dimethyl-2-oxo-1,2-dihydroqui-
nolin-8-yl)ethyl)amino)methyl)-2-oxooxazolidin-3-yl)-
2H-pyrazino[2,3-b][1,4]oxazin-3(4H)-one (Example 28)

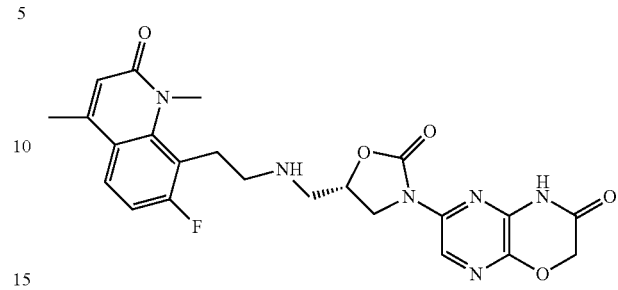

(S)-6-(5-(((2-(3-fluoro-5-methyl-6-oxo-5,6-dihydro-1,5-
naphthyridin-4-yl)ethyl)amino)methyl)-2-oxooxazolidin-
3-yl)-2H-pyrazino[2,3-b][1,4]oxazin-3(4H)-one (Ex-
ample 29)

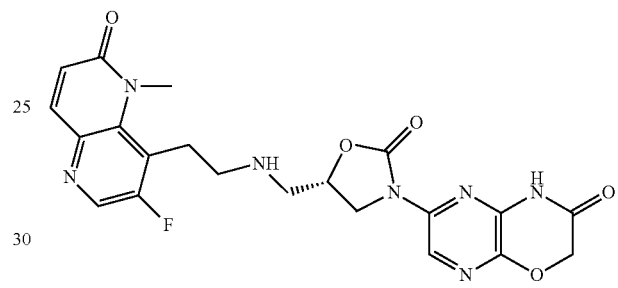

(S)-6-(5-(((2-(6-fluoro-4-methyl-3-oxo-3,4-dihydroqui-
noxalin-5-yl)ethyl)amino)methyl)-2-oxooxazolidin-3-
yl)-2H-pyrazino[2,3-b][1,4]oxazin-3(4H)-one (Example
30)

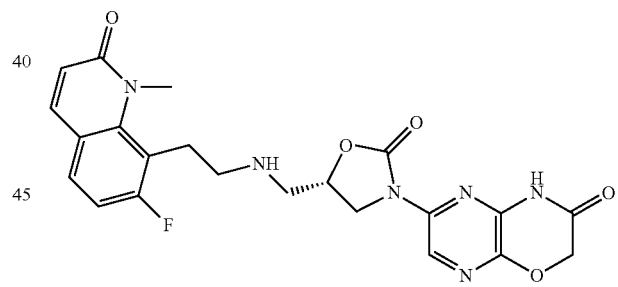 [SMILES: Cc1cc(=O)n(C)c2c(CCNC[C@H]3CN(c4cnc5c(n4)NC(=O)CO5)C(=O)O3)c(F)ccc12]

According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms, and pharmaceutically active derivatives thereof. Said process comprises reacting Formula (A), and Formula (B)

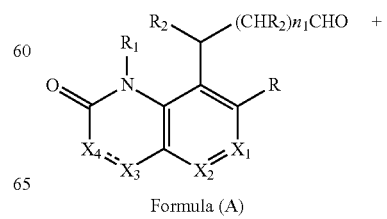

Formula (A)

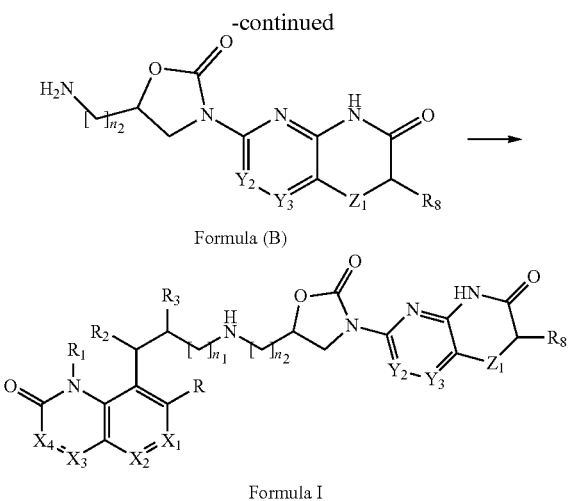

Formula (B)

Formula I in presence of at least one reducing agent and an adsorbent to obtain the compounds of Formula I.

According to an embodiment, the present disclosure relates a process of preparation of compound of Formula I, wherein $R_1$ of Formula (A) is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, 4-7 membered carbocyclyl or heterocyclyl ring which may be fully saturated or unsaturated or partially unsaturated optionally having up to three heteroatom independently selected from O, N, or S, each of which is unsubstituted or substituted with 1 to 3 groups independently selected from halogen, amino, hydroxyl, $C_{1-6}$ alkoxy, $SO_3H$, $SO_2R_9$, $COOR_9$, $CONHR_9$, or $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatom independently selected from O, N, or S, $C_{3-6}$ cycloalkylamino, $C_{3-6}$ aminocycloalkyl, $C_{1-6}$ alkylamino, or di ($C_{1-6}$ alkyl)amino; $R_2$ and $R_3$ are independently selected from the group consisting of hydrogen, $C_{1-6}$ alkyl, fluorine, $OC_{1-6}$ alkyl, hydroxyl, and amino; R is selected from the group consisting of hydrogen, fluorine, cyano, $OC_{1-6}$ alkyl, and hydroxyl; $X_1$ is N or $CR_4$; $R_4$ is selected from the group consisting of hydrogen, halogen, cyano, $-OC_{1-6}$ alkyl, $C_{1-6}$ haloalkyl, $-OC_{1-6}$ haloalkyl, and $C_{1-6}$ alkyl; $X_2$ is N or $CR_5$; $R_5$ is selected from the group consisting of hydrogen, halogen, cyano, $-OC_{1-6}$ alkyl, $C_{1-6}$ haloalkyl, $-OC_{1-6}$ haloalkyl, and $C_{1-6}$ alkyl; $X_3$ is N or $CR_6$; and $X_4$ is CH or C—$C_{1-6}$ alkyl when dotted line (----) represents a bond, wherein $R_6$ is selected from the group consisting of hydrogen, halogen, cyano, $-OC_{1-6}$ alkyl, $-OC_{1-6}$ haloalkyl, and $C_{1-6}$ alkyl, wherein $C_{1-6}$ alkyl is optionally substituted with hydroxyl or amino; $X_4$ is $CH_2$ or O; and $X_3$ is $CH_2$ when dotted line (---) represents no bond; $n_1$ is 0 or 1; $Y_2$ and $Y_3$ of Formula (B) are independently selected from —N or $CR_7$; $R_7$ is selected from the group consisting of hydrogen, halogen, cyano, $-OC_{1-6}$ alkyl, $C_{1-6}$ haloalkyl, $-OC_{1-6}$ haloalkyl, and $C_{1-6}$ alkyl; $Z_1$ is selected from the group consisting of O, S, and $CH_2$; $n_2$ is 0 to 2; and $R_8$ is selected from the group consisting of hydrogen, $C_{1-6}$ alkyl, and fluorine.

According to an embodiment, the present disclosure relates a process of preparation of compound of Formula I, wherein the at least one reducing agent is selected from the group consisting of sodium borohydride, 2-picoline-borane complex, sodium cyano borohydride, sodium triacetoxy borohydride, and combinations thereof.

According to an embodiment, the present disclosure relates a process of preparation of compound of Formula I, wherein the adsorbent is selected from the group consisting of molecular sieves, silicagel, zeolites, anhydrous sodium sulphate, anhydrous magnesium sulphate, activated charcoal, and combinations thereof.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use as a medicament.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in the preparation of medicaments for inhibiting microbial growth.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in the preparation of medicaments for inhibiting bacterial growth.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in killing or inhibiting the growth of a microorganism selected from the group consisting of bacteria, virus, fungi and protozoa.

According to an embodiment, the present disclosure relates to use of a compound of Formula I or its stereoisomers, pharmaceutically acceptable salts, complexes, hydrates, solvates, tautomers, polymorphs, racemic mixtures, optically active forms, and pharmaceutically active derivatives thereof, in killing or inhibiting the growth of a microorganism selected from the group consisting of bacteria, virus, fungi and protozoa.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in killing or inhibiting the growth of Gram-positive and Gram-negative bacteria.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in treatment of bacterial infection caused by Gram-positive bacterium or a Gram-negative bacterium.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in killing or inhibiting the growth of drug sensitive and drug resistance bacterium selected from a group consisting of *Escherichia coli, Staphylococcus aureus, Salmonella typhi, Salmonella paratyphi, Salmonella* typhimurium, Salmonella enteritidis, Shigella dysenteriae, Shigella flexneri, Shigella boydii, Shigella sonnei, Staphylococcus epidermidis, Streptococcus pneumoniae, Streptococcus pygenes, Stenotrophomonas maltophilia, Haemophilus influenza, Legionella pneumophila, Mycoplasma pneumonia, Acinetobacter haemolyticus Acinetobacter junii, Acinetobacter lwoffi, Burkholderia cepacia, Chlamydophila pneumoniae, Clostridium difficili, Enterobacter aerogenes, Enterobacter cloacae. Moraxella catarrhalis, Enterococcus faecium Neisseria gonorrhoeae, Neisseria meningitides, Proteus mirabilis, Citrobacter freundii, Citrobacter kosari, Citrobacter barakii, Seratia marcescens, Klebsiella pneumoniae, Acinetobacter baumannii, Pseudomonas aeruginosa, Enterococcus faecalis, Enterococcus faecium, or any combinations thereof.

According to an embodiment, the present disclosure relates to a compound of Formula I or its stereoisomers, pharmaceutically acceptable salts, complexes, hydrates, solvates, tautomers, polymorphs, racemic mixtures, optically active forms, and pharmaceutically active derivatives thereof, for use in treating a disease or condition in a patient wherein said disease or condition is caused by a microorganism selected from the group consisting of Gram negative, and Gram positive pathogens.

According to an embodiment, the present disclosure relates to use of a compound of Formula I or its stereoisomers, pharmaceutically acceptable salts, complexes, hydrates, solvates, tautomers, polymorphs, racemic mixtures, optically active forms, and pharmaceutically active derivatives thereof, in treating disease or condition in a patient, wherein said disease or condition is caused by a microorganism selected from the group consisting of Gram negative, and Gram positive pathogens. The patient is a typically a mammal, preferably a human.

According to an embodiment, the present disclosure relates to a method of treating a disease or condition in a patent, said method comprising administering to a patient a compound of Formula I, or its stereoisomers, pharmaceutically acceptable salts, complexes, hydrates, solvates, tautomers, polymorphs, racemic mixtures, optically active forms, and pharmaceutically active derivatives thereof, wherein said disease or condition is caused by microorganism selected from the group consisting of Gram negative, and Gram positive pathogens.

According to an embodiment, the present disclosure relates to medicaments that include a compound of Formula I, or an addition salt of the compound of Formula I with a pharmaceutically acceptable acid or base. These medicaments find their use in therapeutics, especially in the treatment of bacterial infection caused by both drug sensitive and drug resistance bacterium including quinolone resistance belonging to Gram positive and Gram negative species; especially of those caused by Escherichia coli, Staphylococcus aureus, Salmonella typhi, Salmonella paratyphi, Salmonella typhimurium, Salmonella enteritidis, Shigella dysenteriae, Shigella flexneri, Shigella boydii, Shigella sonnei, Staphylococcus epidermidis, Streptococcus pneumoniae, Streptococcus pygenes, Stenotrophomonas maltophilia, Haemophilus influenza, Legionella pneumophila. Mycoplasma pneumonia, Acinetobacter haemolyticus Acinetobacter junii, Acinetobacter lwoffi, Burkholderia cepacia, Chlamydophila pneumoniae, Clostridium difficili, Enterobacter aerogenes, Enterobacter cloacae. Moraxella catarrhalis, Enterococcus faecium Neisseria gonorrhoeae, Neisseria meningitides, Klebsiella pneumoniae, Acinetobacter baumannii, Pseudomonas aeruginosa, and Enterococcus faecalis/Enterococcus faecium.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms, and pharmaceutically active derivatives thereof, in the manufacture of a medicament for the treatment of an infection caused by bacterial species in a warm-blooded animal, such as man.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms and pharmaceutically active derivatives thereof, in the manufacture of a medicament for the production of an antibacterial effect in a warm-blooded animal such as man.

According to an embodiment, the present disclosure relates to a method for treating bacterial infections caused by bacterial species in a warm-blooded animal such as man, said method including administering to said animal an effective amount of a compound of Formula I, or a pharmaceutically acceptable salt thereof.

According to an embodiment, the present disclosure relates to a method for producing an antibacterial effect in a warm-blooded animal such as man, said method including administering to said animal an effective amount of a compound of Formula I, or a pharmaceutically acceptable salt thereof.

According to an embodiment, the present disclosure relates to a compound of Formula I, or a pharmaceutically acceptable salt thereof, for use in the treatment and/or prophylaxis of bacterial infections in a warm-blooded animal, such as man.

According to an embodiment, the present disclosure relates to a compound of Formula I, or a pharmaceutically acceptable salt thereof, for the therapeutic and prophylactic treatment of mammals including humans, in particular in treating bacterial infections caused by bacterial species, is normally formulated in accordance with standard pharmaceutical practice as a pharmaceutical composition.

According to an embodiment, the present disclosure relates to a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivatives thereof, and at least one pharmaceutically acceptable carrier, diluent, or excipient.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivatives thereof, in the manufacture of a medicament for the treatment of a bacterial infection caused by bacterial species in a warm-blooded animal such as man.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivatives thereof, in the manufacture of a medicament for the production of an antibacterial effect in a warm-blooded animal such as man.

According to an embodiment, the present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivatives thereof together with a pharmaceutically acceptable carrier, and in combination with at least one antibiotic.

According to an embodiment, the present disclosure relates to a method for treating infection caused by bacterial species in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivatives thereof.

According to an embodiment, the present disclosure relates to a method for producing an antibacterial effect in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivatives thereof.

According to an embodiment, the present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivatives thereof, together with a pharmaceutically acceptable carrier, optionally in combination with one or more other pharmaceutical compositions.

According to an embodiment, the present disclosure relates to a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivatives thereof, and a pharmaceutically acceptable diluent or carrier.

According to an embodiment, the present disclosure relates to a composition comprising a compound of Formula I, or its stereoisomers, pharmaceutically acceptable salts, complexes, hydrates, solvates, tautomers, polymorphs, racemic mixtures, optically active forms and pharmaceutically active derivatives thereof, and a carrier.

According to an embodiment, the present disclosure relates to a composition comprising a compound of Formula I, or its stereoisomers, pharmaceutically acceptable salts, complexes, hydrates, solvates, tautomers, polymorphs, racemic mixtures, optically active forms and pharmaceutically active derivatives thereof, and a pharmaceutically acceptable carrier.

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The present disclosure relates to a process of preparation of a composition comprising a compound of Formula I or its stereoisomers, pharmaceutically acceptable salts, complexes, hydrates, solvates, tautomers, polymorphs, racemic mixtures, optically active forms and pharmaceutically active derivatives thereof together with a pharmaceutically acceptable carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivatives thereof, together with a pharmaceutically acceptable carrier, optionally in combination with one or more other pharmaceutical compositions.

The compositions of the present disclosure may be obtained by conventional procedures using conventional pharmaceutical excipients well known in the art. Thus, compositions intended for oral use may contain, for example, one or more colouring, sweetening, flavouring and/or preservative agents Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents or procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the disclosure may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penetrate the cells of interest or stratum corneum, and fuse with the cell membrane, resulting in delivery of the contents of the liposome into the cell. Other suitable formulations can employ niosomes. Niosomes are lipid vesicles similar to liposomes, with membrane consisting largely of nonoinic lipids, some forms of which are effective for transporting compounds across the stratum corneum.

Compositions for administration may also be formulated as a depot preparation, which may be administered by implantation or by intramuscular injection. The compositions may be formulated with suitable polymeric or hydrophobic material (as an emulsion in acceptable oil), ion exchange resins, or sparingly soluble derivatives.

The compound of the present disclosure can also be administered in sustained release forms or from sustained release drug delivery systems.

For further information on formulation, drug delivery as well as processing techniques the reader is referred to Remington's Pharmaceutical Sciences (21$^{st}$ Edition, 2005, University of the sciences in Philadelphia, Lippincott William & Wilkins)

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990 and Remington's Pharmaceutical Sciences (21$^{st}$ Edition, 2005, University of the sciences in Philadelphia, Lippincott William & Wilkins).

As stated above the size of the dose required for the therapeutic or prophylactic treatment of a particular disease state will necessarily be varied depending on the host treated, the route of administration and the severity of the illness being treated. Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the disclosure described herein also apply.

The compounds disclosed herein may be applied as a sole therapy or may involve, in addition to a compound of the disclosure, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following: i) other antibacterial agents for example macrolides e.g. erythromycin, azithromycin or clarithromycin; quinolones e.g. ciprofloxacin or levofloxacin; B lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability increasing protein (BPI) products; and/or iv) one or more antibacterial agents useful in the treatment of Mycobacterium tuberculosis such as one or more of rifampicin, isoniazid, pyrizinamide, ethambutol, quinolones e.g. moxifloxacin or gatifloxacin, streptomycin and/or v) efflux pump inhibitors.

According to an embodiment, the present disclosure relates to a compound of the Formula I, or a pharmaceutically acceptable salt thereof and a chemotherapeutic agent selected from: i) one or more additional antibacterial agents; and/or ii) one or more anti-infective agents; and/or iii) biological protein therapeutics for example antibodies, cytokines, bactericidal/permeability increasing protein (BPI) products; iv) one or more antibacterial agents useful in the treatment of pulmonary tuberculosis, extra-pulmonary tuberculosis, avium infections, buruli ulcers and/or v) one or more efflux pump inhibitors.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to Advanced Organic Chemistry, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, published by John Wiley and Sons, 1991) and as described hereinabove.

Abbreviations

The following abbreviations are employed in the examples and elsewhere herein:

TLC—thin layer chromatography;
HPLC—high pressure liquid chromatography;
MPLC—medium pressure liquid chromatography;
NMR—nuclear magnetic resonance spectroscopy;
DMSO—dimethylsulfoxide;
$CDCl_3$—deuterated chloroform;
MeOD—deuterated methanol, i.e. $D_3COD$;
MS—mass spectroscopy; ESP (or ES)—electrospray; EI—electron impact; APCI—atmospheric pressure chemical ionization;
THF—tetrahydrofuran;
DCM—dichloromethane;
MeOH—methanol;
DMF—dimethylformamide;
EtOAc—ethyl acetate;
LC/MS—liquid chromatography/mass spectrometry;
h—hour(s); min is minute(s);
d—day(s);
MTBD—N-methyl-1,5,7-triazabicyclo[4.4.0]dec-5-ene;
TFA—trifluoroacetic acid; v/v—ratio of volume/volume;
Boc—t-butoxycarbonyl;
Cbz—benzyloxycarbonyl;
Bz—benzoyl;
Atm—atmospheric pressure;
rt—room temperature;
mg—milligram; g denotes gram;
µL—microliter;
mL—milliliter;
L—liter;
µM—micromolar;
mM—millimolar; M denotes molar;
DMAP—dimethyaminopyridine;
TBDMS—tert-butyldimethylsilyl
N—normal; and
nm—nanometer.

EXAMPLES

The following examples provide the details about the synthesis, activities and applications of the compounds of the present disclosure. It should be understood the following is representative only, and that the invention is not limited by the details set forth in these examples.

Materials and Methods:

Evaporations were carried out by rotary evaporation in vacuo and work up procedures were carried out after removal of residual solids by filtration; temperatures are quoted as ° C.; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kieselgel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the invention was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (* scale) and peak multiplicities are shown thus: s, singlet; d, doublet; dd, doublet of doublets; dt, doublet of triplets; dm, doublet of multiplets; t, triplet, m, multiplet; br, broad.

Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 Å particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

General Process for the Preparation of the Compounds of Formula A

Compounds of Formula (A) may be prepared as Formula (J) and Formula (L) where in $R_2$ and $R_3$=H and $n_1$=0 or 1 from compounds of Formula (C) via Allyation using tributylallyltin and tetrakis (triphenylphosphine) palladium (0) catalyst. (Scheme 1).

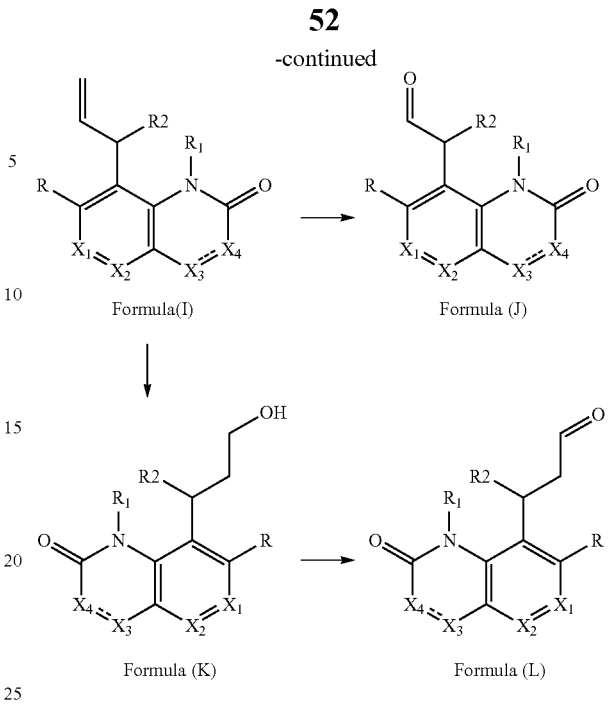

Formula(I)    Formula (J)

Formula (K)    Formula (L)

Compounds of Formula (J) was obtained from oxidative cleavage olefene of Formula (I) using suitable oxiding agent, whereas compounds of Formula (L) was obtained oxidation of Formula K which in turn obtained from Formula(I) via hydroboration.

General Process for the Preparation of the Compounds of Formula B

The compounds of Formula (B) were obtained from compounds of Formula (E) and compounds of Formula I as summarised in the below Scheme. Palladium catalysed Buchwald coupling of compounds of Formula (E) with Formula (F) under optimal reaction conditions provided the compounds of Formula (G). Further compounds of Formula (G) was converted to compounds of Formula (H) via azidation reaction and reduction of azide functionality provided the compounds Formula (B).

Scheme 1

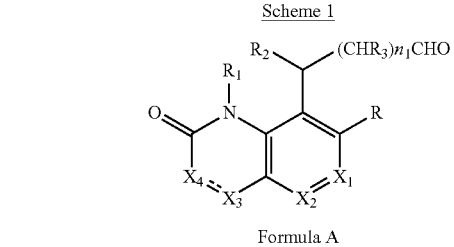

Formula A

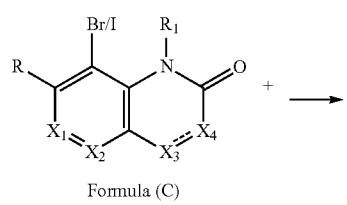

Formula (C)

Scheme 2

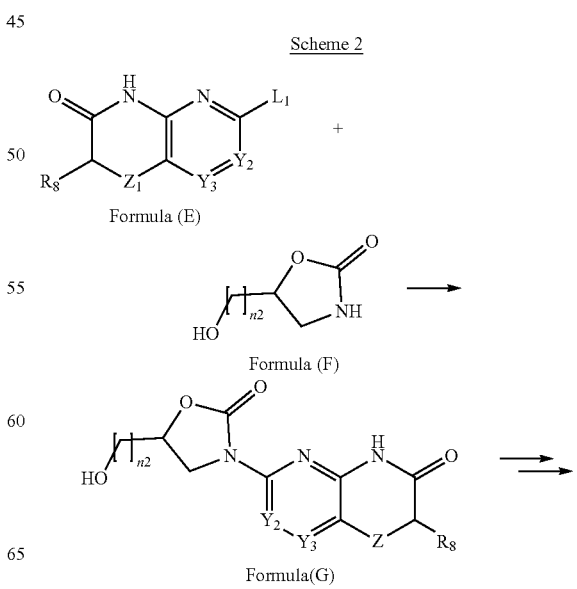

Formula (E)

Formula (F)

Formula(G)

-continued

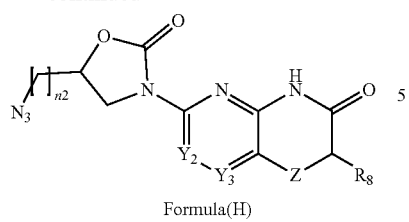
Formula(H)

↓

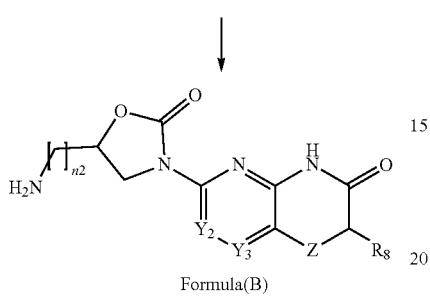
Formula(B)

In another embodiment, the compounds of Formula Ia where in $Z_1$ is O; $n_2$=1 or 2; $R_8$ is H; can be prepared reacting compounds of Formula (B) with compounds of Formula (D) as shown Scheme 3

Scheme 3

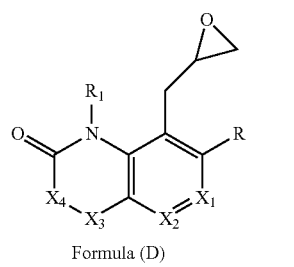
Formula (D)
+

-continued

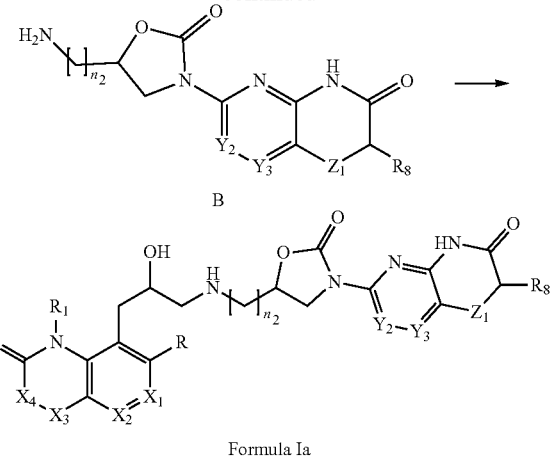
B

Formula Ia

In an embodiment, the disclosure provides a process for the preparation of compounds of Formula (I) and the compounds of Formula (I) may be prepared in a variety of ways. The processes and Examples shown below illustrate some methods useful for the synthesis of compounds of Formula (I) and intermediates which may be used for the synthesis of compounds of Formula (I). Where a particular solvent or reagent is shown or referred to in the accompanying text, it is to be understood that the chemist of ordinary skill in the art will be able to modify and/or replace that solvent or reagent as necessary.

Synthesis of Intermediates

Synthesis of 6-(5-(2-aminoethyl)-2-oxooxazolidin-3-yl)-2H-pyrido[3,2-b][1,4]oxazin-3(4H)-one (Intermediate I)

Intermediate I, 6-(5-(2-aminoethyl)-2-oxooxazolidin-3-yl)-2H-pyrido[3,2-b][1,4]oxazin-3(4H)-one (CAS number 2156619-15-5) was synthesized as reported earlier in WO2017199265.

Synthesis of 6-(5-(aminomethyl)-2-oxooxazolidin-3-yl)-2H-pyrido[3,2-b][1,4]oxazin-3(4H)-one, II

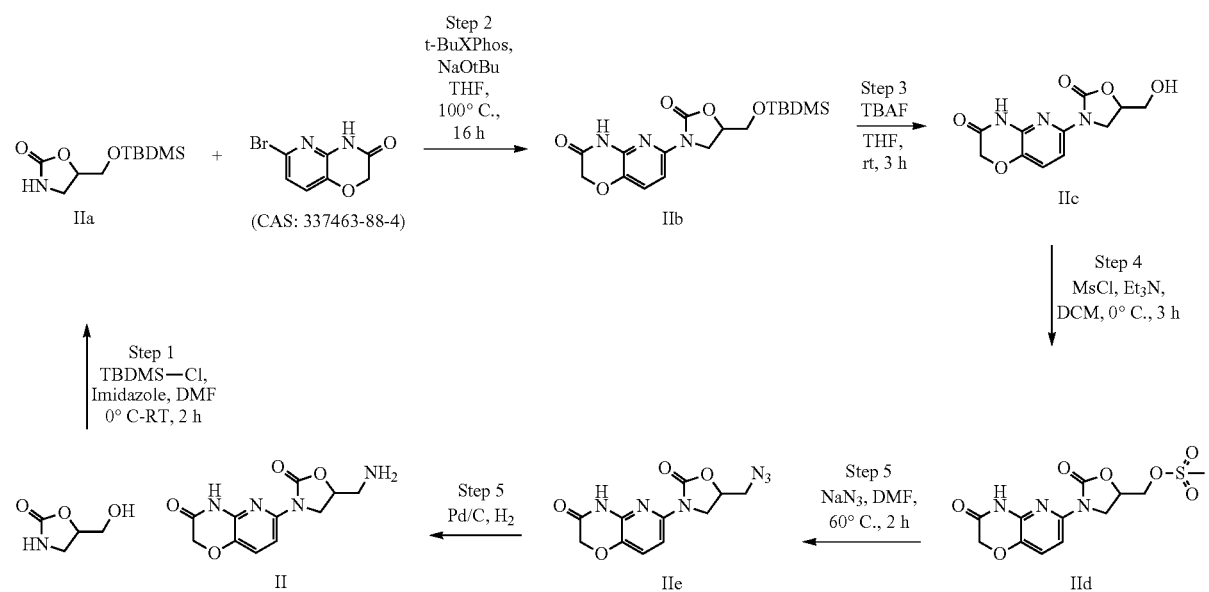

Step 1: 5-(((Tert-butyldimethylsilyl)oxy)methyl) oxazolidin-2-one (IIa)

To a stirred solution of TBDMS-Cl (5.74 g, 0.0384 mol), imidazole (3.4 g, 0.0512 mol), DMAP (0.31 g, 0.0025 mol) in DMF (15 mL), cooled to 0° C., 5-(hydroxymethyl) oxazolidin-2-one (3 g, 0.0256 mmol) in DMF (15 mL) was added and stirred at 25° C. for 2 h. After completion of the reaction, reaction mixture was quenched with water and extracted with ethyl acetate (3×150 ml). The separated organic layer was washed with water, brine, dried over $Na_2SO_4$, filtered and concentrated under reduced pressure. It was purified by column chromatography on silica gel (230-400 mesh, 20-25% ethyl acetate in pet ether) to obtain IIa (3.6 g, 61%); LC-MS Calculated for $C_{10}H_{21}NO_3Si$, 231.37; Observed 232.1. $^1H$ NMR (400 MHz, $CDCl_3$): δ5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H).

Step 2: 6-(5-(((Tert-butyldimethylsilyl)oxy)methyl)-2-oxooxazolidin-3-yl)-2H-pyrido[3,2-b][1,4]oxazin-3(4H)-one (IIb)

To a stirred solution of IIa (3.92 g, 0.0171 mol) and I (3.6 g, 0.0155 mol) in dry 1,4-dioxane (50 mL), were added t-butyl-X-Phos mesyl chloride complex (0.618 g, 0.0077 mol) and sodium tert-butoxide (2.24 g, 0.0234 mol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford IIb (3.5 g, 59%); LC-MS Calculated for $C_{17}H_{25}N_3O_5Si$, 379.49, Observed 380.0; $^1H$ NMR (400 MHz, DMSO-$d_6$): δ 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H).

Step 3: 6-(5-(Hydroxymethyl)-2-oxooxazolidin-3-yl)-2H-pyrido[3,2-b][1,4]oxazin-3(4H)-one (IIc)

To a stirred solution of IIb (5 g, 0.0132 mol) in THF (25 mL), cooled to 0° C., tert-butyl ammonium fluoride (1 M in THF) (29.38 mL, 0.0293 mol) was added dropwise and stirred at 25° C. for 3 hours. After completion of the reaction, reaction mixture was quenched with water obtained solid filtered and dried in vacuum to obtain white solid of IIc (3.0 g, 85%); LC-MS Calculated for $C_{11}H_{11}N_3O_5$, 265.23, Observed=265.9; $^1H$ NMR (400 MHz, DMSO-$d_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-4.07 (m, 1H), 3.92-3.88 (m, 1H), 3.69-3.65 (m, 1H), 3.54-3.34 (m, 1H).

Step 4: 2-Oxo-3-(3-oxo-3,4-dihydro-2H-pyrido[3,2-b][1,4]oxazin-6-yl)oxazolidin-5-yl)methyl methanesulfonate (IId)

To a stirred solution of IIc (3 g, 0.0113 mol) in dry DMF (30 mL), cooled to 0° C., triethylamine (3.15 mL, 0.0226 mol) and mesyl chloride (1.05 mL, 0.0135 mol) were added and stirred at 25° C. for 2 h. After completion of the reaction, reaction mixture was quenched with water obtained solid filtered dried in vacuum to obtain white solid of IId (2.8 g, 73%); LC-MS Calculated for $C_{12}H_{13}N_3O_7S$, 343.31; Observed 344.0; $^1H$ NMR (400 MHz, DMSO-d6): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H).

Step 5: 6-(5-(Azidomethyl)-2-oxooxazolidin-3-yl)-2H-pyrido[3,2-b][1,4]oxazin-3(4H)-one (IIe)

To a stirred solution of IId (2.8 g, 0.00816 mol) in DMF (28 mL), cooled to 0° C., sodium azide (1.3 g, 0.0204 mol) was added and heated at 60° C. for 3 h. After completion of the reaction, reaction mixture was quenched with water obtained solid filtered and dried in vacuo to obtain white solid of IIe (1.9 g, 80%); LC-MS Calculated for $C_{11}H_{10}N_6O_4$, 290.24; Observed 290.9; $^1H$ NMR (400 MHz, DMSO-$d_6$): δ 11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.84-3.70-3.84 (m, 3H).

Step 6: 6-(5-(Aminomethyl)-2-oxooxazolidin-3-yl)-2H-pyrido[3,2-b][1,4]oxazin-3(4H)-one (II)

To a stirred solution of IIe (1.9 g, 0.00653 mol) in THF:MeOH (1:1) (40 ml), 10% palladium on carbon (0.6 g) was added and stirred at 25° C. under $H_2$ for 4 h. After completion of the reaction, reaction mixture was filtered through celite bed using THF and MeOH and concentrated under reduced pressure to obtain II (1.22 g, 70%). The crude material was taken for final step without any purification. LC-MS Calculated for $C_{11}H_{12}N_4O_4$, 264.24; Observed 265.1; $^1H$ NMR (400 MHz, DMSO-$d_6$): δ 7.61 (d, J=8.80 Hz, 1H), 7.43 (d, J=8.80 Hz, 1H), 4.61 (s, 2H), 4.10 (t, J=8.80 Hz, 1H), 3.91-3.86 (m, 1H), 2.88-2.79 (m, 2H).

Synthesis of (S)-6-(5-(aminomethyl)-2-oxooxazolidin-3-yl)-2H-pyrido[3,2-b][1,4]oxazin-3(4H)-one, III

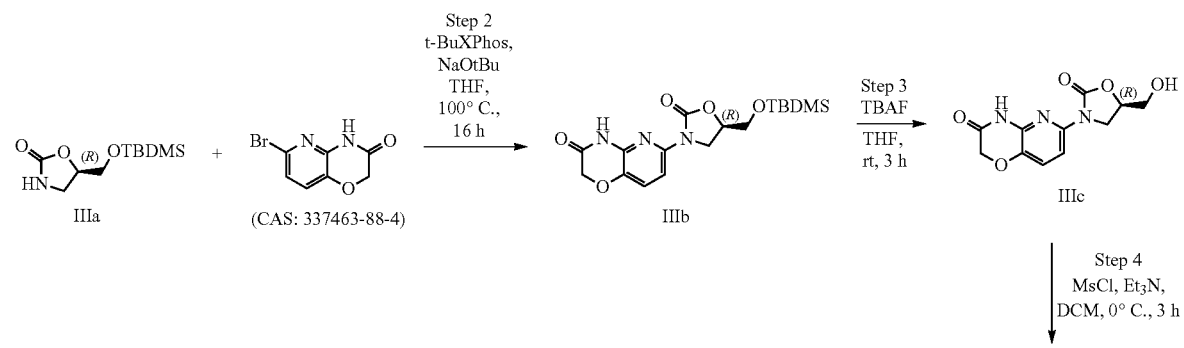

-continued

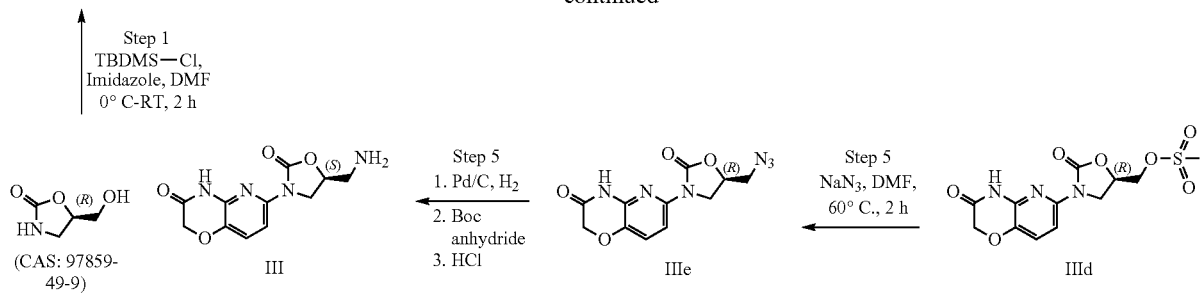

Step 1: (R)-5-(((tert-butyldimethylsilyl)oxy)methyl) oxazolidin-2-one (IIIa)

To a stirred solution of TBDMS-Cl (38.46 g, 0.256 mol), imidazole (23.2 g, 0.341 mol), DMAP (2.08 g, 0.017 mol) in DMF (200 mL), cooled to 0° C., (R)-5-(hydroxymethyl) oxazolidin-2-one (CAS: 97859-49-9, 20 g, 0.1709 mmol) in DMF (25 mL) was added and stirred at 25° C. for 2 h. After completion of the reaction, reaction mixture was quenched with water and extracted with ethyl acetate. The separated organic layer was washed with water, brine (200. mL), dried over $Na_2SO_4$, filtered, and concentrated under reduced pressure. It was purified by column chromatography on silica gel (230-400 mesh, 20-25% ethyl acetate in pet ether) to obtain IIIa (32 g, 81%). LC-MS Calculated for $C_{10}H_{21}NO_3Si$, 231.37, Observed 232.1. $^1$H NMR (400 MHz, $CDCl_3$): δ 5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H).

Step 2: (R)-6-(5-(((tert-butyldimethylsilyl)oxy) methyl)-2-oxooxazolidin-3-yl)-2H-pyrido[3,2-b][1,4]oxazin-3(4H)-one (IIIb)

To a stirred solution of IIIa (32 g, 0.139 mol) and 6-bromo-2H-pyrido[3,2-b][1,4]oxazin-3(4H)-one (WO2017199265, 31.7 g, 0.139 mol) in dry 1,4-dioxane (50 mL), were added t-butyl-X-Phos mesyl chloride complex (5.5 g, 0.0069 mol) and sodium tert-butoxide (19.94 g, 0.207 mol) and was degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford Mb (45.6 g, 86%); LC-MS Calculated for $C_{17}H_{25}N_3O_5Si$, 379.49, Observed 380.0; $^1$H NMR (400 MHz, DMSO-$d_6$): δ 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H).

Step 3: (R)-6-(5-(Hydroxymethyl)-2-oxooxazolidin-3-yl)-2H-pyrido[3,2-b][1,4]oxazin-3(4H)-one (IIIc)

To a stirred solution of IIIb (45 g, 0.118 mol) in THF (250 mL), cooled to 0° C., tert-butyl ammonium fluoride (1 M in THF) (296 mL, 0.296 mol) was added drop wise and stirred at 25° C. for 3 hours. After completion of the reaction, reaction mixture was quenched with water obtained solid filtered and dried in vacuum to obtain white solid of IIIc (29 g, 92%); LC-MS Calculated for $C_{11}H_{11}N_3O_5$, 265.23, Observed=265.9; $^1$H NMR (400 MHz, DMSO-$d_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-4.07 (m, 1H), 3.92-3.88 (m, 1H), 3.69-3.65 (m, 1H), 3.54-3.34 (m, 1H).

Step 4: (R)-(2-oxo-3-(3-oxo-3,4-dihydro-2H-pyrido[3,2-b][1,4]oxazin-6-yl)oxazolidin-5-yl)methyl methanesulfonate (IIId)

To a stirred solution of IIIc (29 g, 0.109 mol) in dry DMF (300 mL), cooled to 0° C., triethylamine (45.7 mL, 0.328 mol) and mesyl chloride (17 mL, 0.218 mol) were added and stirred at 25° C. for 2 h. After completion of the reaction, reaction mixture was quenched with water obtained solid filtered dried in vacuum to obtain white solid of IIId (30 g, 80%). LC-MS Calculated for $C_{12}H_{13}N_3O_7S$, 343.31; Observed 344.0. $^1$H NMR (400 MHz, DMSO-$d_6$): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H).

Step 5: (R)-6-(5-(azidomethyl)-2-oxooxazolidin-3-yl)-2H-pyrido[3,2-b][1,4]oxazin-3(4H)-one (IIIe)

To a stirred solution of IIId (30 g, 0.087 mol) in DMF (300 mL), cooled to 0° C., sodium azide (17 g, 0.262 mol) was added and heated at 60° C. for 3 h. After completion of the reaction, reaction mixture was quenched with water obtained solid filtered and dried in vacuo to obtain white solid of IIIe (22 g, 87%). LC-MS Calculated for $C_{11}H_{10}N_6O_4$, 290.24; Observed 290.9. $^1$H NMR (400 MHz, DMSO-$d_6$): δ 11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.70-3.84 (m, 3H).

Step 6: (S)-6-(5-(aminomethyl)-2-oxooxazolidin-3-yl)-2H-pyrido[3,2-b][1,4]oxazin-3(4H)-one (III)

To a stirred solution of IIIe (22 g, 0.075 mol) in THF: MeOH (1:1) (400 ml), 10% palladium on carbon (7 g) was added and stirred at 25° C. under $H_2$ for 4 h. After completion of the reaction, reaction mixture was filtered through celite bed using THF and MeOH and concentrated under reduced pressure to obtain III (15 g, 75%). LC-MS Calculated for $C_{11}H_{12}N_4O_4$, 264.24; Observed 265.1.

Purification of Intermediate III: Boc Protection: To a stirred solution of crude III (15 g, 0.056 mol) in 1,4 dioxane:water (1:1, 200 mL) was added $Na_2CO_3$ (12 g, 0.113 mol) followed by the addition of $(Boc)_2O$ (25 g, 0.113 mol) at 0° C. and allowed to stir at room temperature for 12 h. The reaction mixture was diluted with EtOAc (250 mL) and washed with water (2×250 mL). The combined organic layers were washed with brine (50 mL), dried over sodium sulphate and evaporated under reduced pressure to get the crude. Crude was purified by column chromatography (230/400 mesh, 4% DCM in MeOH) to get desire Boc protected III as white solid (12 g, 58%). Analytical data for Boc protected III; LC-MS Calc. for $C_{16}H_{20}N_4O_6$: 364.36; Obs. 265.1; $^1$H NMR (400 MHz, DMSO-D6): δ 11.23 (s, 1H), 7.61 (d, 1H, J=8.8 Hz), 7.45 (d, 1H, J=8.8 Hz), 7.24 (m, 1H), 4.71 (m, 1H), 4.60 (s, 2H), 4.16-4.11 (m, 1H), 3.84-3.80 (m, 1H), 3.25 (m, 2H), 1.36 (s, 9H).

The Boc protected III (12 g, 0.033 mmol) was taken in 1, 4 dioxane (60 mL) and 4M HCl in dioxane (120 mL) was added at 0° C. to it. The resulting mixture was stirred at room temperature for 3 h. The reaction mixture was concentrated to obtain crude amine HCl salt. The crude was dissolved in dry MeOH/DCM (200 mL) and neutralized with resin, filtered and concentrated to afford pure amine III as off white solid (8 g, 92%). LC-MS Calc. for $C_{11}H_{12}N_4O_4$, 264.24; Obs. 265.1 [M+H]; $^1$H NMR (400 MHz, DMSO-D6): δ 11.05 (brs, 1H), 7.62 (d, 1H, J=8.8 Hz), 7.45 (d, 1H, J=8.8 Hz), 7.05 (brs, 2H), 4.83 (m, 1H), 4.62 (s, 2H), 4.23-4.20 (m, 1H), 3.87-3.82 (m, 1H), 3.19-3.10 (m, 2H).

Synthesis of (R)-6-(5-(aminomethyl)-2-oxooxazolidin-3-yl)-2H-pyrido[3,2-b][1,4]oxazin-3(4H)-one, IV g, 61%). $^1$H NMR (400 MHz, CDCl$_3$): δ5.11 (s, 1H), 4.72-4.66 (m, 1H), 3.86-3.82 (m, 1H), 3.79-3.76 (m, 1H), 3.66-3.62 (m, 1H), 3.58-3.55 (m, 1H), 0.91 (s, 9H), 0.11 (s, 6H). LC-MS Calculated for $Cl_0H_{21}NO_3Si$, 231.37, Observed 232.1.

Step 2: (S)-6-(5-(((tert-butyldimethylsilyl)oxy)methyl)-2-oxooxazolidin-3-yl)-2H-pyrido[3,2-b][1,4]oxazin-3(4H)-one (IVb)

To a stirred solution of IVa (3.92 g, 0.0171 mol) and 6-bromo-2H-pyrido[3,2-b][1,4]oxazin-3(4H)-one (WO2017199265, 3.6 g, 0.0155 mol) in dry 1,4-Dioxane (50 mL), were added t-butyl-X-Phos mesyl chloride complex (0.618 g, 0.0077 mol) and sodium tert-butoxide (2.24 g, 0.0234 mol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford IVb (3.5 g, 59%). $^1$H NMR (400 MHz, DMSO-d$_6$): δ 7.60 (d, J=8.68 Hz, 1H), 7.43 (d, J=8.68 Hz, 1H), 4.77-4.73 (m, 1H), 4.67 (s, 2H), 4.15-4.10 (m, 1H), 3.93-3.89 (m, 3H), 0.79 (s, 9H), 0.04 (s, 6H); LC-MS Calculated for $C_{17}H_{25}N_3O_5Si$, 379.49, Observed 380.0.

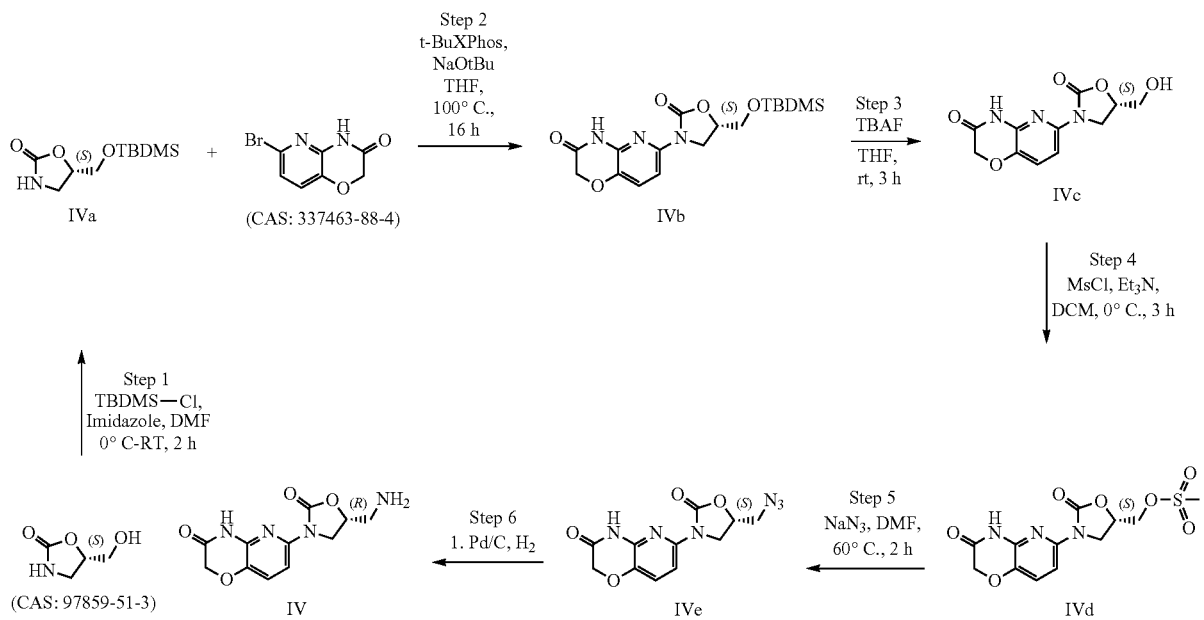

Step 1: (S)-5-(((tert-butyldimethylsilyl)oxy)methyl)oxazolidin-2-one (IVa)

To a stirred solution of TBDMS-Cl (5.74 g, 0.0384 mol), imidazole (3.4 g, 0.0512 mol), DMAP (0.31 g, 0.0025 mol) in DMF (15 mL), cooled to 0° C., (S)-5-(hydroxymethyl)oxazolidin-2-one (3 g, 0.0256 mmol) in DMF (15 mL) was added and stirred at 25° C. for 2 h. After completion of the reaction, reaction mixture was quenched with water and extracted with ethyl acetate. The separated organic layer was washed with water, brine (50. mL), dried over Na$_2$SO$_4$, filtered and concentrated under reduced pressure. It was purified by column chromatography on silica gel (230-400 mesh, 20-25% ethyl acetate in pet ether) to obtain IVa (3.6

Step 3: (S)-6-(5-(Hydroxymethyl)-2-oxooxazolidin-3-yl)-2H-pyrido[3,2-b][1,4]oxazin-3(4H)-one (IVc)

To a stirred solution of IVb (5 g, 0.0132 mol) in THF (25 mL), cooled to 0° C., tert-butyl ammonium fluoride (1 M in THF) (29.38 mL, 0.0293 mol) was added dropwise and stirred at 25° C. for 3 hours. After completion of the reaction, reaction mixture was quenched with water. The obtained solid was filtered and dried in vacuum to obtain white solid of IVc (3.0 g, 85%). $^1$H NMR (400 MHz, DMSO-d$_6$): δ 11.22 (s, 1H), 7.60 (d, J=8.80 Hz, 1H), 7.42 (d, J=8.40 Hz, 1H), 5.21 (bs, 1H), 4.70-4.66 (m, 1H), 4.60 (s, 2H), 4.12-

4.07 (m, 1H), 3.92-3.88 (m, 1H), 3.69-3.65 (m, 1H), 3.54-3.34 (m, 1H); LC-MS Calculated for $C_{11}H_{11}N_3O_5$, 265.23, Observed=265.9.

Step 4: (S)-(2-oxo-3-(3-oxo-3,4-dihydro-2H-pyrido[3,2-b][1,4]oxazin-6-yl)oxazolidin-5-yl)methyl methanesulfonate (IVd)

To a stirred solution of IVc (3 g, 0.0113 mol) in dry DMF (30 mL), cooled to 0° C., triethylamine (3.15 mL, 0.0226 mol) and mesyl chloride (1.05 mL, 0.0135 mol) were added and stirred at 25° C. for 2 h. After completion of the reaction, reaction mixture was quenched with water and filtered. Obtained solid was dried in vacuum to obtain white solid of IVd (2.8 g, 73%). $^1$H NMR (400 MHz, DMSO-d$_6$): δ 11.27 (s, 1H), 7.61 (d, J=8.40 Hz, 1H), 7.46 (d, J=8.80 Hz, 1H), 5.00 (bs, 1H), 4.63 (s, 2H), 4.63-4.51 (m, 2H), 4.25-4.20 (m, 1H), 3.90-3.85 (m, 1H), 3.35 (s, 3H); LC-MS Calculated for $C_{12}H_{13}N_3O_7S$, 343.31; Observed 344.0.

Step 5: (S)-6-(5-(azidomethyl)-2-oxooxazolidin-3-yl)-2H-pyrido[3,2-b][1,4]oxazin-3(4H)-one (IVe)

To a stirred solution of IVd (2.8 g, 0.00816 mol) in DMF (28 mL), cooled to 0° C., sodium azide (1.3 g, 0.0204 mol) was added and heated at 60° C. for 3 h. After completion of the reaction, reaction mixture was quenched with water and filtered. Obtained solid was dried in vacuum to obtain white solid of IVe (1.9 g, 80%). $^1$H NMR (400 MHz, DMSO-d$_6$): δ11.26 (s, 1H), 7.61 (d, J=8.40 Hz, 1H), 7.45 (d, J=8.80 Hz, 1H), 4.88 (bs, 1H), 4.63 (s, 2H), 4.16 (t, J=9.60 Hz, 1H), 3.84-3.70-3.84 (m, 3H); LC-MS Calculated for $C_{11}H_{10}N_6O_4$, 290.24; Observed 290.9.

Step 6: (R)-6-(5-(aminomethyl)-2-oxooxazolidin-3-yl)-2H-pyrido[3,2-b][1,4]oxazin-3(4H)-one (IV)

To a stirred solution of IVe (1.9 g, 0.00653 mol) in THF:MeOH (1:1) (40 ml), 10% palladium on carbon (0.6 g) was added and stirred at 25° C. under H$_2$ for 4 h. After completion of the reaction, reaction mixture was filtered through celite bed using THF and MeOH and concentrated under reduced pressure to obtain IV (1.22 g, 70%). The crude material was taken for next step without any purification. $^1$H NMR (400 MHz, DMSO-d$_6$): δ7.61 (d, J=8.80 Hz, 1H), 7.43 (d, J=8.80 Hz, 1H), 4.61 (s, 2H), 4.10 (t, J=8.80 Hz, 1H), 3.91-3.86 (m, 1H), 2.88-2.79 (m, 2H); LC-MS Calculated for $C_{11}H_{12}N_4O_4$, 264.24; Observed 265.1.

Synthesis of 6-chloro-2H-pyrazino[2,3-b][1,4]oxazin-3(4H)-one, Va

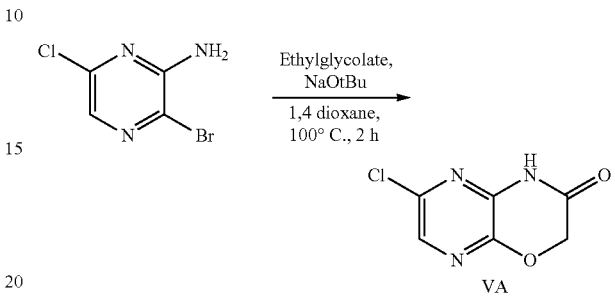

To a stirred solution of 3-bromo-6-chloropyrazin-2-amine (75 g, 0.3598 mol) in 1,4-dioxane (1500 mL) at room temperature under nitrogen atmosphere was added sodium tert-butoxide (110.65 g, 1.1514 mol) and stirred for 30 minutes. Then ethyl glycolate (112.37 g, 1.0794 mol) was added dropwise over a period of 30 minutes at room temperature. The resulting mixture was heated to 100° C. and stirred for 2 hours. The progress of the reaction was monitored by TLC.

After that the reaction mixture was cooled to room temperature and concentrated under reduced pressure to remove the dioxane. The residue obtained was diluted with water (750 mL) and neutralized using HCl (1.5 N). The precipitated solid was filtered out and dried under vacuum to get the compound Va as an off white solid. Yield: 60 g, 89.9%; LC-MS Calc. for $C_6H_4ClN_3O_2$, 185.57, Observed 184.0 (M−1H); $^1$H NMR (400 MHz, DMSO-d6): δ 11.86 (s, 1H), 7.87 (s, 1H), 4.90 (s, 2H).

Synthesis of (S)-6-(5-(aminomethyl)-2-oxooxazolidin-3-yl)-2H-pyrazino[2,3-b][1,4]oxazin-3(4H)-one, V

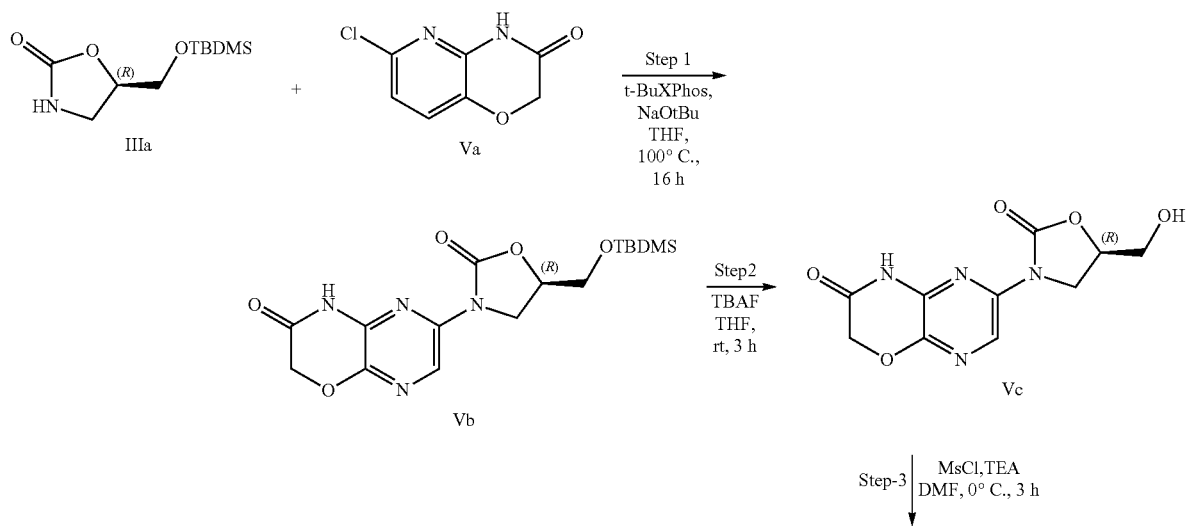

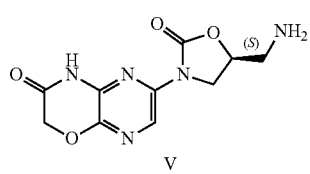
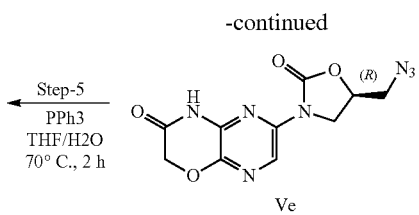
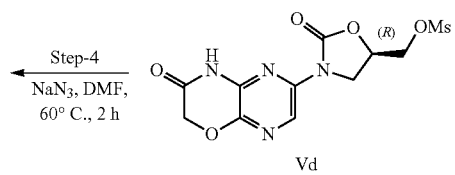

Step 1: (R)-6-(5-(((tert-butyldimethylsilyl)oxy)methyl)-2-oxooxazolidin-3-yl)-2H-pyrazino[2,3-b][1,4]oxazin-3(4H)-one (Vb)

To a stirred solution of Va (2.5 g, 13.51 mmol) and IIIa (3.43 g, 14.86 mmol) in dry 1,4-Dioxane (40 mL), were added t-butyl-X-Phos mesyl chloride complex (0.53 g, 0.67 mmol) and sodium tert-butoxide (1.94 g, 20.27 mmol) and degassed for 20 mins. Then, it was heated in sealed tube at 100° C. for 16 h. After completion of the reaction, reaction mixture was concentrated under reduced pressure. It was purified by column chromatography on silica gel (230-400 mesh, 25-30% ethyl acetate in pet ether) to afford Vb (3 g, 59%). LC-MS Calc. for $C_{16}H_{24}N_4O_5Si$, 380.48, Observed 381.1 (M+1H); $^1$H NMR (400 MHz, DMSO-d$_6$): δ 11.61 (s, 1H), 8.37-8.35 (m, 1H), 4.85-4.79 (m, 3H), 4.12-4.06 (m, 1H), 3.89-3.74 (m, 3H), 0.84-0.71 (m, 9H), 0.03-0.00 (m, 6H).

Step 2: (R)-6-(5-(hydroxymethyl)-2-oxooxazolidin-3-yl)-2H-pyrazino[2,3-b][1,4]oxazin-3(4H)-one (Vc)

To a stirred solution of Vb (3 g, 7.89 mmol) in THF (30 mL), cooled to 0° C., tert-butyl ammonium fluoride (1 M in THF) (15.8 mL, 15.78 mmol) was added dropwise and stirred at room temperature for 3 hours. After completion of the reaction, reaction mixture was quenched with water, extracted with ethyl acetate, dried over sodium sulphate and evaporated. The crude was purified by column chromatography on silica gel (230-400 mesh, 50-50% ethyl acetate in pet ether) to afford Vc (1.5 g, 71%). LC-MS Calc. for $C_{10}H_{10}N_4O_5$, 266.21, Observed 267.1 (M+1H); $^1$H NMR (400 MHz, DMSO-d$_6$): δ 11.62 (s, 1H), 8.38 (s, 1H), 5.23-5.07 (m, 2H), 5.03 (s, 1H), 4.86-4.73 (m, 1H), 4.10-3.86 (m, 2H), 3.70-3.48 (m, 2H).

Alternative Route for the Synthesis of Vc

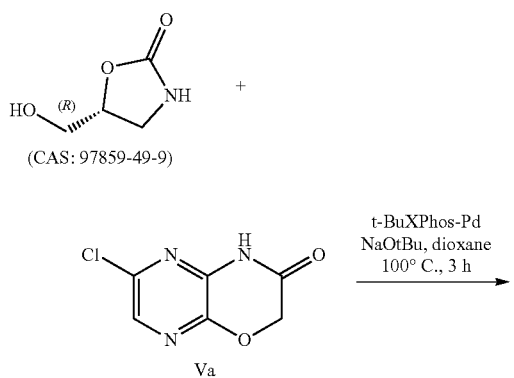

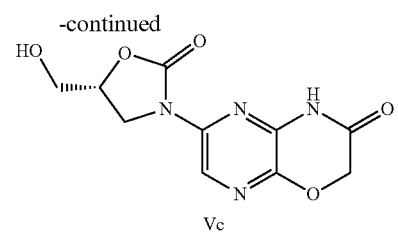

To a stirred solution of Va (40.0 g, 0.215 mol) and (R)-5-(hydroxymethyl)oxazolidin-2-one (CAS: 97859-49-9, 28.0 g, 0.237 mol) in 1,4-dioxane (600 mL) was added sodium tert-butoxide (31.08 g, 0.323 mol) at room temperature. The resulting mixture was degassed with a stream of nitrogen and was added t-butyl-X-Phos Palladacycle (8.56 g, 0.0107 mol) at room temperature. The resulting mixture was then heated to 100° C. and stirred for 3 hours. After that, the reaction mixture was cooled to room temperature, concentrated in vacuo. The residue obtained was diluted with water (500 mL), neutralised with 1.5 N HCl (pH~7). The solid precipitated out was filtered and washed with diethyl ether, dried under vacuo to get compound Vc as brown solid. Yield: 55.0 g (crude), 95.9%.

Step 3: (R)-(2-oxo-3-(3-oxo-3,4-dihydro-2H-pyrazino[2,3-b][1,4]oxazin-6-yl)oxazolidin-5-yl)methyl methanesulfonate (Vd)

To a stirred solution of Vc (1.5 g, 5.63 mmol) in dry DMF (15 mL), cooled to 0° C., Triethylamine (2.3 mL, 16.91 mmol) and mesyl chloride (0.69 mL, 8.45 mmol) were added and stirred at 25° C. for 2 h. After completion of the reaction, reaction mixture was quenched with water, the resultant solid was filtered, washed with pet ether and dried by vacuum to afford brown solid of Vd (1.2 g, 63%). LC-MS Calc. for $C_{11}H_{12}N_4O_7S$, 344.30, Observed 345.0 (M+1H); $^1$H NMR (400 MHz, DMSO-d$_6$): δ 11.67 (s, 1H), 8.38 (s, 1H), 5.06-5.04 (m, 1H), 4.87 (s, 2H), 4.57-4.54 (m, 2H), 4.23-4.20 (m, 1H), 3.86-3.82 (m, 1H), 3.28 (s, 3H), 3.25-3.23 (m, 1H).

Step 4: (R)-6-(5-(azidomethyl)-2-oxooxazolidin-3-yl)-2H-pyrazino[2,3-b][1,4]oxazin-3(4H)-one (Ve)

To a stirred solution of Vd (1.2 g, 3.48 mmol) in DMF (12 mL), cooled to 0° C., sodium azide (0.56 g, 8.72 mmol) was added and heated at 65° C. for 3 h. After completion of the reaction, reaction mixture was quenched with water, the obtained solid was filtered, washed with pet ether and dried to afford the brown solid Ve (0.7 g, 70%). LC-MS Calc. for $C_{10}H_9N_7O_4$, 291.23, Observed 290.1 (M−1H); $^1$H NMR (400 MHz, DMSO-d$_6$): δ 11.66 (s, 1H), 4.94-4.86 (m, 3H), 4.18-4.13 (m, 1H), 3.81-3.75 (m, 3H).

Step 5 (S)-6-(5-(aminomethyl)-2-oxooxazolidin-3-yl)-2H-pyrazino[2,3-b][1,4]oxazin-3(4H)-one (V)

To a stirred solution of Ve (0.7 g, 2.40 mmol) in THF:MeOH (1:1) (40 ml) was added PPh$_3$ (1.9 g, 7.21 mmol) at room temperature. The reaction mixture was heated at 70° C. for 3 h. After completion of the reaction by TLC, reaction mixture was cooled to room temperature, and was extracted with ethyl acetate (2×100 ml) for 2 times. Further the aqueous layer was concentrated and dried to afford V (0.3 g, 47%).

LC-MS Calc. for $C_{10}H_{11}N_5O_4$, 265.23, Observed 264.1 (M−1H); $^1$H NMR (400 MHz, DMSO-$d_6$): δ 8.38 (s, 1H), 4.85 (s, 2H), 4.69-4.67 (m, 1H), 4.11-4.06 (m, 1H), 3.88-3.84 (m, 1H), 3.17 (s, 1H), 2.91-2.83 (m, 2H).

Synthesis of (R)-6-(5-(aminomethyl)-2-oxooxazolidin-3-yl)-2H-pyrazino[2,3-b][1,4]oxazin-3(4H)-one, VI

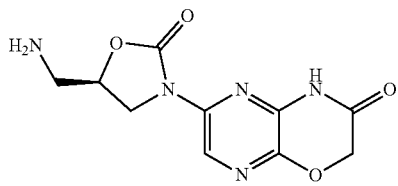 [SMILES: NC[C@@H]1CN(c2cnc3c(n2)NC(=O)CO3)C(=O)O1]

Intermediate VI was synthesized using scheme and procedures analogues to Intermediate V involving (S)-5-(hydroxymethyl)oxazolidin-2-one (CAS: 97859-49-9) and 6-chloro-2H-pyrazino[2,3-b][1,4]oxazin-3(4H)-one (Va) as starting materials.

LC-MS Calc. for $C_{10}H_{11}N_5O_4$, 265.23, Observed 264.2 (M−1H); $^1$H NMR (400 MHz, DMSO-$d_6$): δ 8.36 (s, 1H), 4.84 (s, 2H), 4.69-4.65 (m, 1H), 4.12-4.06 (m, 1H), 3.89-3.84 (m, 1H), 3.16 (s, 1H), 2.92-2.83 (m, 2H).

Synthesis of (S)-2-(5-(aminomethyl)-2-oxooxazolidin-3-yl)-6H-pyrimido[5,4-b][1,4]oxazin-7(8H)-one, VII

Intermediate VII was synthesized using scheme and procedures analogues to Intermediate V involving (R)-5-(hydroxymethyl) oxazolidin-2-one (CAS: 97859-51-3) and 6-chloro-2H-pyrazino[2,3-b][1,4]oxazin-3(4H)-one (CAS: 943995-32-2) as starting materials; LC-MS Calc. for $C_{10}H_{11}N_5O_4$, 265.23, Observed 266 (M+);

$^1$H NMR (400 MHz, DMSO-$d_6$): δ 8.37 (s, 1H), 4.87 (s, 2H), 4.69-4.63 (m, 1H), 4.13-4.06 (m, 1H), 3.90-3.84 (m, 1H), 3.19 (s, 1H), 2.91-2.83 (m, 2H).

Synthesis of 6-(5-(2-aminoethyl)-2-oxooxazolidin-3-yl)-2H-pyrazino[2,3-b][1,4]oxazin-3(4H)-one, XXI

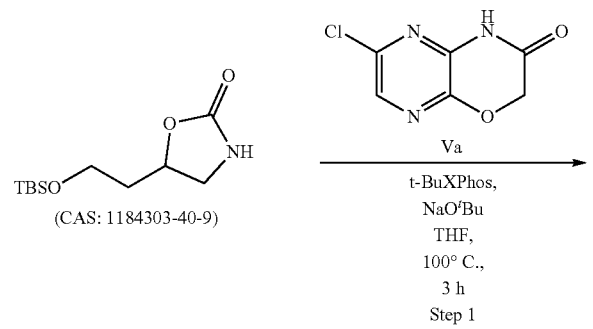

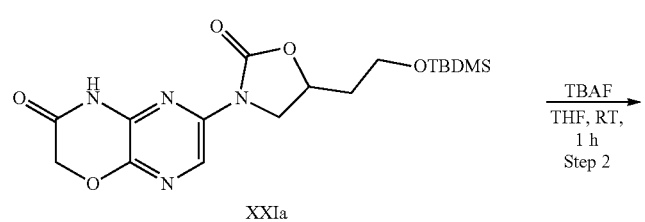

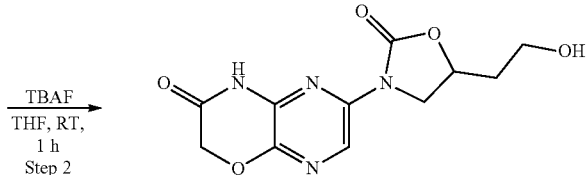

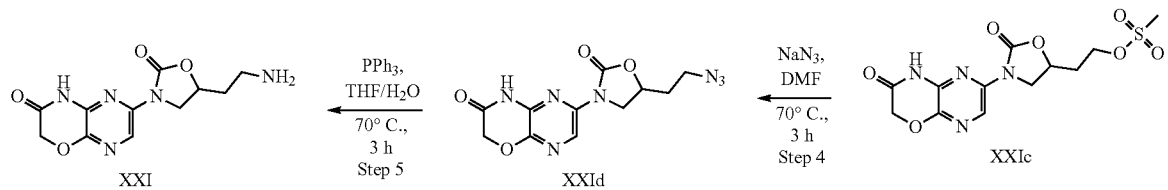

Step 1: 6-(5-(2-((tert-butyldimethylsilyl)oxy)ethyl)-2-oxooxazolidin-3-yl)-2H-pyrazino[2,3-b][1,4]oxazin-3(4H)-one (XXIa)

To a stirred solution of compound Va (40.0 g, 0.174 mol) and 5-(2-((tert-butyldimethylsilyl)oxy)ethyl)oxazolidin-2-one (CAS: 1184303-40-9, 47.12 g, 0.192 mmol) in 1.4-dioxane (600 ml) at room temperature under nitrogen atmosphere was added sodium tert-butoxide (25.16 g, 0.2619 mmol). The resulting mixture was degassed with a stream of nitrogen and was added t-butyl-X-Phos Palladacycle (6.9 g, 0.008732 mmol) at room temperature. The reaction mixture was then heated to 100° C. and stirred for 3 hours. After that, the reaction mixture was cooled to 0° C., filtered through celite pad and the filtrate was concentrated in vacuo. The obtained crude product was purified by column chromatography using silica gel (230-400 mesh) eluting with 25% ethyl acetate in petroleum ether to get compound XXIa as a pale-yellow solid. Yield: 51.0 g, 59.64%; LC-MS Calc. for $C_{17}H_{26}N_4O_5Si$ 395.52, Obs.: 393.1 [M$^+$–H]; $^1$H NMR (300 MHz, DMSO-$d_6$): δ 11.59 (s, 1H), 8.25 (d, J=72.60 Hz, 1H), 4.85-4.79 (m, 2H), 4.22-4.10 (m, 1H), 3.77-3.70 (m, 2H), 1.96 (d, J=6.00 Hz, 2H), 1.22 (t, J=7.20 Hz, 2H), 0.87 (s, 9H), 0.05 (s, 6H).

Step 2: 6-(5-(2-hydroxyethyl)-2-oxooxazolidin-3-yl)-2H-pyrazino[2,3-b][1,4]oxazin-3(4H)-one (XXIb)

To a stirred solution of compound XXIa (52.0 g, 0.1321 mol) in THF (500 mL) at 0° C. under nitrogen atmosphere was added tetra-n-butylammonium fluoride (264.6 mL, 0.2646 mol). The resulting mixture was warmed to room temperature and stirred for 1 hour. After that, the reaction mixture was quenched with water, the solid precipitated was filtered and dried under vacuum to get the compound XXIb as an off-white solid, which was taken for the next step without any purification. Yield: 32 g (crude); LC-MS Calc. for $C_{11}H_{12}N_4O_5$, 280.24, Obs.: 281.1 [M$^+$+H]; $^1$H NMR (300 MHz, DMSO-$d_6$): δ 11.63 (s, 1H), 8.39 (s, 1H), 4.85-4.82 (m, 3H), 4.69 (t, J=4.80 Hz, 1H), 4.23-4.13 (m, 1H), 3.80 (d, J=7.20 Hz, 1H), 3.57 (d, J=4.80 Hz, 2H), 1.94-1.88 (m, 2H).

Step 3: 2-(2-oxo-3-(3-oxo-3,4-dihydro-2H-pyrazino[2,3-b][1,4]oxazin-6-yl)oxazolidin-5-yl)ethyl methanesulfonate (XXIc)

To a stirred solution of compound XXIb (32 g, 0.114 mol) in N, N dimethylformamide (320 mL) at 0° C. under nitrogen atmosphere were added triethylamine (31.97 mL, 0.229 mol) and methanesulfonyl chloride (11.59 mL, 0.149 mol) successively. The resulting mixture was warmed to room temperature and stirred for 3 hours. After that, the reaction mixture was cooled to 0° C., diluted with water, the precipitated solid was filtered and dried under vacuum to get the compound XXIc as a pale-brown solid, which was taken for the next step without any purification. Yield: 38 g (crude); LC-MS Calc. for $C_{12}H_{14}N_4O_7S$, 358.34, Obs.: 359.0 [M$^+$+H]; $^1$H NMR (300 MHz, DMSO-$d_6$): δ 11.66 (s, 1H), 8.38 (s, 1H), 4.85-4.81 (m, 3H), 4.36-4.12 (m, 2H), 3.79-3.75 (m, 1H), 3.22 (s, 3H), 3.08 (d, J=9.20 Hz, 1H), 2.22 (d, J=8.00 Hz, 2H).

Step 4: 6-(5-(2-Azidoethyl)-2-oxooxazolidin-3-yl)-2H-pyrazino[2,3-b][1,4]oxazin-3(4H)-one (XXId)

To a stirred solution of compound XXIc (38.0 g (crude), 0.1063 mol) in DMF (380 mL) at 0° C. under nitrogen atmosphere was added sodium azide (17.28 g, 0.2658 mol). The resulting mixture was heated to 70° C. and stirred for 3 hours. After that, the reaction mixture was cooled to 0° C. and diluted with water. The solid precipitated was filtered and dried under vacuum to get compound XXId as an off-white solid, which was taken for the next step without any purification. Yield: 25 g (crude); LC-MS Calc. for $C_{11}H_{11}N_7O_4$, 305.25, Obs.: 304.1 [M$^+$–H]; $^1$H NMR (300 MHz, DMSO-$d_6$): δ 11.60 (s, 1H), 8.36 (s, 1H), 4.80 (t, J=10.40 Hz, 2H), 4.23-4.11 (m, 2H), 3.76-3.72 (m, 1H), 3.57-3.47 (m, 2H), 2.06-2.01 (m, 2H).

Step 5: 6-(5-(2-Aminoethyl)-2-oxooxazolidin-3-yl)-2H-pyrazino[2,3-b][1,4]oxazin-3(4H)-one (XXI)

To a stirred solution of compound XXId (25 g, 0.081 mol) in a mixture of THF/H$_2$O (1.0 L, 1:1) at 0° C. under nitrogen atmosphere was triphenylphosphene (64.1 g, 0.245 mol). The resulting mixture was then heated to 70° C. and stirred for 3 hours. After that, the reaction mixture was diluted with water (200 mL) and washed with EtOAc (3×250 mL), the aqueous layer was concentrated in vacuo. The crude product obtained was triturated with diethyl ether to afford pure compound XXI as a pale yellow solid. Yield: 18.0 g; LC-MS Calc. for $C_{11}H_{13}N_5O_4$, 279.26, Obs.: 280.1 [M$^+$+H]; $^1$H NMR (300 MHz, DMSO-$d_6$): δ8.35 (s, 1H), 4.83-4.81 (m, 3H), 4.22-4.13 (m, 2H), 3.75-3.71 (m, 1H), 2.75-2.66 (m, 2H), 1.91-1.81 (m, 2H).

Synthesis of 3-(3-fluoro-5-methyl-6-oxo-5,6-dihydro-1,5-naphthyridin-4-yl)propanal, VIII

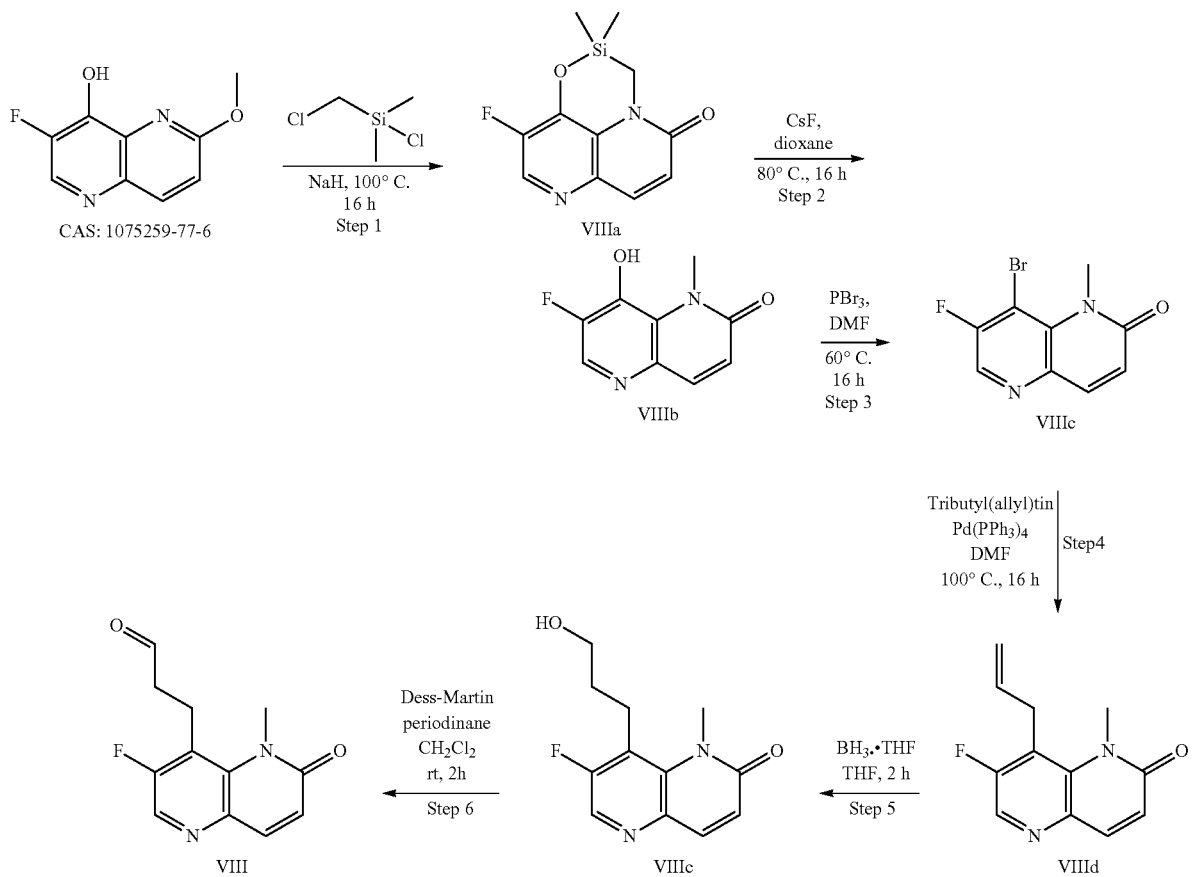

Step 1: 10-Fluoro-2,2-dimethyl-2,3-dihydro-5H-[1,4,2]oxazasilino[6,5,4-de][1,5]naphthyridin-5-one (VIIIa)

To a stirred solution of 3-fluoro-6-methoxy-1,5-naphthyridin-4-ol 1 (CASs: 1075259-77-6, 5 g, 25.77 mmol) in DMF (50 mL) at 0° C. under nitrogen atmosphere was added sodium hydride (1.5 g, 38.65 mmol, 60% dispersed in mineral oil). The resulting mixture was warmed to room temperature and stirred for 1 hour. Then chloro(chloromethyl)dimethylsilane (10 ml) was added to the reaction mixture and allowed to stir at room temperature for another 1.5 hour. The resulting reaction mixture then heated to 100° C. and stirred for 16 hours. After that, the reaction mixture was quenched with methanol (1 mL) and concentrated completely in vacuo. The obtained crude product was further purified by column chromatography using silica gel (60-120 mesh) eluting with 10-15% of Methanol in dichloromethane to get compound VIIa.

Yield: 5.5 g, 85.1%; LC-MS Calc. for $C_{11}H_{11}N_2O_2Si$, 250.30; Obs: 251.0 [M$^+$+H]; $^1$H NMR (300 MHz, DMSO-d$_6$): δ 8.49 (d, J=2.4 Hz, 1H) 7.87 (d, J=9.60 Hz, 1H), 6.84 (d, J=9.90 Hz, 1H), 3.61 (s, 2H), 0.45 (s, 6H).

Step I1: 7-fluoro-8-hydroxy-1-methyl-1,5-naphthyridin-2(1H)-one (VIIIb)

To a stirred solution of compound VIIIa (5.5 g, 22.00 mmol) in mixture of 1,4-dioxane/methanol (100 mL, 2:1) at 60° C. under nitrogen atmosphere was added cesium fluoride (10 g, 66.00 mmol). The resulting mixture was heated to 80° C. and stirred for 16 hours. After that, the reaction mixture was concentrated in vacuo. The residue obtained was dissolved was in water (25 mL) and neutralized with 1.5 N HCl (adjusted pH~6-7). The solid precipitated out was filtered and dried under vacuo to get compound VIIIb as an off white solid, which was used as such for the next step without any purification. Yield: 3.50 g; LC-MS Calc. for $C_9H_7FN_2O_2$, 194.17; Obs.; 195.1; [M$^+$+H]. $^1$H NMR (400 MHz, DMSO-d$_6$): δ 12.29 (brs, 1H), 8.25 (d, J=6.00 Hz, 1H), 7.68 (d, J=9.60 Hz, 1H), 6.82 (d, J=10.00 Hz, 1H), 4.01 (s, 3H).

Step III: 8-Bromo-7-fluoro-1-methyl-1,5-naphthyridin-2(1H)-one (VIIIc)

To a stirred solution of compound VIIIb (3.2 g, 16.5 mmol) in N,N-dimethylformamide (25 mL) at 0° C. under nitrogen atmosphere was added phosphorous tribromide (2.4 mL, 25 mmol) in dropwise. The resulting mixture was then gradually warmed to room temperature, then heated to 60° C. and stirred for 16 hours. After that, the reaction mixture was cooled to room temperature and concentrated in vacuo. The residue obtained was dissolved in dichloromethane (100 mL), washed with 10% aqueous NaHCO$_3$ (2×10 mL), brine (20 mL). The organic phase was dried over Na$_2$SO$_4$ and concentrated in vacuo. The obtained crude product was purified by column chromatography using silica gel (60-120 mesh) eluting with 50% of ethyl acetate in petroleum ether to get compound VIIIc. Yield: 1.6 g, 38.2%; LC-MS Calc. for $C_9H_6BrFN_2O$, 257.06; Obs.; 257.0 [M]. $^1$H NMR (400 MHz, DMSO-d$_6$): δ 8.61 (s, 1H), 7.92 (d, J=9.60 Hz, 1H), 6.89 (d, J=9.60 Hz, 1H), 3.89 (s, 3H).

Step 4: 8-Allyl-7-fluoro-1-methyl-1,5-naphthyridin-2(1H)-one (VIIId)

To a stirring solution of compound VIIIc (1.60 g, 7.05 mmol) in dry DMF (20 mL) was added tributyl(allyl)tin (2.63 mL, 8.46 mmol) and the mixture was purged with $N_2$ for 20 min Pd(PPh$_3$)$_4$ (0.40 g, 0.35 mmol) was added and the reaction mixture was stirred at 80° C. for 16 hours. After cooling to room temperature, water was added and the resulting mixture was extracted with ethyl acetate (2×100 mL). The combined organic phases were washed with brine, dried over $Na_2SO_4$ and concentrated to get crude product which was purified by column chromatography using silica gel (60-120 mesh) eluting with 20-25% ethyl acetate in petroleum ether to afford pure product VIIId as off-white solid. Yield: 0.80 g, 50%; LC-MS: Calc. for $C_{12}H_{11}FN_2O$ 218.09; Obs. 219.1 [M+H]$^+$. $^1$H NMR (400 MHz, DMSO-D$_6$): δ 7.96 (d, J=12.0 Hz, 1H), 7.89 (d, J=9.6 Hz, 1H), 6.80 (d, J=10.0 Hz, 1H), 6.07-6.00 (m, 1H), 5.13-5.08 (m, 2H), 3.65-3.63 (m, 2H), 3.58 (s, 3H).

Step 5: 7-Fluoro-8-(3-hydroxypropyl)-1-methyl-1,5-naphthyridin-2(1H)-one (VIIIe)

To a stiffing solution of compound VIIId (0.80 g, 3.66 mmol) in dry THF (12 mL) was added BH$_3$.THF complex (7.4 mL 7.33 mmol) at 0° C. and stirred at room temperature for 2 hours. Upon completion, the reaction mixture was cooled to 0° C. and 10% aqueous sodium bicarbonate solution (4 mL) followed by 30% hydrogen peroxide (8 mL) were added and stirred at room temperature for 1 hour. The reaction mixture was diluted with ethyl acetate (100 mL) and washed with water, brine. The organic layer was dried over $Na_2SO_4$ and concentrated to get the crude product. The crude was purified by column chromatography using silica gel (230-400 mesh) by eluting with 80% ethyl acetate in petroleum ether to afford pure product IIIe as brown solid. Yield: 0.18 g, 21%; LC-MS: Calc. for $C_{12}H_{13}FN_2O_2$ 236.25; Obs. 237.0.

Step 6: 3-(3-Fluoro-5-methyl-6-oxo-5, 6-dihydro-1,5-naphthyridin-4-yl)propanal (VIII)

To a stirring solution of compound VIIIe (0.18 g, 0.76 mmol) in dry dichloromethane (7.2 mL) was added Dess-Martin periodinane (0.48 g 1.14 mmol) at 0° C. and stirred at room temperature for 2 hours. Upon completion, the reaction mixture was cooled to 0° C., quenched with sodium thiosulphate dissolved in 10% sodium bicarbonate solution and extracted with ethyl acetate (75 mL). The organic layer was separated and washed with water, brine. The organic layer was dried over $Na_2SO_4$ and concentrated to get the crude product VIII. The crude was used for the next step without further purification. Yield: 0.14 g, 79%; LC-MS: Calc. for $C_{12}H_{11}FN_2O_2$ 234.23; Obs. 235.1 [M+H]$^+$.

Synthesis of 2-(3-fluoro-5-methyl-6-oxo-5,6-dihydro-1,5-naphthyridin-4-yl)acetaldehyde, IX

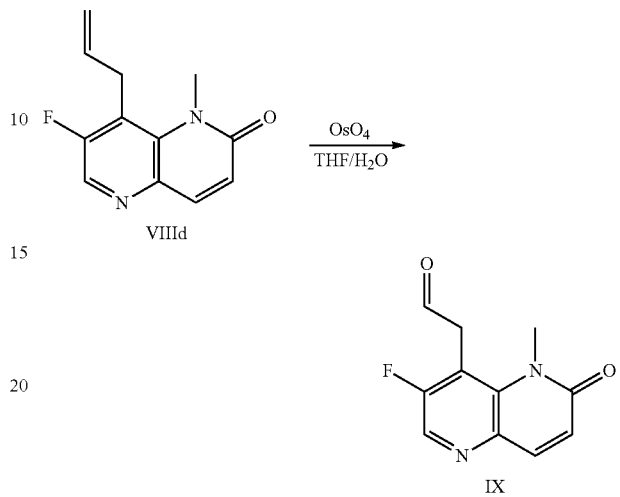

To a stirred solution of compound VIIId (0.06 g, 0.275 mmol) in a mixture of THF/H$_2$O (4 mL, 1:1) at 0° C. under nitrogen atmosphere were added NaIO$_4$ (0.18 g 0.825 mmol) and osmium tetroxide (2.5% wt in t-BuOH, 0.12 mL 0.013 mmol) successively. The resulting mixture was then warmed to room temperature and stirred for 2 hours. After that, the reaction mixture quenched with water and extracted with ethyl acetate (2×20 mL). The combined organic phase was washed with 2% sodium thiosulfate solution (10 mL), brine (10 mL), dried over anhydrous sodium sulfate and concentrated in vacuo. The obtained crude product was further purified by column chromatography using silica gel (60-120 mesh) eluting with 100% ethyl acetate in petroleum ether to get compound IX as a brown gummy solid and the crude material was taken for next step without further purification. Yield: 0.04 g, 66.6%; LC-MS Calc. for $C_{11}H_9FN_2O_2$, 220.20; Obs.; 221.1 [M$^+$+H].

Synthesis of 2-(7-fluoro-1-methyl-2-oxo-1,2,3,4-tetrahydroquinolin-8-yl)acetaldehyde, X

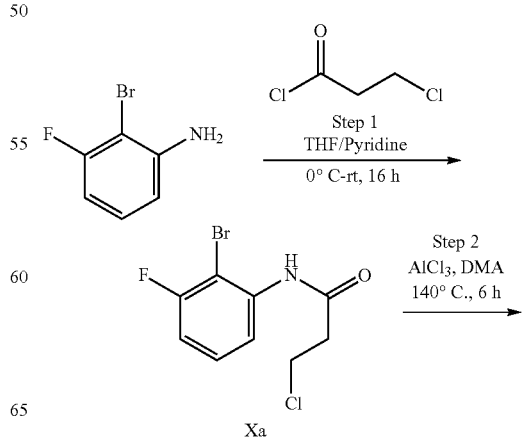

-continued

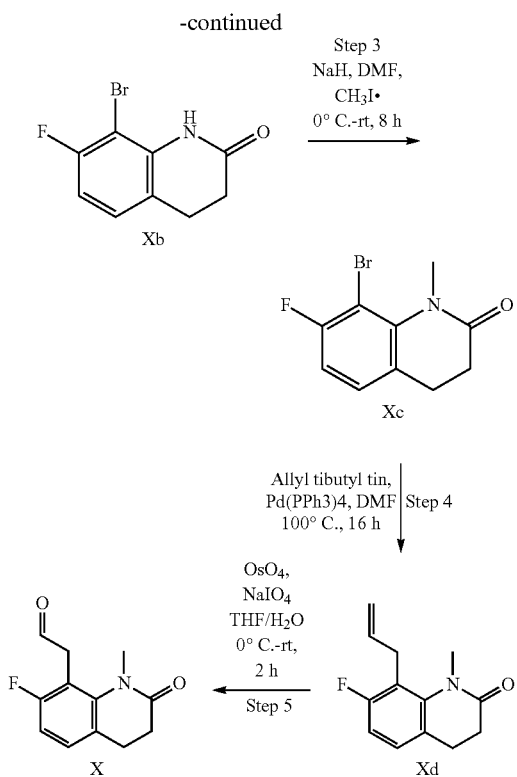

Step 1:
N-(2-Bromo-3-fluorophenyl)-3-chloropropanamide (Xa)

To a stirred solution of 2-bromo-3-fluoroaniline (5.00 g, 26.3 mmol) in dry THF (50 mL) at 0° C. under nitrogen atmosphere was added pyridine (3.18 mL). Then 3-chloropropanoyl chloride (3.02 mL g, 31.6 mmol) was added in dropwise carefully. Then the reaction mixture was warmed to room temperature and stirred for 16 hours. After that the reaction mixture was concentrated under reduced pressure. The residue obtained was diluted with water (100 mL) and extracted with ethyl acetate (3×75 mL). The combined extract was washed with water, brine, dried over $Na_2SO_4$ and concentrated in vacuo to get compound Xa (crude), which was used for the next step without any further purification. Yield: 6.40 g; $^1$H-NMR (400 MHz, DMSO-$d_6$): δ9.77 (s, 1H), 7.48-7.39 (m, 2H), 7.24-7.19 (m, 1H), 3.88 (t, J=6.4 Hz, 2H), 2.91 (t, J=6.4 Hz, 2H)

Step 2: 8-Bromo-7-fluoro-3,4-dihydroquinolin-2 (1H)-one (Xb)

To a mixture of compound Xa (5.00 g, 17.8 mmol) and $AlCl_3$ (11.8 g, 89.28 mmol) at 0° C. under nitrogen atmosphere was added DMA (1 mL) Then the reaction mixture was heated to 140° C. for 6 hours. After that the reaction mixture was cooled to room temperature, quenched with ice water (100 mL) and extracted with ethyl acetate (3×75 mL). The combined organic phase was washed with brine (2×50 mL), dried over $Na_2SO_4$ and concentrated in vacuo. The obtained crude product was purified by column chromatography using silica gel (230-400 mesh) eluting with 25% ethyl acetate in petroleum ether to get compound Xb as an off-white solid. Yield: 2.10 g, 48.27%. $^1$H-NMR (400 MHz, DMSO-$d_6$): δ9.41 (s, 1H), 7.27-7.23 (m, 1H), 6.95 (t, J=8.4 Hz, 1H), 2.92 (t, J=7.6 Hz, 2H), 2.51-2.48 (m, 2H).

Step 3: 8-Bromo-7-fluoro-1-methyl-3,4-dihydroquinolin-2(1H)-one (Xc)

To a stirred solution of compound Xb (2.00 g, 8.19 mmol) in DMF (40 mL) was added NaH (60% dispersion in oil, 0.49 g, 12.3 mmol) in portions. The resulting mixture was stirred at 0° C. for 30 minutes and was added MeI (0.61 mL, 9.82 mmol) in dropwise. The reaction mixture was then gradually warmed to room temperature and stirred for 8 hours. After that, the reaction mixture was quenched with ice cold water (50 mL) and extracted with ethyl acetate (3×200 mL). The combined organic phase was washed with brine (3×50 mL), dried over $Na_2SO_4$ and concentrated in vacuo. The obtained crude product was further purified by column chromatography using silica gel (230-400 mesh) eluting with 15% ethyl acetate in petroleum ether to get compound Xc as an off-white solid. Yield: 1.60 g, 75.82%. $^1$H-NMR (400 MHz, $CDCl_3$): δ7.10-7.08 (m, 1H), 6.87-6.85 (m, 1H), 3.49 (s, 3H), 2.86-2.83 (m, 2H), 2.61-2.58 (m, 2H).

Step 4: 8-Allyl-7-fluoro-1-methyl-3,4-dihydroquinolin-2(1H)-one (Xd)

To a stirred solution of compound Xc (0.60 g, 2.32 mmol) in DMF (10 mL) was added tributylallyltin (1.06 mL, 3.48 mmol) at room temperature. The resulting mixture was degassed with a stream of nitrogen for 30 minutes and was added $Pd(PPh_3)_4$ (0.27 g, 0.23 mmol) at room temperature. The reaction mixture was then heated to 100° C. and stirred for 16 hours. After that the reaction mixture was cooled to 0° C., quenched with water and extracted with ethyl acetate (2×50 mL). The combined organic phase was washed with water (50 mL), brine (50 mL), dried over $Na_2SO_4$ and concentrated in vacuo. The obtained crude product was further purified by column chromatography using silica gel (230-400 mesh) eluting with 20% ethyl acetate in petroleum ether to compound Xd as a colourless liquid. Yield: 0.45 g, 88.40%. $^1$H-NMR (400 MHz, $CDCl_3$): δ7.05-7.01 (m, 1H), 6.78 (t, J=8.8 Hz, 1H), 6.09-6.00 (m, 1H), 5.16-5.12 (m, 1H), 5.05-5.00 (m, 1H), 3.45-3.43 (m, 2H), 3.33 (s, 3H), 2.81-2.75 (m, 2H), 2.58-2.53 (m, 2H)

Step 5: 2-(7-Fluoro-1-methyl-2-oxo-1,2,3,4-tetrahydroquinolin-8-yl) acetaldehyde (X)

To a stirred solution of compound Xd (0.42 g, 1.94 mmol) in a mixture of THF/$H_2O$ (20 mL, 3:1) at 0° C. under nitrogen atmosphere were added $OsO_4$ (2.5 M solution in t-BuOH, 0.98 mL) and $NaIO_4$ (1.24 g, 5.82 mmol). The reaction mixture warmed to room temperature and stirred for 2 hours. Upon completion, the reaction mixture was quenched with water (20 mL) and extracted with ethyl acetate (3×30 mL). The combined organic phase was dried over $Na_2SO_4$ and concentrated in vacuo. The obtained crude product was further purified by column chromatography using silica gel (230-400 mesh) eluting with 30-35% ethyl acetate in petroleum ether to get compound X as a dark brown solid. Yield: 0.25 g, 59.10%. LC-MS: Calc. for $C_{12}H_{12}FNO_2$ 221.09; Obs.: 222.2 [M+H]$^+$; $^1$H NMR (400 MHz, $CDCl_3$): δ9.86 (s, 1H), 7.14-7.11 (m, 1H), 6.85 (t, J=8.8 Hz, 1H), 3.85 (d, J=1.6 Hz, 2H), 3.27 (s, 3H), 2.85-2.82 (m, 2H), 2.62-2.58 (m, 2H).

Synthesis of 2-(6-Fluoro-4-methyl-3-oxo-3,4-dihydroquinoxalin-5-yl)acetaldehyde, XI

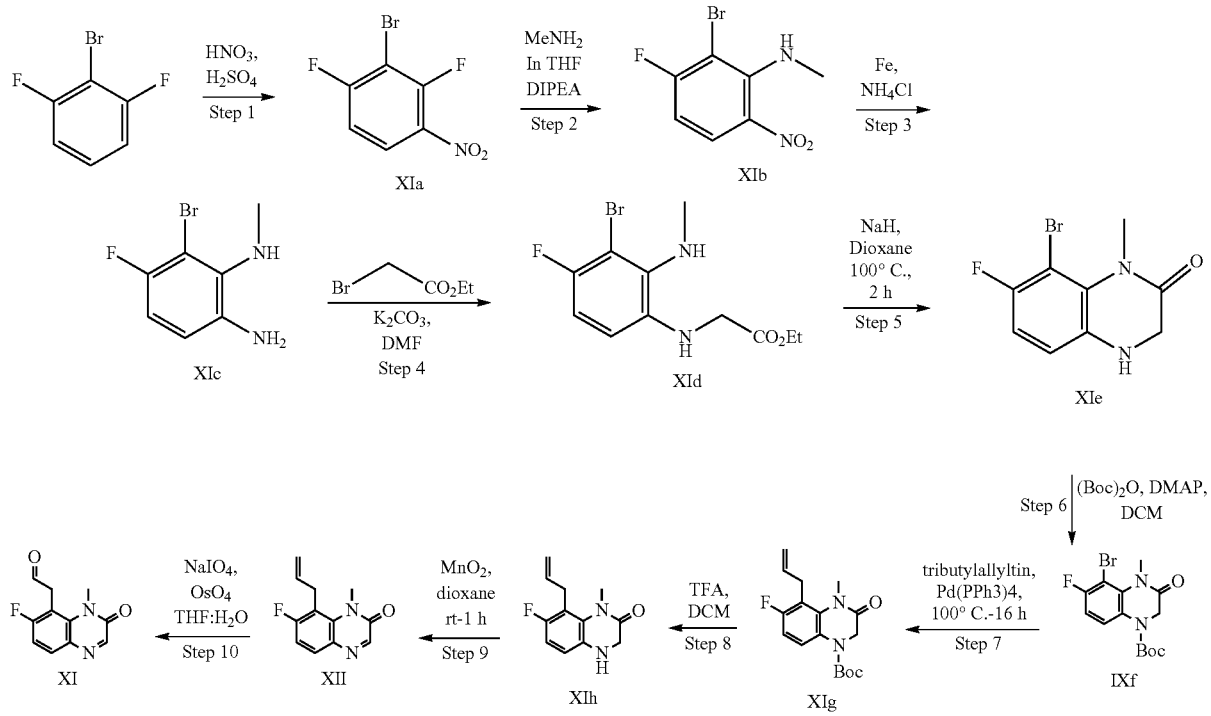

Step 1: 2-Bromo-1,3-difluoro-4-nitrobenzene (XIa)

To a stirred solution of 2-bromo-1,3-diflurobenzene (CAS 64248-56-2, 10.0 g, 51.8 mmol) in $H_2SO_4$ (30 mL) at 0° C. under nitrogen atmosphere was added $HNO_3$ (65%, 25 mL) in dropwise. The resulting mixture was warmed to room temperature and stirred for 1 hour. After that, the reaction mixture was poured onto ice and vigorously stirred for 5 minutes. The resulting suspension was extracted with $CH_2C_{12}$ (4×125 mL), washed with brine (200 mL), dried over $Na_2SO_4$ and concentrated in vacuo to get compound XIa (crude). The obtained crude product was taken for the next step without any further purification. Yield: 9.00 g, 72.99%. $^1$H-NMR (400 MHz, DMSO-$d_6$): δ8.34-8.29 (m, 1H), 7.56-7.51 (m, 1H).

Step 2: 2-Bromo-3-fluoro-N-methyl-6-nitroaniline (XIb)

To a stirred solution of compound XIa (9.00 g, 37.8 mmol) and DIPEA (13.3 mL, 75.6 mmol) in THF (90 mL) at room temperature under nitrogen atmosphere was added methylamine (2M in THF, 37.8 mL, 75.6 mmol). The resulting mixture was heated to 60° C. and stirred for 3 hours. After that, the reaction mixture was concentrated under reduced pressure and the residue obtained was purified by column chromatography using silica gel (60-120 mesh) eluting with petroleum ether to give compound XIb as pale yellow colour solid. Yield: 7.70 g, 81.74%. $^1$H-NMR (400 MHz, DMSO-$d_6$): δ7.91-7.87 (m, 1H), 6.80-6.76 (m, 2H), 2.75 (s, 3H).

Step 3: 6-Bromo-5-fluoro-N1-methylbenzene-1,2-diamine (XIc)

To a stirred solution of compound XIb (7.70 g, 30.9 mmol) in a mixture of methanol/water (400 mL, 3:1) were added ammonium chloride (8.20 g, 154.6 mmol) and iron powder (6.90 g, 123.7 mmol) successively. The resulting mixture was heated at reflux for 16 hours. After that, the reaction mixture was filtered to the solid material and the filtrate was concentrated under reduced pressure. The residue obtained was diluted with water and extracted with ethyl acetate (2×300 mL). The combined organic phase was washed with brine, dried over $Na_2SO_4$ and concentrated in vacuo. The obtained residue was further purified by column chromatography using silica gel (230-400 mesh) eluting with 15-20% ethyl acetate in petroleum ether to get compound XIc as pale brown colour solid. Yield: 3.50 g, 51.69%; $^1$H NMR (400 MHz, DMSO-$d_6$): δ 6.70 (t, J=8.6 Hz, 1H), 6.61-6.59 (m, 1H), 4.82 (brs, 2H), 3.92 (brs, 1H), 2.61 (s, 3H).

Step 4: Ethyl (3-bromo-4-fluoro-2-(methylamino)phenyl) glycinate (XId)

To a stirred solution of compound XIc (3.50 g, 16.0 mmol) in DMF (70 mL) at 0° C. under nitrogen atmosphere were added $K_2CO_3$ (3.30 g, 23.9 mmol) and ethyl bromoacetate (2.10 mL, 19.2 mmol) successively. The resulting mixture was heated to 75° C. and stirred for 1 hour. Upon completion, the reaction mixture was quenched with ice cold water (50 mL) and extracted with ethyl acetate (4×100 mL). The combined organic phase was washed with brine, dried over Na$_2$SO$_4$ and concentrated in vacuo. The obtained crude product was purified by column chromatography using silica gel (230-400 mesh) eluting with 10-15% of ethyl acetate in petroleum ether to get compound XId. Yield: 3.50 g, 71.86%. $^1$H-NMR (400 MHz, DMSO-d$_6$): δ 6.84 (t, J=8.6 Hz, 1H), 6.41-6.38 (m, 1H), 5.39-5.37 (m, 1H), 4.16-4.08 (m, 1H), 4.01-3.94 (m, 1H), 2.59 (d, J=5.7 Hz, 3H), 1.18 (t, J=7.0 Hz, 3H).

Step 5: 8-Bromo-7-fluoro-1-methyl-3,4-dihydroquinoxalin-2(1H)-one (XIe)

To a stirred solution of compound XId (3.50 g, 11.5 mmol) in 1,4-Dioaxne (70 mL) at 0° C. under nitrogen atmosphere was added NaH (60% dispersion in oil, 0.14 g, 3.44 mmol). The resulting mixture was heated 100° C. and stirred for 2 hours. After that, reaction mixture was quenched with ice cold water (50 mL) and extracted with ethyl acetate (3×100 mL). The combined organic phase was washed with brine (100 mL), dried over Na$_2$SO$_4$ and concentrated in vacuo. The obtained crude product was further purified by column chromatography using silica gel (230-400 mesh) eluting with 25-30% of ethyl acetate in petroleum ether to get compound XIe as off white solid. Yield: 2.70 g, 90.91%. $^1$H-NMR (400 MHz, DMSO-d6): δ6.99-6.94 (m, 1H), 6.88-6.84 (m, 1H), 6.24 (s, 1H), 3.60 (s, 2H), 3.35 (s, 3H).

Step 6: Tert-butyl 5-bromo-6-fluoro-4-methyl-3-oxo-3,4-dihydroquinoxaline-1(2H)-carboxylate (XIf)

To a stirred solution of compound XIe (2.00 g, 7.70 mmol) in dichloromethane (20 mL) at 0° C. under nitrogen atmosphere were added 4-dimethylaminopyridine (1.41 g, 9.25 mmol) and di-tert-butyl dicarbonate successively. The resulting mixture was allowed to stir at room temperature for 8 hours. After that, the reaction mixture was concentrated under reduced pressure to get the crude product, which was further purified by column chromatography using silica gel (230-400 mesh) eluting with 10% ethyl acetate in petroleum ether to get compound XIf as off white solid. Yield: 1.40 g, 50.54%. $^1$H-NMR (400 MHz, CDCl$_3$): δ 7.65-7.62 (m, 1H), 6.97 (t, J=8.4 Hz, 1H), 4.29 (s, 2H), 3.54 (s, 3H), 1.55 (s, 9H).

Step 7: Tert-butyl 5-bromo-6-fluoro-4-methyl-3-oxo-3,4-dihydroquinoxaline-1(2H)-carboxylate (XIg)

To a stirred solution of compound XIf (1.40 g, 3.89 mmol) in DMF (20 mL) at room temperature was added tributylallyltin (1.80 mL, 5.84 mmol). The resulting mixture was degassed with stream of nitrogen for 30 minutes. Then Pd(PPh$_3$)$_4$ (0.23 g, 1.94 mmol) was added to the reaction mixture under nitrogen atmosphere. The resulting mixture was then heated to 100° C. and stirred for 16 hours. After that, the reaction mixture was cooled to 0° C., quenched with water and extracted with ethyl acetate (2×50 mL). The combined organic phase were washed with water (50 mL), brine (50 mL), dried over Na$_2$SO$_4$ and concentrated in vacuo. The obtained crude product was further purified by column chromatography using silica gel (230-400 mesh) eluting with 20% ethyl acetate in petroleum ether to get compound XIg as a light yellow viscous liquid. Yield: 0.85 g, 68.00%. $^1$H-NMR (400 MHz, CDCl$_3$): δ7.58-7.53 (m, 1H), 6.91-6.86 (m, 1H), 6.07-5.99 (m, 1H), 5.18-5.15 (m, 1H), 5.04 (d, J=17.4 Hz, 1H), 4.38 (s, 1H), 4.25 (s, 2H), 3.47-3.45 (m, 2H), 3.37 (s, 3H), 1.54 (s, 9H).

Step 8: 8-Allyl-7-fluoro-1-methyl-3,4-dihydroquinoxalin-2(1H)-one (XIh)

To a stirred solution of compound XIg (0.85 g, 2.65 mmol) in dichloromethane (15 mL) at 0° C. under nitrogen atmosphere was added trifluoroacetic acid (4.0 mL, 5.32 mmol). The resulting mixture was allowed to stir at 0° C. for 1 hour. After that, the reaction mixture was diluted with water (20 mL) and extracted with dichloromethane (3×25 mL). The combined organic phase was washed with 10% NaHCO$_3$ solution, dried over Na$_2$SO$_4$ and concentrated in vacuo. The obtained crude product was further purified by column chromatography using silica gel (230-400 mesh) eluting with 20% ethyl acetate in petroleum ether to compound XIh as a pale yellow liquid. Yield: 0.39 g, 66.78%. LC-MS: Calc. for C$_{12}$H$_{13}$FN$_2$O 220.1; Obs.: 221.1 [M+H]

Step 9: 8-Allyl-7-fluoro-1-methylquinoxalin-2(1H)-one (XII)

To a stirred solution of compound XIh (0.39 g, 1.77 mmol) in 1,4-dioxane (5 mL) at room temperature under nitrogen atmosphere was added MnO$_2$ (90%, 1.53 g, 17.7 mmol) at once. The resulting mixture was allowed to stir at room temperature for 30 minutes. After that, the reaction mixture was filtered and the filtrate was concentrated under reduced pressure to get compound XIi (crude) as a pale yellow solid, which was used for the next step without any further purification. Yield: 0.31 g (crude); $^1$H NMR (400 MHz, DMSO-d$_6$): δ8.18 (s, 1H), 7.81-7.77 (m, 1H), 7.29 (t, J=9.1 Hz, 1H), 6.21-6.14 (m, 1H), 5.19 (d, J=10.3 Hz, 1H), 4.87 (d, J=17.2 Hz, 1H), 3.76 (s, 2H), 3.73 (s, 3H). LC-MS: Calc. for C$_{12}$H$_{11}$FN$_2$O 218.1; Obs. 219.2 [M+H]$^+$.

Step 10: 2-(6-Fluoro-4-methyl-3-oxo-3,4-dihydroquinoxalin-5-yl)acetaldehyde (XI)

To a stirred solution of compound XIi (0.19 g, 0.87 mmol) in a mixture of THF/H$_2$O (10 mL: 5 mL, 2:1) at 0° C. under nitrogen atmosphere were added O$_s$O$_4$ (2.5 M solution in t-BuOH) (0.88 mL, 0.08 mmol) and NaIO$_4$ (0.55 g, 2.61 mmol) successively. The resulting mixture was warmed to room temperature and stirred for 3 hours. After that, the reaction mixture was quenched with water (20 mL) and extracted with ethyl acetate (3×20 mL). The combined organic phase was washed with brine, dried over Na$_2$SO$_4$ and concentrated in vacuo. The obtained crude product was further purified by column chromatography using silica gel (230-400 mesh) eluting with 30% ethyl acetate in petroleum ether to get compound XIi as a pale yellow solid. Yield: 0.085 g, 44.50%. LC-MS: Calc. for C$_{11}$H$_9$FN$_2$O$_2$ 220.1; Obs.: 221.0 [M+H]$^+$.

Synthesis of 2-(7-Fluoro-1-methyl-2-oxo-1,2-dihydroquinolin-8-yl)acetaldehyde, XII

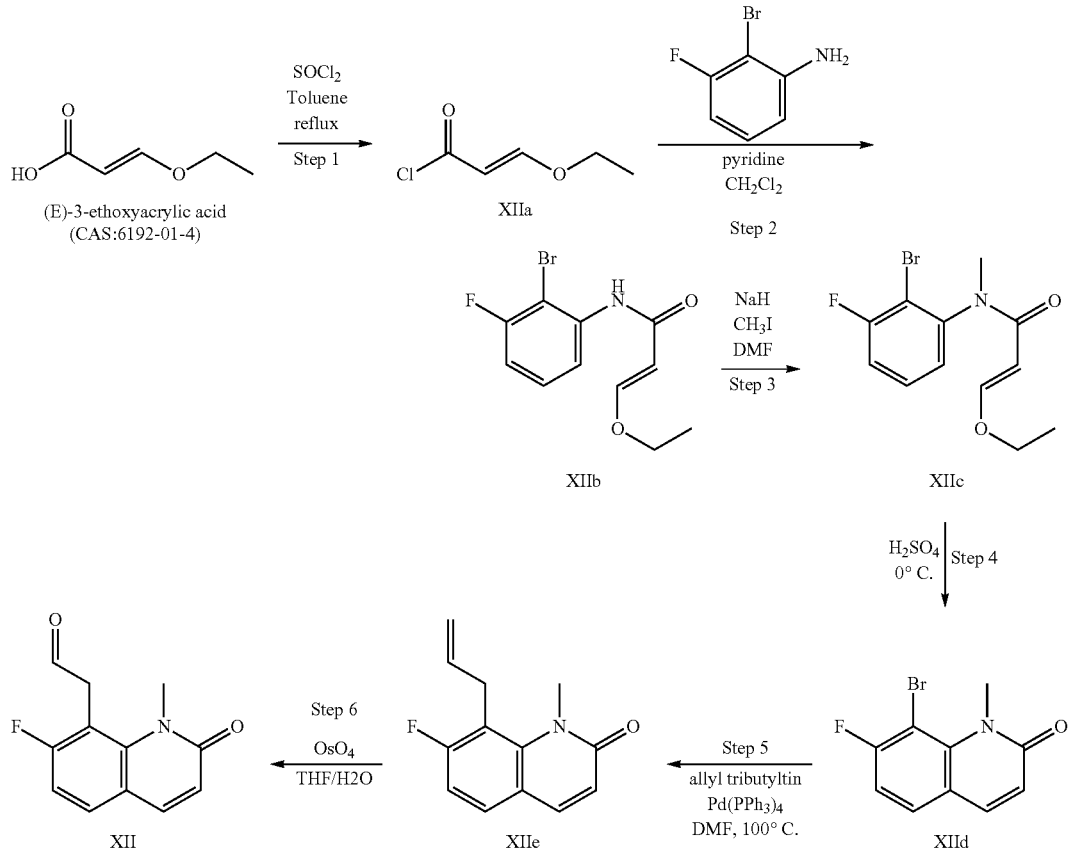

Step 1: (E)-3-Ethoxyacryloyl chloride (XIIa)

To a mixture of (E)-3-ethoxyacrylic acid (150 g, 1.29 mmol) in toluene (1 L) at room temperature was added $SOCl_2$ (121 mL, 1.68 mmol) in dropwise. The resulting mixture was heated to 90° C. and stirred for 2 hours. After that, the reaction mixture was completely concentrated under reduced pressure to get compound XIIa (crude), which was used as such for the next step. Yield: 155 g (crude).

Step 2: (E)-N-(2-bromo-3-fluorophenyl)-3-ethoxyacrylamide (XIIb)

To a stirred solution of compound XIIa (155 g, 1.15 mmol) in dichloromethane (2 L) at 0° C. under nitrogen atmosphere were added pyridine (750 mL, 5 vol) and 2-bromo-3-fluroaniline (218.0 g, 1.15 mmol). The resulting mixture was continued to stir at room temperature for 16 hours. After that the reaction mixture was quenched with water extracted with dichloromethane (2×5 L). The combined organic phase was washed with 1.5N HCl solution (2×3 L), brine (1×2 L), dried over $Na_2SO_4$ and concentrated in vacuo. The obtained crude product was purified by column chromatography using silica gel (60-120 mesh) eluting with 20% of ethyl acetate in petroleum ether to get compound XIIb. Yield: 240 g, 64.67% (over a two steps); LC-MS Calc. for $C_{11}H_{11}BrFNO_2$, 288.12; Obs: 290.0 [M$^+$+ 2H]; $^1$H NMR (300 MHz, DMSO-d$_6$): δ 9.26 (s, 1H), 7.61-7.59 (d, 1H, J=8.19 Hz), 7.54-7.49 (m, 1H), 7.41-7.34 (m, 1H), 7.17-7.11 (m, 1H), 5.79-5.75 (d, 1H, J=12.33 Hz), 3.97-3.95 (m, 2H), 1.30-1.25 (m, 3H).

Step 3: (E)-N-(2-Bromo-3-fluorophenyl)-3-ethoxy-N-methylacrylamide (XIIc)

To a stirred solution of compound XIIb (240 g, 0.832 mmol) in DMF (1.5 L) at 0° C. under nitrogen atmosphere was added NaH (60%) (39.9 g, 0.993 mmol) in portions over a period of 30 min and stirred for 30 minutes. Then methyl iodide (77.7 mL, 1.248 mmol) was added in dropwise at 0° C. The resulting mixture was warmed to room temperature and stirred for 1 hour. Upon completion, the reaction mixture was cooled to 0° C., quenched with ice cold water (3 L) and extracted with ethyl acetate (2×2 L). The combined organic phase was washed with brine (1×2 L), dried over $Na_2SO_4$ and concentrated under in vacuo. The crude was further purified by column chromatography using silica gel (60-120 mesh) eluting with 35-40% of ethyl acetate in petroleum ether to get compound XIIc. Yield: 200 g, 79.19%; LC-MS Calc. for $C_{12}H_{13}BrFNO_2$, 302.14; Obs.; 302.1 [M]; $^1$H NMR (300 MHz, DMSO-d$_6$): δ 7.54-7.31 (m, 4H), 4.80-4.76 (d, 1H, J=12.0 Hz), 3.78-3.71 (m, 2H), 3.10 (s, 3H), 1.14-1.10 (m, 3H).

Step 4: 8-Bromo-7-fluoro-1-methylquinolin-2(1H)-one (XIId)

A solution of compound XIIc (50 g, 0.165 mmol) in 1,4-dioxane (100 mL) was added to the precooled solution of Conc. H₂SO₄ (250 mL, 5 v) under nitrogen atmosphere. The resulting mixture was warmed to room temperature and stirred for 2 days. Upon completion, the reaction mixture was cooled to 0° C., quenched with ice cold water (3 L) and extracted with ethyl acetate (2×2 L). The combined organic extract was washed with water, brine, dried over Na₂SO₄ and concentrated in vacuo. The obtained crude product was purified by column chromatography using silica gel (60-120 mesh) eluting with 50% of ethyl acetate in petroleum ether to get compound XIId. Yield: 30 g, 70.77%. LC-MS Calc. for C₁₀H₇BrFNO, 256.07; Obs.; 256.0 [M]; 1H-NMR (300 MHz, DMSO-d₆): δ 7.92-7.89 (d, 1H, J=9.6 Hz), 7.82-7.77 (m, 1H), 7.33-7.27 (t, 1H, J=8.4 Hz) 6.64-6.60 (d, 1H, J=9.6 Hz), 3.84 (s, 3H).

Step 5: 8-Allyl-7-fluoro-1-methylquinolin-2(1H)-one (XIIe)

To a stirred solution of compound XIId (30 g, 117.18 mmol) in DMF (300 mL) was added tributylallyltin (46.5 mL, 140.62 mmol) at room temperature. The resulting mixture was degassed with a stream of nitrogen for 30 minutes. Then tetrakis (triphenylphosphine) palladium (0) (13.5 g, 11.71 mmol) was added. The reaction was then heated to 100° C. and stirred for 12 hours. After that, the reaction mixture was cooled room temperature and concentrated in vacuo. The obtained crude product was further purified by column chromatography (60-120 mesh, 20% ethyl acetate in petroleum ether) to get compound XIIe as pale yellow liquid. Yield: 21 g, 82.61%. LC-MS Calc. for C₁₃H₁₂FNO, 217.2; Obs.; 218.1; [M⁺+H]; ¹H NMR (400 MHz, DMSO-d₆): δ 7.65-7.62 (d, 1H, J=9.6 Hz), 7.47-7.43 (dd, 1H, J₁=8.4, J₂=6.4 Hz), 7.05-7.00 (t, 1H, J=9.2 Hz) 6.71-6.68 (d, 1H, J=9.6 Hz), 6.22-6.16 (m, 1H), 5.27-5.24 (d, 1H, J=10.4 Hz), 5.03-4.99 (d, 1H, J=17.2 Hz), 3.84 (s, 3H), 3.76 (d, 2H, J=2.0 Hz).

Step 5: 2-(7-Fluoro-1-methyl-2-oxo-1,2-dihydroquinolin-8-yl)acetaldehyde (XII)

To a stirred solution of compound XIIe (10 g, 46 mmol) in a mixture of THF/water (500 mL, 1:1) at 0° C. under nitrogen atmosphere were added sodium meta periodate (29.54 g 138 mmol) and osmium tetroxide (2.5% wt in t-BuOH, 23.4 mL 2.3 mmol) successively. The resulting mixture was warmed to room temperature and stirred for 4 hours. After that, the reaction mixture quenched with water and extracted with ethyl acetate (2×500 mL). The combined organic phase was washed with 2% sodium thiosulfate solution (200 mL), brine (200 mL), dried over anhydrous sodium sulfate and concentrated in vacuo. The obtained crude product was further purified by column chromatography (60-120 mesh, 80% ethyl acetate in petroleum ether) to get compound XII as an off white solid. Yield: 7.35 g, 72.84%. ¹H-NMR (400 MHz, DMSO-d₆): δ 9.83 (s, 1H), 7.90-7.88 (d, 1H, J=8.0 Hz), 7.75-7.71 (m, 1H, J=8.4), 7.21-7.16 (t, 1H, J=9.2 Hz) 6.57-6.55 (d, 1H, J=9.2 Hz), 4.33-4.32 (d, 2H, J=2.8 Hz), 3.52 (s, 3H).

Synthesis of 3-(7-Fluoro-1-methyl-2-oxo-1,2-dihydroquinolin-8-yl)propanal, XIII

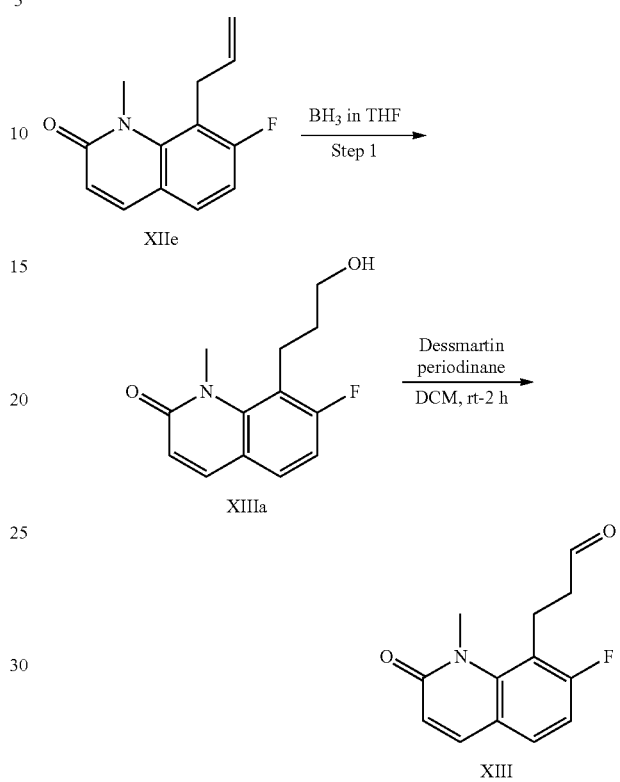

Step 1: 7-Fluoro-8-(3-hydroxypropyl)-1-methylquinolin-2(1H)-one (XIIIa)

To a stirred solution of compound XIIe (2.7 g, 12.442 mmol) in dry THF (40 mL) at 0° C. under nitrogen atmosphere was added BH₃. THF complex (24.8 mL, 24.887 mmol) in dropwise, [effervescences was observed during the reaction]. The resulting mixture was warmed to room temperature and stirred for 1 hour. After that, the reaction mixture was diluted with ethyl acetate (100 mL) and quenched with saturated aqueous NH₄Cl solution (50 mL). The two layers were separated. The organic layer was washed with brine (100 mL), dried over anhydrous sodium sulphate and concentrated in vacuo. The obtained crude was further purified by column chromatography using silica gel (230-400 mesh) by eluting with 75-100% ethyl acetate in petroleum ether to get compound 7 as an off-white solid. Yield: 1.5 g, 51.36%. LC-MS Calc. for C₁₃H₁₄FNO₂ 235.26; Obs.: 236.1 [M⁺+H]; ¹H NMR (400 MHz, DMSO-d₆) δ7.85 (d, J=9.39 Hz, 1H), 7.62 (t, J=10.92 Hz, 1H), 7.12 (t, J=9.39 Hz, 1H), 6.54 (d, J=9.36 Hz, 1H), 4.62-4.58 (m, 1H), 3.70 (s, 3H), 3.50-3.44 (m, 2H), 2.98-3.04 (m, 2H), 1.75-1.70 (m, 2H).

Step 2: 3-(7-Fluoro-1-methyl-2-oxo-1,2-dihydroquinolin-8-yl) propanal (XIII)

To a stirred solution of compound XIIIa (2.0 g, 8.510 mmol) dry dichloromethane (40 mL) at 0° C. under nitrogen atmosphere was added dess martin periodinane (5.41 g, 12.765 mmol). The resulting mixture was warmed to room temperature and stirred for 2 hours. After that, the reaction mixture was diluted with dichloromethane (50 mL), washed with 10% aqueous NaHCO$_3$ solution brine (50 mL), dried over anhydrous Na$_2$SO$_4$ and concentrated in vacuo. The obtained crude product was further purified by silica gel (230-400 mesh) by eluting with 40-50% ethyl acetate in petroleum ether to get compound XIII as an off-white solid. Yield: 1.5 g, 75.76%. LC-MS Calc. for C$_{13}$H$_{12}$FNO$_2$ 233.24; Obs. 234.2 [M$^+$+H].

Synthesis of 2-(7-fluoro-1,4-dimethyl-2-oxo-1,2-dihydroquinolin-8-yl)acetaldehyde, XIV

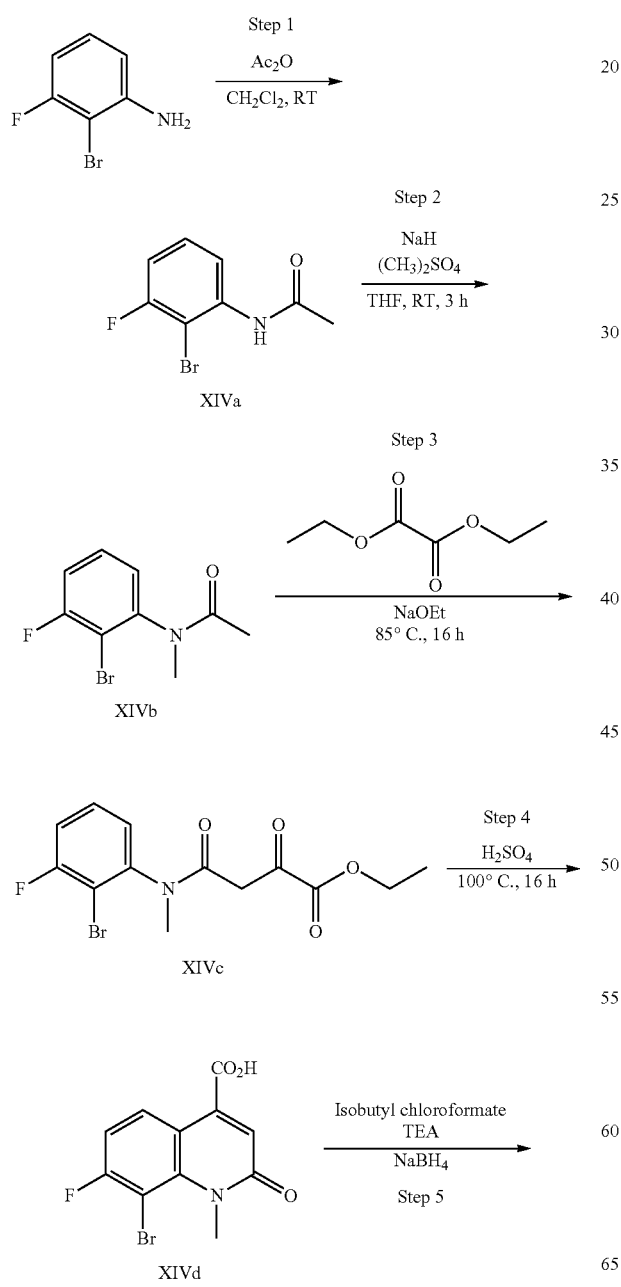

Step 1: N-(2-Bromo-3-fluorophenyl) acetamide (XIVa)

To a stirred solution of 2-bromo-3-fluoro aniline (25.0 g, 131.57 mmol) in dichloromethane (500 mL) at 0° C. under nitrogen was added acetic anhydride (18.65 mL, 197.36 mmol). The resulting mixture was warmed to room temperature and stirred for 16 hours. After that, the reaction mixture was diluted water and extracted with dichloromethane (2×500 mL). The combined organic phase was washed with brine, dried over anhydrous Na$_2$SO$_4$ and concentrated in vacuo to get compound XIVa (crude), which was taken as such for the next step without further purification. Yield: 25 g, 81.91%. LC-MS Calc. for $C_8H_7BrFNO$, 232.05; Obs.; 232.0 [M+]; $^1$H-NMR (300 MHz, DMSO-$d_6$): δ 9.57 (s, 1H), 7.49-7.34 (m, 2H), 7.20-7.14 (m, 1H), 2.09 (s, 3H).

Step 2: N-(2-Bromo-3-fluorophenyl)-N-methylacetamide (XIVb)

To a stirred solution of compound XIVa (25.0 g, 107.73 mmol) in dry THF (500 mL) under nitrogen atmosphere was added sodium hydride (60% in mineral oil, 5.38 g, and 134.66 mmol) and stirred for 30 minutes. Then dimethyl sulphate (13.79 mL, 145.44 mmol) was added to the reaction mixture at 0° C. The resulting mixture was warmed to room temperature and stirred at room temperature for 3 hours. After that, the reaction mixture was diluted with water and extracted with ethyl acetate (2×500 mL). The combined organic phase was washed with brine, dried over sodium sulfate and concentrated in vacuo to get compound XIVb as a white solid, which was used as such for the next step without further purification. Yield: 20 g, 75.47%. LC-MS Calc. for $C_9H_9BrFNO$ 246.08; Obs.: 248.0; [M++2H]; $^1$H NMR (300 MHz, DMSO-$d_6$): δ 7.58-7.32 (m, 3H), 3.05 (s, 3H), 1.67 (s, 3H).

Step 3: Ethyl 4-((2-bromo-3-fluorophenyl)(methyl) amino)-2,4-dioxobutanoate (XIVc)

To a stirred solution of compound XIVb (20.0 g, 81.95 mmol) in sodium ethoxide (20% in ethanol, 55 mL, 163.90 mmol) at room temperature under nitrogen atmosphere was added diethyl oxalate (47.89 g, 327.81 mmol). The resulting mixture was then heated at 80° C. and stirred for 16 hours. After that, the reaction mixture was completely evaporated under reduced pressure to get crude compound, which was further purified by column chromatography silica gel (230-400 mesh, 40% EtOAc in Petroleum ether) to get compound XIVc as a colorless oil. Yield: 15.0 g, 53.32%. LC-MS Calc. for $C_{13}H_3BrFNO_4$ 346.15; Obs.: 347.0 [M++H]; $^1$H NMR (400 MHz, DMSO-$d_6$): δ 7.63-7.48 (m, 3H), 5.37 (s, 1H), 4.18-4.13 (m, 2H), 3.22 (s, 3H), 1.30-1.15 (m, 3H).

Step 4: 8-Bromo-7-fluoro-1-methyl-2-oxo-1,2-dihydroquinoline-4-carboxylic acid (XIVd)

A solution of compound XIVc (23.0 g, 66.44 mmol) in Con $H_2SO_4$ (230 mL) was heated to 90° C. and stirred for 16 hours. After that, the reaction mixture was quenched with ice cold water and extracted with ethyl acetate (2×500 mL), washed with water, brine, dried over sodium sulfate and concentrated in vacuo. The obtained crude product was further triturated with diethyl ether, filtered and dried to get compound XIVd as a white solid, which was used as such for the next step without further purification. Yield: 15 g, 75.26%. LC-MS Calc. for $C_{11}H_7BrFNO_3$ 300.08; Obs.: 300.0; [M+]; $^1$H NMR (400 MHz, DMSO-$d_6$): δ 14.22 (s, br, 1H), 8.25-8.22 (m, 1H), 7.40-7.35 (m, 1H), 6.95 (s, 1H), 3.81 (s, 3H).

Step 5: 8-Bromo-7-fluoro-4-(hydroxymethyl)-1-methylquinolin-2(1H)-one (XIVe)

To a stirred solution of compound XIVd (12.0 g, 40.00 mmol) in THF (120 mL) at 0° C. under nitrogen atmosphere were added triethylamine (7.23 mL, 52.00 mmol) and isobuyl chloroformate (6.55 g, 48 mmol) successively and stirred for 1 hour. Then NaBH$_4$ (3.80 g, 100.00 mmol) in portions and methanol (10 mL) were added to the reaction mixture and continued to stir for 10 minutes. After that, the reaction mixture was diluted with water and extracted with ethyl acetate (2×500 mL). The combined organic phase was washed with brine, dried over sodium sulfate and concentrated in vacuo. The obtained crude product was purified by column chromatography silica gel (230-400 mesh, 40% EtOAc in petroleum ether) to get compound XIVe as a white solid. Yield: 6.5 g, 56.82%. LC-MS Calc. for $C_{11}H_9BrFNO_2$, 286.10; Obs.: 288.0 [M++2H]; $^1$H NMR (400 MHz, DMSO-$d_6$): δ 7.82-7.78 (m, 1H), 7.34-7.30 (m, 1H), 6.68 (s, 1H), 5.61-5.58 (m, 1H), 4.74-4.72 (m, 2H), 3.80 (s, 3H).

Step 6: 8-Bromo-4-(chloromethyl)-7-fluoro-1-methylquinolin-2(1H)-one (XIVf)

To a stirred solution of compound XIVe (3.0 g, 10.48 mmol) in dichloromethane (60 mL) at 0° C. under nitrogen atmosphere was added thionyl chloride (2.34 mL, 31.46 mmol) in dropwise. The resulting mixture was then warmed to room temperature and stirred for 5 hours. After that, the reaction mixture was quenched with 10% aqueous NaHCO$_3$ solution and extracted with dichloromethane (2×100 mL) The combined organic extract was washed with brine, dried over sodium sulfate and concentrated in vacuo. The obtained crude product was further purified by column chromatography using silica gel (230-400 mesh) eluting with 20% EtOAc in petroleum ether) to get compound XIVf as an off-white solid. Yield: 1.5 g, 47.16%. LC-MS Calc. for $C_{11}H_8BrClFNO$, 304.54; Obs.: 306.0 [M++2H]; $^1$H-NMR (300 MHz, DMSO-$d_6$): δ 7.98-7.93 (m, 1H), 7.44-7.39 (m, 1H), 6.87 (s, 1H), 5.04 (s, 2H), 3.81 (s, 3H).

Step 7: 8-Bromo-7-fluoro-1,4-dimethylquinolin-2(1H)-one (XIVg)

To a stirred solution of compound XIVf (1.5 g, 4.93 mmol) in DMF (30 mL) at 0° C. under nitrogen atmosphere was added NaBH4 (93 mg, 2.46 mmol). The resulting mixture was warmed to room temperature and stirred for 3 hours. After that, the reaction mixture was cooled to 0° C., quenched with water (60 mL) and extracted with ethyl acetate (2×100 mL). The combined organic phase was washed with brine, dried over sodium sulfate and concentrated in vacuo. The obtained crude product was further purified by column chromatography using silica gel (230-400 mesh) 20% ethyl acetate in petroleum ether) to get compound XIVg as an off-white solid. Yield: 0.7 g, 53.84%. LC-MS Calc. for $C_{11}H_9BrFNO$, 270.10; Obs.: 272.0 [M++2H]; $^1$H NMR (400 MHz, DMSO-$d_6$): δ 7.83 (m, 1H), 7.31 (m, 1H), 6.55 (s, 1H), 3.78 (s, 3H), 2.40 (s, 3H).

Step 8: 8-Allyl-7-fluoro-1,4-dimethylquinolin-2(1H)-one (XIVh)

To a stirred solution of compound XIVg (0.7 g, 2.59 mmol) in DMF (15 mL) at room temperature was added allyltributyltin (1.02 g, 3.11 mmol). The resulting mixture was degassed with a stream of nitrogen for 30 minutes. Then tetrakis(triphenylphosphine)palladium(0) (0.149 g, 0.12 mmol) was added to reaction mixture at room temperature. The resulting mixture was then heated to 100° C. and stirred for 16 hours. After that, the reaction mixture was cooled to 0° C., diluted with water (40 mL) and extracted with ethyl acetate (2×100 mL). The combined organic phase was washed with brine, dried over sodium sulfate and concentrated in vacuo. The obtained crude product was further purified by column chromatography using silica gel (230-400 mesh) eluting with 25% ethyl acetate in petroleum ether to get compound XIVh as a pale brown solid. Yield: 0.4 g, 66.66%. LC-MS Calc. for $C_{14}H_{14}FNO$, 231.27; Obs.: 232.1 $[M^++H]$.

Step 9: 2-(7-Fluoro-1,4-dimethyl-2-oxo-1,2-dihydroquinolin-8-yl)acetaldehyde (XIV)

To a stirred solution of compound XIVh (0.2 g, 0.865 mmol) in a mixture of THF/$H_2O$ (3 mL, 2:1) at 0° C. under nitrogen atmosphere were added sodium metaperiodate (0.55 g 2.59 mmol) and osmium tetroxide (2.5% in t-BuOH, 0.45 mL, 0.043 mmol) successively. The resulting mixture was warmed to room temperature and stirred for 8 hours. After that, the reaction mixture was diluted with water and extracted with ethyl acetate (2×30 mL). The combined organic phase was washed with sodium thiosulfate, brine, dried over sodium sulfate and concentrated in vacuo. The obtained crude product was further purified by column chromatography silica gel (230-400 mesh) eluting with 40% ethyl acetate in petroleum ether) to get compound XIV as a pale brown solid. Yield: 0.08 g, 39.80%. LC-MS Calc. for $C_{13}H_{12}FNO_2$, 233.24; Obs.: 234.1 $[M^++H]$; $^1H$ NMR (400 MHz, DMSO-$d_6$): δ 9.83 (s, 1H), 7.80-7.77 (m, 1H), 7.23-7.18 (m, 1H), 6.50 (s, 1H), 4.31 (d, 2H), 3.48 (s, 3H), 2.42 (s, 3H).

Synthesis of 2-(1-Ethyl-7-fluoro-2-oxo-1,2-dihydroquinolin-8-yl)acetaldehyde, XV

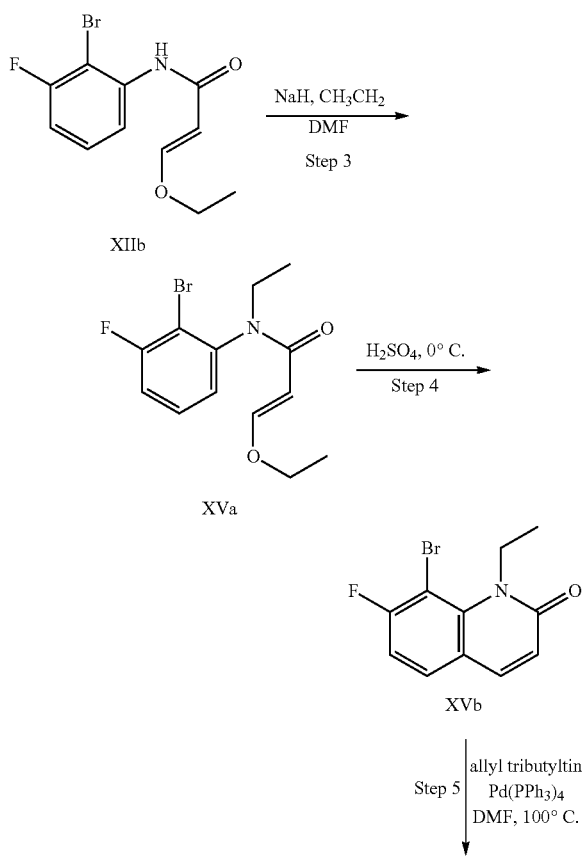

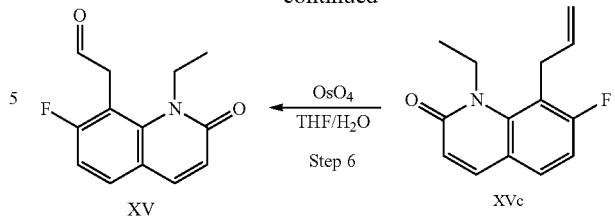

Step 1: (E)-N-(2-bromo-3-fluorophenyl)-3-ethoxy-N-ethylacrylamide (XVa)

To a stirred solution of compound XIIb (20.0 g, 69.65 mmol) in DMF (200 mL) at 0° C. under nitrogen atmosphere was added NaH (60%) (3.3 g, 83.27 mmol) in portions over a period of 30 minutes and stirred for 30 minutes. Then ethyl iodide (8.3 mL, 104 mmol) was added in dropwise at 0° C. The resulting mixture was warmed to room temperature and stirred for 1 hour. After that, the reaction mixture was cooled to 0° C., quenched with ice cold water (500 mL) and extracted with ethyl acetate (2×400 mL). The combined organic phase was washed with brine (500 mL), dried over $Na_2SO_4$ and concentrated under in vacuo. The obtained crude was further purified by column chromatography using silica gel (60-120 mesh) eluting with 30-40% ethyl acetate in petroleum ether to get compound XVa. Yield: 16 g, 72.92%. LC-MS Calc. for $C_{13}H_{15}BrFNO_2$, 316.17; Obs.; 317.2 $[M^++H]$; $^1H$ NMR (400 MHz, DMSO-$d_6$): δ 7.41-7.54 (m, 4H), 7.26 (d, J=7.60 Hz, 1H), 4.73 (d, J=11.60 Hz, 1H), 3.90-3.95 (m, 1H), 3.71-3.77 (m, 2H), 1.12 (t, J=7.20 Hz, 3H), 1.02 (t, J=7.20 Hz, 3H).

Step 2: 8-Bromo-1-ethyl-7-fluoroquinolin-2(1H)-one (XVb)

A solution of compound XVa (16 g, 50.60 mmol) in 1,4-dioxane (30 mL) was added to the precooled solution of Conc. $H_2SO_4$ (80 mL, 5 v) at 0° C. under nitrogen atmosphere. The resulting mixture was warmed to room temperature and stirred for 2 days. After that, the reaction mixture was cooled to 0° C., quenched with ice cold water (500 mL) and extracted with ethyl acetate (2×500 mL). The combined organic extract was washed with water, brine, dried over $Na_2SO_4$ and concentrated in vacuo. The obtained crude product was purified by column chromatography using silica gel (60-120 mesh) eluting with 50% of ethyl acetate in petroleum ether to get compound XVb. Yield: 5.5 g, 40.26%. LC-MS Calc. for $C_{11}H_9BrFNO$, 270.1; Obs.; 272.0; $[M+2]$; $^1H$ NMR (400 MHz, DMSO-$d_6$): δ 7.54-7.93 (m, 2H), 7.27-7.35 (m, 1H), 6.60-6.64 (m, 1H), 4.54-4.60 (m, 2H), 1.41-1.36 (m, 3H).

Step 3: 8-Allyl-1-ethyl-7-fluoroquinolin-2(1H)-one (XVc)

To a stirred solution of compound XVb (3 g, 11.10 mmol) in DMF (60 mL) was added tributylallyltin (4.13 mL, 13.32 mmol) at room temperature. The resulting mixture was degassed with a stream of nitrogen for 10 minutes. Then tetrakis(triphenylphosphine)palladium (0) (0.63 g, 0.555 mmol) was added at room temperature. The resulting mixture was then heated to 100° C. and stirred for 16 hours. After that, the reaction mixture was cooled room temperature and concentrated in vacuo. The obtained crude product was further purified by column chromatography using silica gel (60-120 mesh) eluting with 20% ethyl acetate in petroleum ether to get compound XVc as a pale yellow liquid. Yield: 1.7 g, 66.40%. LC-MS Calc. for $C_{14}H_{14}FNO$, 231.2; Obs.: 232.1 [M$^+$+H]; $^1$H NMR (400 MHz, DMSO-d$_6$): δ 7.88 (d, J=9.60 Hz, 1H), 7.71 (t, J=7.60 Hz, 1H), 7.18 (t, J=8.80 Hz, 1H), 6.43 (t, J=131.60 Hz, 1H), 6.13-6.21 (m, 1H), 5.17 (d, J=10.40 Hz, 1H), 4.85 (d, J=17.20 Hz, 1H), 4.14-4.19 (m, 2H), 3.68 (s, 2H), 1.33-1.30 (m, 3H).

Step 4: 2-(1-Ethyl-7-fluoro-2-oxo-1,2-dihydroquinolin-8-yl)acetaldehyde (XV)

To a stirred solution of compound XVc (0.08 g, 0.34 mmol) in a mixture of THF/water (60 mL, 1:1) at 0° C. under nitrogen atmosphere were added sodium meta periodate (0.22 g 1.03 mmol) and osmium tetroxide (2.5% wt in t-BuOH, 0.68 mL 0.017 mmol) successively. The resulting mixture was warmed to room temperature and stirred for 3 hours. After that, the reaction mixture quenched with water and extracted with ethyl acetate (2×50 mL). The combined organic phase was washed with 2% sodium thiosulfate solution (50 mL), brine (50 mL), dried over anhydrous sodium sulfate and concentrated in vacuo. The obtained crude product was further purified by column chromatography using silica gel (60-120 mesh) eluting with 50% ethyl acetate in petroleum ether to get compound XV as an off white solid. Yield: 0.4 g, 80.06%. $^1$H NMR (400 MHz, DMSO-d$_6$): δ 9.85 (s, 1H), 7.99-7.97 (m, 1H), 7.75 (t, J=6.44 Hz, 1H), 7.19-7.27 (m, 1H), 6.55-6.66 (m, 1H), 4.26 (s, 2H), 4.01 (d, J=6.60 Hz, 2H), 1.29 (d, J=2.24 Hz, 3H).

Synthesis of 2-(1-(2-((Tert-butyldimethylsilyl)oxy)ethyl)-7-fluoro-2-oxo-1,2-dihydroquinolin-8-yl)acetaldehyde, XVI

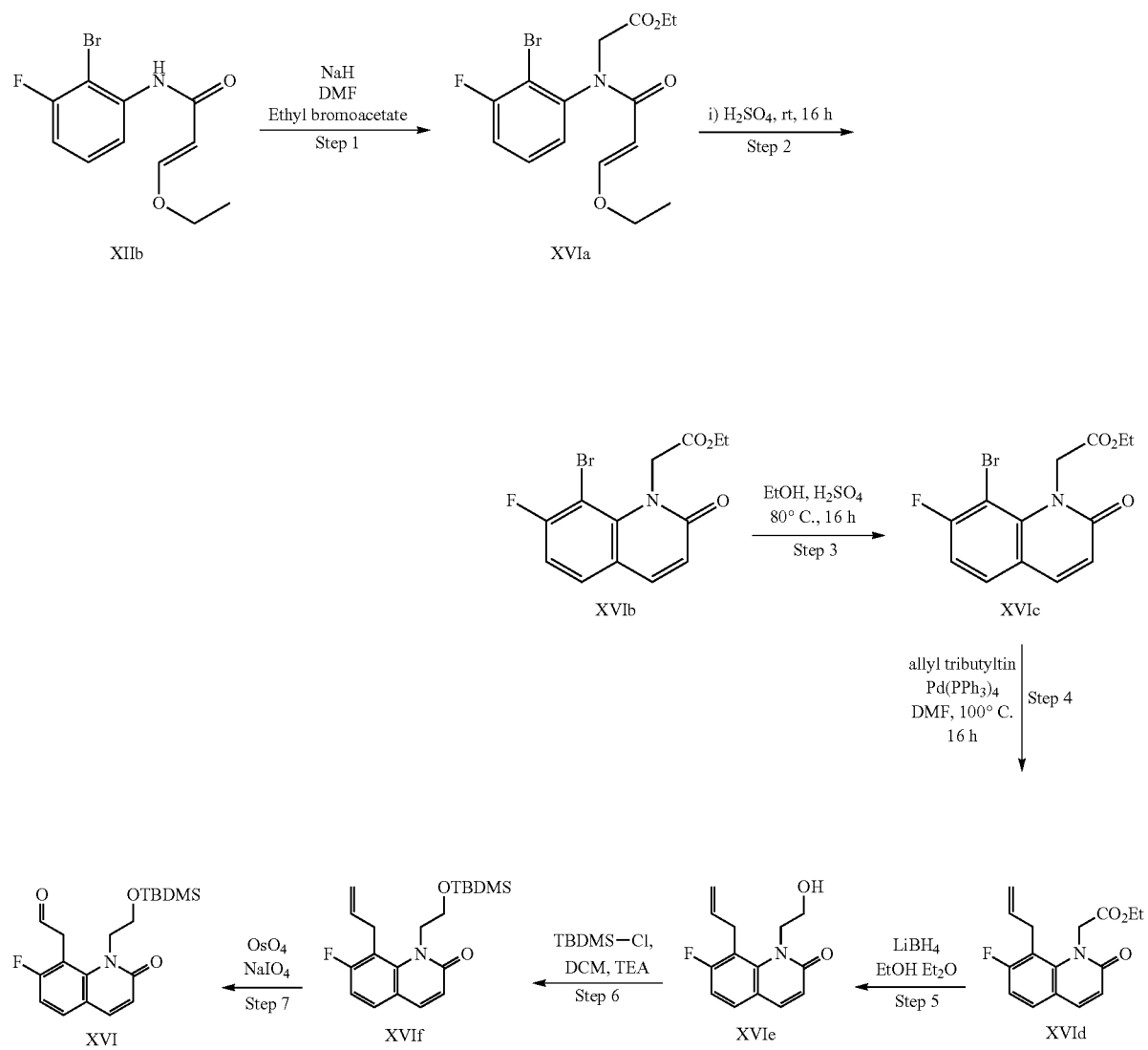

Step 1: Ethyl (E)-N-(2-bromo-3-fluorophenyl)-N-(3-ethoxyacryloyl)glycinate (XVIa)

To a stirred solution of compound XIIb (115.0 g, 399.30 mmol) in DMF (1.15 L) at 0° C. under nitrogen atmosphere was added NaH (60%) (23.9 g 598.95 mmol) in portions over a period of 30 min and stirred for 30 minutes. Then ethyl bromoacetate (43.8 mL, 598.95 mmol) was added in dropwise at 0° C. The resulting mixture was warmed to room temperature and stirred for 1 hour. Upon completion, the reaction mixture was cooled to 0° C., quenched with ice cold water (3 L) and extracted with ethyl acetate (2×2 L). The combined organic phase was washed with brine (1×2 L), dried over $Na_2SO_4$ and concentrated under in vacuo. The crude was further purified by column chromatography using silica gel (60-120 mesh) eluting with 30% of ethyl acetate in petroleum ether to get compound XVIa. Yield: 121 g, 81.01%. LC-MS Calc. for $C_{15}H_{18}BrFNO_4$, 374.21; Obs.: 375.1 [M+H]; $^1$H NMR (400 MHz, $CDCl_3$): δ7.58 (d, J=11.92 Hz, 1H), 7.47 (d, J=7.92 Hz, 1H), 7.37-7.31 (m, 2H), 7.18-7.14 (m, 1H), 5.04 (d, J=17.28 Hz, 1H), 4.92 (d, J=11.92 Hz, 1H), 4.25-4.14 (m, 2H), 3.81-3.76 (m, 2H), 3.64 (d, J=17.28 Hz, 1H), 1.31-1.24 (m, 6H).

Step 2: 2-(8-Bromo-7-fluoro-2-oxoquinolin-1(2H)-yl)acetic acid (XVIb)

A compound XVIa (50 g, 267.38 mmol) was dissolved in Conc. $H_2SO_4$ (350 mL, 7 v) at 0° C. under nitrogen atmosphere. The resulting mixture was warmed to room temperature and stirred for 16 hours. Upon completion, the reaction mixture was cooled to 0° C., quenched with ice cold water (2 L) and extracted with ethyl acetate (2×1 L). The combined organic extract was washed with water, brine, dried over $Na_2SO_4$ and concentrated in vacuo. The obtained crude product was further triturated with diethyl ether to afford compound XVIb as an orange solid. Yield: 19.7 g, 49.13%. LC-MS Calc. for $C_{11}H_7BrFNO_3$; 300.08; Obs.: 301.9 [M$^+$+H]; $^1$H NMR (400 MHz, DMSO-$d_6$): δ 12.96 (s, 1H), 8.00 (d, J=9.48 Hz, 1H), 7.89-7.85 (m, 1H), 7.48-7.34 (m, 1H), 6.69 (d, J=9.44 Hz, 1H), 5.26 (s, 2H)

Step 3: Ethyl 2-(8-bromo-7-fluoro-2-oxoquinolin-1(2H)-yl)acetate (XVIc)

To a stirred solution of compound XVIb (23.5 g, 78.33 mmol) in ethanol (450 mL) was added Con $H_2SO_4$ (23.5 mL) at 0° C. under nitrogen atmosphere. The resulting mixture was heated at 80° C. for 16 hours. After that, the reaction mixture was quenched with ice water (400 mL) and extracted with EtOAc (2×500 mL), dried over sodium sulphate concentrated in vacuo. The obtained crude product was purified by column chromatography silica gel (230-400 mesh, 20% ethyl acetate in petroleum ether) to get compound XVIc as a white solid. Yield: 17.5 g, 68.11%. LC-MS Calc. for $C_{13}H_{11}BrFNO_3$; 328.14; Obs.: 330.0 [M$^+$+2]; $^1$H NMR (400 MHz, $CDCl_3$): δ7.65 (d, J=9.48 Hz, 1H), 7.54-7.50 (m, 1H), 7.10-7.06 (m, 1H), 6.72 (d, J=9.48 Hz, 1H), 5.49 (s, 2H), 4.34-4.29 (m, 2H), 1.33 (t, J=7.16 Hz, 3H).

Step 4: Ethyl 2-(8-allyl-7-fluoro-2-oxoquinolin-1(2H)-yl)acetate (XVId)

To a stirred solution of compound XVIc (17.5 g, 53.35 mmol) in DMF (200 mL) at room temperature was added allyltributyltin (26.48 mL, 80.03 mmol). The resulting mixture was degassed with a stream of nitrogen for 30 minutes. Then tetrakis (triphenylphosphine)palladium(0) (3.08 g, 2.66 mmol) was added to reaction mixture at room temperature. The resulting mixture was then heated to 100° C. and stirred for 16 hours. After that, the reaction mixture was cooled to 0° C., diluted with water (200 mL) and extracted with ethyl acetate (2×500 mL). The combined organic phase was washed with brine, dried over sodium sulphate and concentrated in vacuo. The obtained crude product was purified by column chromatography silica gel (230-400 mesh, 30% ethyl acetate in petroleum ether) to get compound XVId as a pale yellow liquid. Yield: 15 g, 97.27%. LC-MS Calc. for $C_{16}H_{16}BrFNO_3$; 289.31; Obs.: 290.1[M$^+$+H]; $^1$H NMR (400 MHz, $CDCl_3$): δ7.66 (d, J=9.44 Hz, 1H), 7.48-7.45 (m, 1H), 7.04-7.02 (m, 1H), 6.65 (d, J=9.44 Hz, 1H), 6.22-6.15 (m, 1H), 5.29 (d, J=10.32 Hz, 1H), 4.99 (d, J=0.88 Hz, 1H), 0.96 (s, 2H), 4.35-4.29 (m, 2H), 3.57 (d, J=1.88 Hz, 2H), 1.33 (t, J=7.08 Hz, 3H).

Step 5: 8-Allyl-7-fluoro-1-(2-hydroxyethyl)quinolin-2(1H)-one (XVIe)

To a stirred solution of compound XVId (7.3 g, 25.25 mmol) in ethanol (75 mL) and diethyl ether (33 mL) at room temperature under nitrogen atmosphere was added a solution of $LiBH_4$ in THF (2M) (75 mL, 151.55 mmol) (22 mg, 0.56 mmol) and allowed to stir for 30 minutes at room temperature. After that, the reaction mixture was cooled to 0° C., quenched with $NH_4Cl$ solution and extracted with ethyl acetate (2×200 mL). The combined organic phase was washed with brine, dried over sodium sulphate and concentrated in vacuo. The obtained crude product was further purified by column chromatography silica gel (230-400 mesh, 40% ethyl acetate in petroleum ether) to get compound XVIe as an off white solid. Yield: 3.5 g, 56.17%. LC-MS Calc. for $C_{14}H_{14}FNO_2$, 247.27; Obs.: 248.1[M$^+$+H]; $^1$H NMR (400 MHz, DMSO-$d_6$): δ7.89 (d, J=9.40 Hz, 1H), 7.73-7.69 (m, 1H), 7.21-7.15 (m, 1H), 6.55 (d, J=9.36 Hz, 1H), 6.19-6.10 (m, 1H), 5.14 (d, J=16.40 Hz, 1H), 4.98 (s, 1H), 4.85 (d, J=17.24 Hz, 1H), 4.26 (t, J=6.64 Hz, 2H), 3.80 (d, J=1.80 Hz, 2H), 3.71 (d, J=4.08 Hz, 2H), 3.35 (d, J=7.32 Hz, 1H).

Step 6: 8-Allyl-1-(2-((tert-butyldimethylsilyl)oxy)ethyl)-7-fluoroquinolin-2(1H)-one (XVIf)

To a stirred solution of compound XVIe (10 g, 40.44 mmol) in dichloromethane (200 mL) at 0° C. under nitrogen atmosphere were added imidazole (8.25 g, 121.32 mmol) and TBDMS chloride (12.2 g, 80.88 mmol) successively. The resulting mixture was warmed to room temperature and stirred for 30 minutes. After that, the reaction mixture was cooled to 0° C., diluted with water (200 mL) and extracted with ethyl acetate (2×500 mL). The combined organic phase was washed with brine, dried over sodium sulphate and concentrated in vacuo. The obtained crude product was further purified by column chromatography silica gel (230-400 mesh, 8% ethyl acetate in petroleum ether) to get compound XVIf as a colourless liquid. Yield: 13 g, 88.91%. LC-MS Calc. for $C_{20}H_{28}FNO_2Si$, 361.53; Obs.: 362.1 [M$^+$+H]; $^1$H NMR (400 MHz, DMSO-$d_6$): δ7.88 (d, J=9.60 Hz, 1H), 7.71-7.67 (m, 1H), 7.15 (t, J=8.80 Hz, 1H), 6.55 (d, J=9.20 Hz, 1H), 6.16-6.09 (m, 1H), 5.20-5.17 (m, 1H), 4.91 (d, J=17.20 Hz, 1H), 4.36 (t, J=6.00 Hz, 2H), 3.86 (t, J=6.00 Hz, 2H), 3.78 (d, J=2.00 Hz, 2H), 0.69 (s, 9H), 0.00 (s, 6H).

Step 7: 2-(1-(2-((Tert-butyldimethylsilyl)oxy)ethyl)-7-fluoro-2-oxo-1,2-dihydroquinolin-8-yl)acetaldehyde (XVI)

To a stirred solution of compound XVIf (13.0 g, 36.01 mmol) in a mixture of THF/$H_2O$ (1 L, 2:1) at 0° C. under nitrogen atmosphere were added sodium meta periodate (23.1 g 0.108 mmol) and osmium tetroxide (2.5% in t-BuOH, 18.3 mL 1.8 mmol) successively. The resulting mixture was warmed to room temperature and stirred for 6 hours. After that, the reaction mixture was diluted with water and extracted with ethyl acetate (2×400 mL). The combined organic phase was washed with sodium thiosulfate, brine, dried over sodium sulphate and concentrated in vacuo to get compound XVI as a pale yellow liquid, which was used as such for the next step without further purification. Yield: 10 g, crude. LC-MS Calc. for $C_{19}H_{26}FNO_3Si$, 363.56; Obs.: 364.1[M$^+$+H].

Synthesis of 2-(7-fluoro-1-(2-methoxyethyl)-2-oxo-1,2-dihydroquinolin-8-yl) acetaldehyde, XVII

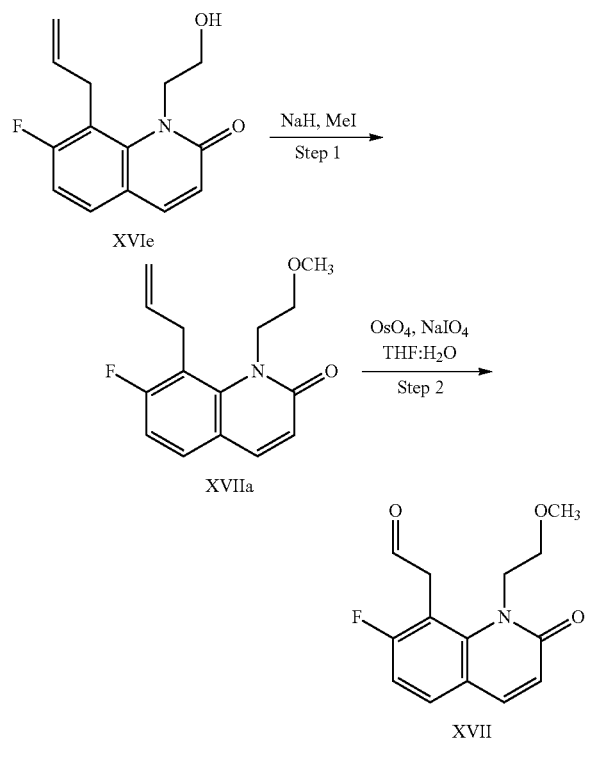

Step 1: 8-Allyl-7-fluoro-1-(2-methoxyethyl)quinolin-2(1H)-one (XVIIa)

To a stirred solution of compound XVIe (1 g, 4.04 mmol) in dry DMF (10 mL) at 0° C. under nitrogen atmosphere was added NaH (0.19 g, 4.85 mmol). The resulting mixture was stirred for 30 minutes at 0° C. and was added MeI (0.68 g, 4.85 mmol) in dropwise. The reaction mixture was warmed to room temperature and stirred for 2 hours.

The reaction mixture was then quenched with ice water and extracted with EtOAc (twice). The combined organic phase was washed with water, brined solution, dried over sodium sulphate and concentrated in vacuo. The obtained crude product was further purified by column chromatography on silica gel (230-400 mesh, 20% ethyl acetate in pet ether) to get XVIIa as an off-white solid. Yield: 0.65 g, 61.55%. LC-MS Calc. for $C_{15}H_{16}FNO_2$, 261.30; Obs: 262.1 [M+H]$^+$; $^1$H NMR (400 MHz, DMSO-d$_6$): δ7.89 (d, J=9.44 Hz, 1H), 7.72 (t, J=6.84 Hz, 1H), 7.19 (t, J=8.72 Hz, 1H), 6.55 (d, J=9.36 Hz, 1H), 6.17-6.10 (m, 1H), 5.18 (d, J=11.68 Hz, 1H), 4.88-4.84 (m, 1H), 4.36 (t, J=6.32 Hz, 2H), 3.74-3.73 (m, 2H), 3.64 (t, J=6.36 Hz, 2H), 3.20 (s, 3H).

Step 2: 2-(7-fluoro-1-(2-methoxyethyl)-2-oxo-1,2-dihydroquinolin-8-yl)acetaldehyde (XVII)

To a stirred solution of compound XVIIa (0.65 g, 2.49 mmol) in THF (40 mL) and water (40 mL) at 0° C. under nitrogen atmosphere were added sodium metaperiodate (1.59 g, 7.47 mmol) and osmium tetroxide (2.5% wt in tert-Butanol, 2.02 mL 0.19 mmol) successively. The resulting mixture was warmed to room temperature and stirred for 4 hours. After that, the reaction mixture was quenched with water and extracted with ethyl acetate (2×50 mL). The combined organic phase was washed with 2% sodium thiosulfate solution (20 mL), brine (20 mL), dried over sodium sulphate and concentrated in vacuo to get crude compound XVII, which was taken for the next step without further purification. Yield: 0.25 g (crude).

Synthesis of Ethyl 7-fluoro-1-methyl-2-oxo-8-(2-oxoethyl)-1,2-dihydroquinoline-4-carboxylate, XVII

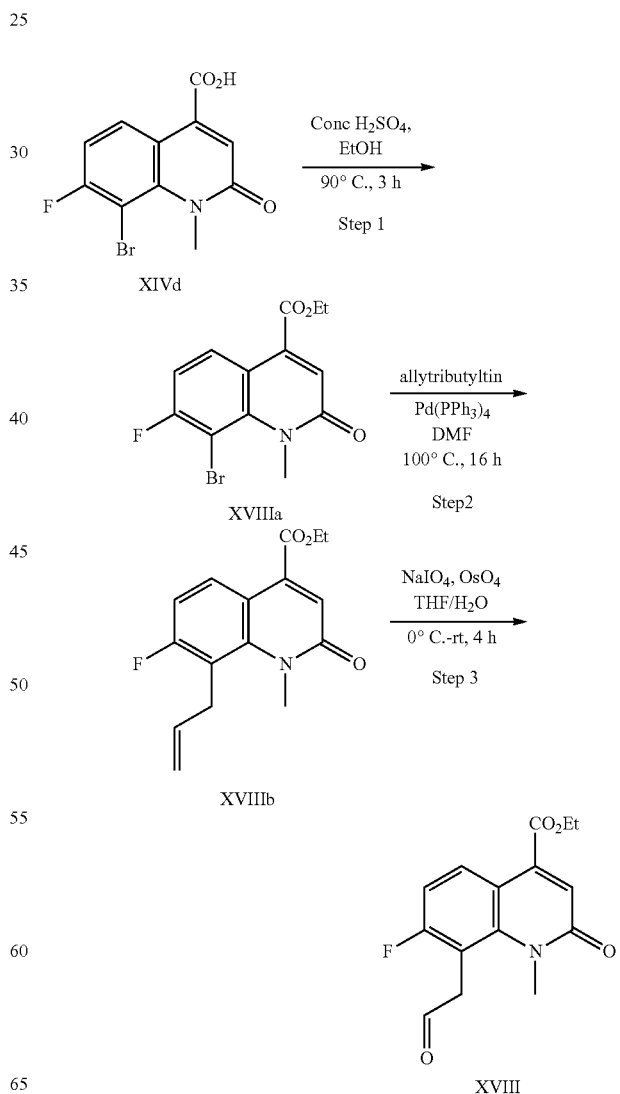

Step 1: Ethyl 8-bromo-7-fluoro-1-methyl-2-oxo-1,2-dihydroquinoline-4-carboxylate (XVIIa)

To a stirred solution of compound XIVd (3.0 g, 10.00 mmol) in ethanol (60 mL) was added Conc. $H_2SO_4$ (1 mL) at 0° C. under nitrogen atmosphere. The resulting mixture was heated at 90° C. and stirred for 3 hours. After that, the reaction mixture was quenched with ice water (50 mL) and extracted with ethyl acetate (2×100 mL), dried over sodium sulphate and concentrated in vacuo. The obtained crude product was further purified by column chromatography using silica gel (230-400 mesh) eluting with 30% ethyl acetate in petroleum ether to get compound XVIIa as a white solid. Yield: 2.0 g, 60.97%. LC-MS Calc. for $C_{13}H_{11}BrFNO_3$, 328.14; Obs.: 330.0 [M$^+$+2H]; $^1$H NMR (400 MHz, DMSO-d$_6$): δ 8.14-8.10 (m, 1H), 7.40-7.36 (m, 1H), 6.98 (s, 1H), 4.42-4.37 (m, 2H), 3.81 (s, 3H), 1.36-1.33 (m, 3H).

Step 2: Ethyl 8-bromo-7-fluoro-1-methyl-2-oxo-1,2-dihydroquinoline-4-carboxylate (XVIIb)

To a stirred solution of compound XVIIa (1.0 g, 3.04 mmol) in DMF (15 mL) at room temperature was added allyltributyltin (1.4 mL, 4.57 mmol). The resulting mixture was degassed with a stream of nitrogen for 30 minutes. Then tetrakis (triphenylphosphine)palladium(0) (0.176 g, 0.15 mmol) was added to reaction mixture at room temperature. The resulting mixture was then heated to 100° C. and stirred for 16 hours under nitrogen atmosphere. After that, the reaction mixture was cooled to 0° C., diluted with water (60 mL) and extracted with ethyl acetate (2×100 mL). The combined organic phase was washed with brine, dried over sodium sulphate and concentrated in vacuo. The obtained crude product was further purified by column chromatography using silica gel (230-400 mesh) eluting with 30% ethyl acetate in petroleum ether to get compound XVIIb as a brown solid. Yield: 0.7 g, 79.54%. LC-MS Calc. for $C_{16}H_{16}FNO_3$, 289.31; Obs.: 290.2; [M$^+$+H]; $^1$H NMR (400 MHz, DMSO-d$_6$): δ8.01-7.96 (m, 1H), 7.52-7.48 (m, 1H), 7.27-7.21 (m, 1H), 6.89 (s, 1H), 6.20-6.09 (m, 1H), 5.21-5.17 (m, 1H), 4.96-4.90 (m, 1H), 4.42-4.35 (m, 2H), 3.71-3.61 (m, 4H), 1.37-1.31 (m, 3H).

Step 3: Ethyl 7-fluoro-1-methyl-2-oxo-8-(2-oxoethyl)-1,2-dihydroquinoline-4-carboxylate (XVII)

To a stirred solution of compound XVIIb (0.5 g, 1.73 mmol) in a mixture of THF/H$_2$O (45 mL, 2:1) at 0° C. under nitrogen atmosphere were added sodium meta periodate (1.10 g 5.18 mmol) and osmium tetroxide (2.5% in t-BuOH, 0.88 mL, 0.08 mmol) successively. The resulting mixture was warmed to room temperature and stirred for 4 hours. After that, the reaction mixture was diluted with water and extracted with ethyl acetate (2×50 mL). The combined organic phase was washed with sodium thiosulfate, brine, dried over sodium sulfate and concentrated in vacuo. The obtained crude product was purified by column chromatography using silica gel (230-400 mesh) eluting with 60% ethyl acetate in petroleum ether to get compound XVII as an off-white solid. Yield: 0.3 g, 56.25%. LC-MS Calc. for $C_{15}H_{14}FNO_4$, 291.28; Obs.: 292.1 [M$^+$+H]; $^1$H NMR (400 MHz, DMSO-d$_6$): δ9.83 (s, 1H), 8.07-8.03 (m, 1H), 7.28-7.24 (m, 1H), 6.92 (s, 1H), 4.42-4.32 (m, 4H), 3.51 (s, 3H), 1.36-1.33 (m, 3H)

Synthesis of 2-(7-Fluoro-1-(2-(methylsulfonyl) ethyl)-2-oxo-1,2-dihydroquinolin-8-yl)acetaldehyde, XVIII

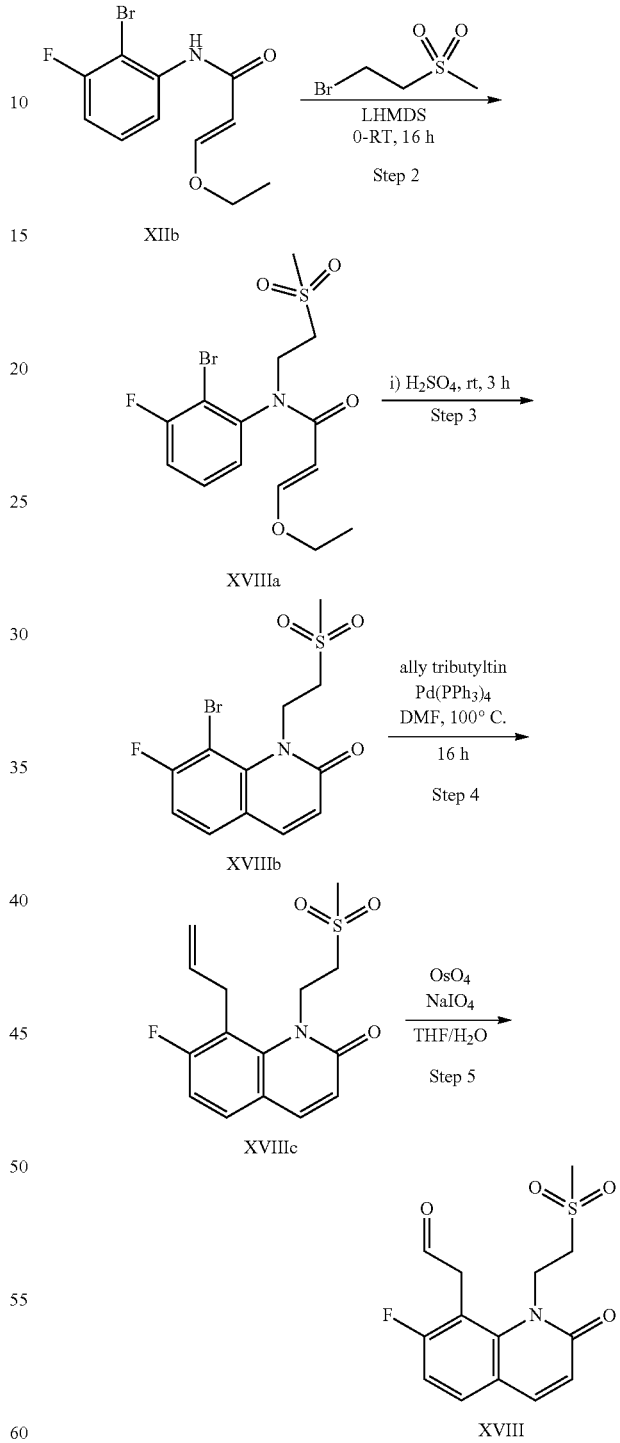

Step 1: (E)-N-(2-bromo-3-fluorophenyl)-3-ethoxy-N-(2-(methylsulfonyl)ethyl) acrylamide (XVIIIa)

To a stirred solution of compound XIIb (1.5 g, 5.208 mmol in dry THF (15 mL) at 0° C. under nitrogen atmosphere was added LiHMDS in THF (1M) (7.8 mL, 7.812 mmol). The resulting reaction mixture was warmed to room temperature and stirred for 16 hours. After that, the reaction mixture was cooled to 0° C., quenched with NH$_4$Cl solution and extracted with ethyl acetate (2×50 mL). The combined organic phase was washed with brine, dried over sodium sulphate and concentrated in vacuo. The obtained crude product was purified by column chromatography silica gel (230-400 mesh, 60% ethyl acetate in petroleum ether) to get compound XVIIIa as an off white solid. Yield: 0.95 g, 46.34%. LC-MS Calc. for C$_{15}$H$_{17}$BrFNO$_4$S: 394.36; Obs.: 397.0 [M$^+$+2]; $^1$H NMR (400 MHz, CDCl$_3$): δ7.58 (d, J=11.88 Hz, 1H), 7.41-7.37 (m, 1H), 7.24-7.16 (m, 2H), 4.86 (d, J=11.88 Hz, 1H), 4.41-4.36 (m, 1H), 3.84-3.77 (m, 3H), 3.41 (t, J=7.48 Hz, 2H), 3.05 (s, 3H), 1.25 (t, J=7.04 Hz, 3H).

Step 2: 8-Bromo-7-fluoro-1-(2-(methylsulfonyl)ethyl)quinolin-2(1H)-one (XVIIIb)

A solution of compound XVIIIa (0.95 g, 2.417 mmol) at 0° C. under nitrogen atmosphere was added Con H$_2$SO$_4$ (5 mL) in dropwise. The resulting mixture was warmed to room temperature and stirred for 3 hours. After that, the reaction mixture was quenched with ice cold water and extracted with ethyl acetate (2×100 mL), washed with water, brine, dried over sodium sulphate and concentrated in vacuo. The obtained crude product was purified by column chromatography silica gel (230-400 mesh, 20% ethyl acetate in petroleum ether) to get compound XVIIIb as an off white solid. Yield: 0.15 g, 18.07%. LC-MS Calc. for C$_{12}$H$_{11}$BrFNO$_3$; 348.19; Obs.: 348.0; $^1$H NMR (400 MHz, CDCl$_3$): δ 7.64 (d, J=9.60 Hz, 1H), 7.54-7.50 (m, 1H), 7.13-7.09 (m, 1H), 6.66 (d, J=9.60 Hz, 1H), 5.01-4.97 (m, 2H), 3.82 (t, J=7.60 Hz, 2H), 3.13 (s, 3H).

Step 3: 8-Allyl-7-fluoro-1-(2-(methylsulfonyl)ethyl)quinolin-2(1H)-one (XVIIIc)

To a stirred solution of compound XVIIIb (0.15 g, 0.431 mmol) in DMF (5 mL) at room temperature was added allyltributyltin (0.17 g, 0.512 mmol). The resulting mixture was degassed with a stream of nitrogen for 30 minutes. Then tetrakis (triphenylphosphine)palladium (0) (0.05 g, 0.043 mmol) was added to the reaction mixture at room temperature. The resulting mixture was then heated to 100° C. and stirred for 16 hours. After that, the reaction mixture was cooled to 0° C., diluted with water (10 mL) and extracted with ethyl acetate (2×25 mL). The combined organic phase was washed with brine, dried over sodium sulphate and concentrated in vacuo. The obtained crude product was further purified by column chromatography silica gel (230-400 mesh, 50% ethyl acetate in petroleum ether) to get compound XVIIIc as an off white solid. Yield: 0.1 g, 75.18%. LC-MS Calc. for C$_{15}$H$_{16}$BrFNO$_3$S; 309.36; Obs.: 310 [M$^+$+H];

Step 4: 2-(7-Fluoro-1-(2-(methylsulfonyl)ethyl)-2-oxo-1,2-dihydroquinolin-8-yl)acetaldehyde (XVIII)

To a stirred solution of compound XVIIIc (0.1 g, 0.323 mmol) in a mixture of THF/H$_2$O (6 mL, 2:1) at 0° C. under nitrogen atmosphere were added sodium meta periodate (0.2 g, 0.970 mmol) and osmium tetroxide (2.5% in t-BuOH, 0.3 mL 0.032 mmol) successively. The resulting mixture was warmed to room temperature and stirred for 4 hours. After that, the reaction mixture was diluted with water and extracted with ethyl acetate (2×100 mL). The combined organic phase was washed with sodium thiosulfate, brine, dried over sodium sulphate and concentrated in vacuo to get the crude compound XVIII as an off white solid, which was used for the next step without any further purification. Yield: 0.07 g, crude. LC-MS Calc. for C$_{14}$H$_{14}$FNO$_4$S, 311.33; Obs.: 312.1[M$^+$+H].

Synthesis of 2-(7-Fluoro-4-(methoxymethyl)-1-methyl-2-oxo-1,2-dihydroquinolin-8-yl)acetaldehyde, XIX

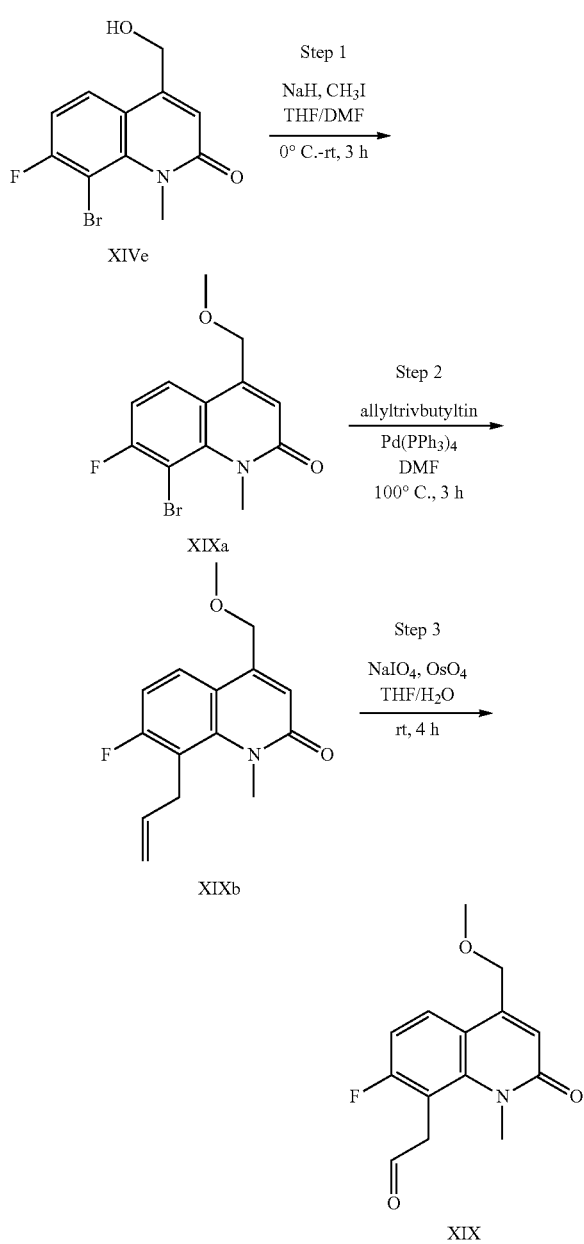

Step 1: 8-Bromo-7-fluoro-4-(methoxymethyl)-1-methylquinolin-2(1H)-one (XIXa)

To a stirred solution of compound XIVe (0.4 g, 1.39 mmol) in a mixture of THF/DMF (8 mL, 3:1) at 0° C. under nitrogen atmosphere was added NaH (84 mg, 2.09 mmol). The resulting mixture was stirred for 30 minutes at 0° C. and was added MeI (0.1 mL, 2.09 mmol) in dropwise. The resulting mixture was warmed to room temperature and stirred for 3 hours. After that, the reaction mixture was quenched with ice water and extracted with ethyl acetate (2×30 mL). The combined organic phase was washed with water, brined solution, dried over sodium sulphate and concentrated in vacuo. The obtained crude product was further purified by column chromatography on silica gel (230-400 mesh) eluting with 20% ethyl acetate in petroleum ether) to get compound XIXa as an off-white solid. Yield: 0.35 g, 83.53%. LC-MS Calc. for $C_{12}H_{11}BrFNO_2$ 300.13; Obs.: 302.0; [M$^+$+2H]; $^1$H NMR (400 MHz, DMSO-d$_6$): δ 7.83-7.79 (m, 1H), 7.36-7.32 (m, 1H), 6.65 (s, 1H), 4.67 (s, 2H), 3.81 (s, 3H), 3.41 (s, 3H).

Step 2: 8-Allyl-7-fluoro-4-(methoxymethyl)-1-methylquinolin-2(1H)-one (XIXb)

To a stirred solution of compound XIXa (0.4 g, 1.33 mmol) in DMF (8 mL) at room temperature was added allyltributyltin (0.62 mL, 1.99 mmol). The resulting mixture was degassed with a stream of nitrogen for 30 minutes. Then tetrakis (triphenylphosphine)palladium(0) (77 mg, 0.06 mmol) was added to reaction mixture at room temperature. The resulting mixture was then heated to 100° C. and stirred for 3 hours under nitrogen atmosphere. After that, the reaction mixture was cooled to 0° C., diluted with water (30 mL) and extracted with ethyl acetate (2×50 mL). The combined organic phase was washed with brine, dried over sodium sulfate and concentrated in vacuo. The obtained crude product was purified by column chromatography on silica gel (230-400 mesh) eluting with 40% ethyl acetate in petroleum ether) to get compound XIXb as a brown solid. Yield: 0.25 g, 71.84%; LC-MS Calc. for $C_{15}H_{16}FNO_2$, 261.30; Obs.: 262.2; [M$^+$+H]; $^1$H NMR (400 MHz, DMSO-d$_6$): δ7.73-7.71 (m, 1H), 7.20-7.18 (m, 1H), 6.58 (s, 1H), 6.20-6.17 (m, 1H), 5.20-5.17 (m, 1H), 4.95-4.91 (m, 1H), 4.68-4.66 (m, 2H), 3.71 (s, 2H), 3.65 (s, 3H), 3.43-3.33 (m, 3H).

Step 3: 2-(7-Fluoro-4-(methoxymethyl)-1-methyl-2-oxo-1,2-dihydroquinolin-8-yl)acetaldehyde (XIX)

To a stirred solution of compound XIXb (0.3 g, 1.14 mmol) in a mixture of THF/H$_2$O (27 mL, 2:1) at 0° C. under nitrogen atmosphere were added sodium meta periodate (0.74 g 3.44 mmol) and osmium tetroxide (2.5% in t-BuOH, 0.6 mL 0.057 mmol) successively. The resulting mixture was warmed to room temperature and stirred for 4 hours under nitrogen atmosphere. After that, the reaction mixture was diluted with water and extracted with ethyl acetate (2×50 mL). The combined organic phase was washed with sodium thiosulfate, brine, dried over sodium sulfate and concentrated in vacuo. The obtained crude product was purified by column chromatography silica gel (230-400 mesh) eluting with 60% ethyl acetate in petroleum ether) to get compound XIX as an off-white solid. Yield: 0.2 g, 66.22%; LC-MS Calc. for $C_{14}H_{14}FNO_3$, 263.27; Obs.: 264.2 [M$^+$+H];

$^1$H NMR (400 MHz, DMSO-d$_6$): δ9.83 (s, 1H), 7.77-7.72 (m, 1H), 7.23-7.17 (m, 1H), 6.58 (s, 1H), 4.66 (s, 2H), 4.31 (s, 2H), 3.49 (s, 3H), 3.39 (s, 3H).

Synthesis of 2-(6-Fluoro-2,4-dimethyl-3-oxo-3,4-dihydroquinoxalin-5-yl)acetaldehyde, XX

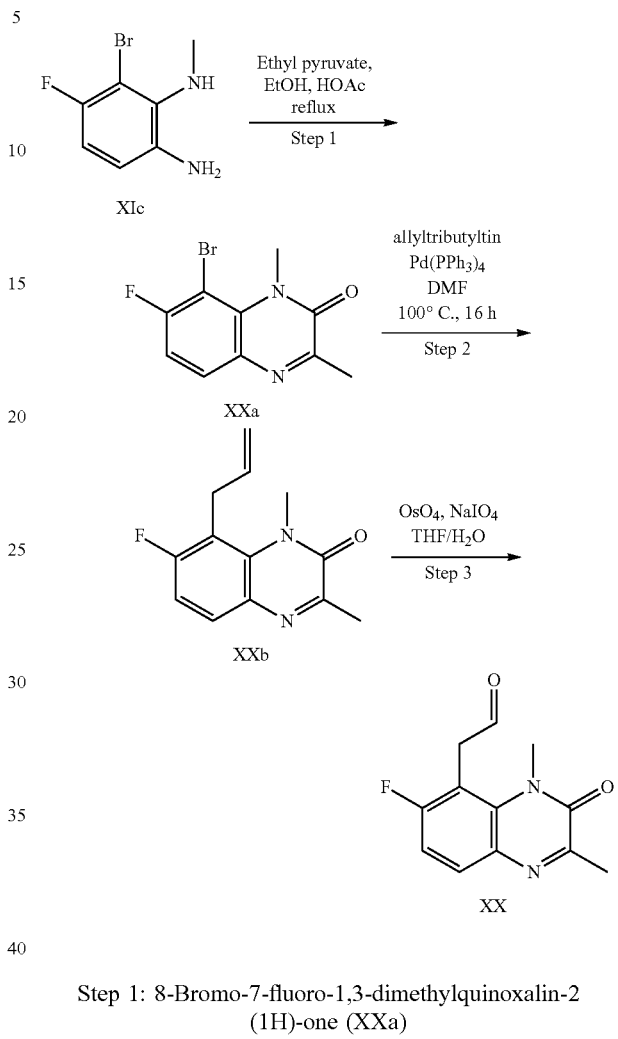

Step 1: 8-Bromo-7-fluoro-1,3-dimethylquinoxalin-2 (1H)-one (XXa)

To a stirred solution of compound XIc (3.00 g, 13.7 mmol) in ethanol (15 mL) at room temperature under nitrogen atmosphere were added ethyl pyruvate (1.52 mL, 13.7 mmol) and acetic acid (15 mL) successively. The resulting mixture was heated to reflux and stirred for 16 hours. After that, the reaction mixture was concentrated under reduced pressure. The residue obtained was diluted with water (100 mL) and extracted with ethyl acetate (2×50 mL). The combined organic phase was washed with brine (50 mL), dried over Na$_2$SO$_4$ and evaporated in vacuo. The obtained crude product was further purified by column chromatography using silica gel (230-400 mesh) eluting with 20-30% ethyl acetate in petroleum ether to get compound XXa as an off-white solid. Yield: 2.30 g, 61.99%; $^1$H-NMR (400 MHz, DMSO-d$_6$): δ7.82-7.78 (m, 1H), 7.41-7.37 (m, 1H), 3.91 (s, 3H), 2.42 (s, 3H).

Step 2: 8-Allyl-7-fluoro-1,3-dimethylquinoxalin-2 (1H)-one (XXb)

To a stirred solution of compound XXa (2.30 g, 8.48 mmol) in DMF (40 mL) at room temperature was added tributylallyltin (3.16 mL, 10.2 mmol). The resulting mixture was degassed with a stream of nitrogen for 30 minutes. Then tetrakis(triphenylphosphine)palladium(0) (0.49 g, 0.42 mmol) was added to the reaction mixture under nitrogen atmosphere. The resulting mixture was heated to 100° C. and stirred for 16 hours. After that, the reaction mixture was cooled to 0° C., quenched with water and extracted with ethyl acetate (2×50 mL). The combined organic phase was washed with water (50 mL), brine (50 mL), dried over $Na_2SO_4$ and concentrated in vacuo. The obtained crude product was further purified by column chromatography using silica gel (230-400 mesh) eluting with 20% ethyl acetate in petroleum ether to get compound XXb as an off-white solid. Yield: 1.08 g, 54.82%; $^1$H-NMR (400 MHz, DMSO-$d_6$): δ7.71-7.67 (m, 1H), 7.24 (t, J=9.2 Hz, 1H), 6.21-6.11 (m, 1H), 5.19-5.16 (m, 1H), 4.86 (d, J=17.2 Hz, 1H), 3.74 (s, 2H), 3.72 (s, 3H), 2.39 (s, 3H).

Step 3: 2-(6-Fluoro-2,4-dimethyl-3-oxo-3,4-dihydroquinoxalin-5-yl)acetaldehyde (XX)

To a stirred solution of compound XXb (0.20 g, 0.86 mmol) in a mixture of THF: $H_2O$ (15 mL, 2:1) at 0° C. under nitrogen atmosphere were added $OsO_4$ (2.5 M solution in t-BuOH) (0.4 mL, 0.05 mmol) and $NaIO_4$ (0.55 g, 2.58 mmol) successively. The resulting mixture was warmed to room temperature and stirred for 2 hours. After that, the reaction mixture was quenched with water (20 mL) at 0° C. and extracted with ethyl acetate (3×20 mL). The combined organic phase was washed with brine, dried over anhydrous $Na_2SO_4$ and concentrated in vacuo. The obtained crude product was further purified by column chromatography using silica gel (230-400 mesh) eluting with 30-35% ethyl acetate in petroleum ether to get compound XX as a dark brown solid. Yield: 0.09 g, 44.77%; LC-MS: Calc. for $C_{12}H_{11}FN_2O_2$ 234.1; Obs.: 235.2 [M+H]$^+$; $^1$H NMR (400 MHz, DMSO-$d_6$): δ9.83 (s, 1H), 7.76-7.72 (m, 1H), 7.27 (t, J=9.2 Hz, 1H), 4.37 (d, J=3.2 Hz, 2H), 3.57 (s, 3H), 2.41 (s, 3H).

Synthesis of Tert-butyl 4-(2-((tert-butyldimethylsilyl)oxy)ethyl)-6-fluoro-3-oxo-5-(2-oxoethyl)-3,4-dihydroquinoxaline-1(2H)-carboxylate, XXII

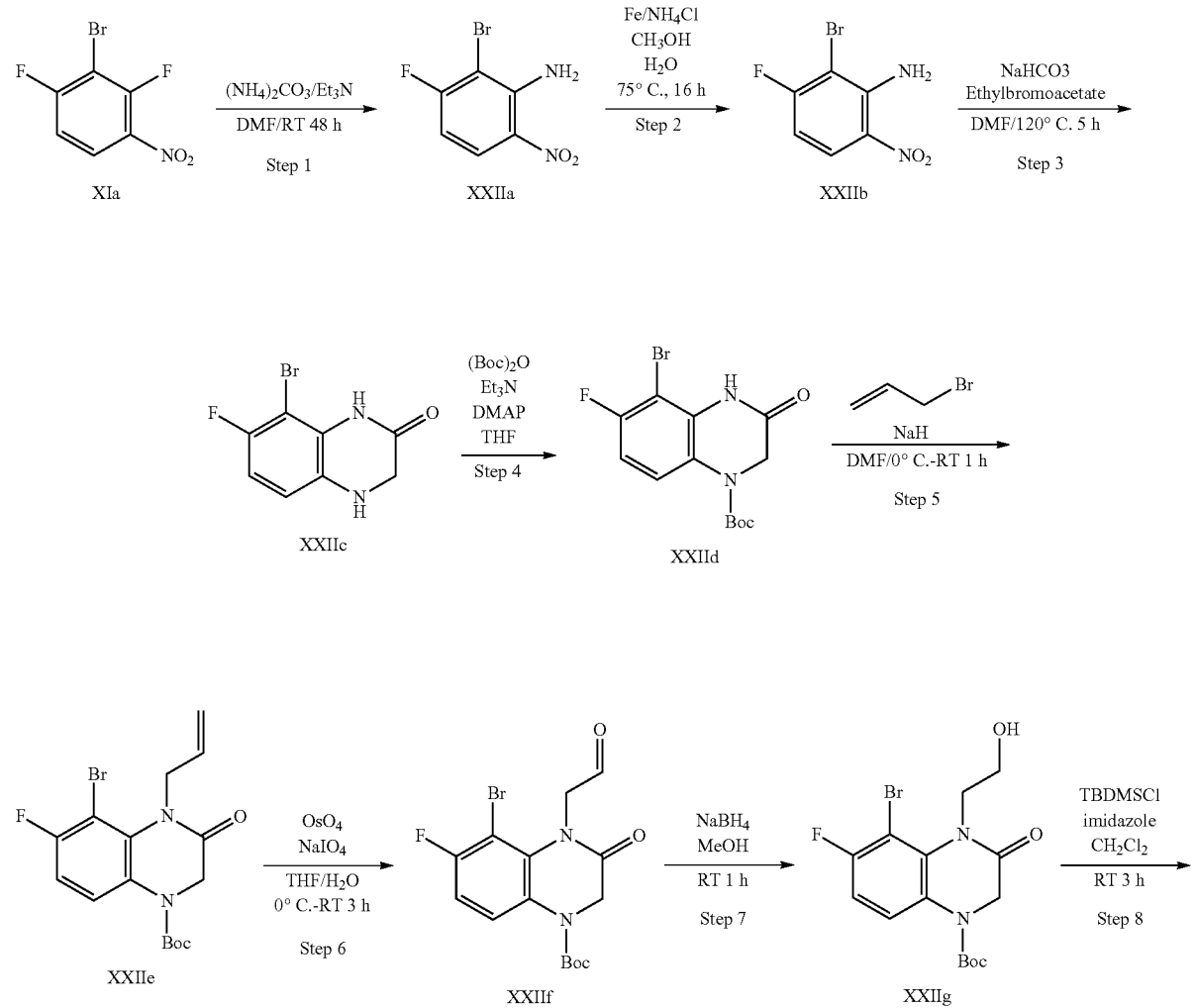

-continued

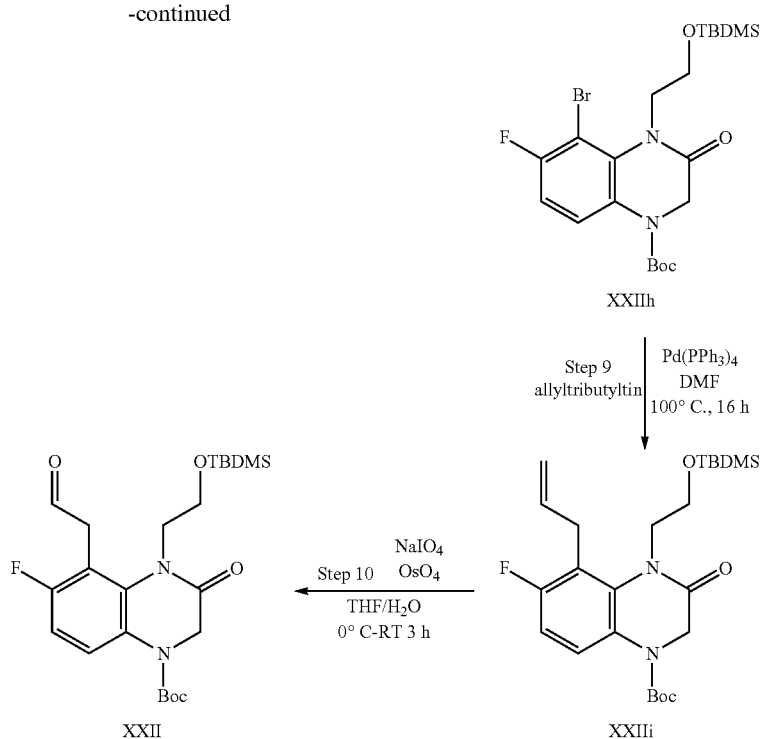

Step 1: 2-Bromo-3-fluoro-6-nitroaniline (XXIIa)

To a stirred solution of compound XIa (10 g, 0.042 mmol) in DMF (100 mL) at 0° C. under nitrogen atmosphere were added ammonium carbonate (4.0 g, 0.042 mmol) and triethylamine (17.6 mL, 0.126 mmol) successively. The resulting mixture was warmed to room temperature and stirred for 48 hours. After that, the reaction mixture was quenched with ice cold water (100 mL) and extracted with ethyl acetate (3×200 mL). The combined organic phase was washed with brine (3×50 mL), dried over $Na_2SO_4$ and concentrated in vacuo to get compound XXIIa as a brown solid, which was used as such for the next step without further purification. Yield: 13 g (crude).

Step 2: 3-Bromo-4-fluorobenzene-1,2-diamine (XXIIb)

To a stirred solution of compound XXIIa (10 g, 0.042 mmol) in a mixture of methanol/water (300 mL, 2:1) under nitrogen atmosphere at room temperature were added ammonium chloride ((6.7 g, 0.127 mmol) and iron powder (7.12 g, 0.127 mmol) successively. The resulting mixture was heated to 70° C. and stirred for 16 hours. After that, the reaction mixture was diluted with water and extracted with ethyl acetate (2×1000 mL). The combined organic phase was washed with brine, dried over sodium sulphate and concentrated in vacuo. The obtained crude product was further purified by column chromatography using silica gel (230-400 mesh) eluting with 30% EtOAc in petroleum ether) to get compound XXIIb as a brown colour solid. Yield: 5.0 g, 57.27%; $^1$H-NMR (400 MHz, DMSO-$d_6$): δ 6.45-6.49 (m, 1H), 6.34 (t, J=8.40 Hz, 1H), 4.93 (s, 2H), 4.65 (s, 2H).

Step 3: 8-Bromo-7-fluoro-3,4-dihydroquinoxalin-2 (1H)-one (XXIIc)

To a stirred solution of compound XXIIb (8.0 g, 0.038 mmol) in dry DMF (800 mL) under nitrogen atmosphere at room temperature were added sodium bicarbonate (3.3 g, 0.0397 mmol) and ethyl bromoacetate (4.49 mL, 0.0397 mmol) successively. The resulting mixture was stirred at 90° C. for 30 minutes and 120° C. for 5 h. After that, the reaction mixture was diluted with water and extracted with ethyl acetate (2×400 mL). The combined organic phase was washed with brine, dried over sodium sulphate and concentrated in vacuo. The obtained crude product was purified by column chromatography using silica gel (230-400 mesh, 30% EtOAc in petroleum ether) to get compound XXIIc as a brown solid. Yield: 6.0 g, 63.69%; LC-MS: Calc. for $C_8H_6BrFN_2O$ 245.05; Obs.: 243 [M−H]; $^1$H NMR (400 MHz, DMSO-$d_6$): δ 9.72 (s, 1H), 6.82 (t, J=8.68 Hz, 1H), 6.69-6.71 (m, 1H), 6.18 (s, 1H), 3.69 (s, 2H).

Step 4: Tert-butyl 5-bromo-6-fluoro-3-oxo-3,4-dihydroquinoxaline-1(2H)-carboxylate (XXIId)

To a stirred solution of compound XXIIc (3.0 g, 0.0115 mmol) in dry dichloromethane (30 mL) at room temperature under nitrogen atmosphere were added triethylamine (4.8 mL, 0.034 mmol), and DMAP (2.1 g, 0.0173 mmol) and Di-tert-butyl dicarbonate (3.7 mL, 0.017 mmol) successively. The resulting mixture was continued to stir for 4 hours at room temperature. After that, the reaction mixture was diluted with water and extracted with ethyl acetate (2×100 mL). The combined organic phase was washed with brine, dried over sodium sulphate and concentrated in vacuo. The obtained crude product was purified by column chromatography using silica gel (230-400 mesh) eluting with 5% ethyl acetated in petroleum ether to get compound XXIId as a pale brown solid. Yield: 1.2 g, 28.44%; LC-MS: Calc. for $C_{13}H_{14}BrFN_2O_3$ 345.05; Obs.: 242.9; $^1$H NMR (400 MHz, DMSO-$d_6$): δ 10.29 (s, 1H), 7.54-7.55 (m, 1H), 7.09 (t, J=8.84 Hz, 1H), 4.24 (s, 2H), 1.45 (s, 9H).

Step 5: Tert-butyl 4-allyl-5-bromo-6-fluoro-3-oxo-3,4-dihydroquinoxaline-1(2H)-carboxylate (XXIIe)

To a stirred solution of compound XXIId (2.0 g, 0.0057 mmol) in dry DMF (20 mL) at 0° C. under nitrogen atmosphere was added sodium hydride (60% in mineral oil, 0.27 g, 0.0069 mmol) and stirred for 20 minutes. Then allyl bromide (0.73 mL, 0.00855 mmol) was added to the reaction mixture at 0° C. The resulting mixture was warmed to room temperature and stirred at room temperature for 1 hours. After that, the reaction mixture was diluted with water and extracted with ethyl acetate (2×100 mL). The combined organic phase was washed with brine, dried over sodium sulphate and concentrated in vacuo. The obtained crude product was purified by column chromatography using silica gel (230-400 mesh) eluting with 10% ethyl acetate in petroleum ether) to get compound XXIIe as a pale-brown solid. Yield: 1.3 g, 58.29%; $^1$H NMR (400 MHz, DMSO-$d_6$): δ 7.59-7.64 (m, 1H), 7.25 (t, J=8.70 Hz, 1H), 5.57-5.66 (m, 1H), 5.02 (d, J=9.90 Hz, 1H), 4.96-4.76 (m, 3H), 4.26 (s, 2H), 1.44 (s, 9H).

Step 6: Tert-butyl 5-bromo-6-fluoro-3-oxo-4-(2-oxoethyl)-3,4-dihydroquinoxaline-1(2H)-carboxylate (XXIIf)

To a stirred solution of compound XXIIe (1.2 g, 0.00311 mmol) in a mixture of THF/H$_2$O (30 mL, 2:1) at 0° C. under nitrogen atmosphere were added sodium meta periodate (3.3 g, 0.0155 mmol) and osmium tetroxide (2.5% in t-BuOH, (3.1 mL, 0.00031 mmol) successively. The resulting mixture was then warmed to room temperature and stirred for 3 hours. After that, the reaction mixture was diluted with water and extracted with ethyl acetate (2×100 mL). The combined organic phase was washed with sodium thiosulfate, brine, dried over sodium sulphate and concentrated in vacuo. The obtained crude product was further purified by column chromatography silica gel (230-400 mesh) eluting with 30% ethyl acetate in petroleum ether) to get compound XXIIf as a pale-yellow solid. Yield: 0.75 g, 62.51%; $^1$H NMR (400 MHz, DMSO-$d_6$): δ 9.46 (s, 1H), 7.60-7.63 (m, 1H), 7.25 (t, J=8.60 Hz, 1H), 4.83 (s, 2H), 4.30 (s, 2H), 1.46 (s, 9H).

Step 7: Tert-butyl 5-bromo-6-fluoro-4-(2-hydroxyethyl)-3-oxo-3,4-dihydroquinoxaline-1(2H)-carboxylate (XXIIg)

To a stirred solution of compound XXIIf (0.75 g, 0.00193 mmol) in methanol (25 mL) at 0° C. under nitrogen atmosphere was added sodium borohydride (0.18 g, 0.0048 mmol). The resulting mixture was warmed to room temperature and stirred for 1 hours. After that, the reaction mixture was diluted with water and extracted with ethyl acetate (2×100 mL). The combined organic phase was washed with brine, dried over anhydrous sodium sulphate and concentrated in vacuo. The obtained crude product was further purified by column chromatography silica gel (230-400 mesh) eluting with 30% ethyl acetate in petroleum ether) to get compound XXIIg as colourless liquid. Yield: 0.7 g, 92.96%; $^1$H NMR (400 MHz, DMSO-$d_6$): δ 7.57 (d, J=5.10 Hz, 1H), 7.24 (t, J=8.40 Hz, 1H), 4.51 (s, 1H), 4.21 (d, J=5.10 Hz, 4H), 1.43 (s, 9H).

Step 8: Tert-butyl 5-bromo-4-(2-((tert-butyldimethylsilyl)oxy)ethyl)-6-fluoro-3-oxo-3,4-dihydroquinoxaline-1(2H)-carboxylate (XXIIh)

To a stirred solution of compound XXIIg (1.2 g, 0.00308 mmol) in dichloromethane (50 mL) at 0° C. under nitrogen atmosphere were added imidazole (0.41 g, 0.00613 mmol) and TBDMS chloride (0.69 g, 0.00462 mmol) successively. The resulting mixture was warmed to room temperature and stirred for 30 minutes. After that, the reaction mixture was cooled to 0° C., diluted with water (100 mL) and extracted with ethyl acetate (2×100 mL). The combined organic phase was washed with brine, dried over anhydrous sodium sulphate and concentrated in vacuo. The obtained crude product was purified by column chromatography using silica gel (230-400 mesh) eluting with 10% ethyl acetate in petroleum ether) to get compound XXIIh as a colorless liquid. Yield: 1.0 g, 64.52%; LC-MS: Calc. for $C_{21}H_{32Br}FN_2O_4Si$, 503.4; Obs. 405.1 [M+H]$^+$; $^1$H NMR (400 MHz, DMSO-$d_6$): δ 7.68 (brs, 1H), 6.94-6.98 (m, 1H), 4.42 (t, J=5.60 Hz, 2H), 3.71 (t, J=5.60 Hz, 2H), 3.72-3.69 (m, 2H), 1.54 (s, 9H), 0.75 (s, 9H), 0.09 (s, 6H).

Step 9: Tert-butyl 5-allyl-4-(2-((tert-butyldimethylsilyl)oxy)ethyl)-6-fluoro-3-oxo-3,4-dihydroquinoxaline-1(2H)-carboxylate (XXIIi)

To a stirred solution of compound XXIIh (0.93 g, 0.0018 mmol) in DMF (20 mL) at room temperature under nitrogen atmosphere was added allyltributyltin (0.7 mL, 0.0022 mmol). The resulting mixture was degassed with a stream of nitrogen for 30 minutes. Then tetrakis(triphenylphosphine) palladium(0) (0.106 g, 0.000092 mmol) was added to the reaction mixture at room temperature. The resulting mixture was then heated to 100° C. and stirred for 16 hours. After that, the reaction mixture was cooled to 0° C., diluted with water (60 mL) and extracted with ethyl acetate (2×100 mL). The combined organic phase was washed with brine, dried over sodium sulphate and concentrated in vacuo. The obtained crude product was further purified by column chromatography using silica gel (230-400 mesh) eluting with 10% ethyl acetate in petroleum ether to get compound XXIIi as a pale yellow liquid. Yield: 0.55 g, 63.95%; LC-MS: Calc. for $C_{24}H_{37}FN_2O_4Si$, 464.65; Obs.: 465.3 [M+H]$^+$.

Step 10: Tert-butyl 4-(2-((tert-butyldimethylsilyl)oxy)ethyl)-6-fluoro-3-oxo-5-(2-oxoethyl)-3,4-dihydroquinoxaline-1(2H)-carboxylate (XXII)

To a stirred solution of compound XXIII (0.7 g, 0.0015 mmol) in a mixture of THF/H$_2$O (30 mL, 2:1) at 0° C. under nitrogen atmosphere were added sodium meta periodate (0.96 g, 0.00455 mmol) and osmium tetroxide (2.5% in t-BuOH, 0.6 mL, 0.000075 mmol) successively. The resulting mixture was warmed to room temperature and stirred for 3 hours. After that, the reaction mixture was diluted with water and extracted with ethyl acetate (2×100 mL). The combined organic phase was washed with sodium thiosulfate, brine, dried over sodium sulphate and concentrated in vacuo. The obtained crude product was purified by column chromatography silica gel (230-400 mesh) eluting with 30% ethyl acetate in petroleum ether) to get compound XXII as a pale yellow solid. Yield: 0.35 g, 50.00%; $^1$H NMR (400

MHz, DMSO-d$_6$): δ 9.79 (d, J=1.60 Hz, 1H), 6.94 (t, J=9.20 Hz, 1H), 3.89 (s, 4H), 3.73 (t, J=5.20 Hz, 2H), 1.55 (s, 9H), 0.77 (s, 9H), 0.06 (s, 9H).

Example 1: 6-(5-(((3-(3-fluoro-5-methyl-6-oxo-5,6-dihydro-1,5-naphthyridin-4-yl)propyl)amino)methyl)-2-oxooxazolidin-3-yl)-2H-pyrido[3,2-b][1,4]oxazin-3(4H)-one

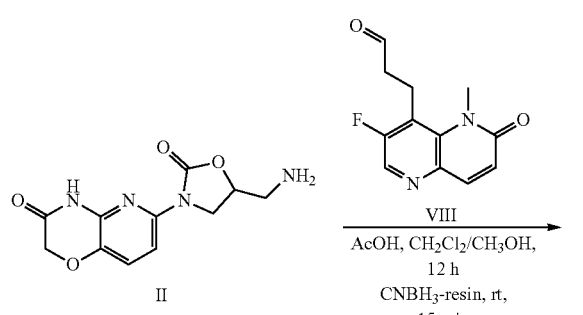

Example 1

To a mixture of VIII (0.14 g, 0.59 mmol) and amine (II, 0.19 g, 0.71 mmol) in dry methanol (7.5 mL) and dichloromethane (7.5 mL) was added AcOH (0.14 mL) and allowed to stir for 12 hours at room temperature. To this was added cyanoborohydride resin (0.48 g, 1.19 mmol) and stirred for 10 minutes. The reaction mixture was filtered and the filtrate was concentrated under reduced pressure. The residue was diluted with dichloromethane (50 mL) and washed with saturated aqueous 10% NaHCO$_3$ solution and brine (2×5 mL). The organic layer was dried over sodium sulphate and concentrated under reduced pressure to get the crude product, which was purified by column chromatography using silica gel (230-400 mesh) by eluting with 8% methanol in dichloromethane to afford the title compound (Example 1) as off-white solid.

Yield: 0.06 g, 21%; LC-MS: Calc. for C$_{23}$H$_{23}$FN$_6$O$_5$ 482.17; Obs. 483.2 [M+H]$^+$ $^1$H NMR (400 MHz, DMSO-D$_6$): δ 11.20 (brs, 1H), 7.94 (d, J=11.2 Hz, 1H), 7.89 (d, J=10.0 Hz, 1H), 7.59 (d, J=8.4 Hz, 1H), 7.42 (d, J=8.4 Hz, 1H), 6.79 (d, J=9.6 Hz, 1H), 4.72-4.69 (m, 1H), 4.61 (s, 2H), 4.16-4.11 (m, 1H), 3.88-3.84 (m, 1H), 3.58 (s, 3H), 3.41-3.38 (m, 1H), 2.89-2.82 (m, 3H), 2.67-2.62 (m, 2H), 1.87-1.80 (m, 2H), 1.11-1.08 (m, 1H); HPLC: 8.87 min; 98.23%; HPLC Column: Atlantis dC18 (250*4.6) mm 5 μm, Mobile Phase A: 0.1% TFA in water, Mobile Phase B: Acetonitrile.

The racemic compound (Example 1) (50 mg) was resolved into its two enantiomers by chiral supercritical fluid chromatography using the following conditions Column: YMC Amylose-SA Eluent: 0.5% DEA in IPA in three batches.

There was no overlap fraction and both enantiomers Example 1a (1$^{st}$ eluting enantiomer) and Example 1b (2$^{nd}$ eluting enantiomer) were isolated in >99.0 ee each.

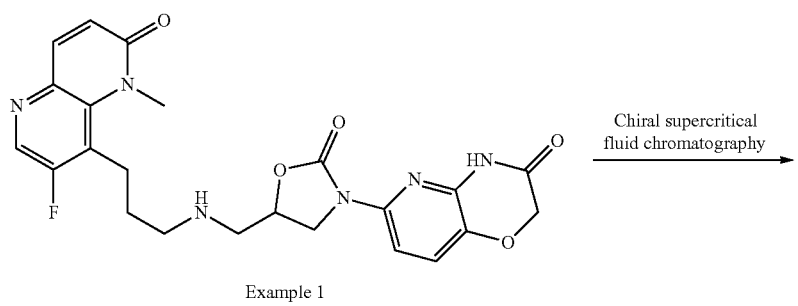

Example 1

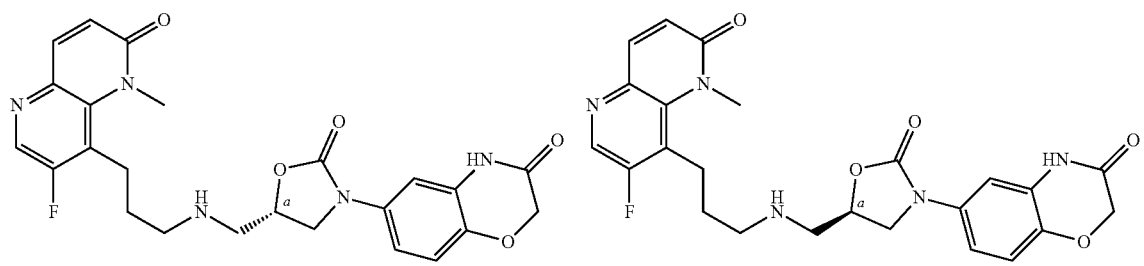

Example 1a (Enantiomer)
a = Absolute configuration unknown

Example 1b (Enantiomer 2)

Example 1a: Chiral 6-(5-(((3-(3-fluoro-5-methyl-6-oxo-5,6-dihydro-1,5-naphthyridin-4-yl)propyl)amino)methyl)-2-oxooxazolidin-3-yl)-2H-pyrido[3,2-b][1,4]oxazin-3(4H)-one (Enantiomer 1)

Yield: 11 mg; LC-MS: Calc. for $C_{23}H_{23}FN_6O_5$ 482.17; Obs. 483.0 $[M+H]^+$. $^1H$ NMR (400 MHz, DMSO-$D_6$): δ 11.20 (brs, 1H), 7.94 (d, J=11.2 Hz, 1H), 7.89 (d, J=10.0 Hz, 1H), 7.59 (d, J=8.4 Hz, 1H), 7.42 (d, J=8.4 Hz, 1H), 6.79 (d, J=9.6 Hz, 1H), 4.72-4.69 (m, 1H), 4.61 (s, 2H), 4.16-4.11 (m, 1H), 3.88-3.84 (m, 1H), 3.58 (s, 3H), 3.41-3.38 (m, 1H), 2.89-2.82 (m, 3H), 2.67-2.62 (m, 2H), 1.87-1.80 (m, 2H), 1.11-1.08 (m, 1H); HPLC: 8.27 min; 98.61%; HPLC Column: Atlantis dC18 (250*4.6) mm 5 μm, Mobile Phase A: 0.1% TFA in water, Mobile Phase B: Acetonitrile; Chiral HPLC: 2.42 min; 100% ee; Column: YMC Amylose-SA, co-solvent: 0.5% DEA in IPA, Flow rate: 5 mL/min, injected volume; 15 μL, Outlet Pressure; 100 bar, Temperature; 35° C.

Example 1b: Chiral 6-(5-(((3-(3-fluoro-5-methyl-6-oxo-5,6-dihydro-1,5-naphthyridin-4-yl)propyl)amino)methyl)-2-oxooxazolidin-3-yl)-2H-pyrido[3,2-b][1,4]oxazin-3(4H)-one (Enantiomer 2)

Yield: 10 mg; LC-MS: Calc. for $C_{23}H_{23}FN_6O_5$ 482.17; Obs. 483.0 $[M+H]^+$. $^1H$ NMR (400 MHz, DMSO-$D_6$): δ 11.20 (brs, 1H), 7.94 (d, J=11.2 Hz, 1H), 7.89 (d, J=10.0 Hz, 1H), 7.59 (d, J=8.4 Hz, 1H), 7.42 (d, J=8.4 Hz, 1H), 6.79 (d, J=9.6 Hz, 1H), 4.72-4.69 (m, 1H), 4.61 (s, 2H), 4.16-4.11 (m, 1H), 3.88-3.84 (m, 1H), 3.58 (s, 3H), 3.41-3.38 (m, 1H), 2.89-2.82 (m, 3H), 2.67-2.62 (m, 2H), 1.87-1.80 (m, 2H), 1.11-1.08 (m, 1H); HPLC: 8.28 min; 97.03%; HPLC Column: Atlantis dC18 (250*4.6) mm 5 μm, Mobile Phase A: 0.1% TFA in water, Mobile Phase B: Acetonitrile.

Chiral HPLC: 4.13 min; 100% ee; Column: YMC Amylose-SA, co-solvent: 0.5% DEA in IPA, Flowrate: 5 mL/min, Injected Volume: 15 μL, Outlet Pressure: 100 bar, Temperature: 35° C.

Example 2: (S)-6-(5-(((2-(7-Fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one

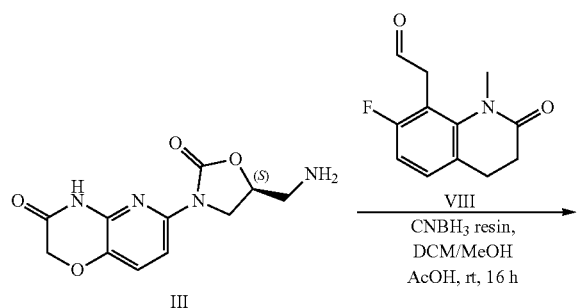

To a stirred solution of compound X (0.08 g, 0.36 mmol) and compound III (0.09 g, 0.36 mmol) in a mixture of dry methanol/dichloromethane (20 mL, 1:1) at room temperature under nitrogen atmosphere was added AcOH (0.10 mL). The resulting mixture was allowed to stir at room temperature for 16 hours. Then cyanoborohydride resin (0.30 g) was added to the reaction mixture at room temperature and stirred for another 15 minutes. After that the reaction mixture was filtered and the filtrate was concentrated under reduced pressure. The residue obtained was diluted with dichloromethane (50 mL) and washed with saturated aqueous NaHCO$_3$ solution and brine (2×15 mL). The organic layer was dried over anhydrous Na$_2$SO$_4$ and concentrated in vacuo. The obtained crude product was purified by column chromatography using silica gel (230-400 mesh) by eluting with 4% methanol in dichloromethane to get Example 2 as an off-white solid. Yield: 50 mg, 29.42%; LC-MS: Calc. for $C_{23}H_{24}FN_5O_5$ 469.18; Obs.: 470.2 $[M+H]^+$; $^1H$ NMR (400 MHz, DMSO-$d_6$): δ 11.21 (s, 1H), 7.60 (d, J=8.7 Hz, 1H), 7.43 (d, J=8.7 Hz, 1H), 7.12-7.08 (m, 1H), 6.89-6.85 (m, 1H), 4.71-4.67 (m, 1H), 4.61 (s, 2H), 4.14-4.09 (m, 1H), 3.86-3.81 (m, 1H), 3.27 (s, 4H), 2.84-2.60 (m, 8H), 2.51-2.41 (m, 2H); HPLC: 9.08 min; 98.35%; HPLC Column: Atlantis dC18 (250*4.6) mm 5 μm, Mobile Phase A: 0.1% TFA in water, Mobile Phase B: Acetonitrile.

Example 3: (R)-6-(5-(((2-(7-Fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one

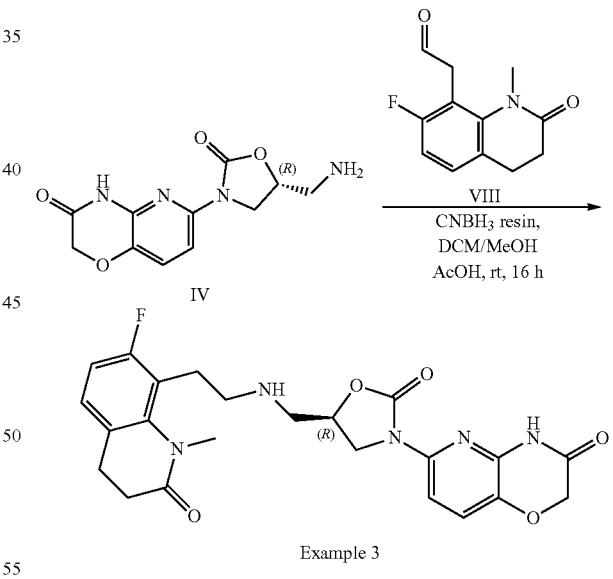

Example 3

To a stirred solution of VII (0.08 g, 0.36 mmol) and IV (0.09 g, 0.36 mmol) in a mixture of dry methanol/dichloromethane (20 mL, 1:1) at room temperature under nitrogen atmosphere was added AcOH (0.10 mL) and stirred for 16 hours. Then cyanoborohydride resin (0.30 g) was added to reaction mixture and stirred for another 15 minutes at room temperature. After that the reaction mixture was filtered and the filtrate was concentrated under reduced pressure. The residue obtained was diluted with dichloromethane (50 mL) and washed with saturated aqueous NaHCO$_3$ solution, brine, dried over anhydrous Na$_2$SO$_4$ and concentrated in vacuo.

The obtained crude product was further purified by column chromatography using silica gel (230-400 mesh) by eluting with 4% methanol in dichloromethane to get Example 3 as an off-white solid. Yield: 55 mg, 32.16%; LC-MS: Calc. for $C_{23}H_{24}FN_5O_5$ 469.18; Obs. 470.2 [M+H]$^+$; $^1$H NMR (400 MHz, DMSO-d$_6$): δ $^1$H NMR (400 MHz, DMSO-d$_6$): δ 11.20 (s, 1H), 7.60 (d, J=8.7 Hz, 1H), 7.43 (d, J=8.7 Hz, 1H), 7.12-7.08 (m, 1H), 6.89-6.85 (m, 1H), 4.71-4.67 (m, 1H), 4.61 (s, 2H), 4.14-4.09 (m, 1H), 3.86-3.81 (m, 2H), 3.27 (s, 3H), 2.84-2.60 (m, 8H), 2.51-2.41 (m, 2H); HPLC: 9.25 min; 98.70%; HPLC Column: Atlantis dC18 (250*4.6) mm 5 μm, Mobile Phase A: 0.1% TFA in water, Mobile Phase B: Acetonitrile Example 4: (S)-6-(5-(((2-(6-Fluoro-4-methyl-3-oxo-3,4-dihydroquinoxalin-5-yl)ethyl) amino)methyl)-2-oxooxazolidin-3-yl)-2H-pyrido[3,2-b][1,4]oxazin-3 (4H)-one

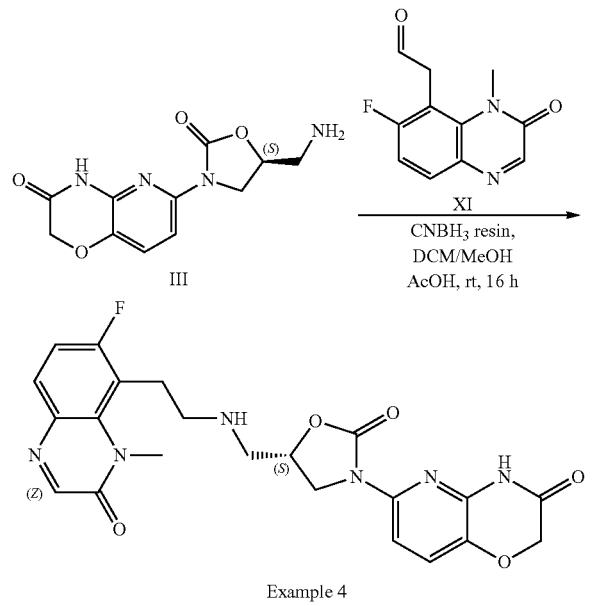

Example 4

To a stirred solution of compound XI (0.085 g, 0.38 mmol) and compound III (0.10 g, 0.38 mmol) in a mixture of dry methanol/dichloromethane (20 mL, 1:1) at room temperature under nitrogen atmosphere was added AcOH (0.10 mL). The resulting mixture was allowed to stir at room temperature for 16 hours. Then cyanoborohydride resin (0.30 g) was added and the resulting mixture continued to stir for another 15 minutes at room temperature. After that the reaction mixture was filtered and the filtrate was concentrated under reduced pressure. The residue was diluted with dichloromethane (50 mL), washed with saturated aqueous NaHCO$_3$ solution, brine (2×15 mL), dried over anhydrous Na$_2$SO$_4$ and concentrated in vacuo. The obtained crude product was purified by column chromatography using silica gel (230-400 mesh) by eluting with 4% methanol in dichloromethane to get compound Example 4 as a pale yellow solid. Yield: 65 mg, 36.31%; LC-MS: Calc. for $C_{22}H_{21}FN_6O_5$ 468.2; Obs.: 469.2 [M+H]$^+$; $^1$H NMR (400 MHz, DMSO-d$_6$): δ11.20 (s, 1H), 8.16-8.15 (m, 1H), 7.73 (t, J=7.3 Hz, 1H), 7.59 (d, J=8.6 Hz, 1H), 7.42 (d, J=8.6 Hz, 1H), 7.26 (t, J=9.2 Hz, 1H), 4.75-4.70 (m, 1H), 4.62 (s, 2H), 4.11 (t, J=9.3 Hz, 1H), 3.86-3.81 (m, 2H), 3.77 (s, 3H), 3.20-3.15 (m, 2H), 2.91-2.86 (4H); HPLC: 8.11 min; 93.12%; HPLC Column: Phenomenex gemini NX-C18 (150*4.6) mm 5 μm, Mobile Phase A: 10 mM Ammonium acetate in water, Mobile Phase B: Acetonitrile.

Example 5: (R)-6-(5-(((2-(6-Fluoro-4-methyl-3-oxo-3,4-dihydroquinoxalin-5-yl) ethyl)amino)methyl)-2-oxooxazolidin-3-yl)-2H-pyrido[3,2-b][1,4]oxazin-3 (4H)-one

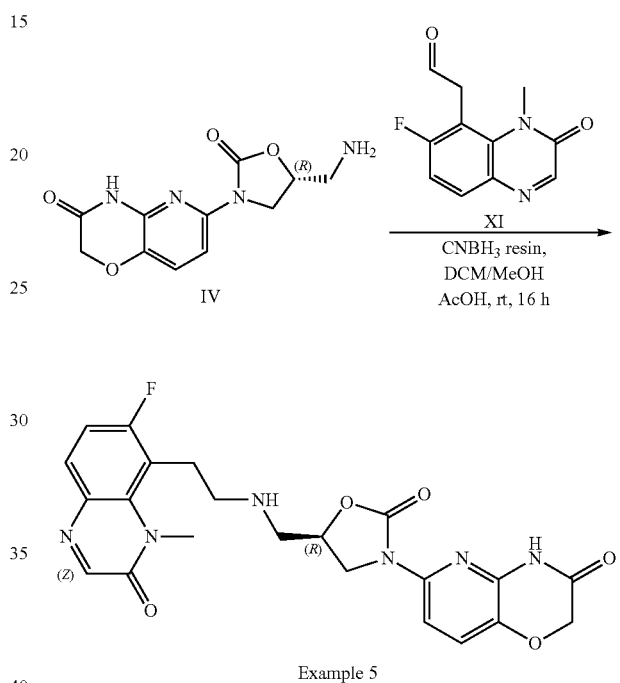

Example 5

To a stirred solution compound XI (0.050 g, 0.22 mmol) and compound IV (0.059 g, 0.22 mmol) in dry methanol/dichloromethane (8 mL, 1:1) at room temperature under nitrogen atmosphere was added AcOH (0.05 mL) and stirred for 16 hours at room temperature. The cyanoborohydride resin (0.22 g) was added at room temperature and continued to stir for another 15 minutes. After that the reaction mixture was filtered and the filtrate was concentrated under reduced pressure. The residue was diluted with dichloromethane (50 mL) and washed with saturated aqueous NaHCO$_3$ solution, brine (2×15 mL), dried over anhydrous Na$_2$SO$_4$ and concentrated in vacuo. The obtained crude product was further purified by reverse phase PREP HPLC to get Example 5 as a pale yellow solid. Yield: 15 mg, 14.15%; LC-MS: Calc. for $C_{22}H_{21}FN_6O_5$ 468.2; Obs. 469.2 [M+H]$^+$; $^1$H NMR (400 MHz, DMSO-d$_6$): δ 11.21 (s, 1H), 8.16-8.15 (m, 1H), 7.73 (t, J=7.3 Hz, 1H), 7.59 (d, J=8.6 Hz, 1H), 7.42 (d, J=8.6 Hz, 1H), 7.26 (t, J=9.2 Hz, 1H), 4.75-4.70 (m, 1H), 4.62 (s, 2H), 4.11 (t, J=9.3 Hz, 1H), 3.86-3.81 (m, 2H), 3.74 (s, 3H), 3.20-3.15 (m, 2H), 2.91-2.86 (4H); HPLC: 8.59 min; 99.16%; HPLC Column: Atlantis dC18 (250*4.6) mm 5 μm, Mobile Phase A: 0.1% TFA in water, Mobile Phase B: Acetonitrile.

Example 6: (S)-6-(5-(((2-(6-fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one

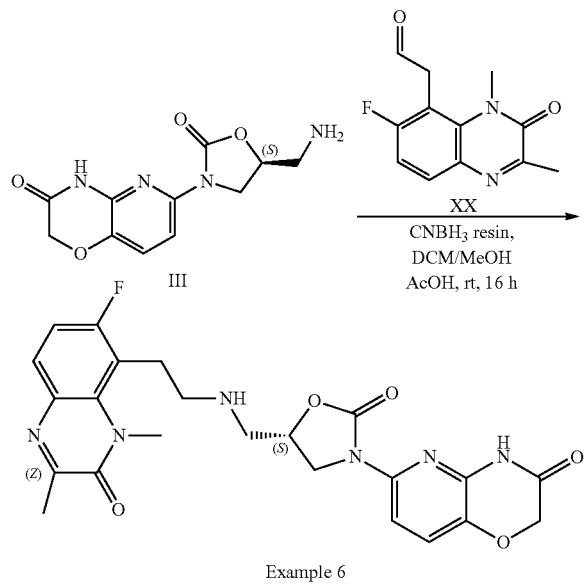

Example 6

To a stirred solution of compound XX (0.09 g, 0.38 mmol) and compound XXX (0.10 g, 0.38 mmol) in dry methanol/dichloromethane (20 mL, 1:1) at room temperature under nitrogen atmosphere was added AcOH (0.10 mL) and allowed to stir for 16 hours at room temperature. Then cyanoborohydride resin (0.30 g) was added to the reaction mixture and continued to stir for 15 minutes at room temperature. After that, the reaction mixture was filtered and the filtrate was concentrated under reduced pressure. The residue obtained was diluted with dichloromethane (50 mL), washed with saturated aqueous NaHCO$_3$ solution and brine (2×15 mL). The organic phase was dried over Na$_2$SO$_4$ and concentrated in vacuo. The obtained crude product, was further purified by column chromatography using silica gel (230-400 mesh) by eluting with 4% methanol in dichloromethane to get Example 6 as an off-white solid. Yield: 60 mg, 33.33%; LC-MS: Calc. for C$_{23}$H$_{23}$FN$_6$O$_5$ 482.17; Obs.: 483.2 [M+H]$^+$; $^1$H-NMR (400 MHz, DMSO-d$_6$): δ 11.19 (s, 1H), 7.65-7.57 (m, 2H), 7.42 (d, J=8.6 Hz, 1H), 7.21 (t, J=9.2 Hz, 1H), 4.77-4.73 (m, 1H), 4.61 (s, 2H), 4.14-4.10 (m, 1H), 3.85-3.81 (m, 1H), 3.77 (s, 3H), 3.18-3.15 (m, 2H), 2.93-2.82 (m, 4H), 2.32 (s, 3H); HPLC: 8.91 min; 98.08%; HPLC Column: Atlantis dC18 (250*4.6) mm 5 μm, Mobile Phase A: 0.1% TFA in water, Mobile Phase B: Acetonitrile.

Example 7: (R)-6-(5-(((2-(6-Fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one

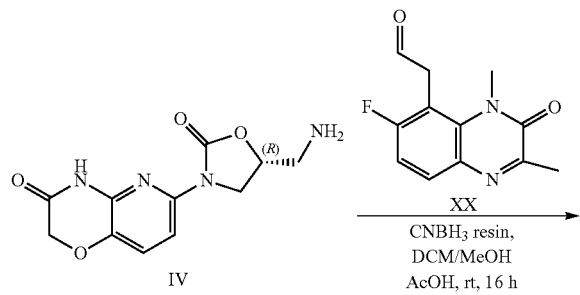

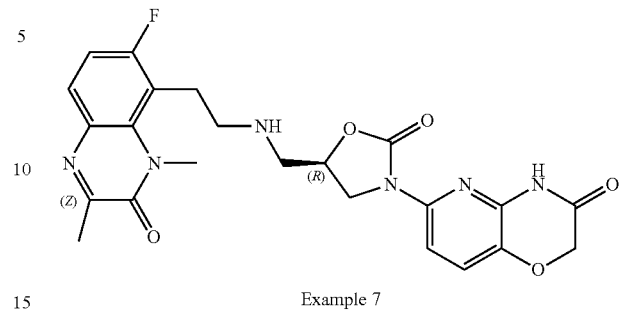

Example 7

To a stirred mixture of compound XX (0.06 g, 0.25 mmol) and compound IV (0.067 g, 0.25 mmol) in a mixture of dry methanol/dichloromethane (16 mL, 1:1) at room temperature under nitrogen atmosphere was added AcOH (0.10 mL) and allowed to stir for 16 hours at room temperature. Then cyanoborohydride resin (0.21 g) was added to reaction mixture and continued to stir for another 15 minutes at room temperature. After that, the reaction mixture was filtered and the filtrate was concentrated under reduced pressure. The residue obtained was diluted with dichloromethane (50 mL) and washed with saturated aqueous NaHCO$_3$ solution and brine (2×15 mL). The organic layer was dried over Na$_2$SO$_4$ and concentrated under reduced pressure to get the crude product, which was further purified by column chromatography using silica gel (230-400 mesh) by eluting with 4% methanol in dichloromethane to get Example 7 as an off-white solid. Yield: 20 mg, 16.26%; LC-MS: Calc. for C$_{23}$H$_{23}$FN$_6$O$_5$ 482.17; Obs.: 483.2 [M+H]$^+$; $^1$H NMR (400 MHz, DMSO-d$_6$): δ 11.20 (s, 1H), 7.65-7.57 (m, 2H), 7.42 (d, J=8.6 Hz, 1H), 7.21 (t, J=9.2 Hz, 1H), 4.77-4.73 (m, 1H), 4.62 (s, 2H), 4.12-4.08 (m, 1H), 3.85-3.81 (m, 1H), 3.77 (s, 3H), 3.18-3.15 (m, 2H), 2.93-2.82 (m, 4H), 2.33 (s, 3H). HPLC: 8.91 min; 98.79%; HPLC Column: Atlantis dC18 (250*4.6) mm 5 μm, Mobile Phase A: 0.1% TFA in water, Mobile Phase B: Acetonitrile.

Example 8: (S)-6-(5-(((2-(7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one

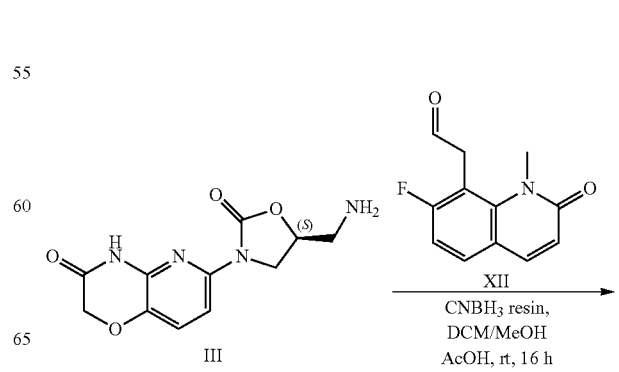

115

-continued

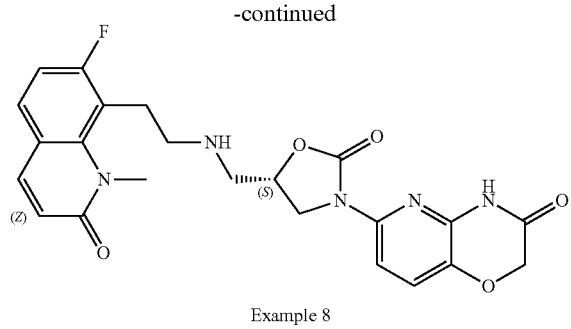

Example 8

To a stirred solution of compound XII (0.5 g, 2.28 mmol) and compound III (0.28 g, 1.07 mmol) in mixture of dry methanol/dichloromethane (50 mL, 1:1) at room temperature under nitrogen atmosphere was added acetic acid (0.5 mL) and allowed to stir for 16 hours.

116

Then cyanoborohydride resin (2.07 g, 4.5 mmol)) was added to reaction mixture and continued to stir for 10 minutes. After that, the reaction mixture was filtered and filtrate was concentrated under reduced pressure. The obtained crude was further purified by preparative HPLC to get Example 8 as formate salt (off-white solid). Yield: 0.140 g, 13.20%; LC-MS Calc. for $C_{23}H_{22}FN_5O_5$, 467.46; Obs.: 468.3 [M$^+$+H]$^+$; $^1$H-NMR (400 MHz, DMSO-d$_6$): δ11.19 (brs, 1H), 7.84 (d, J=9.16 Hz, 1H), 7.64-7.58 (m, 2H), 7.42 (d, J=8.76 Hz, 1H), 7.13 (t, J=9.12 Hz, 1H), 6.53 (d, J=9.28 Hz, 1H), 4.70 (s, 1H), 4.61 (s, 2H), 4.11 (t, J=9.40 Hz, 1H), 3.86-3.82 (m, 1H), 3.71 (s, 3H), 3.13-2.84 (m, 2H), 2.80-2.67 (m, 4H).

Example 9: (S)-6-(5-(((2-(6-fluoro-4-(2-hydroxy-ethyl)-3-oxo-3,4-dihydroquinoxalin-5-yl)ethyl)amino)methyl)-2-oxooxazolidin-3-yl)-2H-pyrido[3,2-b][1,4]oxazin-3(4H)-one

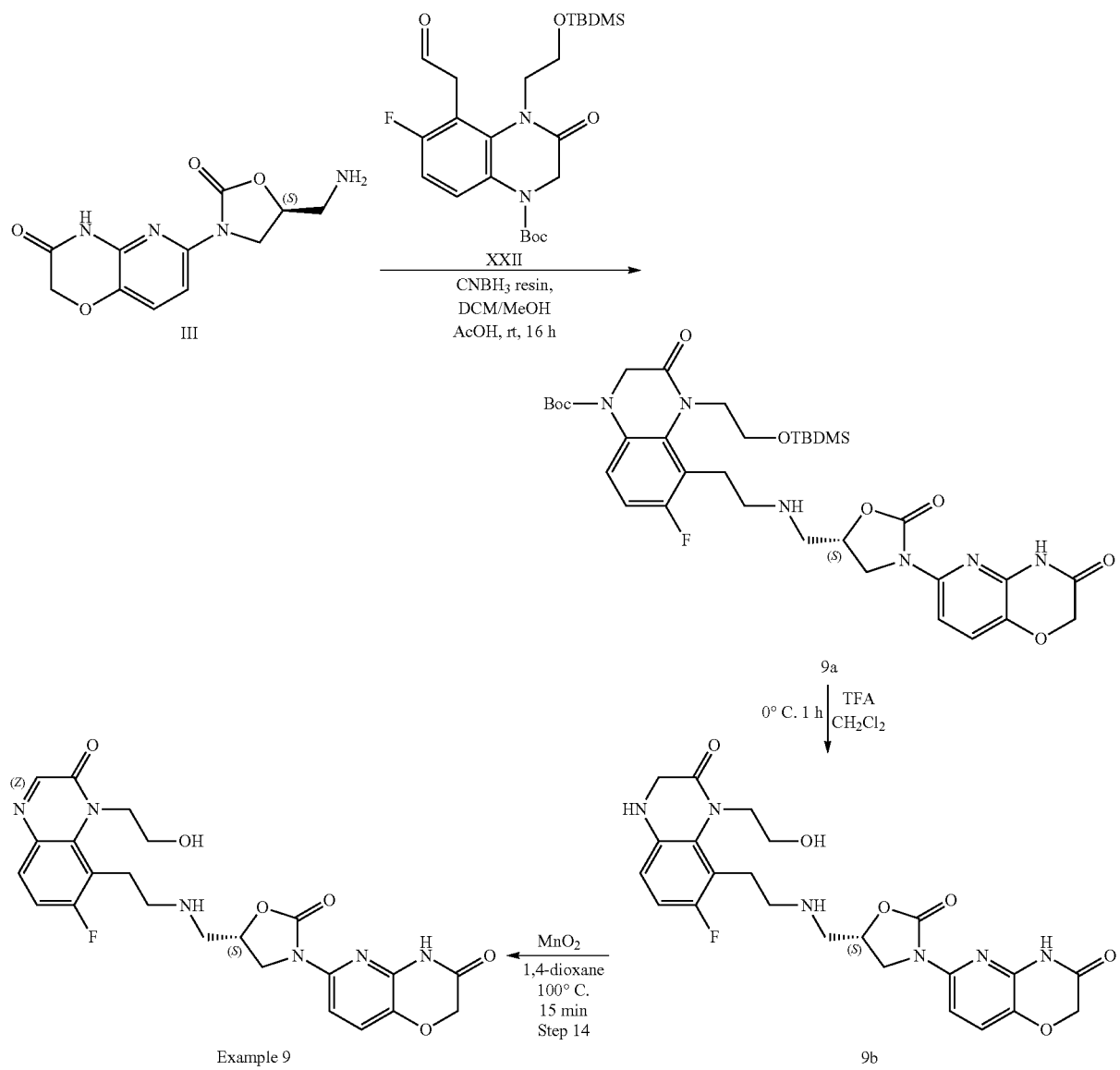

Step 1: Tert-butyl (S)-4-(2-((tert-butyldimethylsilyl)oxy)ethyl)-6-fluoro-3-oxo-5-(2-(((2-oxo-3-(3-oxo-3,4-dihydro-2H-pyrido[3,2-b][1,4]oxazin-6-yl)oxazolidin-5-yl)methyl)amino)ethyl)-3,4-dihydroquinoxaline-1(2H)-carboxylate (9a)

To a stirred mixture of compound XXII (0.35 g, 0.00075 mmol) and compound III (0.337 g, 0.000826 mmol) in dry methanol/dichloromethane (10 mL, 1:1) at room temperature under nitrogen atmosphere was added AcOH (0.35 mL) and allowed to stir for 16 hours. Then cyanoborohydride resin (0.66 g, 0.0015 mmol) was added to the reaction mixture and continued to stir for 10 minutes. After that, the reaction mixture was filtered and the filtrate was concentrated under reduced pressure. The obtained crude product was purified by column chromatography using silica gel (230-400 mesh) eluting with 5% MeOH in dichloromethane to get compound 9a as a pale yellow solid. Yield: 0.3 g, 56.60%; LC-MS: Calc. for $C_{34}H_{47}FN_6O_8Si$, 714.87; Obs.: 715.2 $[M+H]^+$.

Step 2: (S)-6-(5-(((2-(6-Fluoro-4-(2-hydroxyethyl)-3-oxo-1,2,3,4-tetrahydroquinoxalin-5-yl)ethyl)amino)methyl)-2-oxooxazolidin-3-yl)-2H-pyrido[3,2-b][1,4]oxazin-3(4H)-one (9b)

To a stirred solution of compound 9a (0.3 g, 0.42 mmol), in dichloromethane (5 mL) at 0° C. under nitrogen atmosphere was added trifluroacetic acid (10 mL). The resulting mixture was warmed to room temperature and stirred for 1 hour. After that, the reaction mixture was concentrated in vacuo. The residue obtained was diluted with water (10 mL) and basified (pH~8) using 10% $NaHCO_3$ solution and extracted with dichloromethane (2×50 mL). The combined organic phase was washed with brine, dried over sodium sulphate and concentrated in vacuo to get the compound 9b as a yellow solid, which was used as such for the next step without further purification. Yield: 0.15 g (crude); LC-MS: Calc. for $C_{23}H_{25}FN_6O_6$, 500.49; Obs.: 501.1; $^1H$ NMR (400 MHz, DMSO-$d_6$): δ 11.19 (s, 1H), 7.59 (d, J=8.68 Hz, 1H), 7.42 (d, J=8.64 Hz, 1H), 6.68-6.79 (m, 2H), 5.89 (s, 1H), 4.68-4.60 (m, 4H), 4.13 (t, J=9.08 Hz, 1H), 3.82-3.91 (m, 3H), 3.45 (s, 2H), 2.82 (d, J=36.44 Hz, 6H), 1.23 (s, 3H).

Step 3: (S)-6-(5-(((2-(6-Fluoro-4-(2-hydroxyethyl)-3-oxo-3,4-dihydroquinoxalin-5-yl)ethyl)amino)methyl)-2-oxooxazolidin-3-yl)-2H-pyrido[3,2-b][1,4]oxazin-3(4H)-one To a stirred solution of compound 9b (0.15 g, 0.30 mmol) in 1,4-dioxane (10 mL) at room temperature under nitrogen atmosphere was added $MnO_2$ (0.26 g, 0.30 mmol). The resulting mixture was heated to 100° C. and stirred for 15 minutes. After that, the reaction mixture was filtered through celite pad and the filtrated was concentrated in vacuo. The obtained crude product was further purified by preparative HPLC to get Example 9 as formate salt (off-white solid). Yield: 0.07 g, 46.97%; LC-MS: Calc. for $C_{23}H_{23}FN_6O_6$ 498.47; Obs. 499.2 $[M+H]^+$; $^1H$ NMR (400 MHz, DMSO-$d_6$): δ 11.20 (s, 1H), 8.16 (d, J=13.40 Hz, 2H), 7.75 (t, J=6.60 Hz, 1H), 7.60 (d, J=8.68 Hz, 1H), 7.43 (d, J=8.68 Hz, 1H), 7.27 (t, J=9.20 Hz, 1H), 4.74-4.72 (m, 1H), 4.62 (s, 2H), 4.43 (t, J=5.88 Hz, 2H), 4.13 (t, J=9.32 Hz, 1H), 3.82-3.86 (m, 1H), 3.67 (t, J=5.92 Hz, 2H), 3.33-3.19 (m, 3H), 2.88 (d, J=8.00 Hz, 4H); HPLC: 8.37 min; 99.8%; HPLC Column: Atlantis dC18 (250*4.6) mm 5 μm, Mobile Phase A: 0.1% TFA in water, Mobile Phase B: Acetonitrile.

Example 10: (S)-6-(5-(((2-(7-Fluoro-1-(2-hydroxyethyl)-2-oxo-1,2-dihydroquinolin-8-yl)ethyl)amino)methyl)-2-oxooxazolidin-3-yl)-2H-pyrido[3,2-b][1,4]oxazin-3(4H)-one

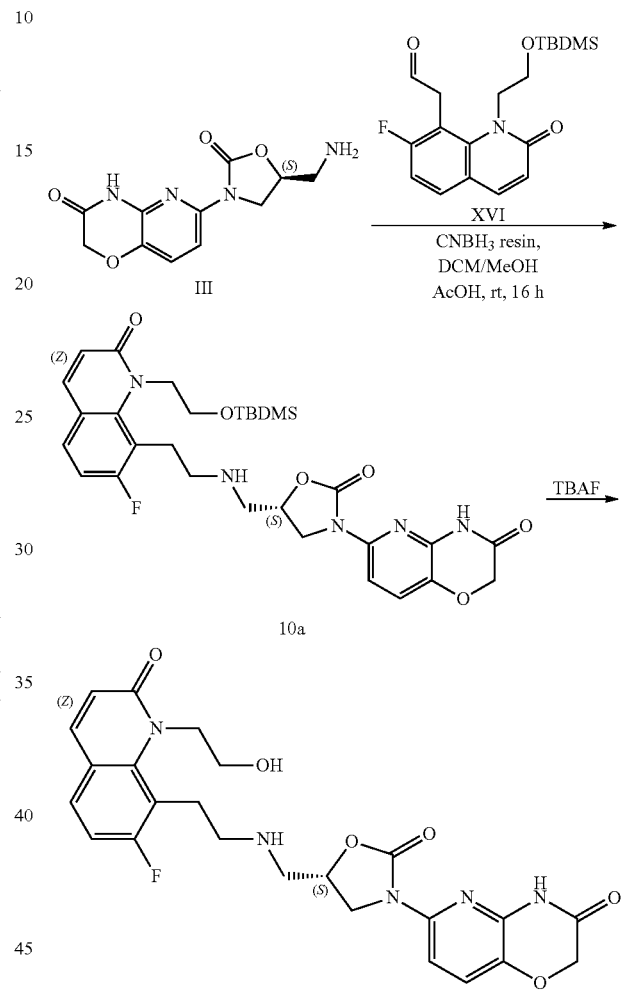

Example 10

Step 1: (S)-6-(5-(((2-(1-(2-((tert-butyldimethylsilyl)oxy)ethyl)-7-fluoro-2-oxo-1,2-dihydroquinolin-8-yl)ethyl)amino)methyl)-2-oxooxazolidin-3-yl)-2H-pyrido[3,2-b][1,4]oxazin-3(4H)-one (10a)

To a stirred mixture of compound XVI (10 g, 27.51 mmol) and compound III (5.83 g, 22.0 mmol) in dry methanol/dichloromethane (600 mL, 1:1) at room temperature under nitrogen atmosphere was added AcOH (10 mL) and allowed to stir for 16 hours. Then cyanoborohydride resin (25 g, 55.02 mmol) was added to the reaction mixture and continued to stir for another 10 minutes. After that the reaction mixture was filtered and the filtrate was concentrated in vacuo. The obtained crude product was further purified by column chromatography using silica gel (230-400 mesh) eluting with 5% methanol in dichloromethane to get compound 10a as an off-white solid. Yield: 7.0 g, 41.61%;

LC-MS Calc. for $C_{30}H_{38}FN_5O_6Si$, 611.75; Obs.: 612.3 [M$^+$+H]; $^1$H NMR (400 MHz, DMSO-d$_6$): δ11.18 (s, 1H), 7.83 (d, J=9.44 Hz, 1H), 7.60 (d, J=8.52 Hz, 1H), 7.42 (d, J=8.64 Hz, 1H), 7.10 (t, J=9.52 Hz, 1H), 6.53 (d, J=9.28 Hz, 1H), 4.75-4.61 (m, 2H), 4.52 (s, 3H), 4.12 (s, 1H), 3.84 (s, 3H), 3.78-3.74 (m, 2H), 3.33 (t, J=18.04 Hz, 2H), 3.11 (t, J=6.48 Hz, 2H), 2.83 (t, J=6.00 Hz, 2H), 0.62 (s, 9H), 0.21 (s, 6H).

Step 2: (S)-6-(5-(((2-(7-Fluoro-1-(2-hydroxyethyl)-2-oxo-1,2-dihydroquinolin-8-yl)ethyl)amino)methyl)-2-oxooxazolidin-3-yl)-2H-pyrido[3,2-b][1,4]oxazin-3(4H)-one To a stirred solution of compound 10a (7 g 11.44 mmol) in THF (35 mL) at 0° C. under nitrogen atmosphere was added tetra-n-butyl ammonium fluoride (22 mL 22.88 mmol). The resulting mixture was warmed to room temperature and stirred for 1 hour. After that, the reaction mixture was concentrated completely under reduced pressure. The obtained crude product compound was further stirred with 7 mL water for 5 minutes. The solid formed was filtered and washed with 10% MeOH in water followed by 10% MeOH in ether and dried under vacuo.

The product obtained was subsequently stirred in 5% formic acid in acetonitrile was stirred at 0° C. for 30 minutes, filtered, washed with 10% MeOH in diethyl ether and dried under vacuo to get Example 10 as formic acid salt (white solid). Yield: 2.5 g, 43.93%; LC-MS Calc. for $C_{24}H_{24}FN_5O_6$, 497.48; Obs.: 498.1[M$^+$+H]; $^1$H NMR (400 MHz, DMSO-d$_6$): δ 11.19 (s, 1H), 8.15 (s, 1H), 7.83 (d, J=9.40 Hz, 1H), 7.64-7.58 (m, 2H), 7.42 (d, J=8.68 Hz, 1H), 7.12 (t, J=9.20 Hz, 1H), 6.52 (d, J=9.36 Hz, 1H), 4.73 (s, 1H), 4.61 (s, 2H), 4.36 (t, J=6.24 Hz, 2H), 4.11 (t, J=9.28 Hz, 1H), 3.86-3.82 (m, 1H), 3.63 (t, J=6.36 Hz, 3H), 3.12 (s, 2H), 2.85 (t, J=7.08 Hz, 4H).

Example 11: (S)-6-(5-(((2-(7-fluoro-1-(2-(methylsulfonyl)ethyl)-2-oxo-1,2-dihydroquinolin-8-yl)ethyl)amino)methyl)-2-oxooxazolidin-3-yl)-2H-pyrido[3,2-b][1,4]oxazin-3(4H)-one

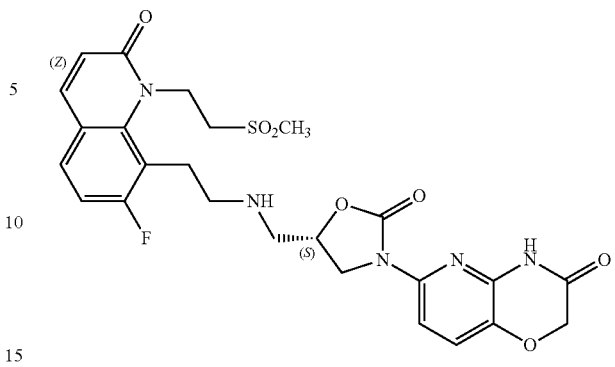

Example 11

To a stirred mixture of compound XVIII (0.07 g, 0.225 mmol) and compound III (0.06 g, 0.225 mmol) in dry MeOH/dichloromethane (10 mL, 1:1) at room temperature under nitrogen atmosphere was added AcOH (0.10 mL) and allowed to stir for 16 hours. Then cyanoborohydride resin (0.16 g, 0.337 mmol) was added to the reaction mixture at room temperature and continued to stir for 10 minutes. After that, the reaction mixture was filtered and the filtrate was concentrated vacuo. The obtained crude product was further purified by preparative HPLC to get Example 11 as formic acid salt (off-white solid). Yield: 16 mg, 12.8%; LC-MS Calc. for $C_{25}H_{26}FN_5O_7S$, 559.57; Obs.: 560.2[M$^+$+H]; $^1$H NMR (400 MHz, DMSO-d$_6$): δ 8.15 (s, 1H), 7.88 (d, J=9.40 Hz, 1H), 7.66 (t, J=7.04 Hz, 1H), 7.58 (d, J=8.64 Hz, 1H), 7.42 (d, J=8.64 Hz, 1H), 7.18 (t, J=9.04 Hz, 1H), 6.56 (d, J=9.32 Hz, 1H), 4.71-4.65 (m, 3H), 4.62 (s, 2H), 4.11 (t, J=9.12 Hz, 1H), 3.84-3.80 (m, 2H), 3.63 (t, J=6.84 Hz, 4H), 3.07 (s, 3H), 2.90 (t, J=6.08 Hz, 4H); HPLC Purity=98.10% (HPLC Column: Atlantis dC18 (250×4.6) mm 5 μm, Mobile Phase A: 0.1% TFA in water, Mobile Phase B: Acetonitrile).

Example 12: (S)-6-(5-(((2-(7-fluoro-4-(hydroxymethyl)-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one

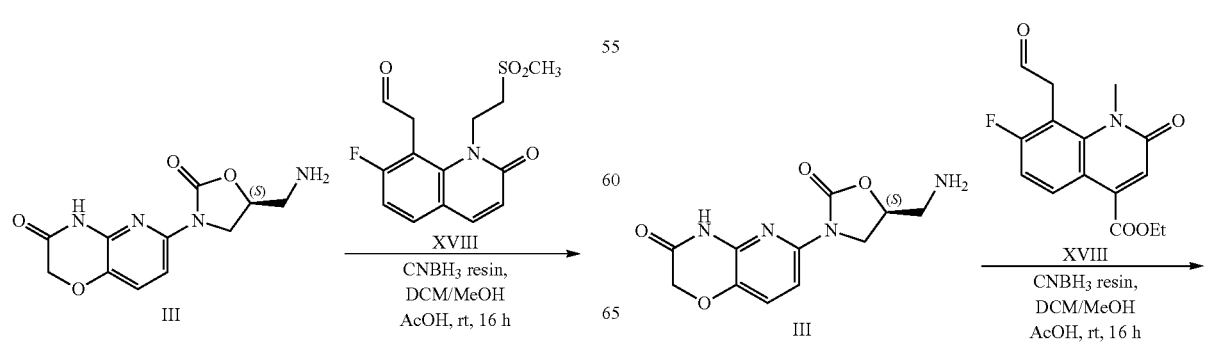

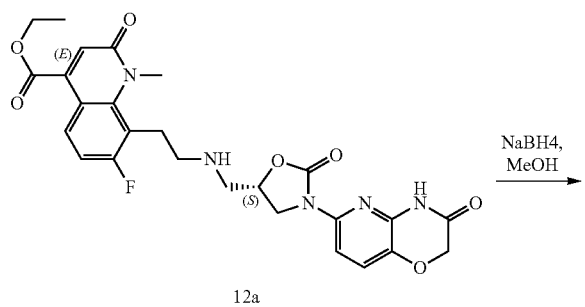

12a

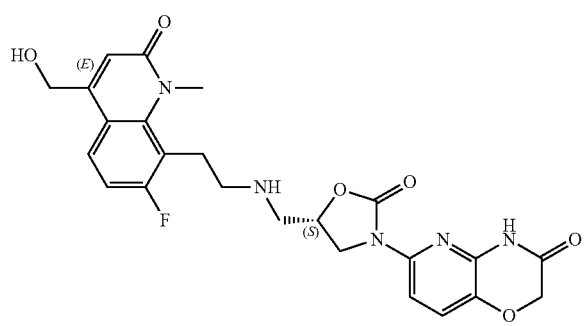

Example 12

Step 1: Ethyl (S)-7-fluoro-1-methyl-2-oxo-8-(2-(((2-oxo-3-(3-oxo-3,4-dihydro-2H-pyrido[3,2-b][1,4]oxazin-6-yl)oxazolidin-5-yl)methyl)amino)ethyl)-1,2-dihydroquinoline-4-carboxylate (12a)

To a stirred mixture of compound XVIII (0.20 g, 0.68 mmol) and compound III (0.182 g, 0.68 mmol) in dry methanol/dichloromethane (20 mL, 1:1) at room temperature under nitrogen atmosphere was added AcOH (0.20 mL) and allowed to stir for 16 hours. Then cyanoborohydride resin (0.565 g, 1.37 mmol) was added to the reaction mixture and continued to stir for another 10 minutes. After that the reaction mixture was filtered and the filtrate was concentrated in vacuo. The obtained crude product was further purified by column chromatography silica gel (230-400 mesh) eluting with 7% methanol in dichloromethane to get compound 12a as white solid. Yield: 0.18 g, 48.65%; LC-MS Calc. for $C_{26}H_{26}FN_5O_7$, 539.52; Obs.: 540.2; [M$^+$+H].

Step 2: (S)-6-(5-(((2-(7-fluoro-4-(hydroxymethyl)-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one To a stirred solution of compound 12a (0.15 g, 0.28 mmol) in dry methanol (5 mL) at 0° C. under nitrogen atmosphere was added sodium borohydride (22 mg, 0.56 mmol) at once. The resulting mixture was warmed to room temperature and stirred for 30 minutes. After that, the reaction mixture was diluted with water and extracted with ethyl acetate (2×50 mL). The combined organic phase was washed with brine, dried over sodium sulfate and concentrated in vacuo. The obtained crude product was further purified by preparative HPLC to get Example 12 as formate salt (white solid). Yield: 25 mg, 20.23%. LC-MS Calc. for $C_{24}H_{24}FN_5O_6$, 497.17; Obs.: 496.2 [M$^+$–H]; $^1$H NMR (400 MHz, DMSO-d$_6$): δ 11.24 (s, 1H), 9.14 (s, 2H), 7.73-7.71 (m, 1H), 7.69-7.52 (m, 1H), 7.47-7.45 (m, 1H), 7.23-7.20 (m, 1H), 6.64 (s, 1H), 5.56 (s, 1H), 4.98 (brs, 1H), 4.71 (s, 3H), 4.28-4.23 (m, 2H), 3.70 (s, 3H), 3.49-3.42 (m, 4H), 3.39-3.27 (m, 4H); HPLC Purity=96.35% (HPLC Column: Atlantis dC18 (250*4.6) mm 5 μm, Mobile Phase A: 0.1% TFA in water, Mobile Phase B: Acetonitrile.)

Example 13: (S)-6-(5-(((2-(4-(Aminomethyl)-7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one

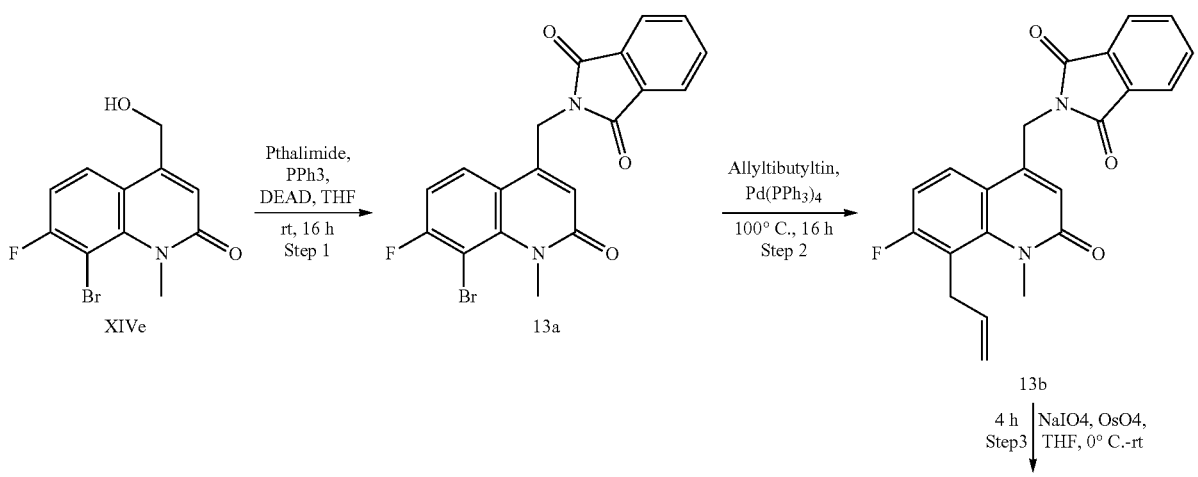

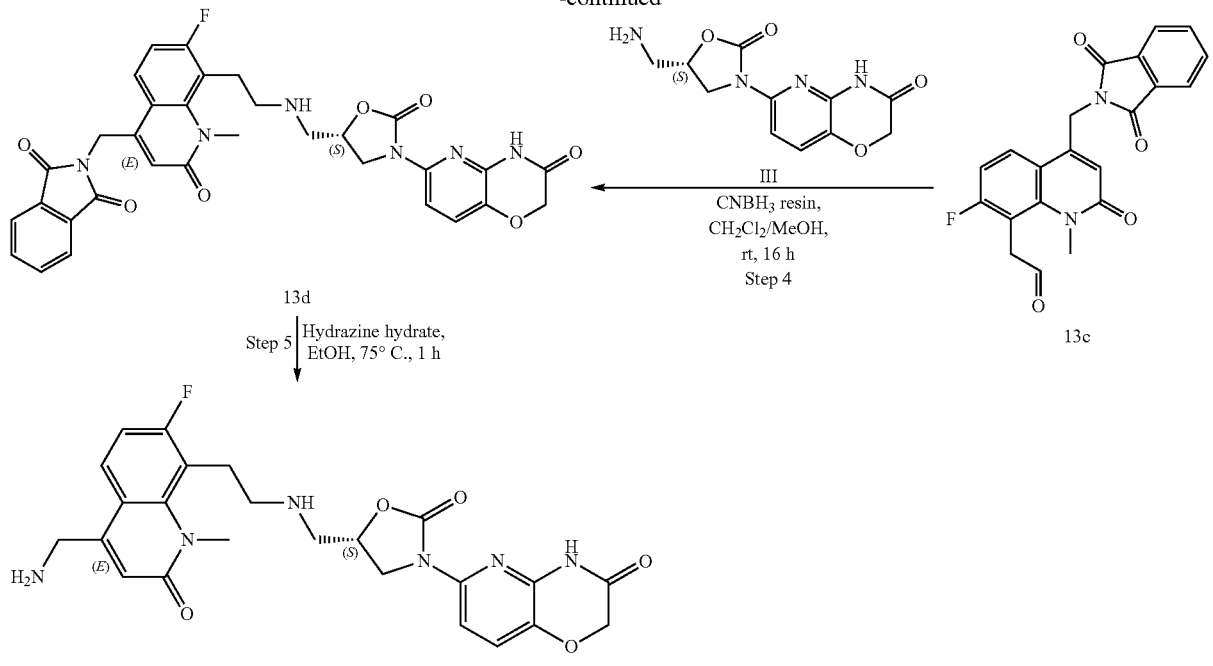

Step 1: 2-((8-Bromo-7-fluoro-1-methyl-2-oxo-1,2-dihydroquinolin-4-yl) methyl) isoindoline-1,3-dione (13a)

To a stirred solution of compound XIVe (3.0 g, 10.48 mmol) in THF (60 mL) at 0° C. under nitrogen atmosphere were added triphenylphosphine (4.13 g, 15.72 mmol) and pthalimide (2.30 g, 15.72 mmol) followed by dropwise addition of DEAD (3.30 mL, 20.97 mmol). The resulting mixture was then warmed to room temperature and stirred for 16 hours. After that, the reaction m mixture was diluted with water and extracted with EtOAc (2×100 mL). The combined organic extract was washed with brine, dried over sodium sulfate and concentrated in vacuo. The obtained crude product was further purified by column chromatography silica gel (230-400 mesh, 20% EtOAc in petroleum ether) to get compound 13a as a white solid. Yield: 2.5 g, 57.47%; LC-MS Calc. for $C_{19}H_{12}BrFN_2O_3$ 415.20; Obs.: 416.0; [M$^+$+H].

Step 2: 2-((8-Allyl-7-fluoro-1-methyl-2-oxo-1,2-dihydroquinolin-4-yl)methyl)isoindoline-1,3-dione (13b)

To a stirred solution of compound 13a (3.0 g, 7.22 mmol) in DMF (45 mL) at room temperature was added allyltributyltin (3.3 mL, 10.83 mmol). The resulting mixture was degassed with a stream of nitrogen for 30 minutes. Then tetrakis (triphenylphosphine)palladium(0) (0.417 g, 0.36 mmol) was added to reaction mixture at room temperature. The resulting mixture was then heated to 100° C. and stirred for 16 hours. After that, the reaction mixture was cooled to 0° C., diluted with water (60 mL) and extracted with ethyl acetate (2×100 mL). The combined organic phase was washed with brine, dried over sodium sulfate and concentrated in vacuo. The obtained crude product was purified by column chromatography silica gel (230-400 mesh, 50% ethyl acetate in petroleum ether) to get compound 13b as a brown solid. Yield: 1.8 g, 65.69%; LC-MS Calc. for $C_{22}H_{17}FN_2O_3$, 376.39; Obs.: 377.1; [M$^+$+H].

Step 3: 2-(4-((1,3-Dioxoisoindolin-2-yl) methyl)-7-fluoro-1-methyl-2-oxo-1,2-dihydroquinolin-8-yl) acetaldehyde (13c)

To a stirred solution of compound 13b (1.6 g, 4.25 mmol) in a mixture of THF/H$_2$O (120 mL, 2:1) at 0° C. under nitrogen atmosphere were added sodium meta periodate (2.73 g 12.75 mmol) and osmium tetroxide (2.5% in t-BuOH, 2.20 mL 0.21 mmol) successively. The resulting mixture was warmed to room temperature and stirred for 4 hours. After that, the reaction mixture was diluted with water and extracted with ethyl acetate (2×100 mL). The combined organic phase was washed with sodium thiosulfate, brine, dried over sodium sulfate and concentrated in vacuo. The obtained crude product was further purified by column chromatography silica gel (230-400 mesh) eluting with 60% ethyl acetate in petroleum ether) to get compound 13c as an off-white solid. Yield: 0.9 g, 56.25%; LC-MS Calc. for $C_{21}H_{15}FN_2O_4$, 378.36; Obs.: 379.1 [M$^+$+H]; $^1$H NMR (400 MHz, DMSO-d$_6$): δ 9.83 (s, 1H), 8.03-7.85 (m, 6H), 7.31-7.25 (m, 1H), 5.03 (s, 2H), 4.32 (d, 2H, J=3.6 Hz), 3.48 (s, 3H).

Step 4: (S)-2-((7-fluoro-1-methyl-2-oxo-8-(2-(((2-oxo-3-(3-oxo-3,4-dihydro-2H-pyrido[3,2-b][1,4] oxazin-6-yl)oxazolidin-5-yl)methyl)amino)ethyl)-1,2-dihydroquinolin-4-yl)methyl)isoindoline-1,3-dione (13d)

To a stirred mixture of compound 13c (0.30 g, 0.79 mmol) and compound III (0.25 g, 0.95 mmol) in dry MeOH/dichloromethane (20 mL, 1:1) at room temperature under nitrogen atmosphere was added AcOH (0.30 mL) and allowed to stir for 16 hours. Then cyanoborohydride resin (0.77 g, 1.58 mmol) was added to the reaction mixture and continued to stir for 10 minutes. After that, the reaction mixture was filtered and the filtrate was concentrated under reduced pressure. The obtained crude was further purified by column chromatography silica gel (230-400 mesh) eluting with 7% MeOH in dichloromethane) to get compound 13d [racemic] as a white solid. Yield: 0.18 g, 36.29%; LC-MS Calc. for $C_{32}H_{27}FN_6O_7$, 626.60; Obs.: 627.2; [M$^+$+H]

Step 5: (S)-6-(5-(((2-(4-(Aminomethyl)-7-fluoro-1-methyl-2-oxo-1,2-dihydroquinolin-8-yl)ethyl)amino) methyl)-2-oxooxazolidin-3-yl)-2H-pyrido[3,2-b][1,4]oxazin-3(4H)-one To a solution of compound 13d (0.35 g, 0.56 mmol) in ethanol (7 mL) at room temperature under nitrogen atmosphere was added hydrazine hydrate (84 mg, 1.67 mmol). The resulting mixture was heated to 75° C. and stirred for 1 hours. After that, the reaction mixture was completely concentrated under reduced pressure. The obtained crude product was further purified by preparative HPLC to get example 13 as a white solid. Yield: 0.2 g, 72.20%; LC-MS Calc. for $C_{24}H_{25}FN_6O_5$, 496.50; Obs.: 497.1 [M$^+$+H]; $^1$H NMR (400 MHz, DMSO-d$_6$): δ 8.20 (s, 2H), 7.72-7.69 (m, 1H), 7.61-7.58 (m, 1H), 7.45-7.41 (m, 1H), 7.18-7.12 (m, 1H), 6.65 (s, 1H), 4.70 (s, br, 1H), 4.62 (s, 2H), 4.13-4.08 (m, 2H), 4.01 (s, 2H), 3.86-3.81 (m, 2H), 3.68 (s, 3H), 3.26 (s, br, 2H), 2.87-2.80 (m, 4H); HPLC Purity=96.35% (HPLC Column: Atlantis dC18 (250*4.6) mm 5 μm, Mobile Phase A: 0.1% TFA in water, Mobile Phase B: Acetonitrile.)

Example 14: (R)-6-(5-(((2-(7-Fluoro-1-methyl-2-oxo-1,2-dihydroquinolin-8-yl)ethyl)amino)methyl)-2-oxooxazolidin-3-yl)-2H-pyrazino[2,3-b][1,4]oxazin-3(4H)-one

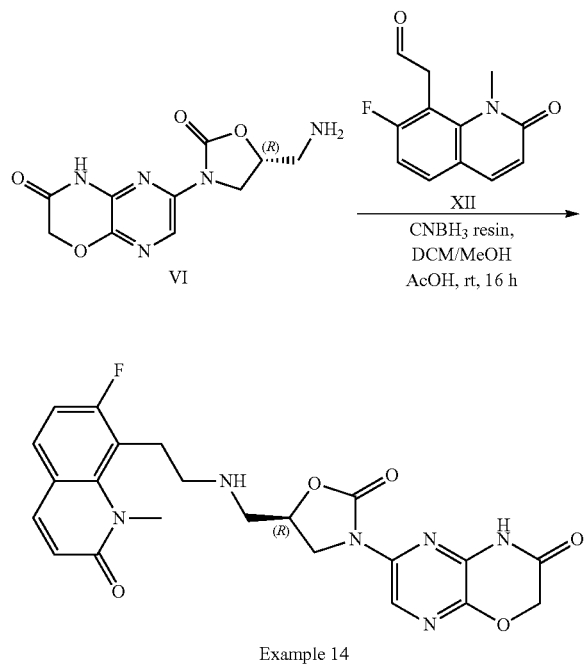

Example 14

To a stirred mixture of compound XII (0.41 g, 1.88 mmol) and compound VI (0.5 g, 1.88 mmol) in dry methanol/ dichloromethane (40 mL, 1:1) at room temperature under nitrogen atmosphere was added AcOH (0.50 mL) and allowed to stir for 16 hours. Then cyanoborohydride resin (1.53 g, 3.39 mmol) was added to the reaction mixture and continued to stir for another 10 minutes. After that the reaction mixture was filtered and the filtrate was concentrated under reduced pressure. The obtained crude product was further purified by preparative HPLC to get example 14 as formate salt (pale yellow solid). Yield: 0.2 g; 22.98%; LC-MS Calc. for $C_{22}H_{21}FN_6O_5$, 468.45; Obs.: 467.1 [M$^+$−H]; $^1$H NMR (400 MHz, DMSO-d$_6$): δ 11.62 (s, 1H), 9.16 (brs, 1H), 8.40-8.38 (m, 1H), 7.89-7.86 (m, 1H), 7.73-7.69 (m, 1H), 7.22-7.17 (m, 1H), 6.59-6.55 (m, 1H), 5.01 (brs, 1H), 4.88-4.87 (m, 2H), 4.23-4.19 (m, 1H), 3.83-3.79 (m, 1H), 3.73-3.72 (m, 3H), 3.40-3.34 (m, 4H), 3.14 brs, 2H). HPLC Purity=96.38% (HPLC Column: Atlantis dC18 (250*4.6) mm 5 μm, Mobile Phase A: 0.1% TFA in water, Mobile Phase B: Acetonitrile).

Example 15: (R)-6-(5-(((2-(7-Fluoro-1-methyl-2-oxo-1,2-dihydroquinolin-8-yl)ethyl)amino)methyl)-2-oxooxazolidin-3-yl)-2H-pyrazino[2,3-b][1,4]oxazin-3(4H)-one

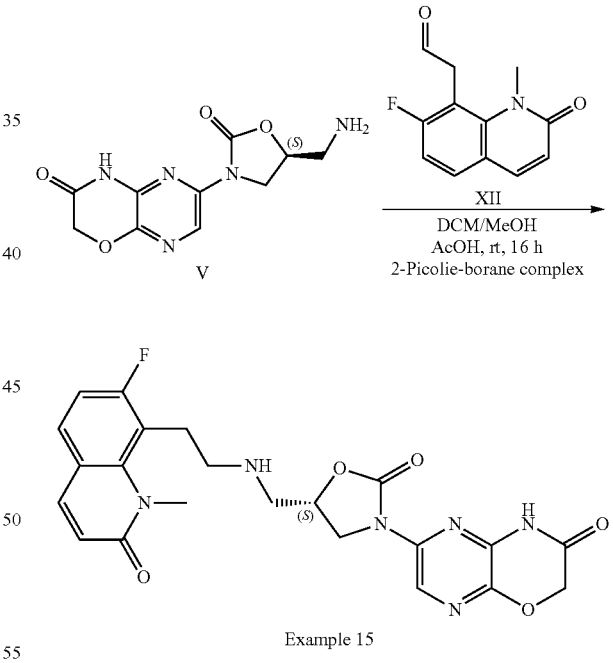

Example 15

To a stirred solution of compound XII (3 g, 13.69 mmol) and compound V (3.63 g, 0.68 mmol) in a mixture of dry MeOH/dichloromethane (200 mL, 1:1) at room temperature under nitrogen atmosphere was added AcOH (3 mL) and allowed to stir for 16 hours. Then 2-picoline borane complex (0.73 g, 6.8 mmol) was added at room temperature and continued to stir for 10 minutes. After that the reaction mixture was quenched with formic acid (2 mL), filtered and concentrated to remove MeOH to get the crude product, which was further purified by GRACE (reverse phase) to get Example 15 as formate salt (off white solid). Yield: 2.54 g, 39.62%; LC-MS Calc. for $C_{22}H_{21}FN_6O_5$, 468.45; Obs.: 469.1; [M++H]; ¹H NMR (400 MHz, DMSO-d₆): δ 11.61 (bs, 1H), 8.38-8.37 (d, 1H, J=3.2 Hz), 8.14 (s, 1H), 7.84-7.82 (d, 1H, J=9.2 Hz), 7.64-7.60 (dd, 1H, $J_1$=8.8, $J_2$=6.4 Hz), 7.15-7.10 (t, 1H, J=8.8 Hz), 6.54-6.52 (d, 1H, J=9.2 Hz), 4.85 (s, 2H), 4.79-4.76 (m, 1H), 4.11-4.06 (m, 1H), 3.83-3.79 (m, 1H), 3.71 (s, 3H), 3.16-3.13 (m, 2H), 2.95-2.91 (m, 2H), 2.89-2.82 (m, 2H). HPLC Purity=97.52%, Column: Atlantis dC18 (250×4.6) mm, 5 μm, Mobile Phase A: 0.1% TFA in water, Mobile Phase B: Acetonitrile.

Example 16: (S)-2-(5-(((2-(7-fluoro-1-methyl-2-oxo-1,2-dihydroquinolin-8-yl) ethyl) amino) methyl)-2-oxooxazolidin-3-yl)-6H-pyrimido[5,4-b][1,4]oxazin-7(8H)-one

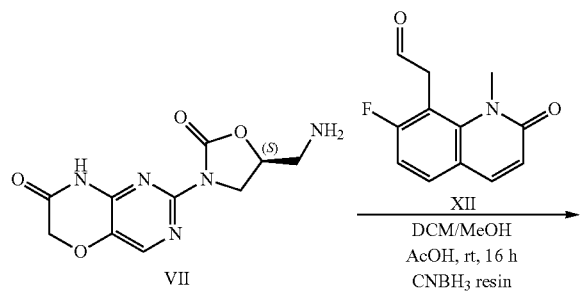

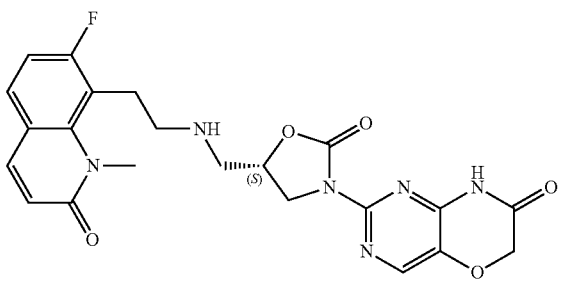

Example 16

To a stirred solution of compound XII (0.3 g, 1.36 mmol) and compound VII (0.43 g, 1.64 mmol) in dry MeOH/DCM (30 mL, 1:1) at room temperature under nitrogen atmosphere was added AcOH (0.3 mL) and allowed to stir for 16 hours. Then cyanoborohydride resin (1.36 g, 2.73 mmol) was added to the reaction mixture at rt and continued to stir for 10 minutes. After that, the reaction mixture was filtered and concentrated in vacuo. The obtained crude product further was purified by preparative HPLC to get Example 16 as formate salt (off white solid) Yield: 0.12 g, 18.75%; LC-MS: Calc. for $C_{22}H_{21}FN_6O_5$, 468.45; Obs. 469.1 [M+H]+; ¹H-NMR (400 MHz, DMSO-d₆): δ 8.22 (s, 1H), 8.16 (s, 1H), 7.85 (d, J=9.20 Hz, 1H), 7.64 (t, J=6.80 Hz, 1H), 7.15 (t, J=8.80 Hz, 1H), 6.55 (d, J=9.20 Hz, 1H), 4.72 (s, 3H), 4.13 (t, J=9.20 Hz, 1H), 3.89-3.85 (m, 1H), 3.73 (s, 3H), 3.17-3.15 (m, 2H), 2.92-2.84 (m, 4H).

Example 17: (S)-2-(5-(((2-(6-fluoro-4-methyl-3-oxo-3,4-dihydroquinoxalin-5-yl)ethyl)amino) methyl)-2-oxooxazolidin-3-yl)-6H-pyrimido[5,4-b][1,4]oxazin-7(8H)-one

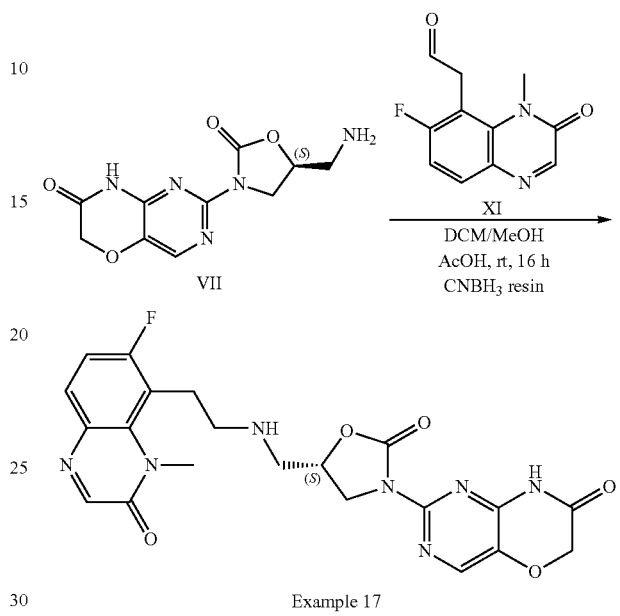

Example 17

To a stirred mixture of compound XI (0.1 g, 0.45 mmol) and compound VII (0.12 g, 0.45 mmol) in dry methanol/dichloromethane (20 mL, 1:1) at room temperature under nitrogen atmosphere was added AcOH (0.1 mL) and allowed to stir for 16 hours. Then cyanoborohydride resin (0.45 g, 0.90 mmol) was added to the reaction mixture at rt and continued to stir for another 10 minutes. After that the reaction mixture was filtered and the filtrate was concentrated under reduced pressure. The obtained crude product was further purified by preparative HPLC to get Example 17 as an off-white solid. Yield: 10 mg, 4.76%. LC-MS: Calc. for $C_{21}H_{20}FN_7O_5$, 469.43; Obs.: 470.2 [M+H]+.

Example 18: 6-((S)-5-((((S)-3-(7-Fluoro-1-methyl-2-oxo-1,2-dihydroquinolin-8-yl)-2-hydroxypropyl)amino)methyl)-2-oxooxazolidin-3-yl)-2H-pyrido[3,2-b][1,4]oxazin-3(4H)-one (Isomer 1) and Example 19: 6-((S)-5-((((R)-3-(7-Fluoro-1-methyl-2-oxo-1,2-dihydroquinolin-8-yl)-2-hydroxypropyl)amino) methyl)-2-oxooxazolidin-3-yl)-2H-pyrido[3,2-b][1,4]oxazin-3(4H)-one (Isomer 2)

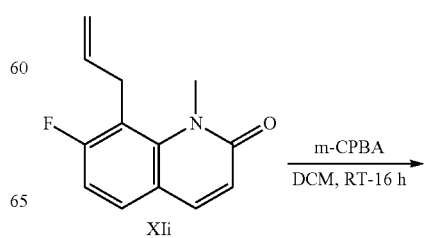

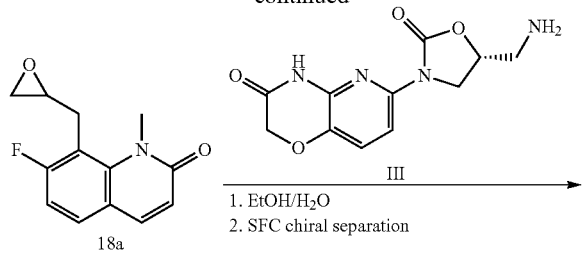

Step 1: 7-Fluoro-1-methyl-8-(oxiran-2-ylmethyl) quinolin-2(1H)-one (18a)

To a stirred solution of compound XII (2.35 g, 10.829 mmol) in dry dichloromethane (46 mL) at 0° C. under nitrogen atmosphere was added mCPBA (4.67 g, 27.73 mmol). The resulting reaction mixture was warmed room temperature and stir for 16 hours. After that the reaction mixture was further diluted with dichloromethane, washed with 10% aqueous NaHCO$_3$ solution (repeatedly) and brine. The organic layer was dried over anhydrous sodium sulphate, filtered and concentrated in vacuo. The obtained crude product was further purified by column chromatography using silica gel (230-400 mesh) by eluting with 35-50% ethyl acetate in petroleum ether to get compound 18a as an off white solid. Yield: 0.6 g, 23.80%; LC-MS Calc. for C$_{13}$H$_{12}$FNO$_2$ 233.23; Obs.: 234.1 [M$^+$+H]; $^1$H NMR (400 MHz, CDCl$_3$): δ 7.61 (d, J=9.4 Hz, 1H), 7.47-7.44 (m, 1H), 7.01 (t, J=8.88 Hz, 1H), 6.66 (d, J=9.36 Hz, 1H), 3.90 (s, 3H), 3.51-3.38 (m, 2H), 3.33 (t, J=3.64 Hz, 1H), 2.86 (t, J=4.20 Hz, 1H), 2.62-2.59 (m, 1H).

Step 2: Racemic 6-((5S)-5-(((3-(7-Fluoro-1-methyl-2-oxo-1,2-dihydroquinolin-8-yl)-2-hydroxypropyl) amino)methyl)-2-oxoxazolidin-3-yl)-2H-pyrido[3,2-b][1,4]oxazin-3(4H)-one A stirred suspension of compound 18a (0.55 g, 2.360 mmol) and compound III (0.625 g, 2.360 mmol) in mixture of EtOH/H$_2$O (12 mL, 2:1) in a seal tube was heated to 100° C. and stirred for 16 hours. The reaction mixture was cooled to room temperature and concentrated completely under reduced pressure to get the crude, which was subsequently purified by preparative HPLC to get racemic mixture (Yield: 0.33 g). The racemic mixture was further subjected chiral SFC (Chiral HPLC) purification to get two isomers Example 18 (Yield: 0.11 g) and Example 19 (Yield: 0.32 g, 27.35%) as an off-white solid; LC-MS Calc. for C$_{24}$H$_{24}$FN$_5$O$_6$ 497.48, Obs. 498.1 & 499.1; [M$^+$+H]; $^1$H-NMR (400 MHz, DMSO-d$_6$): δ 11.21 (s, 1H), 8.15 (s, 1H), 7.87 (d, J=9.44 Hz, 1H), 7.66-7.59 (m, 2H), 7.41-7.44 (m, 1H), 7.15 (t, J=9.16 Hz, 1H), 6.55 (d, J=9.40 Hz, 1H), 4.76 (s, 1H), 4.61 (s, 2H), 4.14 (t, J=8.84 Hz, 1H), 3.86 (t, J=8.60 Hz, 1H), 3.75 (s, 4H), 3.18-3.13 (m, 2H), 2.91 (s, 2H), 2.68-2.61 (m, 2H); Chiral HPLC: Purity: 99.99% (47:52) (RT-5.91, RT-7.33 min) Column: YMC cellulose SB Co-solvent 40% (0.5% Isopropyl amine in IPA), Example 18 Analytical Data: LC-MS Calc. for C$_{24}$H$_{24}$FN$_5$O$_6$ 497.48; Obs. 498.1 & 499.1; [M$^+$+H]; $^1$H NMR (400 MHz, DMSO-d$_6$): δ 11.19 (s, 1H), 7.85 (d, J=9.4 Hz, 1H), 7.63-7.56 (m, 2H), 7.39 (d, J=8.6 Hz, 1H), 7.12 (t, J=9 Hz, 1H), 6.55 (d, J=9.40 Hz, 1H), 4.87-4.86 (m, 1H), 4.73-4.69 (m, 1H), 4.59 (s, 2H), 4.14 (t, J=9.2 Hz, 1H) 3.88-3.85 (m, 1H), 3.75 (s, 4H), 3.13-3.10 (m, 2H), 2.82-2.81 (m, 2H), 2.56-2.55 (m, 2H); Chiral HPLC: Purity: 98.77% (RT-5.84 min) Column: YMC cellulose SB Co-solvent 40% (0.5% Isopropyl amine in IPA).

Example 19 Analytical Data: LC-MS

Calc. for C$_{24}$H$_{24}$FN$_5$O$_6$ 497.48, Obs. 498.1; [M$^+$+H]; Chiral HPLC: Purity: 97.45 (RT-6.84 min) Column: YMC cellulose SB Co-solvent 40% (0.5% Isopropyl amine in IPA).

Example 20: (S)-6-(5-(((2-(7-Fluoro-1-(2-hydroxyethyl)-2-oxo-1,2-dihydroquinolin-8-yl)ethyl)amino) methyl)-2-oxoxazolidin-3-yl)-2H-pyrido[3,2-b][1,4]oxazin-3(4H)-one

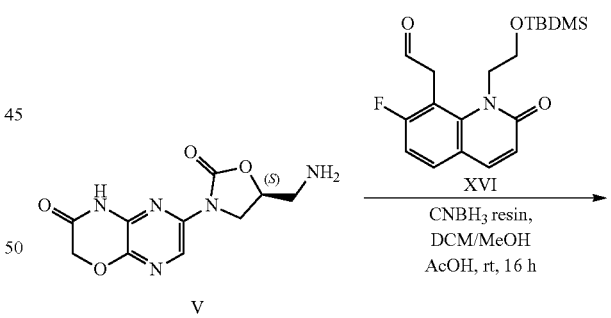

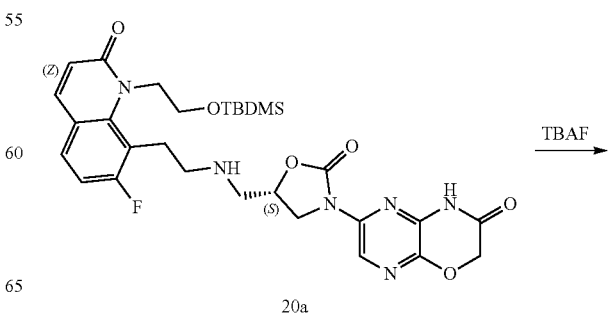

-continued

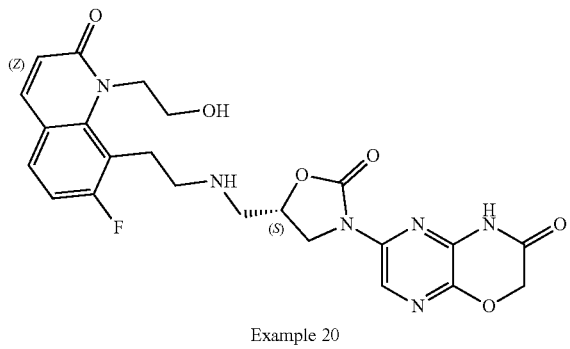

Example 20

Step 1: (S)-6-(5-(((2-(1-(2-((tert-butyldimethylsilyl)oxy)ethyl)-7-fluoro-2-oxo-1,2-dihydroquinolin-8-yl)ethyl)amino)methyl)-2-oxooxazolidin-3-yl)-2H-pyrazino[2,3-b][1,4]oxazin-3(4H)-one (20a)

To a stirred mixture of compound XVI (0.2 g, 0.55 mmol) and compound V (0.14 g, 0.55 mmol) in dry methanol/dichloromethane (40 mL, 1:1) at room temperature under nitrogen atmosphere was added AcOH (0.2 mL) and allowed to stir for 16 hours. Then cyanoborohydride resin (0.5 g, 1.10 mmol) was added to the reaction mixture and continued to stir for another 10 minutes. After that the reaction mixture was filtered and the filtrate was concentrated in vacuo. The obtained crude product was further purified by column chromatography using silica gel (230-400 mesh) eluting with 5% methanol in dichloromethane to get compound 20a as an off-white solid; Yield: 0.11 g, 33.33%; LC-MS Calc. for $C_{29}H_{37}FN_6O_6Si$, 612.73; Obs.: 613.3 [M$^+$+H].

Step 2: (S)-6-(5-(((2-(7-Fluoro-1-(2-hydroxyethyl)-2-oxo-1,2-dihydroquinolin-8-yl)ethyl)amino)methyl)-2-oxooxazolidin-3-yl)-2H-pyrido[3,2-b][1,4]oxazin-3(4H)-one To a stirred solution of compound 20a (0.11 g 0.179 mmol) in THF (5 mL) at 0° C. under nitrogen atmosphere was added tetra-n-butylammonium fluoride (22 mL 0.269 mmol). The resulting mixture was warmed to room temperature and stirred for 1 hour. After that, the reaction mixture was concentrated completely under reduced pressure. The obtained crude product was further purified by preparative HPLC to get example 20 as formate slat (white solid). Yield: 0.035 g 39.32%; LC-MS Calc. for $C_{23}H_{23}FN_6O_6$, 498.47; Obs.: 499.1 [M$^+$+H]; $^1$H NMR (400 MHz, DMSO-d$_6$): δ 11.65 (s, 1H), 8.39 (s, 1H), 8.15 (s, 1H), 7.84 (d, J=9.40 Hz, 1H), 7.63 (t, J=6.96 Hz, 1H), 7.15 (t, J=8.80 Hz, 1H), 6.53 (d, J=9.40 Hz, 1H), 4.87 (s, 2H), 4.78 (s, 1H), 4.39-4.36 (m, 2H), 4.10 (t, J=8.92 Hz, 1H), 3.84-3.80 (m, 1H), 3.66-3.63 (m, 2H), 3.12-3.11 (m, 2H), 2.96-2.87 (m, 4H).

Example 21: (S)-6-(5-(((2-(7-fluoro-1-(2-methoxyethyl)-2-oxo-1,2-dihydroquinolin-8-yl)ethyl)amino)methyl)-2-oxooxazolidin-3-yl)-2H-pyrazino[2,3-b][1,4]oxazin-3 (4H)-one

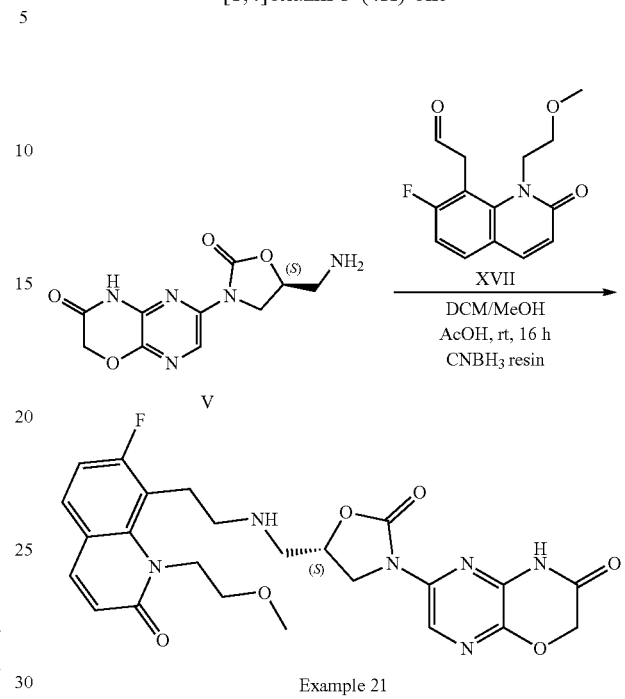

Example 21

To a stirred solution of compound XVII (0.1 g, 0.38 mmol) and amine V (0.11 g, 0.41 mmol) in a mixture of dry MeOH and dichloromethane (16 mL, 1:1) at room temperature under nitrogen was added AcOH (0.1 mL) and allowed to stir for 16 hours. Then cyanoborohydride resin (0.34 g, 0.68 mmol) was added at room temperature and continued stir for 15 minutes. The obtained crude product was further purified by preparative HPLC to get example 21 as formate salt (off white solid). Yield: 15 mg. 7.89%; LC-MS Calc. for $C_{24}H_{25}FN_6O_6$, 512.50; Obs: 513.2; [M+H]$^+$; $^1$H NMR (400 MHz, DMSO-d$_6$): δ 11.78 (brs, 1H), 8.38 (s, 1H), 8.16 (brs, 1H) 7.84 (d, J=8.4 Hz, 1H), 7.65-7.62 (m, 1H), 7.17-7.13 (m, 1H), 7.17-7.13 (m, 1H), 6.53 (d, J=9 Hz, 1H), 4.86 (s, 2H), 4.77 (brs, 1H), 4.47 (brs, 2H), 4.09-4.07 (m, 1H), 3.83-3.80 (m, 1H), 3.59-3.58 (m, 3H), 3.13 (s, 3H), 3.07 (brs, 2H), 2.89-2.67 (m, 4H).

Example 22: (S)-6-(5-(((2-(7-Fluoro-1-(2-methoxyethyl)-2-oxo-1,2-dihydroquinolin-8-yl)ethyl)amino)methyl)-2-oxooxazolidin-3-yl)-2H-pyrazino[2,3-b][1,4]oxazin-3(4H)-one

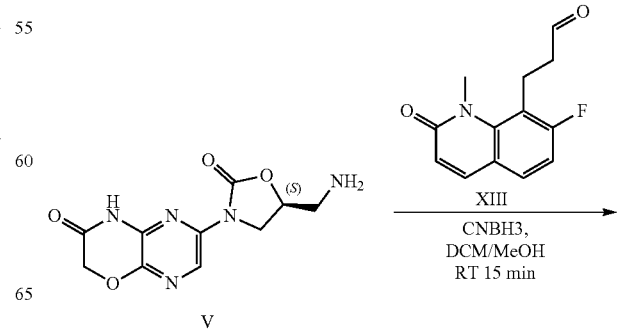

133

-continued

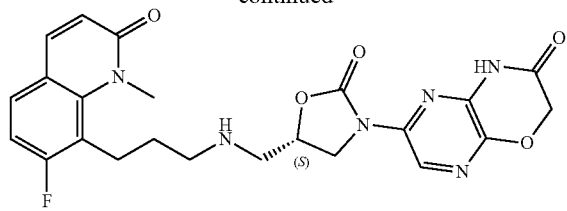

Example 22

134

-continued

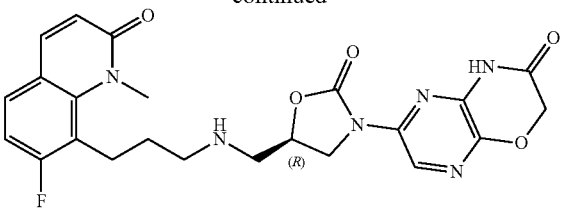

Example 23

To a stirred solution of compound XIII (0.25 g, 1.07 mmol) and compound V (0.28 g, 1.07 mmol) in mixture of dry methanol/dichloromethane (30 mL, 1:1) at room temperature under nitrogen atmosphere was added acetic acid (0.25 mL) and allowed to stir for 16 hours. Then cyanoborohydride resin (1.07 g, 2.14 mmol) was added to reaction mixture and continued to stir for 10 minutes. After that, the reaction mixture was filtered, and filtrate was concentrated under reduced pressure. The obtained crude was further purified by preparative HPLC to get Example 22 as formate salt (off-white solid). Yield: 0.052 g, 11.55%; LC-MS Calc. for $C_{23}H_{23}FN_6O_5$ 482.47; Obs.: 483.2 & 484.2 [M$^+$+H]; $^1$H-NMR (400 MHz, DMSO-d$_6$) δ 11.66 (s, 1H), 8.38 (s, 1H), 8.13 (s, 1H), 7.87 (d, J=9.44 Hz, 1H), 7.65 (t, J=8.24 Hz, 1H), 7.16 (t, J=9.60 Hz, 1H), 6.56 (d, J=9.36 Hz, 1H), 4.87 (s, 3H), 4.17 (brs, 1H), 3.86-3.81 (m, 1H), 3.69 (brs, 3H), 3.69 (brs, 2H), 3.00 (t, J=7.40 Hz, 2H), 2.85 (brs, 2H), 1.83 (s, 2H).

Example 23: (R)-6-(5-(((2-(7-Fluoro-1-(2-methoxyethyl)-2-oxo-1,2-dihydroquinolin-8-yl)ethyl)amino)methyl)-2-oxooxazolidin-3-yl)-2H-pyrazino[2,3-b][1,4]oxazin-3(4H)-one

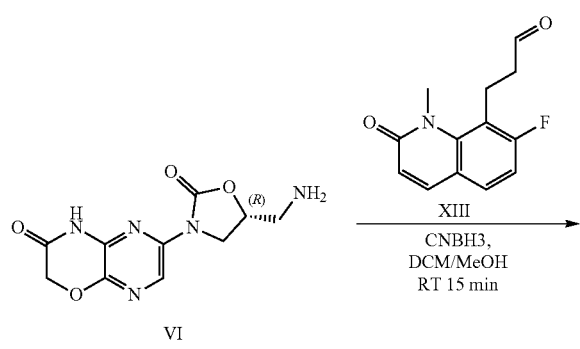

To a stirred mixture of compound XIII (0.7 g, 3.00 mmol) and compound VI (0.79 g, 3.00 mmol) in a mixture dry MeOH/dichloromethane (80 mL, 1:1) at room temperature under nitrogen atmosphere was added AcOH (0.7 mL) and allowed to stir for 16 hours. Then cyanoborohydride resin (2.73 g, 6.00 mmol) was added to the reaction mixture and continued to stir at room temperature for 10 minutes. After that, the reaction mixture was filtered and the filtrate was concentrated under reduced pressure. The obtained crude product was further purified by preparative HPLC to get example 23 as formate salt (white solid); Yield: 0.14 g 11.02%; LC-MS Calc. for $C_{23}H_{23}FN_6O_5$, 482.47; Obs.: 481.1 [M$^+$–H]; $^1$H NMR (400 MHz, DMSO-d$_6$): δ11.68 (s, 1H), 8.38 (s, 1H), 7.89 (d, 1H, J=9.2 Hz), 7.70-7.67 (m, 1H), 7.22-7.17 (m, 1H), 6.58 (d, 1H, J=9.2 Hz), 5.03-5.01 (m, 1H), 4.88 (s, 2H), 4.25-4.20 (m, 1H), 3.82-3.77 (m, 1H), 3.72 (s, 3H), 3.44 (s, br, 3H), 3.06-3.04 (m, 4H), 1.95 (s, br, 2H); HPLC Purity=93.45% (HPLC Column: Atlantis dC18 (250*4.6) mm 5 μm, Mobile Phase A: 0.1% TFA in water, Mobile Phase B: Acetonitrile.)

Example 24: (S)-6-(5-(2-((2-(7-Fluoro-1-methyl-2-oxo-1,2-dihydroquinolin-8-yl)ethyl)amino)ethyl)-2-oxooxazolidin-3-yl)-2H-pyrazino[2,3-b][1,4]oxazin-3(4H)-one and Example 25: (R)-6-(5-(2-((2-(7-Fluoro-1-methyl-2-oxo-1,2-dihydroquinolin-8-yl)ethyl)amino)ethyl)-2-oxooxazolidin-3-yl)-2H-pyrazino[2,3-b][1,4]oxazin-3(4H)-one Step

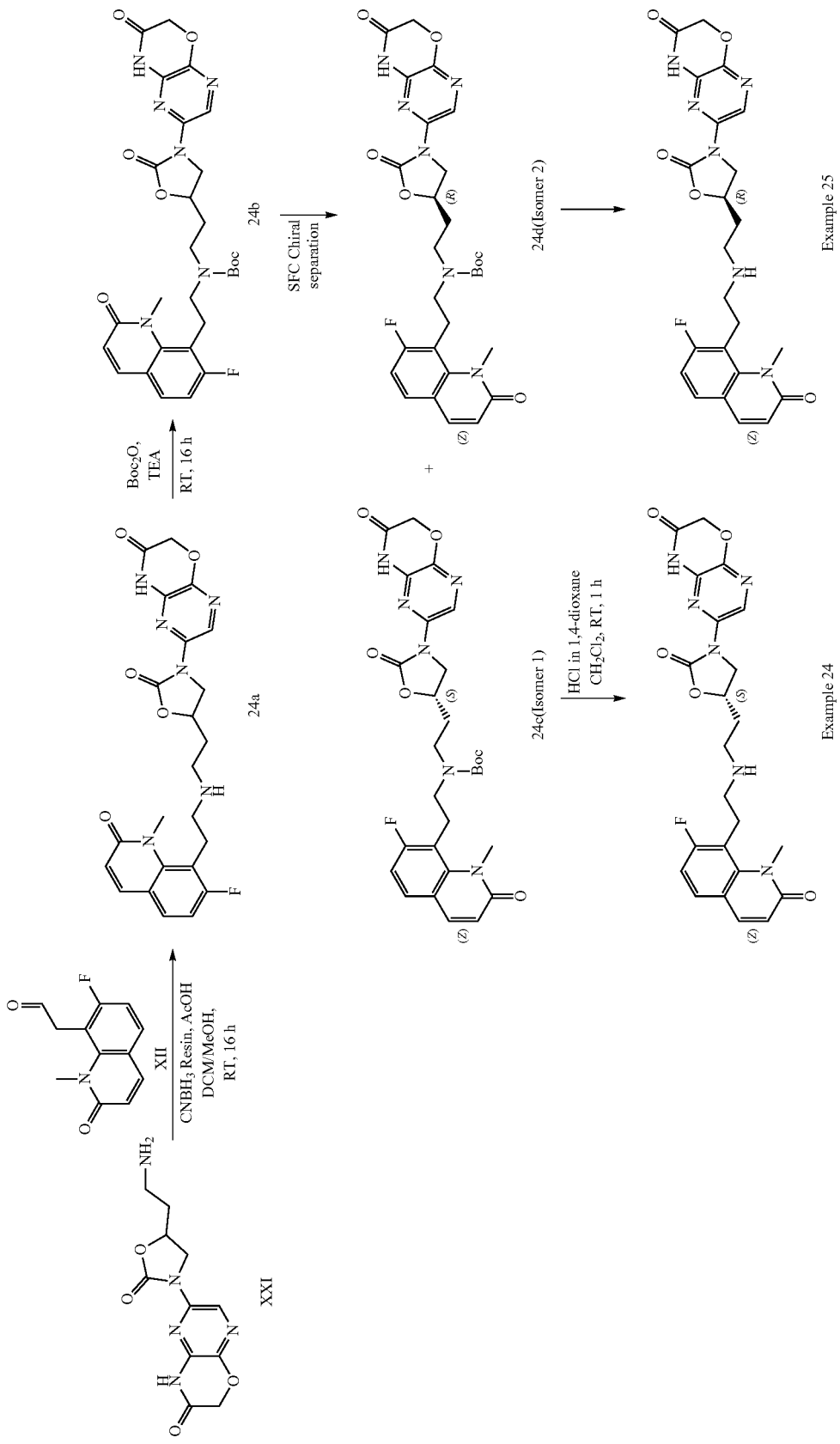

Step 1: Racemic 6-(5-(2-((2-(7-Fluoro-1-methyl-2-oxo-1,2-dihydroquinolin-8-yl)ethyl)amino)ethyl)-2-oxooxazolidin-3-yl)-2H-pyrazino[2,3-b][1,4]oxazin-3(4H)-one (24a)

To a stirred mixture of compound XII (4.71 g, 21.48 mmol) and compound XXI (5 g, 21.48 mmol) in a mixture of dry MeOH/dichloromethane (800 mL, 1:1) at room temperature under nitrogen atmosphere was added AcOH (6 mL). The resulting mixture was continued to stir at room temperature for 16 hours. Then cyanoborohydride resin (17.90 g, 36.52 mmol) was added to the reaction mixture and allowed to stir at room temperature for 1 hour. After that, the reaction mixture was filtered and the filtrate was concentrated under reduced pressure. The obtained crude was further purified by column chromatography using silica gel (230-400 mesh) eluting in 7% MeOH in dichloromethane) to get compound 24a as racemic mixture (pale yellow solid). Yield: 5.0 g 48.26%; LC-MS Calc. for $C_{23}H_{23}FN_6O_5$, 482.47; Obs.: 483.2 [M$^+$+H]; $^1$H-NMR (400 MHz, DMSO-d$_6$): δ 8.31 (s, 1H), 7.84 (d, 1H, J=9.6 Hz), 7.66-7.59 (m, 1H), 7.17-7.12 (m, 1H), 6.55-6.53 (m, 1H), 4.79-4.76 (m, 3H), 4.24-4.14 (m, 1H), 3.78-3.70 (m, 4H), 3.58-3.29 (m, 2H), 3.28-3.16 (m, 1H), 2.83-2.71 (m, 3H), 1.96-1.87 (m, 4H); HPLC Purity=90.25% (HPLC Column: XBridge C18 (50*4.6) mm 3.5 μm, Mobile Phase A: 0.1% TFA in water, Mobile Phase B: 0.1% TFA in Acetonitrile.)

Step 2: Tert-butyl (2-(7-fluoro-1-methyl-2-oxo-1,2-dihydroquinolin-8-yl)ethyl)(2-(2-oxo-3-(3-oxo-3,4-dihydro-2H-pyrazino[2,3-b][1,4]oxazin-6-yl)oxazolidin-5-yl)ethyl)carbamate (24b)

To a stirred solution of compound 24a (10.0 g, 20.72 mmol) in dry dichloromethane (400 mL) at room temperature under nitrogen atmosphere were added TEA (8.65 mL, 62.18 mmol) followed by dropwise addition of Boc anhydride (6.87 mL, 31.09 mmol). The resulting mixture was allowed to stir for 16 hours at room temperature. After that, the reaction mixture was concentrated under reduced pressure. The obtained crude product was further purified by column chromatography using silica gel (230-400 mesh) eluting with 3% MeOH in dichloromethane) to get compound 24b (racemic mixture) as a white solid. Yield: 9.0 g, 74.56%. The racemic mixture was subsequently purified by chiral SFC purification to get 24c (enantiomer 1) and 24d (enantiomer 2). LC-MS Calc. for $C_{28}H_{31}FN_6O_7$, 582.47; Obs.: 581.2 [M$^+$–H]; $^1$H-NMR (400 MHz, DMSO-d$_6$): δ 11.64 (s, 1H), 8.38 (s, 1H), 7.87 (d, 1H, J=8.8 Hz), 7.66 (d, 1H, J=6.4 Hz), 7.20-7.15 (m, 1H), 6.56 (d, 1H, J=9.2 Hz), 4.86 (s, 2H), 4.68 (brs, 1H), 4.21-4.12 (m, 1H), 3.76 (s, 3H), 3.69-3.40 (m, 3H), 3.38-3.16 (m, 3H), 1.94-1.92 (m, 2H), 1.47-1.24 (m, 9H); HPLC Purity=96.22% (HPLC Column: XBridge C18 (50*4.6) mm 3.5 μm, Mobile Phase A: 0.1% TFA in water, Mobile Phase B: 0.1% TFA in Acetonitrile.)

Tert-butyl (S)-(2-(7-fluoro-1-methyl-2-oxo-1,2-dihydroquinolin-8-yl)ethyl)(2-(2-oxo-3-(3-oxo-3,4-dihydro-2H-pyrazino[2,3-b][1,4]oxazin-6-yl)oxazolidin-5-yl)ethyl)carbamate (24c, Isomer 2)

Yield: 3.8 g, 42.22%; LC-MS Calc. for $C_{28}H_{31}FN_6O_7$, 582.47; Obs.: 581.2 [M$^+$–H]; $^1$H NMR (400 MHz, DMSO-d$_6$): δ 11.64 (s, 1H), 8.38 (s, 1H), 7.87 (d, 1H, J=9.2 Hz), 7.67 (d, 1H, J=6.8 Hz), 7.20-7.15 (m, 1H), 6.56 (d, 1H, J=9.6 Hz), 5.76 (s, 2H), 4.86 (s, 2H), 4.69 (brs, 1H), 4.19-4.17 (m, 1H), 3.77 (s, 3H), 3.74-3.69 (m, 1H), 3.49-3.38 (m, 2H), 3.27-3.19 (m, 3H), 1.93 (brs, 2H), 1.37-1.24 (m, 9H). HPLC Purity=96.65% (HPLC Column: XBridge C18 (50*4.6) mm 3.5 μm, Mobile Phase A: 0.1% TFA in water, Mobile Phase B: 0.1% TFA in Acetonitrile.)

Tert-butyl (R)-(2-(7-fluoro-1-methyl-2-oxo-1,2-dihydroquinolin-8-yl)ethyl)(2-(2-oxo-3-(3-oxo-3,4-dihydro-2H-pyrazino[2,3-b][1,4]oxazin-6-yl)oxazolidin-5-yl)ethyl)carbamate (24d, Isomer 2)

Yield: 3.75 g, 41.66%; LC-MS Calc. for $C_{28}H_{31}FN_6O_7$, 582.47; Obs.: 581.2; [M$^+$–H]; $^1$H NMR (400 MHz, DMSO-d$_6$): δ 11.64 (s, 1H), 8.38 (s, 1H), 7.87 (d, 1H, J=8.4 Hz), 7.67 (d, 1H, J=6.0 Hz), 7.20-7.15 (m, 1H), 6.56 (d, 1H, J=9.2 Hz), 4.86 (s, 2H), 4.69 (brs, 1H), 4.19-4.17 (m, 1H), 3.77 (s, 3H), 3.71-3.50 (m, 1H), 3.48-3.38 (m, 2H), 3.28-3.20 (m, 3H), 1.93 (brs, 2H), 2.09 (s, 1H), 1.37-1.30 (m, 9H). HPLC Purity=99.32% (HPLC Column: XBridge C18 (50*4.6) mm 3.5 μm, Mobile Phase A: 0.1% TFA in water, Mobile Phase B: 0.1% TFA in Acetonitrile.)

Example 24: (S)-6-(5-(2-((2-(7-fluoro-1-methyl-2-oxo-1,2-dihydroquinolin-8-yl)ethyl)amino)ethyl)-2-oxooxazolidin-3-yl)-2H-pyrazino[2,3-b][1,4]oxazin-3(4H)-one (Enantiomer 1)

To a stirred solution of 24c (4.50 g, 7.72 mmol) in dry dichloromethane (45 mL) at 0° C. was added HCl in 1,4-dioxane (4N, 23 mL) in dropwise, and allowed to stir for 1 h at room temperature. The resulting mixture was warmed to room temperature and stirred for 1 hour. After that, the reaction mixture was concentrated under reduced pressure. The residue obtained was further triturated with diethyl ether, the solid obtained was filtered and dried to get example 24 as hydrochloride salt (white solid). Yield: 3.8 g, 95.23%. LC-MS Calc. for $C_{23}H_{23}FN_6O_5$, 482.47; Obs.: 481.1; [M$^+$–H]; $^1$H-NMR (400 MHz, DMSO-d$_6$): δ 11.66 (s, 1H), 9.45 (brs, 2H), 8.38 (s, 1H), 7.89 (d, 1H, J=9.2 Hz), 7.74-7.70 (m, 1H), 7.23-7.19 (m, 1H), 6.58 (d, 1H, J=9.2 Hz), 4.90-4.87 (m, 3H), 3.79-3.74 (m, 4H), 3.46-3.42 (m, 2H), 3.18-3.12 (m, 4H), 2.20-2.19 (m, 2H). HPLC Purity=98.99% (HPLC Column: Atlantis dC18 (250*4.6) mm 5 μm, Mobile Phase A: 0.1% TFA in water, Mobile Phase B: Acetonitrile.

Example 25: (R)-6-(5-(2-((2-(7-fluoro-1-methyl-2-oxo-1,2-dihydroquinolin-8-yl)ethyl)amino)ethyl)-2-oxooxazolidin-3-yl)-2H-pyrazino[2,3-b][1,4]oxazin-3(4H)-one (Enantiomer 2)

To a stirred solution of 24d (4.40 g, 7.55 mmol) in dry dichloromethane (44 mL) at 0° C. was added HCl in 1,4-dioxane (4 N, 22 mL) in dropwise. The resulting mixture was warmed to room temperature and stirred for 1 hour. After that, the reaction mixture was concentrated under reduced pressure. The residue obtained was further triturated with diethyl ether, the solid obtained was filtered and dried to get example 25 as hydrochloride (white solid). Yield: 3.70 g, 94.87%. LC-MS Calc. for $C_{23}H_{23}FN_6O_5$, 482.47; Obs.: 481.2 [M$^+$–H]; $^1$H-NMR (400 MHz, DMSO-d$_6$): δ 11.67 (s, 1H), 9.63 (brs, 2H), 8.37 (s, 1H), 7.88 (d, 1H, J=9.6 Hz), 7.74-7.70 (m, 1H), 7.23-7.18 (m, 1H), 6.57 (d, 1H, J=9.6 Hz), 4.92-4.86 (m, 3H), 4.27-4.22 (m, 1H), 3.77-3.74 (m, 4H), 3.45-3.43 (m, 2H), 3.16-3.12 (m, 4H), 2.22-2.20 (m, 2H). HPLC Purity=99.33% (HPLC Column: Atlantis dC18

(250*4.6) mm 5 µm, Mobile Phase A: 0.1% TFA in water, Mobile Phase B: Acetonitrile.

Example 26: (S)-6-(5-(((2-(1-Ethyl-7-fluoro-2-oxo-1,2-dihydroquinolin-8-yl) ethyl) amino)methyl)-2-oxooxazolidin-3-yl)-2H-pyrazino[2,3-b][1,4]oxazin-3(4H)-one

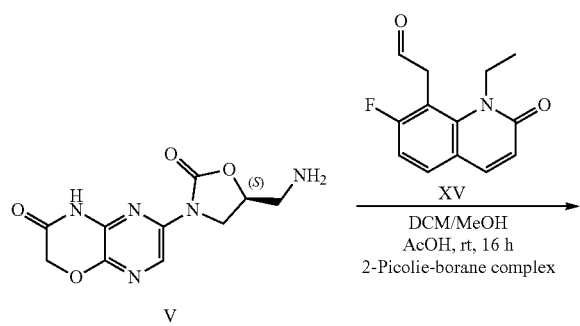

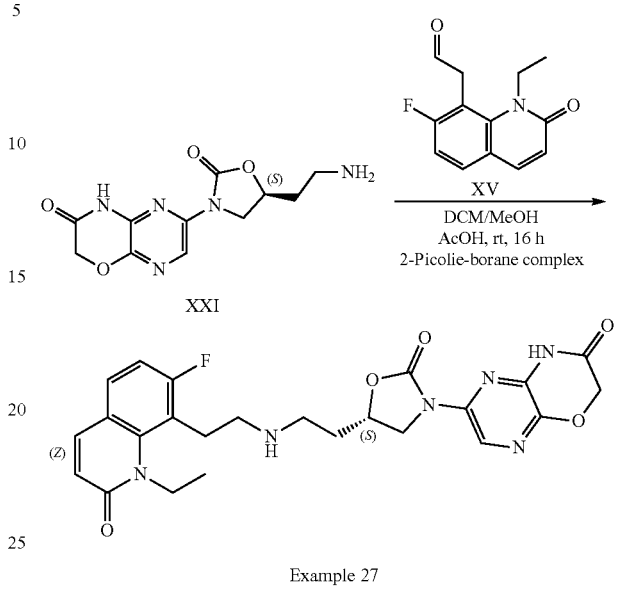

To a stirred solution of compound XV (0.17 g, 0.72 mmol) and compound V (0.21 g, 0.8017 mmol) in a mixture of dry MeOH/dichloromethane (30 mL, 1:1) at room temperature under nitrogen atmosphere was added AcOH (0.2 mL) and allowed to stir for 16 hours. Then 2-picoline borane complex (0.046 g, 0.43 mmol) was added at room temperature and continued to stir for 1 hour. After that the reaction mixture was quenched with formic acid (0.1%, 2 mL), filtered and the filtrate was concentrated in vacuo. The obtained crude product was further purified by column chromatography using silica gel (230-400 mesh) eluting with 5% methanol in dichloromethane to get compound example 26 as formate salt (off white solid). Yield: 0.06 g, 17.14%. LC-MS Calc. for $C_{23}H_{23}FN_6O_5$, 482.47; Obs.: 483.2; [M$^+$+H]; $^1$H NMR (400 MHz, DMSO-d$_6$): δ 11.59 (brs, 1H), 8.39 (s, 1H), 7.84 (d, J=12.40 Hz, 1H), 7.64 (t, J=9.20 Hz, 1H), 7.15 (t, J=12.40 Hz, 1H), 6.53 (d, J=12.40 Hz, 1H), 4.87 (s, 3H), 4.33-4.26 (m, 2H), 4.10 (t, J=12.40 Hz, 1H), 3.86-3.81 (m, 1H), 3.10-3.08 (m, 3H), 2.93-2.81 (m, 4H), 1.26 (t, J=9.20 Hz, 3H). HPLC Purity=95.11%, Column: Atlantis dC18 (250×4.6) mm, 5 µm, Mobile Phase A: 0.1% TFA in water, Mobile Phase B: Acetonitrile.

Example 27: (S)-6-(5-(((2-(1-Ethyl-7-fluoro-2-oxo-1,2-dihydroquinolin-8-yl)ethyl) amino)methyl)-2-oxooxazolidin-3-yl)-2H-pyrazino[2,3-b][1,4]oxazin-3(4H)-one To a stirred solution of compound XV (0.135 g, 0.57 mmol) and compound XXI (0.177 g, 0.63 mmol) in a mixture of dry MeOH/dichloromethane (30 mL, 1:1) at room temperature under nitrogen atmosphere was added AcOH (0.2 mL) and allowed to stir for 16 hours. Then cyanoborohydride resin (0.44 g, 0.98 mmol) was added at room temperature and continued to stir for 1 hour. After that the reaction mixture was filtered and concentrated in vacuo. The obtained crude product was further purified by reverse phase preparative HPLC to get compound Example 27 as formate salt (off white solid). Yield: 0.05 g, 17.42%. LC-MS Calc. for $C_{24}H_{25}FN_6O_6$, 496.50; Obs.: 495.3 [M–H]; $^1$H NMR (400 MHz, DMSO-d$_6$): δ 8.38 (s, 1H), 8.19 (s, 1H), 7.87 (d, J=9.32 Hz, 1H), 7.68 (t, J=7.56 Hz, 1H), 7.18 (t, J=9.28 Hz, 1H), 6.56 (d, J=9.32 Hz, 1H), 4.87-4.82 (m, 4H), 4.33-4.32 (m, 2H), 4.19 (t, J=8.92 Hz, 1H), 3.74 (t, J=9.20 Hz, 2H), 3.14 (brs, 2H), 2.77 (s, 2H), 1.94 (s, 2H), 1.29 (t, J=6.80 Hz, 3H). HPLC Purity=99.13%, Column: Atlantis dC18 (250×4.6) mm, 5 µm, Mobile Phase A: 0.1% TFA in water, Mobile Phase B: Acetonitrile.

Example 28: (S)-6-(5-4(2-(7-Fluoro-1,4-dimethyl-2-oxo-1,2-dihydroquinolin-8-yl)ethyl)amino)methyl)-2-oxooxazolidin-3-yl)-2H-pyrazino[2,3-b][1,4]oxazin-3(4H)-one

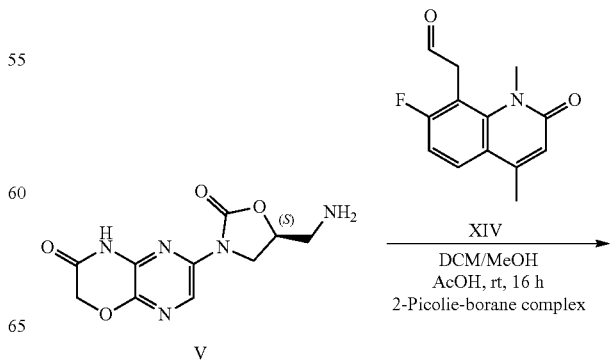

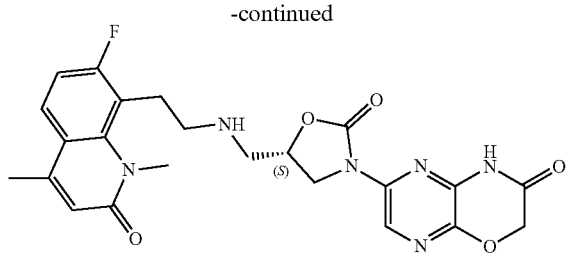

Example 28

To a stirred mixture of compound XIV (80 mg, 0.3433 mmol) and compound V (100 mg, 0.3773 mmol) in a mixture of dry MeOH/dichloromethane (12 mL, 1:1) at room temperature under nitrogen atmosphere were added AcOH (0.3 mL) and 2-picoline-borane complex (22 mg, 0.206 mmol). The resulting mixture was warmed to room temperature for 1 hour. After that, the reaction mixture was quenched with 1% HCOOH in water and concentrated under reduced pressure. The obtained crude product was further purified by preparative HPLC to get example 28 as formate salt (off-white solid). Yield: 20 mg, 12.20%. LC-MS Calc. for $C_{23}H_{23}FN_6O_5$, 482.47; Obs.: 483.2 [M$^+$+H]; $^1$H NMR (400 MHz, DMSO-d$_6$): δ 11.54 (brs, 1H), 8.19 (s, brs, 1H) 7.70-7.68 (m, 1H), 7.17-7.12 (m, 1H), 6.46 (s, 1H), 4.85 (s, 2H), 4.78 (m, 1H), 4.08 (m, 2H), 3.81 (s, 3H), 3.12 (s, brs, 2H), 2.89-2.81 (m, 4H), 2.39 (s, 3H). HPLC Purity=96.37% (HPLC Column: Atlantis dC18 (250*4.6) mm 5 µm, Mobile Phase A: 0.1% TFA in water, Mobile Phase B: Acetonitrile.

Example 29: (S)-6-(5-(((2-(3-Fluoro-5-methyl-6-oxo-5,6-dihydro-1,5-naphthyridin-4-yl)ethyl)amino)methyl)-2-oxooxazolidin-3-yl)-2H-pyrazino[2,3-b][1,4]oxazin-3(4H)-one

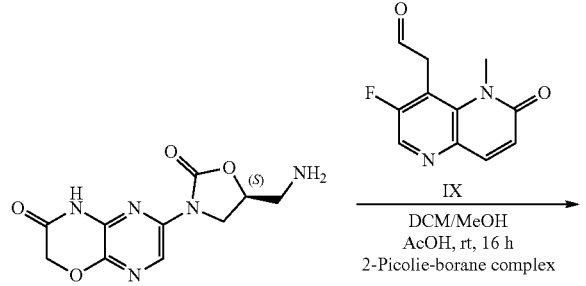

Example 29

To a stirred solution of compound IX (0.04 g, 0.181 mmol) and compound V (0.05 g, 0.181 mmol) in a mixture of dry MeOH/dichloromethane (6 mL, 1:1) at room temperature under nitrogen atmosphere was added AcOH (0.12 mL) and allowed to stir for 10 mins. Then 2-picoline borane complex (0.01 g, 0.108 mmol) was added at 0° C. The resulting mixture was warmed to room temperature and stirred for 3 hours. After that the reaction mixture was concentrated in vacuo. The obtained crude product was purified by preparative HPLC (reverse phase) to get example 29 as formate salt (off white solid). Yield: 0.025 g, 29.76%. LC-MS Calc. for $C_{21}H_{20}FN_7O_5$, 469.43; Obs.: 470.1 [M$^+$+H]; $^1$H NMR (400 MHz, DMSO-d$_6$): δ 11.69 (brs, 1H), 8.50 (s, 1H), 8.38 (s, 1H), 8.14 (s, 1H), 7.86 (d, J=9.68 Hz, 1H), 6.81 (d, J=9.56 Hz, 1H), 4.88 (s, 2H), 4.79-4.83 (brs, 1H), 4.08 (t, J=9.00 Hz, 1H), 3.81-3.79 (m, 1H), 3.76 (s, 3H), 3.26 (d, J=6.60 Hz, 3H), 2.93 (t, J=7.44 Hz, 4H). HPLC Purity=97.04%, Column: Atlantis dC18 (250×4.6) mm, 5 µm, Mobile Phase A: 0.1% HCCOH in water, Mobile Phase B: Acetonitrile.

Example 30: (S)-6-(5-(((2-(6-fluoro-4-methyl-3-oxo-3,4-dihydroquinoxalin-5-yl)ethyl)amino)methyl)-2-oxooxazolidin-3-yl)-2H-pyrazino[2,3-b][1,4]oxazin-3(4H)-one

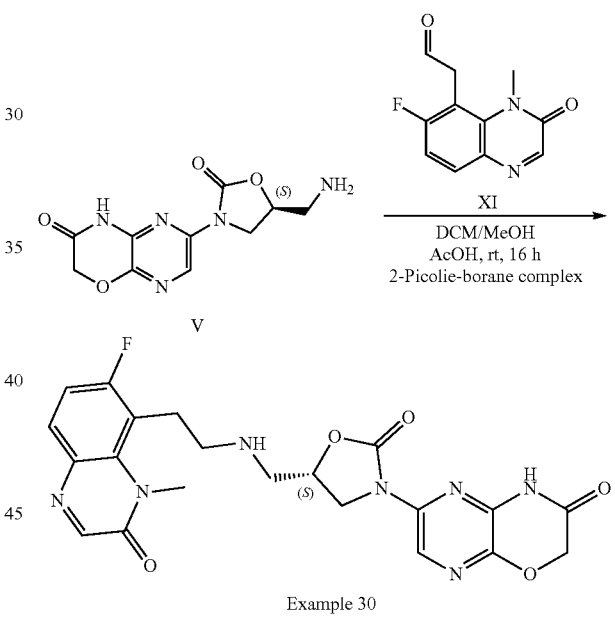

Example 30

To a stirred mixture of compound XI (190 mg, 0.8636 mmol) and compound V (228 mg, 0.8636 mmol) in a mixture of dry MeOH/dichloromethane (10 mL, 1:1) at room temperature under nitrogen atmosphere were added AcOH (0.5 mL) and Pic-BH$_3$ (55 mg, 0.5181 mmol) successively. The resulting mixture was warmed to room temperature and stirred for 1 hour. After that, the reaction mixture was quenched with aqueous HCOOH (1%). The reaction mixture was concentrated under reduced pressure. The obtained crude product was further purified by preparative HPLC (reverse phase) to get example 30 as formate salt (pale yellow solid). Yield: 110 mg, 27.26%. LC-MS Calc. for $C_{21}H_{20}FN_7O_5$, 469.43; Obs.: 468.0 [M$^+$–H]; $^1$H-NMR (400 MHz, DMSO-d$_6$): δ 11.61 (s, 1H), 8.38 (s, 1H), 8.16 (s, 2H), 7.72 (t, J=6.64 Hz, 1H), 7.25 (t, J=9.28 Hz, 1H), 4.87 (s, 2H), 4.77 (brs, 1H), 4.07 (t, J=8.92 Hz, 1H), 4.05-3.75 (m, 4H), 3.17-3.10 (m, 2H), 2.91-2.85 (m, 4H). HPLC Purity=93.26% (HPLC Column: Atlantis dC18 (250*4.6) mm 5 μm, Mobile Phase A: 0.1% AcOH in water, Mobile Phase B: Acetonitrile.

Biological Activity

Example 31: Antibacterial Activity

The compounds of Formula (I) are of interest due to their potent antibacterial effects. The ability of the invention compounds disclosed herein to achieve an antibacterial effect may be evaluated with regard to their ability to inhibit the growth of bacterial species like *Escherichia coli* ATCC 25922, *Staphylococcus aureus* ATCC 29213, *Klebsiella pneumoniae* ATCC 13883, *Acinetobacter baumannii* ATCC 19606, *Pseudomonas aeruginosa* ATCC 27853, *Enterococcus faecalis* ATCC 29212 and *Enterococcus faecalis* ATCC 29212 using an assay based on the following Minimum Inhibitory Concentration (MIC) protocol:

The test bacteria are grown in Luria Bertani Broth (HI-MEDIA M1245), 25 grams of the powder is dissolved in 1000 ml distilled water and sterilized by autoclaving at 15 lbs pressure (121° C.) for 20 minutes. The medium sterility is checked by incubating at 37° C. for a period of 48 h.

Bacterial cultures that are stored as glycerol stocks at −80° C. are sub cultured on LB agar plates to obtain isolated colonies. A single colony of each strain is cultured in LB broth. The cultures are incubated at 37 C, 200 rpm till they reach an optical density (OD at 600 nm) of 0.8 to 1. This log phase culture is diluted in LB broth to a cell number of $5-8*10^5$ CFU/mL to be used as inoculum for MIC experiments. Test compounds are dissolved in dimethyl sulfoxide (DMSO) to a stock concentration of 4 mg/ml. A twofold dilution series of this DMSO stock is prepared in a 96 well V bottom microtitre plate from rows A to H. A 3 μL volume of these dilutions are transferred to a 96-well flat bottom microtitre assay plate. Controls to monitor the effects of DMSO and media sterility are included. Each well is inoculated with 150 μL of the above diluted culture. The plates are incubated at 37° C. overnight in a humidified incubator. The following morning, the plates are read using a Spectrophotometer at 600 nM wavelength. Minimum Inhibitory Concentration (MIC) is defined as the lowest drug concentration containing well which shows no turbidity. The antibacterial activity (MIC) determined against representative Gram positive (*S. aureus*, *E. faecalis*) and Gram negative (*E.coli, -P. aeruginosa* and *A. baumannii*) pathogen were reported Table 1. The exemplified compounds belonging to Formula I demonstrated potent antibacterial activity both Gram positive and Gram negative pathogens.

TABLE 1

| | Minimum Inhibitory Concentration (μg/mL) in LB Media | | | | | |
|---|---|---|---|---|---|---|
| Example | S. aureus ATCC 29213 | E. faecalis ATCC 29212 | E. coli ATCC 25922 | P. aeruginosa ATCC 27853 | K. pneumoniae ATCC 13883 | A. baumannii ATCC 19606 |
| 1 | <4 | <4 | <0.5 | <16 | <1 | <0.5 |
| 1a | <4 | <4 | <0.5 | <16 | <1 | <0.5 |
| 1b | <4 | <4 | <0.5 | <16 | <1 | <0.5 |
| 2 | 0.125 | 1 | 0.125 | 4 | 0.25 | 0.125 |
| 3 | 0.5 | 0.25 | 0.5 | 16 | 2 | 1 |
| 4 | ≤0.015 | 0.06 | 0.03 | 0.25 | 0.03 | ≤0.015 |
| 5 | 0.015 | 0.25 | 0.06 | 1 | 0.125 | 0.03 |
| 6 | 0.015 | 0.125 | 0.06 | 1 | 0.125 | 0.015 |
| 7 | 0.06 | 0.25 | 0.125 | 2 | 0.25 | 0.06 |
| 8 | ≤0.015 | 0.06 | 0.03 | 0.25 | 0.03 | ≤0.015 |
| 9 | 0.03 | 0.125 | 0.06 | 1 | 0.13 | 0.06 |
| 10 | 0.015 | 0.06 | 0.03 | 0.5 | 0.06 | 0.125 |
| 11 | 0.03 | 0.5 | 0.25 | 2 | 0.25 | 0.5 |
| 12 | 0.25 | 0.5 | 0.25 | 1 | 0.5 | 1 |
| 13 | 0.25 | 0.5 | 0.125 | 0.5 | 0.25 | 1 |
| 14 | ≤0.015 | 0.06 | 0.06 | 0.5 | 0.06 | 0.25 |
| 15 | ≤0.015 | 0.06 | 0.03 | 0.25 | 0.03 | 0.06 |
| 16 | 0.06 | 0.25 | 0.06 | 1 | 0.25 | 0.25 |
| 17 | 0.125 | 0.25 | 0.125 | 2 | 0.25 | 1 |
| 18 | 0.125 | 0.5 | 0.125 | 1 | 0.125 | 0.5 |
| 19 | 0.25 | 0.5 | 0.25 | 2 | 0.125 | 1 |
| 20 | 0.03 | 0.125 | 0.125 | 0.5 | 0.5 | 2 |
| 21 | 0.015 | 0.25 | 0.06 | 1 | 0.125 | 0.125 |
| 22 | ≤0.015 | 0.06 | 0.03 | 0.25 | 0.06 | 0.015 |
| 23 | 0.015 | 0.06 | 0.03 | 0.25 | 0.03 | 0.015 |
| 24 | 0.125 | 0.125 | 0.06 | 0.25 | 0.125 | 0.5 |
| 25 | 0.06 | 0.5 | 0.06 | 0.25 | 0.25 | 0.5 |
| 26 | ≤0.015 | 0.03 | 0.03 | 0.5 | 0.03 | 0.03 |
| 27 | 0.015 | 0.06 | 0.03 | 0.5 | 0.125 | 0.06 |
| 28 | ≤0.015 | 0.06 | 0.06 | 0.5 | 0.06 | 0.125 |
| 29 | 0.03 | 0.125 | 0.125 | 0.5 | 0.125 | 0.5 |
| 30 | 0.03 | 0.125 | 0.06 | 0.25 | 0.06 | 0.06 |
| Ciprofloxacin | 0.4 | 0.4 | 0.012 | 0.1 | 0.05 | 0.4 |

Example 33: Enzyme Inhibition Assay:
Determination of $IC_{50}$ Against *E. coli* Gyrase Supercoiling The compounds belonging to Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of Gram-positive and Gram-negative bacteria through inhibition of bacterial Type II topoisomerases namely, DNA gyrase and Topo IV The present invention also provides evidence for treating infection caused both Gram positive and Gram negative bacteria through the inhibition of bacterial topoisomerases using E. coli DNA gyrase and Topo IV enzymes Procedure for E. coli DNA Gyrase Supercoiling Assay E. coli gyrase supercoiling and its inhibition was assayed using a kit procured from Inspiralis (K0001) and the protocol (PMID: 2172086) was adapted with necessary modifications. The compounds to be tested are incubated for 10 minutes with 2.5 nM of E. coli DNA gyrase in a 30 µl volume reaction and 3.2% DMSO. The reactions are then started with the addition of 60 ng relaxed pBR322 plasmid DNA and continued for 45 min at 37° C. The reaction mixture contains 35 mM Tris.HCl (pH 7.5), 24 mM KCl, 1.8 mM spermidine, 4 mM $MgCl_2$, 2 mM DTT, 6.5% (w/v) glycerol, 0.1 mg/mL BSA, and 1 mM ATP. The reaction is then stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH8, 1 mM EDTA, 0.5 mg/ml Bromophenol Blue) and the supercoiled/relaxed forms of plasmid DNA were separated by agarose gel electrophoresis. The 1% agarose gels are run for 3 h at 4 V/cm in 1×TAE (40 mM Tris, 20 mM Acetic acid, 1 mM EDTA). To visualize the DNA the gels are stained for 10 min with 0.7 µg/mL ethidium bromide and excess dye is removed by several washes with water. $IC_{50}$s are determined by quantifying the supercoiled and relaxed DNA in each of the reactions from a gel image by a densitometric method using the Quantity One Software (Bio-rad).

Procedure for E. coli Topoisomerase IV Decatenation Assay

E. coli topoisomerase IV decatenation activity and its inhibition was assayed using a kit procured from Inspiralis (D4002) and the kit protocol was adapted with necessary modifications similar to the gyrase supercoiling assays. The compounds to be tested were incubated for 10 minutes with 5 nM of E. coli topoisomerase IV in a 30 µl volume reaction and 3.2% DMSO. The reactions were started with the addition of 60 ng of kDNA and continued for 40 min at 37° C. The final reaction mixture contains 40 mM Tris.HCl (pH 7.6), 100 mM potassium glutamate, 10 mM magnesium acetate, 10 mM DTT, 1 mM ATP, and 50 µg/ml albumin. The reactions were stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH8, 1 mM EDTA, 0.5 mg/ml Bromophenol Blue) and the kDNA/minicircles forms were separated by agarose gel electrophoresis. The 1% agarose gels were run for 3 h at 4 V/cm in 1×TAE (40 mM Tris, 20 mM Acetic acid, 1 mM EDTA). To visualize the DNA, the gels were stained for 10 min with 0.7 µg/mL ethidium bromide and excess dye was removed by several washes with water. $IC_{50}$s were determined by quantifying the Kinetoplast DNA band inside the gel well and decatenated minicircles that migrate into the gel in each of the reactions from a gel image by a densitometric method using the Quantity One Software (Bio-rad).

Representing examples belonging to Formula I were evaluated against of E. coli DNA gyrase and Topo IV enzyme using gel based supercoiling assay for gyrase inhibition and decatenation assay for Topo IV inhibition. The results of bacterial Type II Topoisomerases (Gyrase and Topo IV) were presented in the Table 2. The results presented in the Table 2 indicates that compounds belonging to formula I exerts its' antibacterial activity through inhibition bacterial type II topoisomerase activity and signifies the dual mode of inhibition for observed antibacterial activity of the compounds.

TABLE 2

| Example | E. coli DNA Gyrase $IC_{50}$ (µM) | E. coli Topo IV $IC_{50}$ (µM) |
|---|---|---|
| 4 | 0.007 | 0.093 |
| 6 | 0.0034 | 0.03 |
| 9 | 0.0032 | 0.175 |
| 10 | 0.0059 | 0.03 |
| 12 | <0.1 | 0.176 |
| 13 | 0.02 | 0.032 |
| 14 | 0.013 | 0.052 |
| 15 | 0.0046 | 0.010 |
| 16 | 0.041 | 0.112 |
| 18 | 0.013 | 0.024 |
| 20 | 0.0106 | 0.090 |
| 22 | 0.0032 | 0.019 |
| 23 | 0.0049 | 0.037 |
| 24 | 0.025 | 0.123 |
| 25 | 0.017 | 0.021 |
| Ciprofloxacin | 0.233 | 14.4 |
| Novobiocin | 0.058 | NA |

Example 34: Antibacterial Susceptibility Studies Using Clinical Isolates of Drug Sensitive and Resistance Strains Gram Negative Bacteria To test if the compounds from the series were able to retain the antibacterial activity against clinical strains of bacteria, antibacterial susceptibility studies ($MIC_{50}$ and $MIC_{90}$ determination) were carried for a representative compound (Example 15, Compound 15) from the series using clinical strains of five gram negative bacterial species (E. coli, P. aeruginosa, K. pneumoniae, A. baumannii, E. cloacae) according the standard CLSI guidelines and the results obtained are presented Table 3. The standard drugs ciprofloxacin and meropenem were used as positive controls in the study.

TABLE 3

Results of $MIC_{50}$ and $MIC_{90}$ studies

|  | Ciprofloxacin | Meropenem | Example 15 |
|---|---|---|---|
| E. coli |  |  |  |
| Number of strains | 201 | 201 | 176 |
| ATCC25922 | 0.015 | 0.06 | 0.06 |
| Minimum | 0.015 | 0.03 | 0.03 |
| $MIC_{50}$ (µg/ml) | 16 | 0.06 | 0.06 |
| $MIC_{90}$ (µg/ml) | 16 | 4 | 0.25 |
| A. baumannii |  |  |  |
| Number of strains | 169 | 169 | 132 |
| ATCC19606 | 0.5 | 0.5 | 0.06 |
| Minimum | 0.06 | 0.03125 | 0.03 |
| $MIC_{50}$ (µg/ml) | 16 | 8 | 0.06 |
| $MIC_{90}$ (µg/ml) | 16 | 32 | 0.125 |
| K. pneumoniae |  |  |  |
| Number of strains | 211 | 211 | 176 |
| ATCC13883 | 0.03 | 0.06 | 0.03 |
| Minimum | 0.015 | 0.03 | 0.06 |
| $MIC_{50}$ (µg/ml) | 4 | 1 | 0.5 |
| $MIC_{90}$ (µg/ml) | 16 | 16 | 1 |

TABLE 3-continued

Results of MIC$_{50}$ and MIC$_{90}$ studies

| | Ciprofloxacin | Meropenem | Example 15 |
|---|---|---|---|
| *P. aeruginosa* | | | |
| Number of strains | 215 | 215 | 176 |
| ATCC27853 | 0.25 | 0.5 | 0.25 |
| Minimum | 0.015 | 0.03 | 0.03 |
| MIC$_{50}$ (µg/ml) | 0.125 | 2 | 0.5 |
| MIC$_{90}$(µg/ml) | 16 | 8 | 1 |
| *E. cloacae* | | | |
| Number of strain | 88 | 88 | 88 |
| Minimum | 0.06 | 0.06 | 0.03 |
| MIC50 (µg/ml) | 0.06 | 0.25 | 0.25 |
| MIC90(µg/ml) | 16 | 16 | 1 |

Example 35: hERG Inhibition Assay

To test if the compounds from the series has any safety risk by inhibiting cardiac ion channel, particularly the potassium channel (IKr, hERG), compounds were tested using electrophysiological assays to evaluate its potential activity on hERG ion channel. The compounds were tested for inhibition of the human ether a go-go related gene (hERG) K+ channel using QPatch HTX automated electrophysiology. 6-Point concentration-response curves were generated using three-fold serial dilutions from a maximum final test concentration of 300 µM and the results are presented in table 4.

Compounds were solubilised to 100 mM in DMSO before dilution in HBPS to 300 µM. 6-Point concentration-response curves were generated using 3.16-fold serial dilutions from the top test concentration.

Procedure:

Electrophysiological recordings were made from a Chinese Hamster Ovary cell line stably expressing the full-length hERG potassium channel. Single cell ionic currents were measured in whole-cell patch clamp configuration at room temperature (21-23° C.) using the QPatch HTX platform (Sophion). Intracellular solution contained (mM): 120 KF, 20 KCl, 10 EGTA, 10 HEPES and was buffered to pH 7.3. The extracellular solution (HEPES-buffered physiological saline, HBPS) contained (mM): 145 NaCl, 4 KCl, 2 CaCl$_2$, 1 MgCl$_2$, 10 HEPES, 10 glucose, buffered to pH7.4. Cells were clamped at a holding potential of −80 mV. Cells were stepped to +20 mV for 2 s then −40 mV for 3 s before returning to the holding potential. This sweep was repeated 10 times at 10 s intervals. hERG currents were measured from the tail step and referenced to the holding current. Compounds were then incubated for 2 minutes prior to a second measurement of ion channel current using an identical pulse train.

TABLE 4 hERG IC$_{50}$ values

| Example | hERG IC$_{50}$ (µM) |
|---|---|
| 3 | 12 |
| 5 | 14 |
| 8 | 17 |
| 9 | 68.7 |
| 10 | 71 |
| 13 | >300 |
| 14 | 41 |

TABLE 4-continued hERG IC$_{50}$ values

| Example | hERG IC$_{50}$ (µM) |
|---|---|
| 15 | 131 |
| 16 | 204 |
| 18 | 237 |
| 20 | >300 |
| 22 | 128 |
| 23 | 35 |
| 24 | >300 |
| 25 | 101 |
| Cisapride | 0.15 |

Example 36: Intravenous Formulation of Example 15 for Pharmacokinetic (PK) Studies Example 15 was formulated in 10% L-Ascorbic acid solution in water to achieve the desirable solubility for intravenous route of administration and adjusted to pH 4 by 1N NaOH.

Procedure: Weighed appropriate amount of the Example 15 to be tested and dissolved in 1 ml of the 10% ascorbic acid solution. (Vortex for a few seconds if the compound doesn't dissolve instantly). Sonicated the compound solution at room temperature for 5 minutes using a bath sonicator to obtain a visually clear solution. The above prepared solution was pH adjusted to pH~4 with 1N NaOH solution (w/v) with sonication (final Formulation pH~4). The details of the Formulation solubility of Example 15 is given in the Table 5.

TABLE 5

IV Formulation solubility

| Formulation Composition | Solubility in 10% L-ascorbic acid in fresh MilliQ water(v/v), Final pH~2.8 |
|---|---|
| Example 15 10% L-Ascorbic acid Water for injection or Fresh MiliQ water 1N NaOH solution for pH adjustment | 25 mg/ml |

The prepared IV formulation of Example 15 were observed to be stable at room temperature for more than 24 hours.

Example 37: In Vivo Pharmacokinetic (PK) Studies in Rats

The rat pharmacokinetic studies were carried out in Sprague-Dawley (SD) rats to estimate the plasma clearance, volume of distribution and terminal half-life of Example 15 following 1 hr intravenous infusion (IV).

The Example 15 exhibited moderate clearance, low volume of distribution and short-half life in SD rats. Dose proportional increase in AUC and Cmax was observed during IV infusion of Example 15 at 5, 10, 30 & 100 mg/kg doses in SD rats. This study suggest that the Example 15 has desirable pharmacokinetic profile to keep blood levels of the parent above the MICs to demonstrate efficacy in rat infection models by IV infusion administration.

Procedure: The objective of this study was to investigate the pharmacokinetic profile of Example 15, following single ascending doses via intravenous (IV) constant rate infusion for 1 h, in male Sprague Dawley rats. The study was performed using the following study design (n=3/group). The pharmacokinetic experimental design for Example 25 is tabulated in the Table 6 below:

TABLE 6

Pharmacokinetic experimental design for Example 15

| Treatment Group | Route [mode] | No. of animals | Dose (mg/kg) | Conc. in formulation (mg/mL) | Infusion rate (mL/min/Kg) | Dose Volume (mL/kg) | Formulation vehicle |
|---|---|---|---|---|---|---|---|
| G1 | IV [Infusion] | 3 | 5 | 0.5 | 0.167 | 10 mL/kg | 10% L-ascorbic acid solution in water for injection and adjusted to pH4 by using 1N NaOH |
| G2 | | 3 | 30 | 3 | | | |
| G3 | | 3 | 100 | 10 | | | |
| G4 | | 3 | 150 | 15 | | | |

Serial blood sampling was used for blood collection. Blood samples were collected at pre-dose, 0.25, 0.5 h (during infusion), 1 h (end of infusion) and 0.033, 0.25, 0.5, 1, 2, 4, 8 and 24 h, post infusion. At each time point about 100 μL of blood was collected from the jugular vein into a labeled microfuge tube containing 200 mM $K_2$EDTA solution (20 μL per mL of blood) and equivalent volume of heparinized saline was replaced following sample collection. The blood samples were processed to obtain the plasma samples within 30 min of scheduled sampling time. All plasma samples were stored below −60° C. until bioanalysis.

Plasma samples were analyzed for Example 15 using a fit-for purpose LC-MS/MS method with a lower limit of quantification (LLOQ) of 8.1 ng/mL. The pharmacokinetic parameters of Example 15 were calculated using the non-compartmental analysis tool of validated Phoenix® WinNonlin® software (version 6.4) with linear up and log down method for estimating AUC.

Male Sprague Dawley rats (8-12 weeks of age, weighing 280±20 g at the time of dosing) used in the study were obtained from Invigo Research laboratories, USA. Anesthetic solution (Ketamine and xylazine) was prepared by mixing 2 mL of Ketamine (50 mg/mL) with 0.5 mL of Xylazine (20 mg/mL) Rats were anaesthetized by ketamine and xylaxine solution by intra-peritoneal route at 1 mL/kg dose. The jugular and femoral veins of rat were cannulated and the study was performed 48 h post cannulation. All animals were fasted overnight before dose administration and food was provided 4 h post dose administration. All animals received water ad libitum during the study period. The IV pharmacokinetic profile Example 15 presented in Table 7

TABLE 7

Pharmacokinetic profile Example 15

| Parameter | 5 mg/kg | 30 mg/kg | 100 mg/kg | 150 mg/kg |
|---|---|---|---|---|
| $C_{max}$ (μg/ml) | 2.4 ± 0.06 | 15.2 ± 2.2 | 62.6 ± 6.7 | 100.7 ± 145.5 |
| $T_{max}$ (h) | 0.77 ± 0.01 | 1.0 ± 0.0 | 1.0 ± 0.0 | 1.0 ± 0.0 |
| $AUC_{inf}$ (h*μg/ml) | 1.7 ± 0.05 | 14.7 ± 0.2 | 73.7 ± 15.3 | 103.9 ± 7.3 |
| $AUC_{last}$ (h*μg/ml) | 1.7 ± 0.05 | 14.7 ± 0.2 | 73.7 ± 15.3 | 103.9 ± 7.3 |
| Vd (L/kg) | 2.21 ± 0.012 | 2.83 ± 0.09 | 9.86 ± 1.68 | 12.9 ± 1 |
| CLp (L/h/kg) | 2.92 ± 0.08 | 2.04 ± 0.03 | 1.40 ± 0.29 | 1.45 ± 0.11 |

TABLE 7-continued

Pharmacokinetic profile Example 15

| Parameter | 5 mg/kg | 30 mg/kg | 100 mg/kg | 150 mg/kg |
|---|---|---|---|---|
| Vss (L/kg) | 0.91 ± 0.05 | 0.84 ± 0.06 | 0.90 ± 0.05 | 0.86 ± 0.04 |
| $t_{1/2}$ (h) | 0.53 ± 0.03 | 0.96 ± 0.02 | 4.93 ± 0.5 | 6.17 ± 0.42 |

Example 38: In Vivo Efficacy of Example 15 in Rat Infection Models: In Vivo Efficacy in Rat Thigh *K. pneumoniae* Model Example 15 was tested in rat thigh infection model following intravenous infusion of compound at doses of 100 mg/kg once, 30 mg/kg once daily over a period of 1 hr to assess its efficacy. This study was performed following all ethical practices as laid down in the guidelines for animal care (Registration number No. 1852/PO/Rc/S/16/CPCSEA). The study was approved by the Institutional Animals Ethics Committee (IAEC) of the test facility. The formulation used was 10% of L-ascorbic acid in fresh MilliQ water (w/v) with pH adjusted to ~4.0 with 1N NaOH. On Day −4 (4 days prior to the desired date of infection), each rat was dosed with a single intra-peritoneal injection of cyclophosphamide equivalent to 150 mg/kg, and returned to its cage. On Day−1 (a day prior to infection) each rat received a dose equivalent to 100 mg/kg of Cyclophosphamide. This procedure ensured that animals will be neutropenic on day 0. On the day of the infection, the overnight culture of the appropriate microorangism [*E. coli* [ATCC25922]/*A. baumannii* [ATCC19606]/*K. pneumoniae* [ATCC13883] was adjusted to 1 OD [equal to ~109 CFU/mL], centrifuged and the cells pelleted. The pelleted cells were suspended in sterile normal saline to obtain 107 CFU/ml and used for infection. The inoculum was serially diluted ten-fold in sterile CSDB broth and 0.05 ml of six dilutions were plated onto CSDA agar plates to determine the viable count (CFU/ml) of inoculum. All animals were divided into different groups as specified in the experimental design for each microorganism. All infections were conducted in a biological safety cabinet, with appropriate personnel protection. Infection was done by injecting 0.2 ml of inoculum [approximately 1×107 CFU/ml in broth] of the appropriate microorgansim using a 1.0 ml syringe and needle, post-laterally into the right thigh of the animal [approximately 2×106 CFU/thigh]. A gentle shaking/mixing of inoculum between two animals was followed for uniform distribution.

Two hours post infection, animals in groups 4, 5 and 6 were administered intravenously with example 15, as a constant rate infusion (duration of infusion 1 h), under Ketamine 60 mg/kg IP+Xylazine 10 mg/kg IP anesthesia, at a dose volume of 10 ml/kg, at the rate of 0.16 ml/min. The dose levels of Example 15 were 10, 30 and 100 mg/kg. Ciprofloxacin [10 mg/kg] and vehicle [10% of L-ascorbic acid in fresh MilliQ water (w/v) with pH adjustment [to pH ~4.0] with 1N Sodium hydroxide solution (w/v)] were dosed intravenously as single bolus doses. The total duration of the study was 10 h.

Animals were sacrificed 10 hr post infection and thigh tissues were harvested to enumerate the bacterial CFU count. Thigh muscles were aseptically excised, weighed, and placed into 1 ml of sterile CSDB broth, and homogenized (Omni Tip (220 V hand held)). Serial ten-fold dilutions of the thigh homogenates were prepared in sterile lactose broth and 0.05 mL of four dilutions for each thigh was plated onto CSDA agar plates. Bacterial colonies were enumerated following overnight incubation at 370 C. Bacterial densities were estimated as Log 10 CFU/gram thigh. The Mean±SD Log 10 CFU/gram thigh was estimated in each group. Significant differences between group means and control will be analyzed by One way ANOVA, followed by a Dunnett's multiple comparison test, using Graphpad Prism at 95% confidence levels. A P value of <0.05 was considered as significant. The results of the efficacy study is presented in Table 8.

cabinet. All infections were conducted in a biological safety cabinet, with appropriate personnel protection. Animals were anaesthetized by intraperitoneal injection of ketamine & xylazine (60+10 mg/kg i.p.) cocktail. Once the animals were in a sufficiently deep plane of anaesthesia as monitored by pedal reflex, the abdominal wall of each rat was shaved with electric clippers and the skin was cleansed with 10% povidine iodine. After a 1.5 to 2 cm lower abdominal wall incision, the abdominal wall muscles were separated with blunt dissection. The urinary bladder was isolated and exposed, the urine inside the bladder was removed and 0.1 ml of sterile saline or bacterial culture $E.\ coli$ (approximately $1\times 10^8$ CFU/animal) was injected into the bladder. After the replacement of the bladder to its original location, the abdominal muscles were approximated using suture and the skin was closed. The wounds were cleansed using 10% povidine iodine.

The IV formulation vehicle used was 10% of L-ascorbic acid in fresh MilliQ water (w/v) with pH adjusted to 4.0 with 1N Sodium hydroxide solution (w/v), and the dose volume was 10 mL/kg. Meropenem was prepared in MilliQ water and the pH of solution was adjusted to 4.5 using HCl. Four hours post infection, animals were dosed intravenously, as single doses (for test compounds), as a constant rate infusion, under Ketamine 60 mg/kg IP+Xylazine 10 mg/kg IP anesthesia, at a dose volume of 10 ml/kg, at the rate of 0.03 ml/min. The dose levels of the test compounds were 3, 10 and 30 mg/kg. Meropenem was administered as a single

TABLE 8

Efficacy of BWC0977 against *K. pneumoniae* [ATCC25922] in a Neutropenic Thigh Infection Model in Rat

| Treatment | Log $_{10}$ CFU/g thigh | | | MEAN ± SD (Log $_{10}$ CFU/g thigh) | Mean Log$_{10}$CFU/g thigh reduction (wrt 2 h PI control: 4.72 Log$_{10}$CFU/g thigh) |
|---|---|---|---|---|---|
| Early Infection Control [ 2 h PI] | 4.58 | 4.78 | 4.79 | 4.72 ± 0.12 | 0.00 |
| Infection control [vehicle] | 7.56 | 6.57 | 6.63 | 6.92 ± 0.56 | −2.20 |
| Ciprofloxacin [10 mg/kg, i.v. bolus] | 3.49 | 3.11 | 3.25 | 3.28 ± 0.19* | 1.44 |
| Example 15 [ 3 mg/kg, i.v., 1 h infusion] | 4.1 | 4.56 | 3.65 | 4.10 ± 0.46# | 0.62 |
| Example 15 [ 10 mg/kg, i.v., 1 h infusion] | 3.18 | 2.85 | 2.71 | 2.91 ± 0.24* | 1.81 |
| Example 15 [ 30 mg/kg, i.v., 1 h infusion] | 1.92 | 1.94 | 2.8 | 2.22 ± 0.50* | 2.50 |

*($P < 0.05$) Significantly different from Infection control 2 hr PI;
($P < 0.05$) Significantly different from Infection control 10 hr PI.

Example 15 showed significant dose dependent efficacy with respect to 2 h Post Infection (PI) control at 10 and 30 mg/kg, and was bacteriostatic at 3 mg/kg when compared to the 2 h PI control and the efficacy was comparable to standard drug ciprofloxacin at similar dose (10 mg/kg).

In Vivo Efficacy in Rat Urinary Tract Infection (UTI) *E. coli* Model:

The purpose of this study is to assess the efficacy of Example 15 against *E. coli* [ATCC25922] following single dose intravenous infusion doses of 3, 10 and 30 mg/kg in a Urinary Tract Infection Rat Model Procedure Prior to the start of the infection process all animals were divided into different groups. All grouped cages of animals were carried to a procedure room, close to a biological safety bolus dose at a dose volume of 5 ml/kg. All the animals were sacrificed at 24 h post infection, as specified in experimental design, by an overdose of $CO_2$ in an appropriate exposure chamber. The group 1 animals were sacrificed at 4 h post infection.

The euthanized animals were dipped into 70% ethanol for surface decontamination. The organs were removed aseptically; the bladder was cut away near the urethra, and the kidneys were removed by blunt dissection to avoid bleeding. The bladder and each kidney separately were be homogenized in PBS. The CFU per milliliter homogenate of bladder, & kidney were determined after 18 to 24 h of incubation at 37° C. The number of bacteria per organ was enumerated and the results of the study are presented in Table 9 and 10.

TABLE 9

Efficacy of Example 15 against *E. coli* [ATCC25922] in Urinary Tract Infection Rat Model—Kidneys

| Treatment | Log$_{10}$ CFU/g (Left Kidney) | | | Log$_{10}$ CFU/g (Right Kidney) | | | MEAN ± SD (Log$_{10}$ CFU/g kidneys) | Mean Log$_{10}$ CFU/g kidney reduction (wrt 4 h PI control: 6.03 Log$_{10}$ CFU/g kidneys) |
|---|---|---|---|---|---|---|---|---|
| Early Infection Control [4 h PI] | 5.62 | 6.74 | 5.51 | 6.41 | 6.10 | 5.82 | 6.03 ± 0.47 | |
| Infection control [vehicle 24 h PI] | 6.95 | 6.18 | 6.76 | 8.18 | 7.44 | 7.92 | 7.23 ± 0.75 | −1.2 |
| Meropenem [30 mg/kg, i.v. bolus] | 4.62 | 4.41 | 5.19 | 4.83 | 3.13 | 4.28 | 4.41 ± 0.70* | 1.62 |
| Example 15[3 mg/kg, i.v., 1 h infusion] | 6.81 | 6.44 | 6.48 | 7.51 | 7.68 | 7.86 | 7.13 ± 0.62 | −1.1 |
| Example 15[ [10 mg/kg, i.v., 1 h infusion] | 4.69 | 5.68 | 4.80 | 6.66 | 6.13 | 6.97 | 5.82 ± 0.94# | 0.21 |
| Example 15[ [30 mg/kg, i.v., 1 h infusion] | 4.98 | 3.84 | 4.12 | 4.66 | 4.05 | 511 | 4.46 ± 0.52* | 1.57 |

*($P < 0.05$) significantly different from Infection control 4 hr PI;
($P < 0.05$) significantly different from Infection control 24 hr PI.

TABLE 10

Efficacy of Example 15 against *E.coli* [ATCC25922] in Urinary Tract Infection Rat Model—bladder

| Treatment | Log$_{10}$ CFU/ml Bladder | | | MEAN ± SD (Log$_{10}$ CFU/ml Bladder) | Mean Log$_{10}$ CFU/ml Bladder reduction (wrt 4 h PI control: 6.49 CFU/ml Bladder) |
|---|---|---|---|---|---|
| Early Infection Control [4 h PI] | 6.80 | 6.58 | 6.11 | 6.49 ± 0.35 | |
| Infection control [vehicle 24 h PI] | 8.05 | 7.92 | 8.37 | 8.11 ± 0.23 | −1.62 |
| Meropenem [30 mg/kg, i.v. bolus] | 4.43 | 4.62 | 3.99 | 4.34 ± 0.32* | 2.15 |
| Example 15 [ 3 mg/kg, i.v., 1 h infusion] | 5.54 | 6.79 | 7.00 | 7.01 ± 0.23 | −0.52 |
| Example 15 [ 10 mg/kg, i.v., 1 h infusion] | 5.54 | 5.97 | 6.05 | 5.85 ± 0.27# | 0.64 |
| Example 15 [ 30 mg/kg, i.v., 1 h infusion] | 4.61 | 4.91 | 4.90 | 4.80 ± 0.17* | 1.69 |

*($P < 0.05$) significantly different from Infection control 4 hr PI;
($P < 0.05$) significantly different from Infection control 24 hr PI.

Example 15 showed significant dose dependent with respect to 4 h PI control at 10 and 30 mg/kg, and was bacteriostatic at 3 mg/kg when compared to the 4 h PI control and the efficacy was comparable to standard drug meropenem at similar dose (30 mg/kg).

In Vivo Efficacy in Rat Lung *P. aeruginosa* Model:

The purpose of this study was to evaluate the efficacy of example 15 against *P. aeruginosa* [ATCC27853], following single dose intravenous infusion doses of 10, 30 and 100 mg/kg in a neutropenic lung infection model in rats Procedure Prior to the start of the infection process, all animals were divided into different groups. All grouped cages of animals were carried to a procedure room, close to a biological safety cabinet. All infections were conducted in a biological safety cabinet, with appropriate personnel protection. Animals were placed into an induction chamber and anaesthesia was induced by exposing the animals to 3-5% Isoflurane in an oxygen flow set at approximately (~) 1 liter per minute (LPM). Once the animals were in a sufficiently deep plane of anaesthesia as monitored by pedal reflex, they were removed and infected (2). Infection was initiated by instilling 0.07 ml (containing ~1×109 CFU/ml) of the inoculum; 35 μl into each nostril of the anesthetized animal using 100 μl pipette (~7×107 CFU/animal). A gentle mixing of inoculum between two animals was followed for uniform distribution.

The IV formulation vehicle used for example 15 was 10% of L-ascorbic acid in fresh MilliQ water (w/v) with pH adjusted to ~4.0 with 1N Sodium hydroxide solution (w/v), and the dose volume was 10 mL/kg. Meropenem was formulated in saline. Four hours post infection, animals were dosed intravenously, as single doses, by infusion, under Ketamine 60 mg/kg IP+Xylazine 10 mg/kg IP anesthesia, at a dose volume of 10 ml/kg, at a constant rate of 0.03 ml/min. The dose levels of the test Example 15 were 10, 30 and 100 mg/kg.

All the animals in groups were sacrificed at 24 h post infection, as specified in experimental design, by an overdose of $CO_2$ in an appropriate exposure chamber. The group 1 animals were sacrificed at 4 hrs post infection. The euthanized animals were dipped into 70% ethanol for surface decontamination. Entire Lung was aseptically isolated, weighed and placed into 1 mL of sterile CSDB broth, and homogenized (Omni Tip (220 V hand held)). Serial ten-fold dilutions of the lungs homogenates were prepared in sterile CSD broth and 0.05 mL of four dilutions for each tissue was plated onto CSDA agar plates. Bacterial colonies were enumerated following overnight incubation at 37° C. Bacterial densities were estimated as $Log_{10}$ CFU/g lung. The Mean±SD $Log_{10}$ CFU/g lung was estimated in each group. Significant differences between group means and control were analyzed by one way ANOVA, followed by a Dunnett's multiple comparison test, using Graphpad Prism at 95% confidence levels. A P value of <0.05 was considered as significant and the results of the study was presented in Table 10.

TABLE 11

Efficacy of Example 15 against P.aeruginosa [ATCC27853] in a Neutropenic Lung Infection Model in Rat

| Treatment | $Log_{10}$ CFU/g Lung | | | MEAN ± SD ($Log_{10}$ CFU/g Lung) | Mean Log 10CFU/g lung reduction (wrt 4 h PI control 5.78 $Log_{10}$CFU/g lung) |
|---|---|---|---|---|---|
| Early Infection Control [ 4 h PI] | 5.74 | 5.72 | 5.89 | 5.78 ± 0.09 | |
| Infection cornrol [vehicle] | 8.84 | 8.99 | 8.73 | 8.85 ± 0.13 | −3.07 |
| Meropenem [30 mg/kg, i.v. bolus] | 5.03 | 5.18 | 4.90 | 5.04 ± 0.14* | 0.74 |
| Example 15 [ 10 mg/g, i.v. 1 h infusion] | 6.68 | 6.75 | 6.47 | 6.63 ± 0.15# | −0.85 |
| Example 15 [ 30 mg/kg, i.v., 1 h infusion] | 4.79 | 4.65 | 4.78 | 4.74 ± 0.08* | 1.04 |
| Example 15 [ 100 mg/kg, i.v., 1 h infusion] | 4.84 | 4.53 | 4.90 | 4.76 ± 0.2* | 1.02 |

Data analysis: One way Annova followed by Dunnett's Multiple Comparison Test;
*(P < 0.05) significantly different from Infection control 4 hr PI.
(P < 0.05) significantly different from Infection control 24 hr PI.

Example 15 showed significant efficacy at 30 mg/kg and 100 mg/kg doses with respect to early infection control, whereas 10 mg/kg was bacteriostatic when compared to the early infection control PI and the efficacy was comparable to standard drug meropenem at similar dose (30 mg/kg).

Advantage

The above-mentioned implementation examples as described on this subject matter and its equivalent thereof have many advantages, including those which are described.

The compounds of the present disclosure show high antibacterial activity against various pathogens including Gram-positive and Gram-negative bacteria through the inhibition of bacterial topoisomerase via a novel mechanism.

The compounds of the present disclosure exhibit high degree of selectivity against hERG channel and may be devoid of cardio toxicity in animal and human.

Representative exemplification of the present disclosure demonstrates of desirable pharmacokinetic profile in rat and efficacious in various rat infection models thus confirming in vivo proof of principle in animal through inhibition of bacterial topoisomerase.

Although the subject matter has been described in considerable detail with reference to certain embodiments thereof, other embodiments are possible. As such, the spirit and scope of the disclosure should not be limited to the description of the embodiments contained herein.

We claim:
1. A compound of Formula I

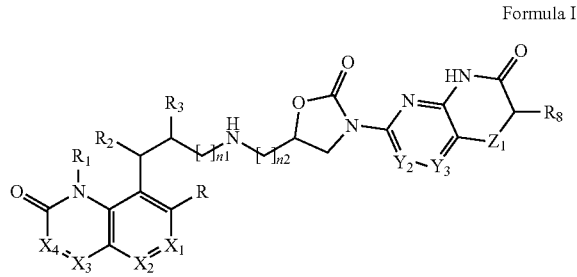

Formula I or its stereoisomers, pharmaceutically acceptable salts, complexes, hydrates, solvates, tautomers, polymorphs, racemic mixtures, optically active forms, and pharmaceutically active derivatives thereof,
wherein
$R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered carbocyclyl or heterocyclyl ring which may be fully saturated or unsaturated or partially unsaturated optionally having up to three heteroatoms independently selected from O, N, and S, each of which is unsubstituted or substituted with 1 to 3 groups independently selected from halogen, amino, hydroxyl, $C_{1-6}$ alkoxy, $SO_3H$, $SO_2R_9$, COORS, $CONHR_9$, and $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatoms independently selected from O, N, and S, $C_{3-6}$ cycloalkylamino, $C_{3-6}$ aminocycloalkyl, $C_{1-6}$ alkylamino, and di ($C_{1-6}$ alkyl)amino;
$R_2$ and $R_3$ are independently selected from the group consisting of hydrogen, $C_{1-6}$ alkyl, fluorine, $OC_{1-6}$ alkyl, hydroxyl, and amino;
R is selected from the group consisting of hydrogen, fluorine, cyano, $OC_{1-6}$ alkyl, and hydroxyl;
$X_1$ is selected from the group consisting of N and $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;

$X_2$ is selected from the group consisting of N and $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is selected from the group consisting of N and $CR_6$; and $X_4$ is CH or C—$C_{1-6}$ alkyl when dotted line ( ---- ) represents a bond, wherein
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl, or amino; or
$X_4$ is selected from the group consisting of $CH_2$ and O; and $X_3$ is $CH_2$ when dotted line ( --- ) represents no bond;
$n_1$ is 0 or 1;
$n_2$ is 0 to 2;
$Y_2$ and $Y_3$ are independently selected from N and $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

2. A compound as claimed in claim 1, or its stereoisomers, pharmaceutically acceptable salts, complexes, hydrates, solvates, tautomers, polymorphs, racemic mixtures, optically active forms, and pharmaceutically active derivatives thereof,
wherein
$R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered carbocyclyl or heterocyclyl ring which may be fully saturated or unsaturated or partially unsaturated optionally having up to three heteroatoms independently selected from O, N, and S, each of which is unsubstituted or substituted with 1 to 3 groups independently selected from halogen, amino, hydroxyl, $C_{1-6}$ alkoxy, $SO_3H$, $SO_2R_9$, COORS, $CONHR_9$, and $SO_2NHR_9$, wherein $R_9$ is selected from H, $C_{1-6}$ alkyl, methylsulfone, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatoms independently selected from O, N, and S, $C_{3-6}$ cycloalkylamino, $C_{3-6}$ aminocycloalkyl, $C_{1-6}$ alkylamino, and di($C_{1-6}$ alkyl)amino;
$R_2$ and $R_3$ are selected from the group consisting of hydrogen, fluorine, methoxy, hydroxyl, and amino; provided that at least one of $R_2$ and $R_3$ is hydrogen;
R is selected from the group consisting of hydrogen, fluorine, methoxy, cyano, and hydroxyl;
$X_1$ is selected from the group consisting of N and $CR_4$;
$R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_2$ is selected from the group consisting of N and $CR_5$;
$R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$X_3$ is selected from the group consisting of N and $CR_6$; and $X_4$ is CH, or C—$C_{1-6}$ alkyl wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is selected from the group consisting of $CH_2$ and O; and $X_3$ is $CH_2$ when dotted line ( --- ) represents no bond;
$n_1$ is 0 or 1;
$n_2$ is 0 to 2;
$Y_2$ and $Y_3$ are independently selected from —N and $CR_7$;
$R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl;
$Z_1$ is selected from the group consisting of O, S, and $CH_2$; and
$R_8$ is selected from the group consisting of hydrogen, $C_{1-6}$ alkyl, and fluorine.

3. A compound as claimed in claim 1, or its stereoisomers, pharmaceutically acceptable salts, complexes, hydrates, solvates, tautomers, polymorphs, racemic mixtures, optically active forms and pharmaceutically active derivatives thereof, wherein
$R_1$ is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered carbocyclyl or heterocyclyl ring which may be fully saturated or unsaturated or partially unsaturated optionally having up to three heteroatoms independently selected from O, N, and S, each of which is unsubstituted or substituted with 1 to 3 groups independently selected from halogen, amino, hydroxyl, $C_{1-6}$ alkoxy, $SO_3H$, $SO_2R_9$, COORS, $CONHR_9$, and $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatoms independently selected from O, N, and S, $C_{3-6}$ cycloalkylamino, $C_{3-6}$ aminocycloalkyl, $C_{1-6}$ alkylamino, and di($C_{1-6}$ alkyl)amino;
$R_2$ and $R_3$ are independently selected from the group consisting of hydrogen, hydroxyl, fluorine, methyl, methoxy, and amino; provided that at least one of $R_2$ and $R_3$ is hydrogen;
R is selected from the group consisting of hydrogen, fluorine, methoxy, cyano, and hydroxyl;
$X_1$ is selected from the group consisting of N and $CR_4$;
$R_4$ is selected from the group consisting of hydrogen, fluorine, cyano, —$OC_{1-3}$ alkyl, and $C_{1-3}$ alkyl;
$X_2$ is selected from the group consisting of N and $CR_5$;
$R_5$ is selected from the group consisting of hydrogen, fluorine, cyano, —$OC_{1-3}$ alkyl, and $C_{1-3}$ alkyl;
$X_3$ is selected from the group consisting of N and $CR_6$; and $X_4$ is selected from the group consisting of CH and C—$CH_3$ wherein dotted line ( ---- ) represents a bond;
$R_6$ is selected from the group consisting of hydrogen, fluorine, cyano, —$OC_{1-3}$ alkyl, and $C_{1-3}$ alkyl, wherein $C_{1-3}$ alkyl is optionally substituted with hydroxyl or amino;
$X_4$ is selected from the group consisting of $CH_2$ and O; and $X_3$ is $CH_2$ when dotted line ( --- ) represents no bond;
$n_1$ is 0 or 1;
$n_2$ is 0 to 2;
$Y_2$ and $Y_3$ are independently selected from —N and $CR_7$;
$R_7$ is selected from the group consisting of hydrogen, halogen, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, $C_{1-6}$ alkyl, and fluorine.

4. A compound as claimed in claim 1, or its stereoisomers, pharmaceutically acceptable salts, complexes, hydrates, solvates, tautomers, polymorphs, racemic mixtures, optically active forms, and pharmaceutically active derivatives thereof, wherein $R_1$ is selected from the group consisting of $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CF_2CH_2NH_2$, $CH_2CH_2SO_2CH_3$,

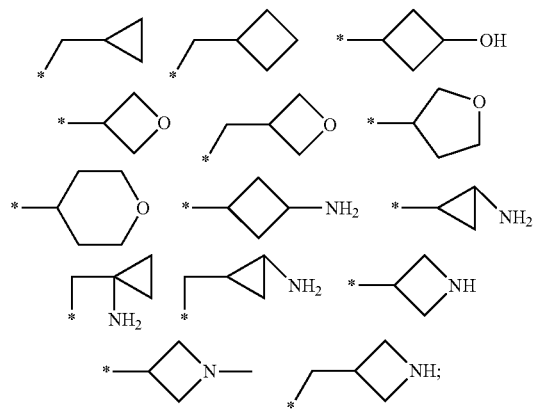

$R_2$ and
$R_3$ are independently selected from the group consisting of hydrogen, fluorine, $C_{1-6}$ alkyl, $OC_{1-6}$ alkyl, hydroxyl, and amino; provided that at least one of $R_2$ and $R_3$ is hydrogen;
R is selected from the group consisting of hydrogen, fluorine, cyano, $OC_{1-6}$ alkyl, and hydroxyl;
$X_1$ is selected from the group consisting of N and $CR_4$;
$R_4$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_2$ is selected from the group consisting of N and $CR_5$;
$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_3$ is selected from the group consisting of N and $CR_6$; and $X_4$ is selected from the group consisting of CH and C—$C_{1-6}$ alkyl wherein dotted line ( ---- ) represents a bond;
$R_6$ is selected from the group consisting of hydrogen, halogen, cyano, —$OC_{1-3}$ alkyl, and $C_{1-3}$ alkyl, wherein $C_{1-3}$ alkyl is optionally substituted with hydroxyl or amino;
$X_4$ is selected from the group consisting of $CH_2$ and O; and $X_3$ is $CH_2$ when dotted line ( --- ) represents no bond;
$n_1$ is 0 or 1;
$n_2$ is 0 to 2;
$Y_2$ and $Y_3$ are independently selected from N and $CR_7$;
$R_7$ is selected from the group consisting of hydrogen, halogen, cyano, —$OC_{1-3}$ alkyl, and $C_{1-3}$ alkyl;
$Z_1$ is selected from the group consisting of O, S, and $CH_2$; and
$R_8$ is selected from the group consisting of hydrogen, $C_{1-6}$ alkyl, and fluorine.

5. A compound as claimed in claim 1, or its stereoisomers, pharmaceutically acceptable salts, complexes, hydrates, solvates, tautomers, polymorphs, racemic mixtures, optically active forms and pharmaceutically active derivatives thereof, wherein $R_1$ is independently selected from the group consisting of $CH_3$, $CH_2CH_3$, $CH(CH_3)_2$, cyclopropyl, cyclobutyl, $CH_2CF_3$, $CH_2CHFCH_3$, $CH_2CF_2CH_3$, $CH_2CH(OH)CH_3$, $CH_2CH_2OH$, $CH_2CH_2OCH_3$, $CH_2CH(OCH_3)CH_3$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $CH_2CH_2SO_2CH_3$,

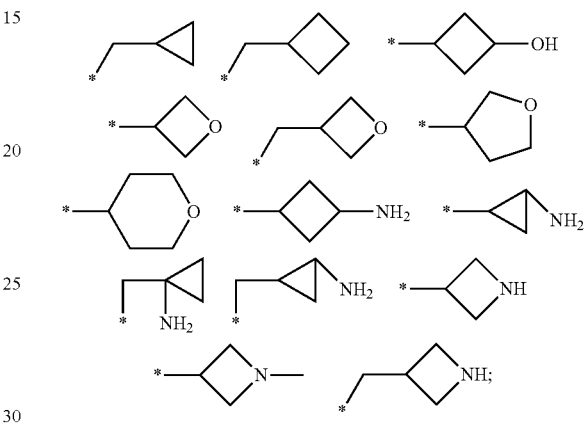

$R_2$ and $R_3$ are is independently selected from the group consisting of hydrogen, hydroxyl, methoxy, fluorine, and amino; provided that at least one of $R_2$ and $R_3$ is hydrogen;
R is selected from the group consisting of hydrogen, fluorine, methoxy, cyano, and hydroxyl;
$X_1$ is selected from the group consisting of N and $CR_4$;
$R_4$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_2$ is selected from the group consisting of N and $CR_5$;
$R_5$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$X_3$ is selected from the group consisting of N and $CR_6$; and $X_4$ is selected from the group consisting of CH and C—$CH_3$ wherein dotted line ( ---- ) represents a bond;
$R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino;
$X_4$ is selected from the group consisting of $CH_2$ and O; and $X_3$ is $CH_2$ when dotted line ( --- ) represents no bond;
$n_1$ is 0 or 1;
$n_2$ is 0 to 2;
$Y_2$ and $Y_3$ are independently selected from —N and $CR_7$;
$R_7$ is selected from the group consisting of hydrogen, halogen, cyano, —$OC_{1-6}$ alkyl, $C_{1-6}$ haloalkyl, $OC_{1-6}$ haloalkyl, and $C_{1-6}$ alkyl;
$Z_1$ is selected from the group consisting of 0, S, and $CH_2$; and
$R_8$ is selected from the group consisting of hydrogen, methyl, and fluorine.

6. A compound as claimed in claim 1, or its stereoisomers, pharmaceutically acceptable salts, complexes, hydrates, solvates, tautomers, polymorphs, racemic mixtures, optically active forms, and pharmaceutically active derivatives thereof, wherein R$_1$ is selected from the group consisting of CH$_3$, CH$_2$CH$_3$, CH(CH$_3$)$_2$, cyclopropyl, cyclobutyl, CH$_2$CF$_3$, CH$_2$CHFCH$_3$, CH$_2$CF$_2$CH$_3$, CH$_2$CH(OH)CH$_3$, CH$_2$CH$_2$OH, CH$_2$CH$_2$OCH$_3$, CH$_2$CH(OCH$_3$)CH$_3$, CH$_2$CH$_2$NH$_2$, CH$_2$CH$_2$NHCH$_3$, CH$_2$CH(NH$_2$)CH$_3$, CH$_2$CH$_2$N(CH$_3$)$_2$, CH$_2$CHFCH$_2$NH$_2$, CH$_2$CF$_2$CH$_2$NH$_2$, CH$_2$CH$_2$SO$_2$CH$_3$,

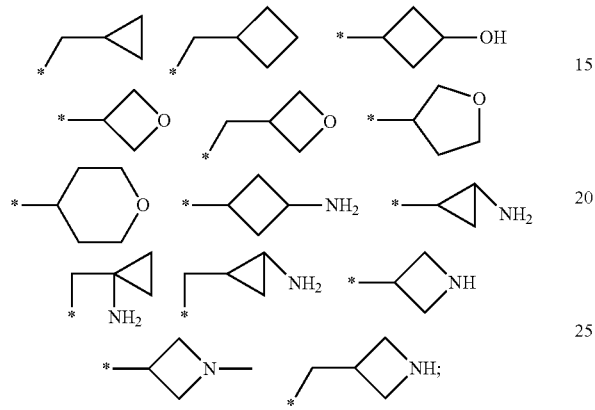

R$_2$ and R$_3$ are independently selected from the group consisting of hydrogen, hydroxyl, methyl, methoxy, and amino; provided that at least one of R$_2$ and R$_3$ is hydrogen;

R is selected from the group consisting of hydrogen, F, CN, and hydroxyl;

X$_1$ is selected from the group consisting of N and CR$_4$;

R$_4$ is selected from the group consisting of hydrogen, fluorine, cyano, —OC$_{1-3}$ alkyl, and C$_{1-3}$ alkyl;

X$_2$ is selected from the group consisting of N and CR$_5$;

R$_5$ is selected from the group consisting of hydrogen, fluorine, cyano, —OC$_{1-3}$ alkyl, and C$_{1-3}$ alkyl;

X$_3$ is selected from the group consisting of N and CR$_6$; and X$_4$ is selected from the group consisting of CH and C—CH$_3$ wherein dotted line ( ---- ) represents a bond;

R$_6$ is selected from the group consisting of hydrogen, fluorine, cyano, —OC$_{1-3}$ alkyl, and C$_{1-3}$ alkyl, wherein C$_{1-3}$ alkyl is optionally substituted with hydroxyl or amino;

X$_4$ is selected from the group consisting of CH$_2$ and O; and X$_3$ is CH$_2$ when dotted line ( --- ) represents no bond;

n$_1$ is 0 or 1;

n$_2$ is 0 to 2;

Y$_2$ and Y$_3$ are independently selected from —N and CR$_7$;

R$_7$ is selected from the group consisting of hydrogen, fluorine, cyano, —OC$_{1-3}$ alkyl, and C$_{1-3}$ alkyl;

Z$_1$ is selected from the group consisting of O, S, and CH$_2$; and

R$_8$ is selected from the group consisting of hydrogen, methyl, and fluorine.

7. A compound as claimed in claim 1, or its stereoisomers, pharmaceutically acceptable salts, complexes, hydrates, solvates, tautomers, polymorphs, racemic mixtures, optically active forms, and pharmaceutically active derivatives thereof, wherein R$_1$ is selected from the group consisting of CH$_3$, CH$_2$CH$_3$, CH(CH$_3$)$_2$, cyclopropyl, cyclobutyl, CH$_2$CF$_3$, CH$_2$CHFCH$_3$, CH$_2$CF$_2$CH$_3$, CH$_2$CH(OH)CH$_3$, CH$_2$CH$_2$OH, CH$_2$CH$_2$OCH$_3$, CH$_2$CH(OCH$_3$)CH$_3$, CH$_2$CH$_2$NH$_2$, CH$_2$CH$_2$NHCH$_3$, CH$_2$CH(NH$_2$)CH$_3$, CH$_2$CH$_2$N(CH$_3$)$_2$, CH$_2$CHFCH$_2$NH$_2$, CH$_2$CF$_2$CH$_2$NH$_2$, CH$_2$CH$_2$SO$_2$CH$_3$,

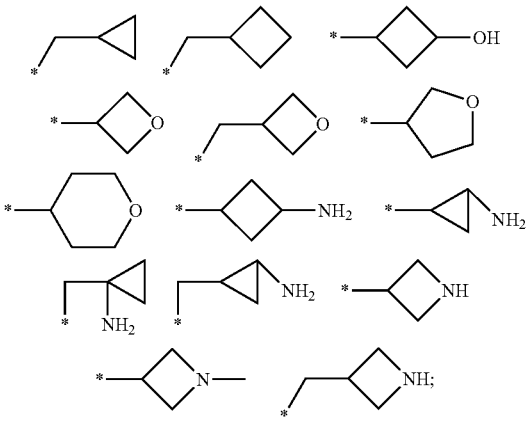

R$_2$ and R$_3$ are independently selected from the group consisting of hydrogen, methoxy, fluorine, and hydroxyl; provided that at least one of R$_2$ and R$_3$ is hydrogen;

R is selected from the group consisting of hydrogen, fluorine, methoxy, cyano, and hydroxyl;

X$_1$ is selected from the group consisting of N and CR$_4$;

R$_4$ is selected from the group consisting of hydrogen, fluorine, cyano, —OC$_{1-3}$ alkyl, and C$_{1-3}$ alkyl;

X$_2$ is selected from the group consisting of N and CR$_5$;

R$_5$ is selected from the group consisting of hydrogen, fluorine, cyano, —OC$_{1-3}$ alkyl, and C$_{1-3}$ alkyl;

X$_3$ is selected from the group consisting of N and CR$_6$; and X$_4$ is selected from the group consisting of CH and C—CH$_3$ wherein dotted line ( ---- ) represents a bond;

R$_6$ is selected from the group consisting of hydrogen, fluorine, cyano, —OC$_{1-3}$ alkyl, and C$_{1-3}$ alkyl, wherein C$_{1-3}$ alkyl is optionally substituted with hydroxyl or amino;

X$_4$ is selected from the group consisting of CH$_2$ and O; and X$_3$ is CH$_2$ when dotted line ( --- ) represents no bond;

n$_1$ is 0 or 1;

n$_2$ is 0 to 2;

Y$_2$ and Y$_3$ are independently selected from —N and CR$_7$;

R$_7$ is selected from the group consisting of hydrogen, fluorine, cyano, —OC$_{1-3}$ alkyl, and C$_{1-3}$ alkyl;

Z$_1$ is selected from the group consisting of O, S, and CH$_2$; and

R$_8$ is selected from the group consisting of hydrogen, C$_{1-6}$ alkyl, and fluorine.

8. A compound as claimed in claim 1, or its stereoisomers, pharmaceutically acceptable salts, complexes, hydrates, solvates, tautomers, polymorphs, racemic mixtures, optically active forms, and pharmaceutically active derivatives thereof, wherein R₁ is selected from the group consisting of CH₃, CH₂CH₃, CH(CH₃)₂, cyclopropyl, cyclobutyl, CH₂CF₃, CH₂CHFCH₃, CH₂CF₂CH₃, CH₂CH(OH)CH₃, CH₂CH₂OH, CH₂CH₂OCH₃, CH₂CH(OCH₃)CH₃, CH₂CH₂NH₂, CH₂CH₂NHCH₃, CH₂CH(NH₂)CH₃, CH₂CH₂N(CH₃)₂, CH₂CHFCH₂NH₂, CH₂CF₂CH₂NH₂, CH₂CH₂SO₂CH₃,

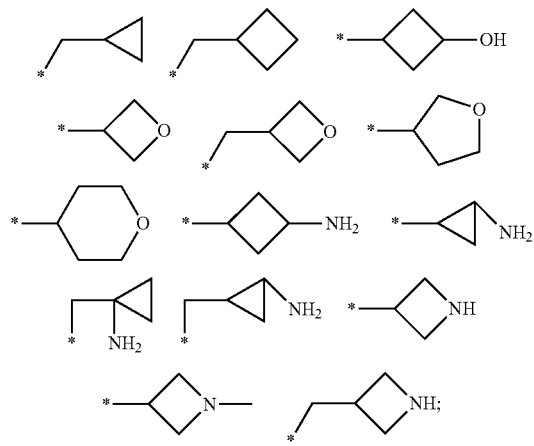

R₂ and R₃ are independently selected from the group consisting of hydrogen, fluorine, methoxy, amino, and hydroxyl;

R is selected from the group consisting of hydrogen, fluorine, cyano methoxy, and hydroxyl;

X₁ is selected from the group consisting of N and CR₄;

R₄ is selected from the group consisting of hydrogen, fluorine, cyano, methoxy, and methyl;

X₂ is selected from the group consisting of N and CR₅;

R₅ is selected from the group consisting of hydrogen, fluorine, cyano, methoxy, and methyl;

X₃ is selected from the group consisting of N and CR₆; and X₄ is selected from the group consisting of CH and C—CH₃ wherein dotted line ( ---- ) represents a bond;

R₆ is selected from the group consisting of hydrogen, fluorine, cyano, methoxy, methyl, CH₂OH, and CH₂NH₂;

X₄ is selected from the group consisting of CH₂ and 0; and X₃ is CH₂ when dotted line ( --- ) represents no bond;

n₁ is 0 or 1;

n₂ is 0 to 2;

Y₂ and Y₃ are independently selected from —N and CR₇;

R₇ is selected from the group consisting of hydrogen, fluorine, cyano, methoxy, and methyl;

Z₁ is 0; and

R₈ is selected from the group consisting of hydrogen, methyl, and fluorine.

9. The compound of Formula I as claimed in claim 1, or its stereoisomers, pharmaceutically acceptable salts, complexes, hydrates, solvates, tautomers, polymorphs, racemic mixtures, optically active forms, and pharmaceutically active derivatives thereof, which is selected from a group consisting of:

6-(5-(((3-(3-fluoro-5-methyl-6-oxo-5,6-dihydro-1,5-naphthyridin-4-yl)propyl)amino)methyl)-2-oxooxazolidin-3-yl)-2H-pyrido[3,2-b][1,4]oxazin-3(4H)-one (Example 1)

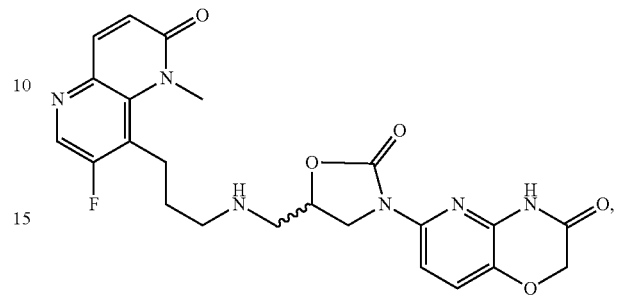

S)-6-(5-(((2-(7-fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one (Example 2)

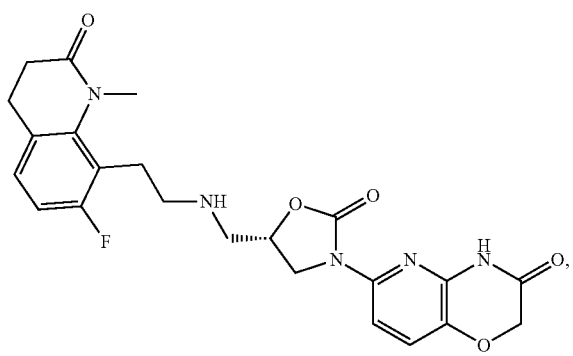 [SMILES: CN1C(=O)CCc2ccc(F)c(CCNC[C@H]3CN(c4ccc5c(n4)NC(=O)CO5)C(=O)O3)c21]

(R)-6-(5-(((2-(7-fluoro-1-methyl-2-oxo-1,2,3,4-tetrahydroquinolin-8-yl)ethyl)amino)methyl)-2-oxooxazolidin-3-yl)-2H-pyrido[3,2-b][1,4]oxazin-3(4H)-one (Example 3)

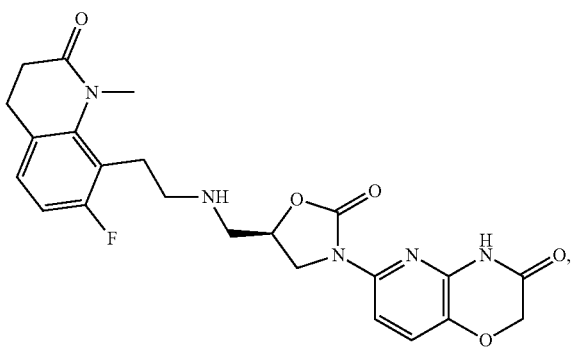 [SMILES: CN1C(=O)CCc2ccc(F)c(CCNC[C@@H]3CN(c4ccc5c(n4)NC(=O)CO5)C(=O)O3)c21]

(S)-6-(5-(((2-(6-fluoro-4-methyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 4)

(R)-6-(5-(((2-(6-fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 7)

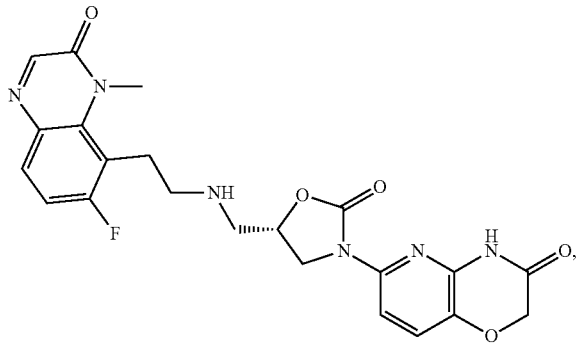 [SMILES: Cn1c(=O)cnc2ccc(F)c(CCNC[C@H]3CN(c4ccc5c(n4)NC(=O)CO5)C(=O)O3)c21]
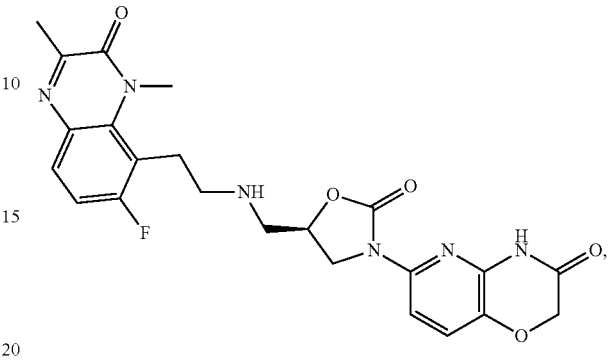

(R)-6-(5-(((2-(6-fluoro-4-methyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 5)

(S)-6-(5-(((2-(7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3(4H)-one (Example 8)

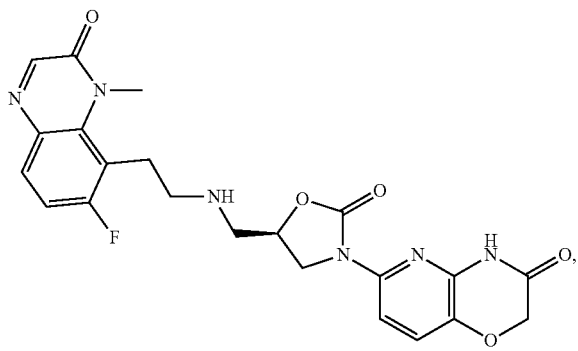 [SMILES: Cn1c(=O)cnc2ccc(F)c(CCNC[C@@H]3CN(c4ccc5c(n4)NC(=O)CO5)C(=O)O3)c21]
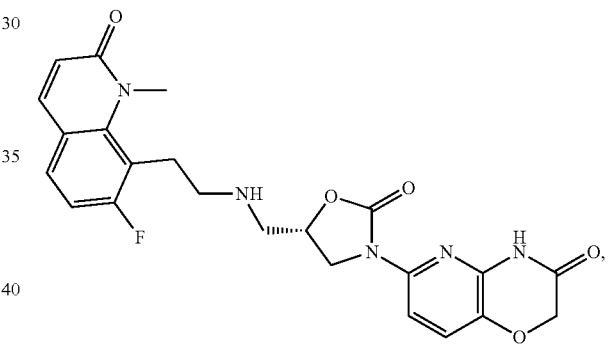

(S)-6-(5-(((2-(6-fluoro-2,4-dimethyl-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 6)

(S)-6-(5-(((2-(6-fluoro-4-(2-hydroxyethyl)-3-oxo-3,4-dihydroquinoxalin-5-yl)ethyl)amino)methyl)-2-oxooxazolidin-3-yl)-2H-pyrido[3,2-b][1,4]oxazin-3(4H)-one (Example 9)

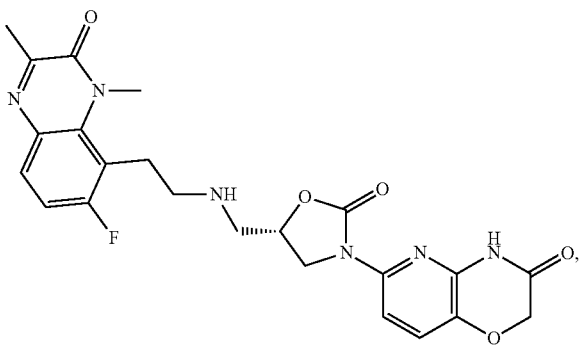 [SMILES: Cc1nc2ccc(F)c(CCNC[C@H]3CN(c4ccc5c(n4)NC(=O)CO5)C(=O)O3)c2n(C)c1=O]
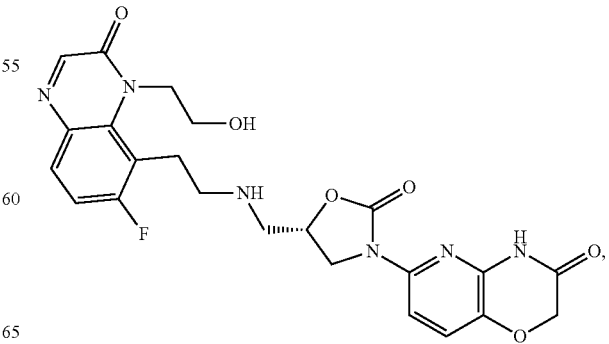

(S)-6-(5-(((2-(7-fluoro-1-(2-hydroxyethyl)-2-oxo-1,2-di-hydroquinolin-8-yl)ethyl)amino)methyl)-2-oxooxazo-lidin-3-yl)-2H-pyrido[3,2-b][1,4]oxazin-3(4H)-one (Example 10)

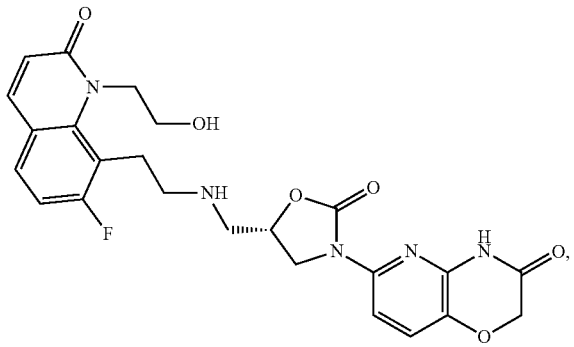 [SMILES: O=C1COc2ccc(N3C[C@H](CNCCc4c(F)ccc5ccc(=O)n(CCO)c45)OC3=O)nc2N1]

(S)-6-(5-(((2-(7-fluoro-1-(2-(methylsulfonyl)ethyl)-2-oxo-1,2-dihydroquinolin-8-yl)ethyl)amino)methyl)-2-oxooxazolidin-3-yl)-2H-pyrido[3,2-b][1,4]oxazin-3(4H)-one (Example 11)

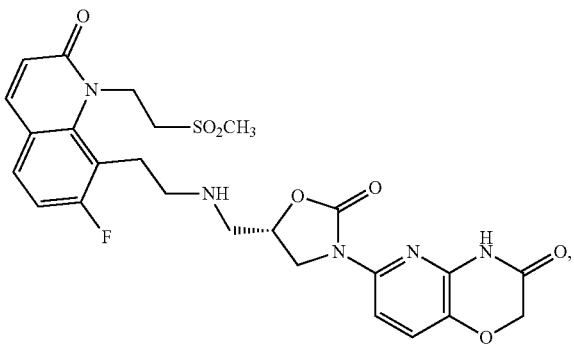 [SMILES: CS(=O)(=O)CCn1c(=O)ccc2ccc(F)c(CCNC[C@H]3CN(c4ccc5c(n4)NC(=O)CO5)C(=O)O3)c21]

(S)-6-(5-(((2-(7-fluoro-4-(hydroxymethyl)-1-methyl-2-oxo-1,2-dihydroquinolin-8-yl)ethyl)amino)methyl)-2-oxooxazolidin-3-yl)-2H-pyrido[3,2-b] [1,4] oxazin-3 (4H)-one (Example 12)

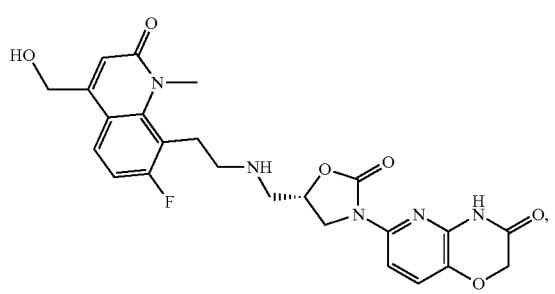 [SMILES: Cn1c(=O)cc(CO)c2ccc(F)c(CCNC[C@H]3CN(c4ccc5c(n4)NC(=O)CO5)C(=O)O3)c21]

S)-6-(5-(((2-(4-(aminomethyl)-7-fluoro-1-methyl-2-oxo-1,2-dihydroquinolin-8-yl)ethyl)amino)methyl)-2-oxooxazolidin-3-yl)-2H-pyrido[3,2-b][1,4]oxazin-3 (4H)-one (Example 13)

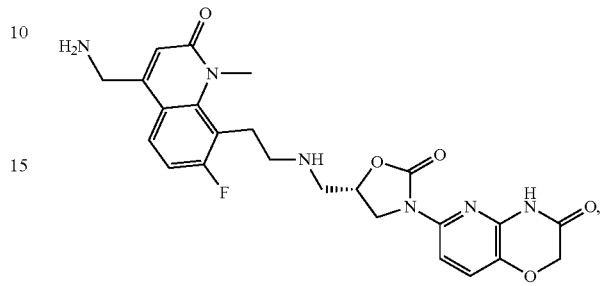

(R)-6-(5-(((2-(7-fluoro-1-methyl-2-oxo-1,2-dihydroqui-nolin-8-yl)ethyl)amino)methyl)-2-oxooxazolidin-3-yl)-2H-pyrazino[2,3-b][1,4]oxazin-3(4H)-one (Example 14)

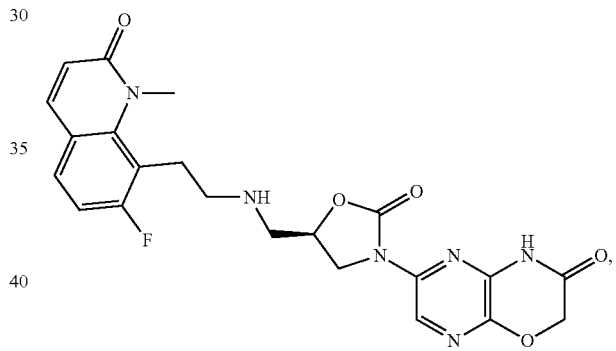

(S)-6-(5-(((2-(7-fluoro-1-methyl-2-oxo-1,2-dihydroqui-nolin-8-yl)ethyl)amino)methyl)-2-oxooxazolidin-3-yl)-2H-pyrazino[2,3-b][1,4]oxazin-3(4H)-one (Example 15)

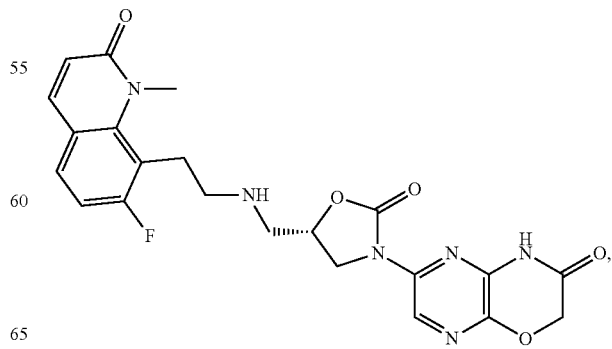

(S)-2-(5-(((2-(7-fluoro-1-methyl-2-oxo-1,2-dihydroquinolin-8-yl)ethyl)amino)methyl)-2-oxooxazolidin-3-yl)-6H-pyrimido[5,4-b][1,4]oxazin-7(8H)-one (Example 16)

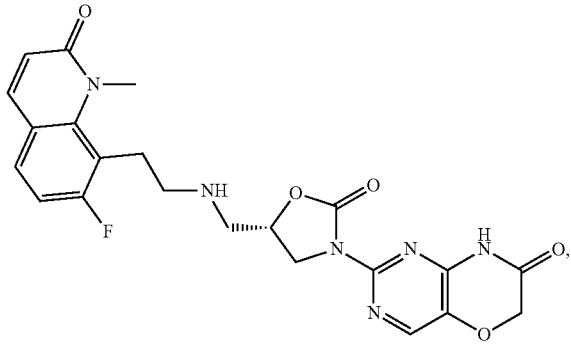 [SMILES: Cn1c(=O)ccc2ccc(F)c(CCNC[C@H]3CN(c4ncc5c(n4)NC(=O)CO5)C(=O)O3)c21]

(S)-2-(5-(((2-(6-fluoro-4-methyl-3-oxo-3,4-dihydroquinoxalin-5-yl)ethyl)amino)methyl)-2-oxooxazolidin-3-yl)-6H-pyrimido[5,4-b][1,4]oxazin-7(8H)-one (Example 17)

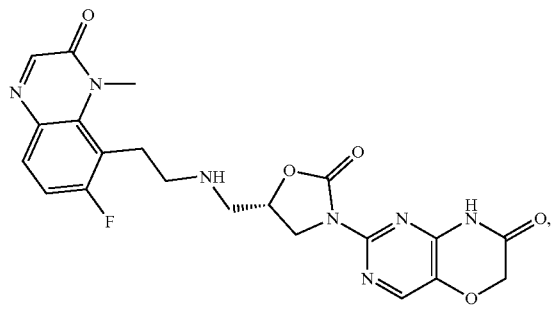 [SMILES: Cn1c(=O)cnc2ccc(F)c(CCNC[C@H]3CN(c4ncc5c(n4)NC(=O)CO5)C(=O)O3)c21]

6-(((S)-5-((((S)-3-(7-fluoro-1-methyl-2-oxo-1,2-dihydroquinolin-8-yl)-2-hydroxypropyl)amino)methyl)-2-oxooxazolidin-3-yl)-2H-pyrido[3,2-b][1,4]oxazin-3(4H)-one (Example 18)

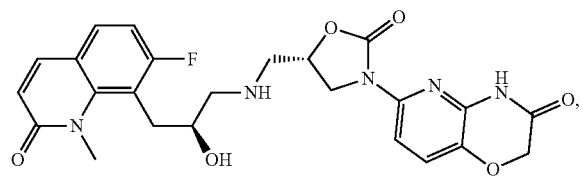 [SMILES: Cn1c(=O)ccc2ccc(F)c(C[C@H](O)CNC[C@H]3CN(c4ccc5c(n4)NC(=O)CO5)C(=O)O3)c21]

6-((S)-5-((((R)-3-(7-fluoro-1-methyl-2-oxo-1,2-dihydroquinolin-8-yl)-2-hydroxypropyl)amino)methyl)-2-oxooxazolidin-3-yl)-2H-pyrido[3,2-b][1,4]oxazin-3(4H)-one (Example 19)

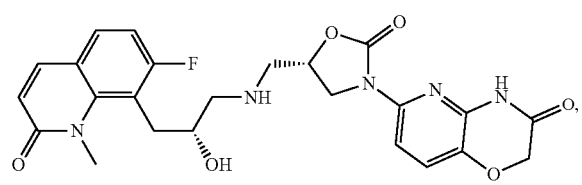 [SMILES: Cn1c(=O)ccc2ccc(F)c(C[C@@H](O)CNC[C@H]3CN(c4ccc5c(n4)NC(=O)CO5)C(=O)O3)c21]

(S)-6-(5-(((2-(7-fluoro-1-(2-hydroxyethyl)-2-oxo-1,2-dihydroquinolin-8-yl)ethyl)amino)methyl)-2-oxooxazolidin-3-yl)-2H-pyrazino[2,3-b][1,4]oxazin-3(4H)-one (Example 20)

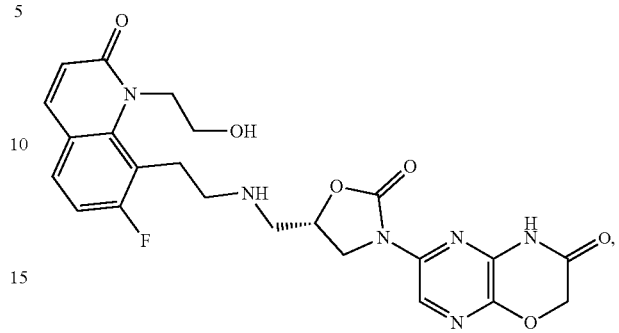

(S)-6-(5-(((2-(7-fluoro-1-(2-methoxyethyl)-2-oxo-1,2-dihydroquinolin-8-yl)ethyl)amino)methyl)-2-oxooxazolidin-3-yl)-2H-pyrazino[2,3-b][1,4]oxazin-3(4H)-one (Example 21)

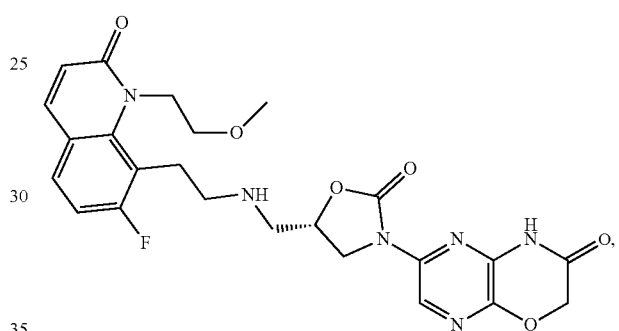

(S)-6-(5-(((3-(7-fluoro-1-methyl-2-oxo-1,2-dihydroquinolin-8-yl)propyl)amino)methyl)-2-oxooxazolidin-3-yl)-2H-pyrazino[2,3-b][1,4]oxazin-3(4H)-one (Example 22)

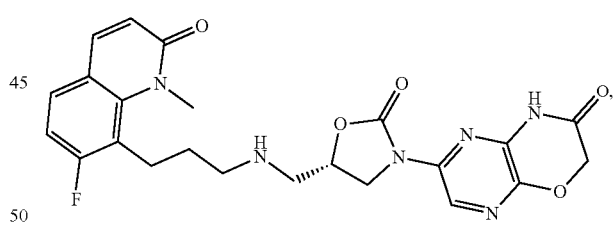

(R)-6-(5-(((3-(7-fluoro-1-methyl-2-oxo-1,2-dihydroquinolin-8-yl)propyl)amino)methyl)-2-oxooxazolidin-3-yl)-2H-pyrazino[2,3-b][1,4]oxazin-3(4H)-one (Example 23)

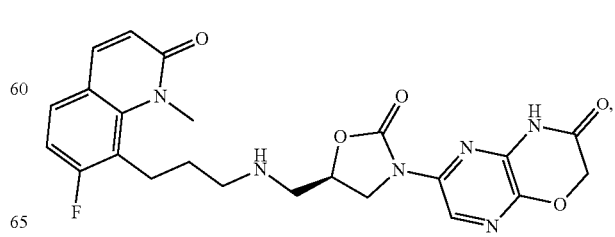

171

(S)-6-(5-(2-(((2-(7-fluoro-1-methyl-2-oxo-1,2-dihydro-quinolin-8-yl)ethyl)amino)ethyl)-2-oxooxazolidin-3-yl)-2H-pyrazino[2,3-b][1,4]oxazin-3(4H)-one (Example 24)

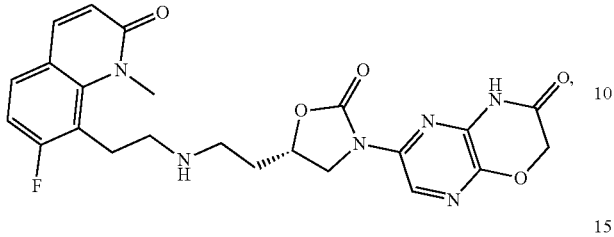

(R)-6-(5-(2-((2-(7-fluoro-1-methyl-2-oxo-1,2-dihydro-quinolin-8-yl)ethyl)amino)ethyl)-2-oxooxazolidin-3-yl)-2H-pyrazino[2,3-b][1,4]oxazin-3(4H)-one (Example 25)

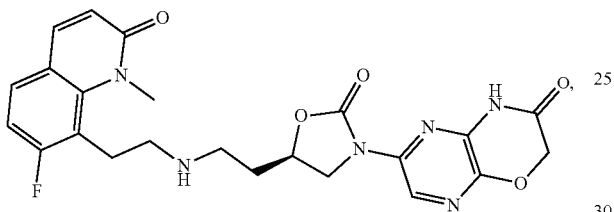

(S)-6-(5-(((2-(1-ethyl-7-fluoro-2-oxo-1,2-dihydroquinolin-8-yl)ethyl)amino)methyl)-2-oxooxazolidin-3-yl)-2H-pyrazino[2,3-b][1,4]oxazin-3(4H)-one (Example 26)

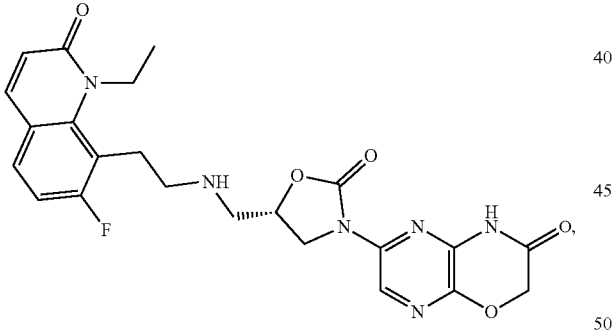

(S)-6-(5-(2-(((2-(1-ethyl-7-fluoro-2-oxo-1,2-dihydroquinolin-8-yl)ethyl)amino)ethyl)-2-oxooxazolidin-3-yl)-2H-pyrazino[2,3-b][1,4]oxazin-3(4H)-one (Example 27)

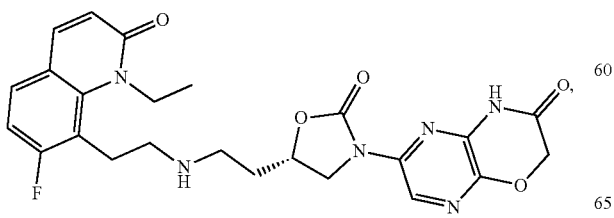

172

(S)-6-(5-(((2-(7-fluoro-1,4-dimethyl-2-oxo-1,2-dihydro-quinolin-8-yl)ethyl)amino)methyl)-2-oxooxazolidin-3-yl)-2H-pyrazino[2,3-b][1,4]oxazin-3(4H)-one (Example 28)

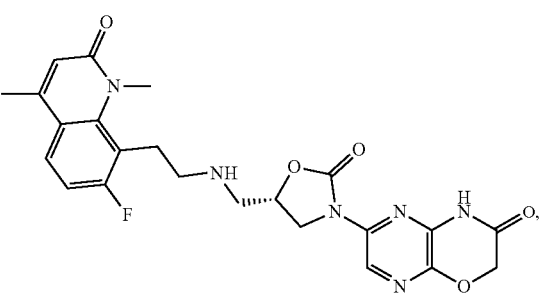 [SMILES: Cc1cc(=O)n(C)c2c(CCNC[C@H]3CN(c4cnc5c(n4)NC(=O)CO5)C(=O)O3)c(F)ccc12]

(S)-6-(5-(((2-(3-fluoro-5-methyl-6-oxo-5,6-dihydro-1,5-naphthyridin-4-yl)ethyl)amino)methyl)-2-oxooxazolidin-3-yl)-2H-pyrazino[2,3-b][1,4]oxazin-3(4H)-one (Example 29)

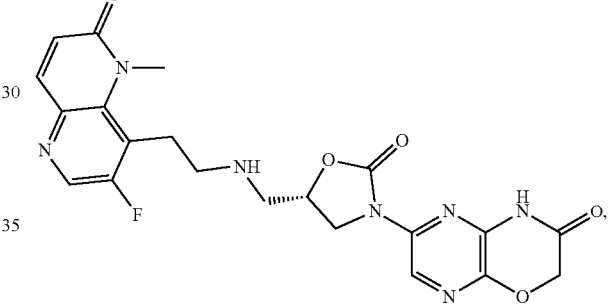

and (S)-6-(5-(((2-(6-fluoro-4-methyl-3-oxo-3,4-dihydroquinoxalin-5-yl)ethyl)amino)methyl)-2-oxooxazolidin-3-yl)-2H-pyrazino[2,3-b][1,4]oxazin-3(4H)-one (Example 30)

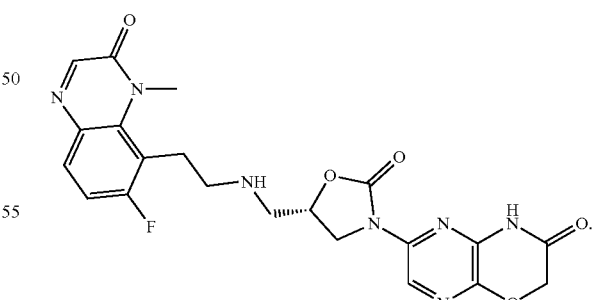

10. A process for preparation of a compound of Formula I as claimed in claim 1, or its stereoisomers, pharmaceutically acceptable salts, complexes, hydrates, solvates, tautomers, polymorphs, racemic mixtures, optically active forms, and pharmaceutically active derivatives thereof, said process comprises reacting Formula (A), and Formula (B)

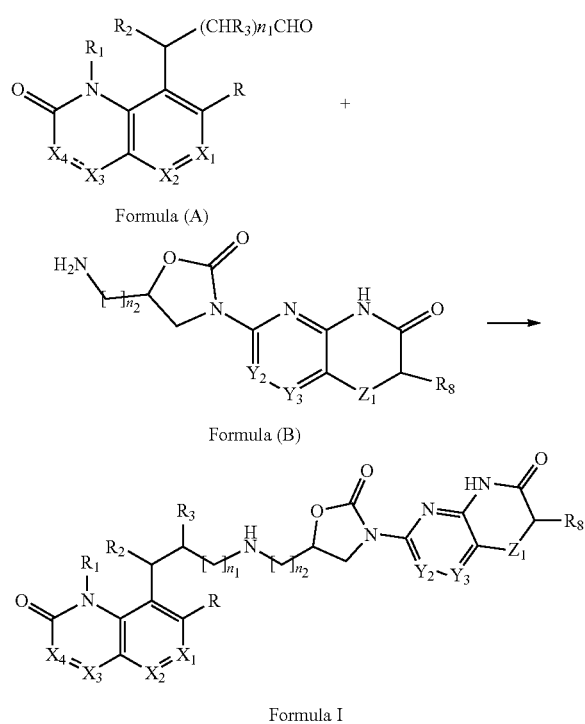

Formula (A)

Formula (B)

Formula I in presence of at least one reducing agent and an adsorbent to obtain the compounds of Formula I.

11. The process as claimed in claim 10, wherein $R_1$ of Formula (A) is selected from the group consisting of $C_{1-6}$ alkyl, $C_{2-6}$ alkenyl, $C_{3-6}$ cycloalkyl, $C_{1-6}$ alkylamino, $C_{1-6}$ aminoalkylene, and 4-7 membered carbocyclyl or heterocyclyl ring which may be fully saturated or unsaturated or partially unsaturated optionally having up to three heteroatoms independently selected from O, N, and S, each of which is unsubstituted or substituted with 1 to 3 groups independently selected from halogen, amino, hydroxyl, $C_{1-6}$ alkoxy, $SO_3H$, $SO_2R_9$, COORS, $CONHR_9$, and $SO_2NHR_9$, wherein $R_9$ is selected from H, $C_{1-6}$ alkyl, methylsulfone, $C_{1-6}$ alkyl, $OC_{1-6}$ alkyl, $OC_{1-6}$ haloalkyl, $C_{3-6}$ cycloalkyl, 3-7 membered heterocyclyl ring which may be fully saturated or unsaturated or partially unsaturated optionally having up to three heteroatoms independently selected from O, N, or S, $C_{3-6}$ cycloalkylamino, $C_{3-6}$ aminocycloalkyl, $C_{1-6}$ alkylamino, and di ($C_{1-6}$ alkyl)amino; $R_2$ and $R_3$ are independently selected from the group consisting of hydrogen, $C_{1-6}$ alkyl, fluorine, $OC_{1-6}$ alkyl, hydroxyl, and amino; R is selected from the group consisting of hydrogen, fluorine, cyano, $OC_{1-6}$ alkyl, and hydroxyl; $X_1$ is selected from the group consisting of N and $CR_4$; $R_4$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl; $X_2$ is selected from the group consisting of N and $CR_5$; $R_5$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl; $X_3$ is selected from the group consisting of N and $CR_6$; and $X_4$ is selected from the group consisting of CH and C—$C_{1-6}$ alkyl when dotted line ( ---- ) represents a bond, wherein $R_6$ is selected from the group consisting of hydrogen, halogen, cyano, —$OC_{1-6}$ alkyl, —$OC_{1-6}$ haloalkyl, and $C_{1-6}$ alkyl, wherein $C_{1-6}$ alkyl is optionally substituted with hydroxyl or amino; $X_4$ is selected from the group consisting of $CH_2$ and O; and $X_3$ is $CH_2$ when dotted line ( --- ) represents no bond; $n_1$ is 0 or 1;

$Y_2$ and $Y_3$ of Formula (B) are independently selected from —N and $CR_7$; $R_7$ is selected from the group consisting of hydrogen, halogen, cyano, —$OC_{1-6}$ alkyl, $C_{1-6}$ haloalkyl, —$OC_{1-6}$ haloalkyl, and $C_{1-6}$ alkyl; $Z_1$ is selected from the group consisting of O, S, and $CH_2$; $n_2$ is 0 to 2; and $R_8$ is selected from the group consisting of hydrogen, $C_{1-6}$ alkyl, and fluorine.

12. The process as claimed in claim 10, wherein the at least one reducing agent is selected from the group consisting of sodium borohydride, sodium cyano borohydride, sodium triacetoxy borohydride, and combinations thereof.

13. The process as claimed in claim 10, wherein the adsorbent is selected from the group consisting of molecular sieves, silica gel, zeolites, anhydrous sodium sulphate, anhydrous magnesium sulphate, activated charcoal, and combinations thereof.

14. A method for killing or inhibiting the growth of a microorganism in a sample, by administering the compound as claimed in claim 1, or its stereoisomers, pharmaceutically acceptable salts, complexes, hydrates, solvates, tautomers, polymorphs, racemic mixtures, optically active forms, and pharmaceutically active derivatives thereof to the sample, wherein the microorganism is selected from the group consisting of bacteria, virus, fungi, and protozoa.

15. A method for treatment of bacterial infection in a subject comprising: administering to the subject an effective amount of the compound as claimed in claim 1.

16. The method as claimed in claim 15, wherein the bacterial infection is caused by a Gram-positive or a Gram-negative pathogen.

17. The method as claimed in claim 15, wherein the bacterial infection is caused by *E. coli, P. aeruginosa, K. pneumonia, A. baumannii, S. aureus, E. faecalis*, or *E. faecium*.

18. A method of treating a disease or condition in a patient comprising administering a compound as claimed in claim 1, its stereoisomers, pharmaceutically acceptable salts, complexes, hydrates, solvates, tautomers, polymorphs, racemic mixtures, optically active forms, and pharmaceutically active derivatives thereof, wherein said disease or condition is caused by a microorganism selected from the group consisting of Gram-positive and Gram-negative pathogens.

19. A pharmaceutical composition comprising a compound of Formula I as claimed in claim 1, or its stereoisomers, pharmaceutically acceptable salts, complexes, hydrates, solvates, tautomers, polymorphs, racemic mixtures, optically active forms, and pharmaceutically active derivatives thereof together with a pharmaceutically acceptable carrier.

20. A pharmaceutical composition comprising a compound of Formula I as claimed in claim 1, or its stereoisomers, pharmaceutically acceptable salts, complexes, hydrates, solvates, tautomers, polymorphs, racemic mixtures, optically active forms and pharmaceutically active derivatives thereof together with a pharmaceutically acceptable carrier, and in combination with at least one antibiotic.

* * * * *